US011229631B2

(12) United States Patent
Xue et al.

(10) Patent No.: US 11,229,631 B2
(45) Date of Patent: *Jan. 25, 2022

(54) THIAZOLECARBOXAMIDES AND PYRIDINECARBOXAMIDE COMPOUNDS USEFUL AS PIM KINASE INHIBITORS

(71) Applicants: Incyte Corporation, Wilmington, DE (US); Incyte Holdings Corporation, Wilmington, DE (US)

(72) Inventors: Chu-Biao Xue, Hockessin, DE (US); Yun-Long Li, Chadds Ford, PA (US); Hao Feng, Glen Mills, PA (US); Jun Pan, Media, PA (US); Anlai Wang, Wilmington, DE (US); Ke Zhang, Wilmington, DE (US); Wenqing Yao, Chadds Ford, PA (US); Fenglei Zhang, Berwyn, PA (US); Jincong Zhuo, Garnet Valley, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/022,803

(22) Filed: Sep. 16, 2020

(65) Prior Publication Data

US 2020/0405702 A1 Dec. 31, 2020

Related U.S. Application Data

(63) Continuation of application No. 16/685,183, filed on Nov. 15, 2019, now Pat. No. 10,828,290, which is a continuation of application No. 16/298,601, filed on Mar. 11, 2019, now Pat. No. 10,517,858, which is a continuation of application No. 15/815,255, filed on Nov. 16, 2017, now Pat. No. 10,265,307, which is a continuation of application No. 15/373,923, filed on Dec. 9, 2016, now Pat. No. 9,849,120, which is a continuation of application No. 14/811,038, filed on Jul. 28, 2015, now Pat. No. 9,550,765, which is a continuation of application No. 14/155,212, filed on Jan. 14, 2014, now Pat. No. 9,200,004.

(60) Provisional application No. 61/859,118, filed on Jul. 26, 2013, provisional application No. 61/790,952, filed on Mar. 15, 2013, provisional application No. 61/752,897, filed on Jan. 15, 2013.

(51) Int. Cl.
| | |
|---|---|
| *A61K 31/444* | (2006.01) |
| *C07D 495/04* | (2006.01) |
| *C07D 401/14* | (2006.01) |
| *C07D 405/14* | (2006.01) |
| *C07D 417/14* | (2006.01) |
| *C07D 471/04* | (2006.01) |
| *C07D 491/048* | (2006.01) |

(52) U.S. Cl.
CPC .......... *A61K 31/444* (2013.01); *C07D 401/14* (2013.01); *C07D 405/14* (2013.01); *C07D 417/14* (2013.01); *C07D 471/04* (2013.01); *C07D 491/048* (2013.01); *C07D 495/04* (2013.01)

(58) Field of Classification Search
CPC .. A61K 31/444; C07D 401/14; C07D 405/14; C07D 417/14; C07D 471/04; C07D 491/048; C07D 495/04
USPC .......................................................... 546/26
See application file for complete search history.

(56) References Cited

U.S. PATENT DOCUMENTS

| | | | |
|---|---|---|---|
| 6,987,116 B2 | 1/2006 | Boschelli et al. | |
| 7,517,990 B2 * | 4/2009 | Ito ........................ | C07D 213/16 546/184 |
| 8,168,794 B2 | 5/2012 | Burger et al. | |
| 8,329,732 B2 | 12/2012 | Burger et al. | |
| 9,200,004 B2 | 12/2015 | Xue | |
| 9,278,950 B2 | 3/2016 | Li et al. | |
| 9,340,546 B2 | 5/2016 | Ahmad | |
| 9,540,347 B2 | 1/2017 | Vechorkin et al. | |
| 9,550,765 B2 | 1/2017 | Xue et al. | |
| 9,556,197 B2 | 1/2017 | Li et al. | |
| 9,580,418 B2 | 2/2017 | Sun et al. | |
| 9,676,750 B2 | 6/2017 | Li et al. | |
| 9,802,918 B2 | 10/2017 | Vechorkin et al. | |
| 9,822,124 B2 | 11/2017 | Vechorkin et al. | |
| 9,849,120 B2 | 12/2017 | Xue et al. | |
| 9,862,705 B2 | 1/2018 | Jia et al. | |
| 9,920,032 B2 | 3/2018 | Vechorkin et al. | |
| 10,000,507 B2 | 6/2018 | Li et al. | |
| 10,265,307 B2 | 4/2019 | Xue et al. | |

(Continued)

FOREIGN PATENT DOCUMENTS

| | | |
|---|---|---|
| CA | 2668255 | 5/2008 |
| CN | 101568527 | 10/2009 |

(Continued)

OTHER PUBLICATIONS

Amson et al., "The human protooncogene product p33pim is expressed during fetal hematopoiesis and in diverse leukemias," Proc. Nat. Acad. Sci., USA, 1989, 86:8857-61.

(Continued)

*Primary Examiner* — Kristin A Vajda
(74) *Attorney, Agent, or Firm* — Fish & Richardson P.C.

(57) ABSTRACT

The present disclosure describes thiazole and pyridine carboxamide derivatives, their compositions and methods of use. The compounds inhibit the activity of the Pim kinases and are useful in the treatment of diseases related to the activity of Pim kinases including, e.g., cancer and other diseases.

4 Claims, No Drawings

(56) References Cited

U.S. PATENT DOCUMENTS

| | | |
|---|---|---|
| 10,336,728 B2 | 7/2019 | Jia et al. |
| 10,450,296 B2 | 10/2019 | Vechorkin et al. |
| 10,517,858 B2 | 12/2019 | Xue et al. |
| 10,828,290 B2 | 11/2020 | Xue et al. |
| 11,053,215 B2 | 7/2021 | Vechorkin et al. |
| 11,066,387 B2 | 7/2021 | Jia et al. |
| 2010/0216839 A1 | 8/2010 | Burger et al. |
| 2011/0059961 A1 | 3/2011 | Wang et al. |
| 2011/0130418 A1 | 6/2011 | Poncelet et al. |
| 2012/0114663 A1 | 5/2012 | Gelfand et al. |
| 2012/0225062 A1 | 9/2012 | Burger et al. |
| 2013/0057956 A1 | 3/2013 | Iwasa |
| 2014/0086941 A1 | 3/2014 | Reddy et al. |
| 2014/0088117 A1 | 3/2014 | Burch et al. |
| 2014/0163000 A1 | 6/2014 | Ahmad |
| 2014/0200216 A1 | 7/2014 | Li et al. |
| 2014/0200227 A1 | 7/2014 | Xue et al. |
| 2015/0057265 A1 | 2/2015 | Li et al. |
| 2015/0329534 A1 | 11/2015 | Xue et al. |
| 2016/0009714 A1 | 1/2016 | Sun et al. |
| 2016/0009726 A1 | 1/2016 | Vechorkin et al. |
| 2016/0137626 A1 | 5/2016 | Li et al. |
| 2016/0347735 A1 | 12/2016 | Vechorkin et al. |
| 2017/0096411 A1 | 4/2017 | Vechorkin et al. |
| 2017/0121310 A1 | 5/2017 | Jia et al. |
| 2017/0158670 A1 | 6/2017 | Vechorkin et al. |
| 2017/0182017 A1 | 6/2017 | Xue et al. |
| 2017/0190716 A1 | 7/2017 | Li et al. |
| 2017/0253587 A1 | 9/2017 | Sun et al. |
| 2018/0170907 A1 | 6/2018 | Jia et al. |
| 2018/0193323 A1 | 7/2018 | Xue et al. |
| 2018/0282302 A1 | 10/2018 | Vechorkin et al. |
| 2019/0209537 A1 | 7/2019 | Xue et al. |
| 2019/0270725 A1 | 9/2019 | Jia et al. |
| 2020/0002309 A1 | 1/2020 | Vechorkin et al. |
| 2020/0155527 A1 | 5/2020 | Xue et al. |
| 2021/0155605 A1 | 5/2021 | Jia et al. |

FOREIGN PATENT DOCUMENTS

| | | |
|---|---|---|
| CN | 102625807 | 8/2012 |
| CN | 102985426 | 3/2013 |
| CN | 103664878 | 3/2014 |
| EP | 2637650 | 9/2013 |
| EP | 2743269 | 6/2014 |
| JP | 2010508278 | 3/2010 |
| JP | 2010533716 | 10/2010 |
| JP | 2010535201 | 11/2010 |
| JP | 2012524085 | 10/2012 |
| JP | 2014527959 | 10/2014 |
| WO | WO 2002/000196 | 1/2002 |
| WO | WO 2002/055489 | 7/2002 |
| WO | WO 2002/093173 | 11/2002 |
| WO | WO 2003/106681 | 12/2003 |
| WO | WO 2004/024895 | 3/2004 |
| WO | WO 2004/090106 | 10/2004 |
| WO | WO 2005/028624 | 3/2005 |
| WO | WO 2005/033310 | 4/2005 |
| WO | WO 2006/006569 | 1/2006 |
| WO | WO 2006/071960 | 7/2006 |
| WO | WO 2006/078228 | 7/2006 |
| WO | WO 2007/002433 | 1/2007 |
| WO | WO 2007/011760 | 1/2007 |
| WO | WO 2007/041712 | 4/2007 |
| WO | WO 2007/044724 | 4/2007 |
| WO | WO 2007/048065 | 4/2007 |
| WO | WO 2007/052843 | 5/2007 |
| WO | WO 2007/084857 | 7/2007 |
| WO | WO 2007/131191 | 11/2007 |
| WO | WO 2008/002676 | 1/2008 |
| WO | WO 2008/022164 | 2/2008 |
| WO | WO 2008/045252 | 4/2008 |
| WO | WO 2008/054749 | 5/2008 |
| WO | WO 2008/058126 | 5/2008 |
| WO | WO 2008/082839 | 7/2008 |
| WO | WO 2008/082840 | 7/2008 |
| WO | WO 2008/106692 | 9/2008 |
| WO | WO 2008/121687 | 10/2008 |
| WO | WO 2008/124323 | 10/2008 |
| WO | WO 2008/127728 | 10/2008 |
| WO | WO 2008/133955 | 11/2008 |
| WO | WO 2008/143759 | 11/2008 |
| WO | WO 2009/014637 | 1/2009 |
| WO | WO 2009/017701 | 2/2009 |
| WO | WO 2009/064486 | 5/2009 |
| WO | WO 2009/065080 | 5/2009 |
| WO | WO 2009/108912 | 9/2009 |
| WO | WO 2009/109576 | 9/2009 |
| WO | WO 2009/151845 | 12/2009 |
| WO | WO 2010/000978 | 1/2010 |
| WO | WO 2010/001169 | 1/2010 |
| WO | WO 2010/002933 | 1/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/048314 | 4/2010 |
| WO | WO 2010/057833 | 5/2010 |
| WO | WO 2010/071885 | 6/2010 |
| WO | WO 2010/135401 | 11/2010 |
| WO | WO 2010/135571 | 11/2010 |
| WO | WO 2010/135581 | 11/2010 |
| WO | WO 2010/135650 | 11/2010 |
| WO | WO 2010/148351 | 12/2010 |
| WO | WO 2011/008487 | 1/2011 |
| WO | WO 2011/025859 | 3/2011 |
| WO | WO 2011/028685 | 3/2011 |
| WO | WO 2011/029802 | 3/2011 |
| WO | WO 2011/031979 | 3/2011 |
| WO | WO 2011/035019 | 3/2011 |
| WO | WO 2011/035022 | 3/2011 |
| WO | WO 2011/053861 | 5/2011 |
| WO | WO 2011/057784 | 5/2011 |
| WO | WO 2011/058139 | 5/2011 |
| WO | WO 2011/060295 | 5/2011 |
| WO | WO 2011/063398 | 5/2011 |
| WO | WO 2011/068667 | 6/2011 |
| WO | WO 2011/075613 | 6/2011 |
| WO | WO 2011/075630 | 6/2011 |
| WO | WO 2011/075643 | 6/2011 |
| WO | WO 2011/079274 | 6/2011 |
| WO | WO 2011/101643 | 8/2011 |
| WO | WO 2011/112662 | 9/2011 |
| WO | WO 2011/124580 | 10/2011 |
| WO | WO 2011/130342 | 10/2011 |
| WO | WO 2011/163195 | 12/2011 |
| WO | WO 2012/004217 | 1/2012 |
| WO | WO 2012/007375 | 1/2012 |
| WO | WO 2012/015474 | 2/2012 |
| WO | WO 2012/016217 | 2/2012 |
| WO | WO 2012/064981 | 5/2012 |
| WO | WO 2012/065297 | 5/2012 |
| WO | WO 2012/065546 | 5/2012 |
| WO | WO 2012/068440 | 5/2012 |
| WO | WO 2012/068450 | 5/2012 |
| WO | WO 2012/078777 | 6/2012 |
| WO | WO 2012/080990 | 6/2012 |
| WO | WO 2012/087881 | 6/2012 |
| WO | WO 2012/101029 | 8/2012 |
| WO | WO 2012/101032 | 8/2012 |
| WO | WO 2012/120415 | 9/2012 |
| WO | WO 2012/120428 | 9/2012 |
| WO | WO 2012/125629 | 9/2012 |
| WO | WO 2012/129338 | 9/2012 |
| WO | WO 2012/135009 | 10/2012 |
| WO | WO 2012/137089 | 10/2012 |
| WO | WO 2012/139930 | 10/2012 |
| WO | WO 2012/145617 | 10/2012 |
| WO | WO 2012/146933 | 11/2012 |
| WO | WO 2012/146936 | 11/2012 |
| WO | WO 2012/148775 | 11/2012 |
| WO | WO 2012/154274 | 11/2012 |
| WO | WO 2012/156367 | 11/2012 |

(56) References Cited

FOREIGN PATENT DOCUMENTS

| | | |
|---|---|---|
| WO | WO 2012/156756 | 11/2012 |
| WO | WO 2012/163942 | 12/2012 |
| WO | WO 2012/170827 | 12/2012 |
| WO | WO 2012/175591 | 12/2012 |
| WO | WO 2012/177606 | 12/2012 |
| WO | WO 2013/013188 | 1/2013 |
| WO | WO 2013/020369 | 2/2013 |
| WO | WO 2013/20370 | 2/2013 |
| WO | WO 2013/020371 | 2/2013 |
| WO | WO 2013/024002 | 2/2013 |
| WO | WO 2013/026025 | 2/2013 |
| WO | WO 2013/033569 | 3/2013 |
| WO | WO 2013/034570 | 3/2013 |
| WO | WO 2013/036611 | 3/2013 |
| WO | WO 2013/041634 | 3/2013 |
| WO | WO 2013/045461 | 4/2013 |
| WO | WO 2013/050446 | 4/2013 |
| WO | WO 2013/050448 | 4/2013 |
| WO | WO 2013/130660 | 9/2013 |
| WO | WO 2013/134079 | 9/2013 |
| WO | WO 2013/066684 | 10/2013 |
| WO | WO 2013/144189 | 10/2013 |
| WO | WO 2013/149909 | 10/2013 |
| WO | WO 2013/151930 | 10/2013 |
| WO | WO 2013/160873 | 10/2013 |
| WO | WO 2013/163279 | 10/2013 |
| WO | WO 2013/170068 | 11/2013 |
| WO | WO 2013/171639 | 11/2013 |
| WO | WO 2013/173720 | 11/2013 |
| WO | WO 2013/175388 | 11/2013 |
| WO | WO 2013/177219 | 11/2013 |
| WO | WO 2013/186692 | 12/2013 |
| WO | WO 2014/001377 | 1/2014 |
| WO | WO 2014/011974 | 1/2014 |
| WO | WO 2014/022752 | 2/2014 |
| WO | WO 2014/033630 | 3/2014 |
| WO | WO 2014/033631 | 3/2014 |
| WO | WO 2014/041131 | 3/2014 |
| WO | WO 2014/048939 | 4/2014 |
| WO | WO 2014/053568 | 4/2014 |
| WO | WO 2014/060411 | 4/2014 |
| WO | WO 2014/071031 | 5/2014 |
| WO | WO 2014/076162 | 5/2014 |
| WO | WO 2014/079011 | 5/2014 |
| WO | WO 2014/079136 | 5/2014 |
| WO | WO 2014/009447 | 6/2014 |
| WO | WO 2014/089379 | 6/2014 |
| WO | WO 2014/097151 | 6/2014 |
| WO | WO 2014/099880 | 6/2014 |
| WO | WO 2014/100158 | 6/2014 |
| WO | WO 2014/100323 | 6/2014 |
| WO | WO 2014/100719 | 6/2014 |
| WO | WO 2014/106706 | 7/2014 |
| WO | WO 2014/110574 | 7/2014 |
| WO | WO 2014/113388 | 7/2014 |
| WO | WO 2014/134426 | 9/2014 |
| WO | WO 2014/138168 | 9/2014 |
| WO | WO 2014/138906 | 9/2014 |
| WO | WO 2014/138907 | 9/2014 |
| WO | WO 2014/139145 | 9/2014 |
| WO | WO 2014/140597 | 9/2014 |
| WO | WO 2014/140644 | 9/2014 |
| WO | WO 2014/140861 | 9/2014 |
| WO | WO 2014/141171 | 9/2014 |
| WO | WO 2014/142290 | 9/2014 |
| WO | WO 2014/142292 | 9/2014 |
| WO | WO 2014/143601 | 9/2014 |
| WO | WO 2014/143768 | 9/2014 |
| WO | WO 2014/145051 | 9/2014 |
| WO | WO 2014/150258 | 9/2014 |
| WO | WO 2014/150276 | 9/2014 |
| WO | WO 2014/151008 | 9/2014 |
| WO | WO 2014/151634 | 9/2014 |
| WO | WO 2015/021153 | 2/2015 |
| WO | WO 2015/027124 | 2/2015 |
| WO | WO 2015/131031 | 9/2015 |
| WO | WO 2015/157257 | 10/2015 |
| WO | WO 2015/168246 | 11/2015 |
| WO | WO 2015/184305 | 12/2015 |
| WO | WO 2015/191677 | 12/2015 |

OTHER PUBLICATIONS

Anderson and Flora, "Preparation of Water-Soluble Organic Compounds Through Salt Formation," Practice of Medicinal Chemistry, Wermuth (Ed.), 1999, vol. 2:347-365.
Arunesh et al., "Small molecule inhibitors of PIM1 kinase: Jul. 2009 to Feb. 2013 patent update," Expert Opin Ther Pat, Jan. 2014, 24(1):5-17.
Asahara, "Solvent Handbook," Incorporated Company Kodansha, 1985, p. 47-51.
Asano et al., "The serine/threonine kinase Pim-2 is a novel anti-apoptotic mediator in myeloma cells," Leukemia, 2011, 25: 1182-1188.
Bamborough, "Assessment of Chemical Coverage of Kinome Space and Its Implications for Kinase Drug Discovery," J. Med. Chem., 2008, 51: 7898-7914.
Baron et al., "PIM1 gene cooperates with human BCL6 gene to promote the development of lymphomas," PNAS, Apr. 2012, 109(15): 5735-5739.
Bastin et al., "Salt Selection and Optimisation Procedures for Pharmaceutical New Chemical Entities," Org Proc Res Dev., Jul. 19, 2000, 4(5):427-435.
Berge et al., "Pharmaceutical Salts," J. Pharm. Sci., 1977, 66(1):1-19.
Blanco-Aparicio, Biochemical Pharmacology, vol. 85, pp. 629-643, 2013.
Blom et al., "Optimizing Preparative LC-MS Configurations and Methods for Parallel Synthesis Purification," J. Comb. Chem., 2003, 5:670-83.
Blom et al., "Preparative LC-MS Purification: Improved Compound Specific Method Optimization," J. Comb. Chem., 2004, 6:874-883.
Blom, "Two-Pump at Column Dilution Configuration for Preparative Liquid Chromatography—Mass Spectrometiy," J. Comb. Chem,, 2002, 4:295-301.
Brault et al., "PIM kinases are progression markers and emerging therapeutic targets in diffuse large B-cell lymphoma," British Journal of Cancer, 2012, 107: 491-500.
Brittain, "Polymorphism in Pharmaceutical Solids,"CRC Press. Marcel Dekker, Inc., New York, 2009, pp. 333-334.
Burger et al. "Structure Guided Optimization, in Vitro Activity, and in Vivo Activity of Pan-PIM Kinase Inhibitors," ACS Med Chem Lett., 2013, 4:1193-1197.
Caira, "Crystalline Polymorphism of Organic Compounds," Topics in Current Chemistry, Jan. 1998, 198: 163-208.
Cancer [online], [retrieved on Jul. 6, 2007] Retrieved from the Internet, URL: http://www.nlm.nih.gov/medlineplus/cancer.html.
Cervantes-Gomez et al., "Biological Effects of the Pim Kinase Inhibitor, SGI-1776, in Multiple Myeloma," Clinical Lymphoma, Myeloma & Leukemia, Sep. 2013, S317-S329.
Chaichian "Targeted Therapies in Systemic Lupus Erythematosus: A State-of-the-Art-Review" J Clin Cell Immunol 2013, S6, 1-8.
Chan et al., "New N- and O-arylations with phenylboronic acids and cupric acetate," Tetrahedron Letters, May 1998, 39(19): 2933-2936.
Chen et al., "Mechanisms of cytotoxicity to Pim kinase inhibitor, SGI-1776, in acute myeloid leukemia," Blood, Jul. 2011, 118(3): 693-702.
Chen et al., "Pim kinase inhibitor, SGI-1776, induces apoptosis in chronic lymphocytic leukemia cells," Blood, 2009, 114:4150-57.
Chilean Office Action, Patent Application No. 1985-2015, dated Jul. 7, 2016, 22 pages (English Translation).
Chinese Office Action in Chinese Application No. 201480012783.3. dated Sep. 6, 2016, 16 pages (English Translation).
Claudio et al., "A molecular compendium of genes expressed in multiple myeloma," Blood, 2002, 100:2175-86.
Colombian Office Action in Colombian Application No. 15-168. 544, dated Aug. 10, 2016, 10 pages.

(56) References Cited

OTHER PUBLICATIONS

Colombian Office Action in Colombian Application No. NC2018/0003739, dated Oct. 13, 2020, 17 pages.
Coperet, "A simple and efficient method for the preparation of pyridine N-Oxides," The Journal of Organic Chemistiy, Jan. 1998, 63: 1740-1741.
Damia "Contemporary pre-clinical development of anticancer agents—What are the optimal preclinical models?" European Journal of Cancer, 2009, 45, 2768-2781.
Database accession No. RN 1795440-67-3, Chemical Abstracts Service, Jul. 6, 2015, 1 page.
Davis et al., "Small Molecule Dual Antagonist of Pim 1 and 3 Kinases Ameliorate Experimental Autoimmune Encephalomyelitis," 26th Congress of the European Committee for Treatment and Research in Multiple Sclerosis, Oct. 13-16, 2010, Gothenburg, Sweden, Poster P436.
Dorwald F. A. Side Reactions in Organic Synthesis, 2005, Wiley: VCH, Weinheim p. IX of Preface PR. 1-15.
Eurasian Office Action in Eurasian Application No. 201690458/28, dated Jan. 25, 2017, 11 pages (with English translation).
Eurasian Office Action in Eurasian Application No. 201890663/28, dated Dec. 10, 2018, 8 pages (with English translation).
European Office Action in European Application No. 16770411.3, dated Mar. 11, 2021, 3 pages.
Freshney, Culture of Animal Cells, A Manual of Basic Technique, Alan R. Liss, Inc., 1983, New York, P4.
Fujii et al., "Aberrant expression of serine-threonine kinase Pim-3 in hepatocellular carcinoma development and its role in the proliferation of human hepatoma cell lines," Int. J. Canc., 2005, 114:209-18.
Georg Pilz, "Modern multiple sclerosis treatment—what is approved, what is on the horizon" Drug Discovery Today Dec. 2008, vol. 13, Nos. 23/24 1013-1025.
Golub et al., "Molecular Classification of Cancer: Class Discovery and Class Prediction by Gene Expression Monitoring," Science, 1999, 286: 531-537.
Gomez-Abad et al., "PIM2 inhibition as a rational therapeutic approach in B-cell lymphoma," Blood, 2011, 118:5517-27.
Gozgit et al., "Effects of the JAK2 Inhibitor, AZ960, on Pim/BAD/BCL-xL Survival Signaling in the Human JAK2 V617F Cell Line SET-2," Journal of Biological Chemistry, Nov. 2008, 283(47): 32334-32343.
Gu and Li, "A concise synthesis of (2S,4R)- and (2S,4S)-4-methylglutamic acid," Tetrahedron Lett., 2003, 44:3203-3205.
Guo et al., "Overexpression of Pim-1 in bladder cancer," J. Experimental & Clinical Cancer Research, 2010, 29: 161-167.
Hammerman et al., "Lymphocyte Transformation by Pim-2 Is Dependent on Nuclear Factor-kB Activation," Cancer Research, Nov. 2004, 64: 8341-8348.
Hirayama, "Handbook for organic compound crystal preparation—Principle and know-how," Marzen Co. Ltd., Jul. 25, 2008, p. 57-84.
Hsi et al., "Ki67 and PIM1 expression predict outcome in mantle cell lymphoma treated with high dose therapy, stem cell transplantation and rituximab: a Cancer and Leukemia Group B 59909 correlative science study," Lenk, Lymph,, 2008, 49:2081-90.
Hsu et al., "Pim-1 knockdown potentiates paclitaxel-induced apoptosis in human hormone-refractory prostate cancers through inhibition of NHEJ DNA repair," Cancer Lett, 2012, 319:214-222.
Hu et al., "PIM-1—specific mAb suppresses human and mouse tumor growth by decreasing PIM-1 levels, reducing Akt phosphorylation and activating apoptosis," J. Clinical Investigation, Feb. 2009, 119(2):362-375.
Huang et al., "Structure-based design and optimization of 2-aminothiazole-4-carboxamide as a new class of CHK1 inhibitors," Bioorganic Med Chem Lett, Mar. 2013, 23(9):2590-2594.
International Preliminary Report on Patentability in International Application No. PCT/US2014/011486, dated Jul. 21, 2015, 7 pages.
International Preliminary Report on Patentability in International Application No. PCT/US2014/011487, dated Jul. 23, 2015, 6 pages.
International Preliminary Report on Patentability in International Application No. PCT/US2014/052214, dated Feb. 23, 2016, 7 pages.
International Preliminary Report on Patentability in International Application No. PCT/US2015/040146, dated Jan. 17, 2017, 8 pages.
International Preliminary Report on Patentability in International Application No. PCT/US2016/034520, dated Dec. 14, 2017, 7 pages.
International Preliminary Report on Patentability in International Application No. PCT/US2016/050925, dated Mar. 22, 2018, 8 pages.
International Search Report and Written Opinion in International Application No. PCT/US2014/011486, mailed Mar. 17, 2014, 12 pages.
International Search Report and Written Opinion in International Application No. PCT/US2014/011487, mailed Apr. 4, 2014, 11 pages.
International Search Report and Written Opinion in International Application No. PCT/US2014/052214, mailed Oct. 28, 2014, 13 pages.
International Search Report and Written Opinion in International Application No. PCT/US2015/040146, dated Oct. 5, 2015, 12 pages.
International Search Report and Written Opinion in International Application No. PCT/US2016/034520, dated Jul. 12, 2016, 11 pages.
International Search Report and Written Opinion in International Application No. PCT/US2016/050925, dated Oct. 21, 2016, 13 pages.
International Search Report and Written Opinion in International Application No. PCT/US2016/054779, dated Dec. 9, 2016, 12 pages.
Isaac et al., "The oncogenic PIM kinase family regulates drug resistance through multiple mechanisms," Drug Resis. Updates, 2011, 14:203-11.
Ishchenko et al., "Structure-based design of low-nanomolar PIM kinase inhibitors," Bioorg Med Chem Lett., 2015, 25:474-480.
Israeli Office Action in Israel Application No. 244,224, dated May 18, 2018, 8 pages (English Translation).
Jiang et al., "3,5-Disubstituted quinolines as novel c-Jun N-terminal kinase inhibitors," Bioorganic & Medicinal Chemistiy Letters, 2007, 17: 6378-6382.
Jin et al., "Expressions of Osteopontin (OPN), anb3 an Pim-1 Associated with Poor Prognosis in Non-small Cell Lung Cancer (NSCLC)," Chin J. Cancer Res, 2012, 24(2): 103-108.
Johnson et al., "Relationship between drug activity in NCI preclinical in vitro and in vivo models and early clinical trials" British Journal of Cancer, 2001, 84, 1424-1437.
Katano et al., "Synthesis and biological activity of (cyclopentenopyridinium)thiomethylcephalosporins," The Journal of Antibiotics, Jan. 1990, 43(9): 1150-1159.
Kelly et al., "Targeting PIM kinase activity significantly augments the efficacy of cytarabine," British Journal of Haematology, 2011, 156: 129-152.
Kirschner, "PIM Kinase Inhibitor AZD1208 for Treatment of MYC-Driven Prostate Cancer," JNCI J Natl Cancer Inst, 2015. 107(2): 1-11.
Kojima, "Iyakuhin Kaihatu niokeru kesyosei sentaku no kourituka wo mezasite (documents indicating well-known arts) for the purpose of improving the selection of a crystalline selection in the development of small or pharmaceutical drug and pharmaceutical drug development," Medicine, Sep. 1, 2008, 68(5):344-349.
Konstantinos Markrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.
Lala et al., "Role of nitric oxide in tumor progression: Lessons from experimental tumors," Cancer and Metastasis Reviews, 1998, 17: 91-106.
Lam et al., "New aryl/heteroaryl C N bond cross-coupling reactions via arylboronic acid/cupric acetate arylation," Tetrahedron Letters, May 1998, 39(19): 2941-2944.

(56) References Cited

OTHER PUBLICATIONS

Li et al., "Pim-3, a Proto-Oncogene with Serine/Threonine Kinase Activity, is Aberrantly Expressed in Human Pancreatic Cancer and Phosphorylates Bad to Block Bad-Mediated Apoptosis in Human Pancreatic Cancer Cell Lines," Canc. Res., 2006, 66:6741-7.
Lin et al., "A small molecule inhibitor of Pim protein kinases blocks the growth of precursor T-cell lymphoblastic leukemia/lymphoma," Blood, Jan. 2010, 115(4): 824-833.
Liu et al., "Overexpression of Pim-1 is associated with poor prognosis in patients with esophageal squamous cell carcinoma," J. Surg. Oncol., 2010,102:683-88.
Liu et al., "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, 2006, 16: 2590-2594.
Lu et al., "Pim2 is required for maintaining multiple myeloma cell growth through modulating TSC2 phosphorylation," Blood, Aug. 2013, 122(9): 1610-1620.
Mahalingam et al., "Targeting PIM kinase enhances the activity of sunitinib in renal cell carcinoma," British J. Cancer, Oct. 2011, 105: 1563-1573.
Magnuson, "Why target PIM1 for cancer diagnosis and treatment?" Future Oncol., Sep. 2010. 6(9): 1461-1478.
Mano, "Pharmaceutical Research in the Early Stages of Drug Discoverysignificance and Practice," Japanese Pharmacological Society, Mar. 1, 2009, 133(3):149-153.
Martin-Sanchez et al., "HDAC inhibitors induce cell cycle arrest, activate the apoptotic extrinsic pathway and synergize with a novel PIM inhibitor in Hodgkin lymphoma-derived cell lines," British J. Haematology, 2010, 152:347-362.
Merkel et al., "PIM1 kinase as a target for cancer therapy," Exp. Opin. Investig. Drugs, 2012, 21:425-38.
Michelotti et al., "Two classes of p38a MAP kinase inhibitors having a common diphenylether core but exhbiting divergent binding modes," 2005, 15: 5274-5279.
Mikkers et al., "High-throughput retroviral tagging to identify components of specific signaling pathways in cancer," Nature Genet, 2002, 32:153-159.
Mikkers et al., "Mice deficient for all PIM kinases display reduced body size and impaired responses to hematopoietic growth factors," Mol. Cell. Biol., 2004, 24:6104-15.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorganic & Medicinal Chemistiy Letters, 2007, 17: 250-254.
Mizuki et al., "Suppression of myeloid transcription factors and induction of STAT response genes by AML-specific Flt3 mutations," Blood, 2003, 101:3164-73.
Morwick, "Pim kinase inhibitors: a survey of the patent literature," Exp. Opin. Ther. Patents, 2010, 20(2):193-212.
Morissette et al., "High-Throughput Crystallization: polymorphs, salts, co-crystals and solvates of pharmaceutical solids," Advanced Drug Delivery Reviews, Feb. 23, 2004, 56:375-300.
Mukaida et al., "Roles of Pim-3, a novel survival kinase, in tumorgenesis," Cancer Science, Aug. 2011, 102(8):1437-1442.
Mulvihill et al., "Novel 2-phenylquinolin-7-yl-derived imidazo [1,5-a]pyrazines as potent insulin-like growth factor-I receptor (IFG-IR) inhibitors," Bioorganic & Medicinal Chemistry, 2008, 16: 1359-1375.
Ocana, A. "Preclinical development of molecular targeted agents for cancer" Nat. Rev. Clin. Oncol. 2011, 8, 200-209.
Ogawa et al., "Insights from Pim1 structure for anti-cancer drug design," Expert Opin Drug Discov, Dec. 2012, 7(12): 1177-92.
Paulekuhn et al., "Trends in Active Pharmaceutical Ingredient Salt Selection based on Analysis of the Orange Book Database," J Med Chem., 2007, 50(26):6665-6672.
Peltola et al., "Pim-1 kinase expression predicts radiation response in squamocellular carcinoma of head and neck and is under the control of epidermal growth factor receptor," Neoplasia, 2009, 11:629-36.
Peturssion, "Protecting Groups in Carbohydrate Chemistry," J. Chem. Educ., 1997, 74(11):1297-1303.
Ravin, "Preformulation," Remington's Pharmaceutical Sciences, 17$^{th}$ Ed., (Mack Publishing Company, Easton, 1985), p. 1409-1423.
Robinson et al., "A Dual PIM 1/3 Kinase Inhibitor Demonstrates Efficacy in Murine Models of Lupus and Multiple Sclerosis," J. Immunol., 2012, 188:119.9.
Schatz, et al., "Targeting cap-dependent translation blocks converging survival signals by AKT and PIM kinases in lymphoma," J. Exp. Med., 2011, 208:1799-1807.
Schwemmers et al., "JAK2$^{V617F}$-negative ET Patients do not display constitutively active JAK/STAT signaling," Exp. Hematol., Nov. 2007, 35(11): 1695-1703.
Search Report, dated Jul. 2, 2014, 6 pages.
Search Report, dated Jul. 3, 2014, 4 pages.
Search Report, dated Jul. 8, 2014, 4 pages.
Sharma "Cell line-based platforms to evaluate the therapeutic efficacy of candidate anticancer agents" Nature Reviews Cancer Apr. 2010, vol. 10, 241-253.
Shen et al., "Inhibition of Pim-1 kinase ameliorates dextran sodium sulfate-induced colitis in mice," Dig. Dis. Sci., 2012, 57:1822-31.
Shinto et al., "Moloney murine leukemia virus infection accelerates lymphomagenesis in Eμ-bcl-2 transfenic mice," Oncogene, 1995, 11:1729-36.
Simone, Oncology: Introduction, Cecil Textbook of Medicine, 20th Edition, 1996 vol. 1, pp. 1004-1010.
Swords et al., "The Pim kinases: new targets for drug development," Curr. Drug Targets, 2011, 12(14):2059-66.
United States Office Action in U.S. Appl. No. 14/155,134, dated Jul. 27, 2015, 12 pages.
usp.org, "Characterization of Crystalline and Partially Crystalline Solids by XRay Powder Diffraction (XRPD)," dated Nov. 23, 2016 [ retrieved on Dec. 30, 2020], retrieved from URL <https://www.usp.org/sites/default/files/usp/document/harmonization/genchapter/g14_pf_35_3_2009.pdf>, 11 pages.
Venkatesh et al., "Role of the Development Scientist in Compound Lead Selection and Optimization," J. Pharm. Sci., 2000, 89:145-54.
Wang et al., "Inhibition of Pim1 kinase prevents peanut allergy by enhancing Runx3 expression and suppressing T(H)2 and T(H)17 T-cell differentiation," J, All. Clin. Immunol., 2012, 130:932-44.
www.leukaemia.org' [online]. "Myeloproliferative neoplasms (MPN)," 2016, [retrieved on Dec. 5, 2016], Retrieved from the Internet: URL<http://www.leukaemia.org.au/blood-cancers/myeloproliferative-neoplasms-mpn>, 3 pages.
Yan et al., "Clinical and therapeutic relevance of PIM1 kinase in gastric cancer," Gastric Cancer, 2012, 15:188-197.
Yang et al., "Proviral integration site 2 is required for interleukin-6 expression induced by interleukin-1, tumour necrosis factor-α and lipopolysaccharide," Immunol., 2010, 131:174-182.
Zippo, et al., "PIM 1-dependent phosphorylation of histone H3 at serine 10 is required for MYC-dependent transcriptional activation and oncogenic transformation," Nature Cell Biol,, 2007, 9:932-44.
Argentina Office Action in Argentina Application No. P140100129, dated Nov. 27, 2019, 10 pages.
Australian Office Action in Australian Application No. 2014207691, dated Aug. 17, 2017, 4 pages.
Australian Office Action in Australian Application No. 2018217210, dated Feb. 22, 2019, 4 pages.
Australian Office Action in Australian Application No. 2016/320892, dated Dec. 2, 2020, 4 pages.
Australian Notice of Allowance in Australian Application No. 2016320892, dated Feb. 26, 2021, 8 pages.
Brazilian Office Action in Brazilian Application No. BR112015016793-4, dated Sep. 19, 2019, 5 pages.
Brazilian Office Action in Brazilian Application No. BR112018004596-9, dated Feb. 2, 2021, 6 pages.
Canadian Office Action in Canadian Application No. 2897200, dated Feb. 14, 2020, 4 pages.

(56) References Cited

OTHER PUBLICATIONS

Canadian Office Action in Canadian Application No. 2897200, dated Sep. 16, 2020, 3 pages.
Chinese Office Action in Chinese Application No. 201480057613.7, dated Apr. 5, 2017, 15 pages (English Translation).
Chilean Office Action in Chilean Application No. 1985-2015, dated Mar. 23, 2017, 13 pages (English Translation).
Chilean Office Action in Chilean Application No. 201600398, dated Jul. 27, 2017, 16 pages (English Translation).
Chilean Office Action in Chilean Application No. 611-2018. dated May 16, 2019, 21 pages.
Chilean Office Action in Chilean Application No. 2079-2019, dated May 15, 2020, 28 pages.
Chilean Office Action in Chilean Application No. 2079-2019, dated Oct. 15, 2020, 21 pages.
Chilean Office Action in Chilean Application No. 20/192,078, dated Dec. 15, 2020, 43 pages.
Chinese Office Action in Chinese Application No. 201680057727.0, dated Aug. 18, 2020, 13 pages.
Chinese Office Action in Chinese Application No. 201810718274.2, dated Nov. 24, 2020, 16 pages.
Colombian Office Action in Colombian Application No. 16-070.957, dated Sep. 13, 2017, 7 pages.
Colombian Office Action in Colombian Application No. NC2018/0003739, dated Apr. 1, 2020, 27 pages.
Costa Rican Office Action in Costa Rican Application No. 2015-0412 dated Jul. 12, 2019, 14 pages.
Costa Rican Office Action in Costa Rican Application No. 2018-0207, dated Jan. 13, 2021, 10 pages.
Eurasian Office Action in Eurasian Application No. 201591339, dated Nov. 5, 2019, 2 pages.
Eurasian Office Action in Eurasian Application No. 201591339, dated Mar. 26, 2019, 4 pages.
European Office Action in European Application No. 14702389.9-1109, dated Jun. 11, 2018.
Indian Office Action in Indian Application No. 201627008738, dated May 16, 2019, 6 pages.
Indian Office Action in Indian Application No. 201918025994, dated Feb. 3, 2021, 3 pages.
Indonesian Office Action in Indonesian Application No. P00201807826, dated Apr. 17, 2020, 10 pages.
Indonesian Office Action in Indonesian Application No. PID201802590, dated Mar. 27, 2020, 6 pages.
Israeli Office Action in Israeli Application No. 239,886, dated Apr. 2, 2019, 4 pages.
Israeli Office Action in Israeli Application No. 239,886, dated Dec. 16, 2019, 9 pages.
Japanese Office Action in Japanese Application No. 2015-552896, dated Nov. 28, 2017, 8 pages (English Translation).
Japanese Office Action in Japanese Application No. 2016-536470, dated Apr. 24, 2018, 4 pages (English Translation).
Japanese Office Action in Japanese Application No. 2018-512592, dated Aug. 25, 2020, 14 pages.
Japanese Office Action in Japanese Application No. 2018-512592, dated Mar. 9, 2021, 10 pages.
Korean Office Action in Korean Application No. 10-2015-7022084, Jul. 30, 2020, 15 pages.
Korean Office Action in Korean Application No. 10-2015-7022084, Feb. 4, 2021, 7 pages.
Malaysian Office Action in Malaysian Application No. PI 2015001776, dated Jul. 22, 2019, 2 pages.
Malaysian Office Action in Malaysian Application No. PI 2018000356, dated Nov. 9, 2020, 3 pages.
Mexican Office Action in Mexican Application No. MX/a/2015/009057, dated Dec. 9, 2019, 3 pages.
New Zealand Office Action in New Zealand Application No. 749911, dated Jul. 19, 2019, 4 pages.
New Zealand Office Action in New Zealand Application No. 749911, dated Oct. 7, 2019, 2 pages.
Peruvian Office Action in Peruvian Application No. 1345.15, dated Mar. 21, 2019, 18 pages.
Philippine Office Action in Philippine Office Application No. 1/2015/501567, dated Jan. 13, 2020, 2 pages.
Taiwanese Office Action in Taiwanese Application No. 103101314, dated Dec. 28, 2017, 18 pages (English Translation).
Taiwanese Office Action in Taiwanese Application No. 105129102, dated Oct. 30, 2020, 12 pages.
Thailand Office Action in Thailand Application No. 1801001409, dated Mar. 11, 2021, 3 pages.
Ukraine Office Action in Ukraine Application No. a 201508119, dated Jul. 15, 2019, 8 pages.
Ukraine Grant in Ukraine Application No. a201508119, dated Nov. 21, 2019, 6 pages.
Ukraine Office Action in Ukraine Application No. a201803689, dated Dec. 18, 2020, 11 pages.
Vietnamese Office Action in Vietnamese Application No. 1-2020-07115, dated Dec. 28, 2020, 2 pages.
Vietnamese Office Action in Vietnamese Application No. 1-2015-02935, dated Dec. 28, 2018, 2 pages.
Baselga et al., "CLEOPATRA: A Phase III Evaluation of Pertuzumab and Trastuzumab for HFR2-Positive Metastatic Breast Cancer," Clinical Breast Cancer, Dec. 2010, 10(6):489-491.
Roche.com, "Pertuzumab combined with Herceptin and chemotherapy significantly extended the time people with HER2-positive metastatic breast cancer lived without their disease getting worse," Jul. 15, 2011[retreived on Aug. 24, 2021], retrieved from URL <https://www.roche.com/media/releases/med-cor-2011-07-15.htm>.
Korean Notice of Allowance in Korean Application No. 10-2015-7022084, dated Jul. 5, 2021, 3 pages.

* cited by examiner

THIAZOLECARBOXAMIDES AND PYRIDINECARBOXAMIDE COMPOUNDS USEFUL AS PIM KINASE INHIBITORS

CROSS-REFERENCE TO RELATED APPLICATIONS

The present application is a continuation of U.S. patent application Ser. No. 16/685,183, filed Nov. 15, 2019, with is a continuation of U.S. patent application Ser. No. 16/298, 601, filed Mar. 11, 2019, now issued U.S. Pat. No. 10,517, 858, issued Dec. 31, 2019, which is a continuation of U.S. patent application Ser. No. 15/815,255, filed Nov. 16, 2017, now issued U.S. Pat. No. 10,265,307, issued Apr. 23, 2019, which is a continuation of U.S. patent application Ser. No. 15/373,923, filed Dec. 9, 2016, now issued U.S. Pat. No. 9,849,120, issued Dec. 26, 2017, which is a continuation of U.S. patent application Ser. No. 14/811,038, filed Jul. 28, 2015, now issued U.S. Pat. No. 9,550,765, issued Jan. 24, 2017, which is a continuation of U.S. patent application Ser. No. 14/155,212, filed Jan. 14, 2014, now issued U.S. Pat. No. 9,200,004, issued Dec. 1, 2015, and claims the benefit of U.S. Provisional Application No. 61/752,897, filed Jan. 15, 2013, U.S. Provisional Application No. 61/790,952, filed Mar. 15, 2013, and U.S. Provisional Application No. 61/859, 118, filed Jul. 26, 2013, the entire disclosures of which are incorporated herein by reference in their entirety.

TECHNICAL FIELD

The present application is concerned with pharmaceutically useful compounds. The disclosure provides new compounds as well as their compositions and methods of use. The compounds inhibit the activity of Pim kinases and are therefore useful in the treatment of diseases related to the activity of Pim kinases including, e.g., cancers and other diseases.

BACKGROUND

Protein kinases regulate diverse biological processes including cell growth, survival, differentiation, organ formation, morphogenesis, neovascularization, tissue repair, and regeneration, among others. Protein kinases also play specialized roles in a host of human diseases including cancer. The three members of the Pim kinase family, one example of a protein kinase family, were initially identified as preferential integration sites of Moloney leukemia virus in mouse models of cancer. Although possessing modest but measurable oncogenic activity alone, they potentiate pro-proliferative and pro-survival oncogenes, e.g., causing a dramatic acceleration of lymphomagenesis in Myc-transgenic or Bl2-transgenic mice. Mikkers et al., *Nature Genet.*, 2002, 32, 153-159; Shinto et al., *Oncogene*, 1995, 11, 1729-35.

The three non-receptor serine/threonine kinases Pim1, Pim2 and Pim3 regulate cell proliferation and survival by impacting gene transcription and protein translation. Zippo, et al., *Nature Cell Biol.*, 2007, 9, 932-44; Schatz, et al., *J Exp. Med.*, 2011, 208, 1799-1807. As opposed to numerous other protein kinases which require activation by phosphorylation, the Pim kinases are constitutively activated and family members have overlapping substrate targets and biological functions, with differences between family members dictated, in part, by their varied tissue distribution. Expression of the Pim kinases is induced by cytokines and growth factors. Among the cytokines activating Pim kinase expression are cytokines which signal through the JAK/STAT pathway. Pim kinases act in parallel to the PI3K/AKT pathway, and they share several phosphorylation targets (e.g., pBAD, p4EBP1). Inhibitors of Pim kinases may therefore potentiate regimens including inhibitors of either the JAK pathway or the PI3K/AKT pathway.

Overexpression of Pim kinases is detected in a wide variety of hematologic and solid cancers. Overexpression of various family members have been noted in multiple myeloma, AML, pancreatic and hepatocellular cancers. Claudio et al., *Blood* 2002, 100, 2175-86; Amson et al., *Proc. Nat. Acad. Sci. USA*, 1989, 86, 8857-61; Mizuki et al., *Blood*, 2003, 101, 3164-73; Li et al., *Canc. Res.*, 2006, 66, 6741-7; Fujii et al., *Int. J Canc.*, 2005, 114, 209-18. Pim1 overexpression is associated with poor prognosis in mantle cell lymphoma, esophageal and head and neck cancers. Hsi et al., *Leuk. Lymph.*, 2008, 49, 2081-90; Liu et al., *J Surg. Oncol.*, 2010, 102, 683-88; Peltola et al., *Neoplasia*, 2009, 11, 629-36. Pim2 overexpression is associated with an aggressive clinical course in a subset of DLBCL patients. Gomez-Abad et al., *Blood*, 2011, 118, 5517-27. Overexpression is often seen where Myc is overexpressed and Pim kinases can convey resistance to traditional chemotherapeutic agents and radiation. Chen et al., *Blood*, 2009, 114, 4150-57; Isaac et al., *Drug Resis. Updates*, 2011, 14, 203-11; Hsu et al., *Cancer Lett.*, 2012, 319, 214; Peltola et al., *Neoplasia*, 2009, 11, 629-36.

As such, these data indicate that inhibition of Pim kinases will be useful to provide therapeutic benefit in cancer patients.

Data from mice deficient for one or multiple Pim kinase family members suggests that pan-Pim inhibitor would have a favorable toxicity profile. Triple knockout mice are viable, but are slightly smaller than their wild type littermates. Mikkers et al., *Mol. Cell. Biol.*, 2004, 24. 6104-15. Since Pim kinases are also involved in a variety of immunologic and inflammatory responses and these indications require drug agents with fewer side effects, Pim kinase inhibitors are expected to be useful in treating patients with colitis (Shen et al., *Dig. Dis. Sci.*, 2012, 57, 1822-31), peanut allergy (Wang et al., *J. All. Clin. Immunol.*, 2012, 130, 932-44), multiple sclerosis and lupus (Davis et al., "Small Molecule Dual Antagonist of Pim 1 and 3 Kinases Ameliorate Experimental Autoimmune Encephalomyelitis", 26th Congress of the European Committee for Treatment and Research in Multiple Sclerosis, 13-16 Oct. 2010, Gothenburg, Sweden, Poster P436; Robinson et al., *J Immunol.*, 2012, 188, 119.9) and rheumatoid arthritis (Yang et al., *Immunol.* 2010, 131, 174-182), and other immunological and inflammatory disorders.

The Pim kinases have therefore been identified as useful targets for drug development efforts. Swords et al., *Curr. Drug Targets*, 2011, 12 (14), 2059-66; Merkel et al., *Exp. Opin. Investig. Drugs*, 2012, 21, 425-38; Morwick et al., *Exp. Opin. Ther. Patents*, 2010, 20 (2), 193-212.

Accordingly, there is a need for new compounds that inhibit Pim kinases. The present application describes new inhibitors of Pim kinases that are useful for treating diseases associated with the expression or activity of one or more Pim kinases, e.g., cancer and other diseases.

SUMMARY

The present disclosure provides, inter alia, a compound of formula (I):

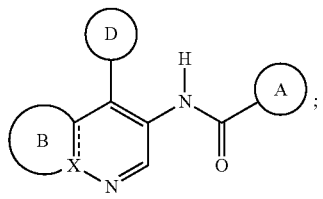

or a pharmaceutically acceptable salt thereof; wherein the variables are as defined below.

The present disclosure also provides a composition comprising a compound of formula (I), or a pharmaceutically acceptable salt thereof, and at least one pharmaceutically acceptable carrier.

The present disclosure also provides methods of treating cancer and other diseases comprising administering to a patient a therapeutically effective amount of a compound of formula (I), or a pharmaceutically acceptable salt thereof.

The details of one or more embodiments are set forth in the description below. Other features, objects, and advantages will be apparent from the description and from the claims.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

I. Compounds

The present disclosure provides, inter alia, a compound of formula (I):

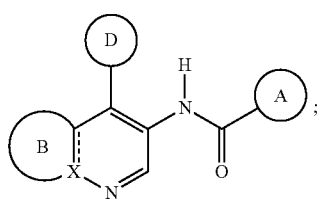

or a pharmaceutically acceptable salt thereof, wherein:

X is C or N;

A, B and D are rings;

the bond ═══ represents a normalized bond within the aromatic ring containing both an N and X, which formally is represented by a C═C bond when X is C and a single bond when X is N;

ring A is of the formula (A-1) or (A-2):

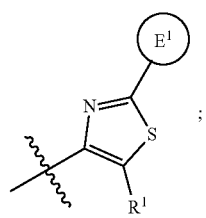

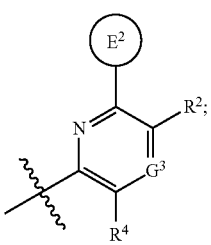

or
ring A is of the formula (A-1) or (A-2a):

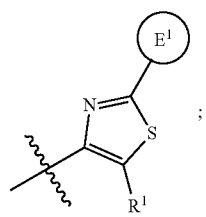

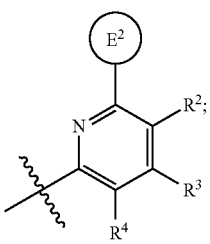

wherein $E^1$ and $E^2$ are rings;

ring B is a fused 3-7 membered carbocycle or a fused 4-7 membered heterocycle, each of which is substituted by n substituents independently selected from $R^B$, wherein n is 0, 1, 2 or 3;

ring D is a $C_{3-7}$ cycloalkyl group or a 4-10 membered heterocycloalkyl group, each of which is substituted by k substituents independently selected from $R^D$, wherein k is 0, 1, 2 or 3;

ring $E^1$ is selected from $C_{3-7}$ cycloalkyl, $C_{6-10}$ aryl, 4-10 membered heterocycloalkyl, and 5-10 membered heteroaryl, each of which is optionally substituted by 1, 2 or 3 substituents independently selected from $R^E$;

ring $E^2$ is selected from $C_{3-7}$ cycloalkyl, $C_{6-10}$ aryl, 4-10 membered heterocycloalkyl, and 5-10 membered heteroaryl, each of which is optionally substituted by 1, 2 or 3 substituents independently selected from $R^E$;

$R^1$ is selected from H, F and $NH_2$;

$R^2$ is selected from H, halo and CN;

$R^3$ is selected from H, halo and CN;

$R^4$ is selected from H, F and $NH_2$;

each $R^B$ is independently selected from $Cy^B$, halo, $C_{1-6}$ alkyl, $C_{2-6}$ alkenyl, $C_{2-6}$ alkynyl, $C_{1-6}$ haloalkyl, CN, NO$_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo; wherein said $C_{1-6}$ alkyl, $C_{2-6}$ alkenyl, and $C_{2-6}$ alkynyl substituents of $R^B$ are each optionally substituted with 1, 2 or 3 substituents independently selected from $Cy^B$, halo, CN, NO$_2$, $OR^{a1}$, $SR^{a1}$, $C(O)R^{b1}$, $C(O)NR^{c1}R^{d1}$, $C(O)OR^{a1}$, $OC(O)R^1$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$ each $R^D$ is independently selected from $Cy^D$, halo, $C_{1-6}$ alkyl, $C_{2-6}$ alkenyl, $C_{2-6}$ alkynyl, $C_{1-6}$ haloalkyl, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{b2}S(O)R^{b2}$, $NR^{b2}S(O)_2R^{b2}$, $NR^{b2}S(O)_2NR^{e2}R^{d2}$, $S(O)R^{b2}$, $S(O)NR^{c2}R^{d2}$, $S(O)_2R^{b2}$, $S(O)_2NR^{c2}R^{d2}$ and oxo; wherein said $C_{1-6}$ alkyl, $C_{2-6}$ alkenyl, and $C_{2-6}$ alkynyl substituents of $R^D$ are each optionally substituted with 1, 2 or 3 substituents independently selected from $Cy^D$, halo, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{e2}R^{d2}$, $S(O)_2R^{b2}$ and $S(O)_2NR^{c2}R^{d2}$;

each $R^E$ is independently selected from $Cy^E$, halo, $C_{1-6}$ alkyl, $C_{2-6}$ alkenyl, $C_{2-6}$ alkynyl, $C_{1-6}$ haloalkyl, CN, NO$_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo; wherein said $C_{1-6}$ alkyl, $C_{2-6}$ alkenyl, and $C_{2-6}$ alkynyl of $R^E$ are each optionally substituted with 1, 2 or 3 substituents independently selected from $Cy^E$, halo, CN, NO$_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$;

$Cy^B$, $Cy^D$ and $Cy^E$ are each independently selected from $C_{6-10}$ aryl, $C_{3-10}$ cycloalkyl, 5-10 membered heteroaryl and 4-10 membered heterocycloalkyl, each of which is optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, NO$_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{3-10}$ cycloalkyl, 5-10 membered heteroaryl, and 4-10 membered heterocycloalkyl substituents of $Cy^B$, $Cy^D$ or $Cy^E$ are each optionally substituted with 1, 2 or 3 substituents independently selected from halo, $C_{1-4}$ haloalkyl, CN, NO$_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$ and $S(O)_2NR^{c4}R^{d4}$;

each $R^{a1}$, $R^{b1}$, $R^{c1}$, $R^{d1}$, $R^{a2}$, $R^{b2}$, $R^{e2}$, $R^{d2}$, $R^{a3}$, $R^{b3}$, $R^{c3}$, $R^{d3}$, $R^{a4}$, $R^{b4}$, $R^{c4}$ and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl and (4-10 membered heterocycloalkyl)-$C_{1-4}$ alkyl is optionally substituted with 1, 2, 3, 4 or 5 substituents independently selected from $C_{1-4}$ alkyl, $C_{1-4}$ haloalkyl, halo, CN, $OR^{a5}$, $SR^{a5}$, $C(O)R^{b5}$, $C(O)NR^{c5}R^{d1}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{c5}$, $NR^{c5}S(O)_2NR^{c5}R^{d5}$ and $S(O)_2NR^{c5}R^{d5}$;

or any $R^{c1}$ and $R^{d1}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl and 5-6 membered heteroaryl are optionally substituted by 1, 2 or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl and 5-6 membered heteroaryl are optionally substituted by 1, 2 or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}R^{d5}$, $NR^{c5}C(=NR^{e5})NR^{c5}R^{d5}$, $S(O)R^{b5}$, $S(O)NR^{c5}R^{d1}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2 or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2 or 3 substituents independently selected from halo, $C_{1-4}$ alkyl, $C_{1-4}$ haloalkyl, $C_{1-4}$ cyanoalkyl, CN $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$ and $S(O)_2NR^{c5}R^{d5}$;

each $R^{a5}$, $R^{b5}$, $R^{c5}$ and $R^{d5}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2 or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c5}$ and $R^{d5}$ attached to the same N atom, together with the N atom to which they are attached, form a 3-, 4-, 5-, 6-, or 7-membered heterocycloalkyl group optionally substituted with 1, 2 or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl and $C_{1-4}$ haloalkoxy; and each $R^{e1}$, $R^{e2}$, $R^{e3}$, $R^{e4}$ and $R^{e5}$ is independently selected from H, $C_{1-4}$ alkyl and CN.

In some embodiments, X is C.

In some embodiments, X is N.

In some embodiments, ring B is a fused 3-7 membered carbocycle optionally substituted by 1, 2 or 3 substituents independently selected from $R^B$.

In some embodiments, ring B is a fused benzo ring according to formula (B-1):

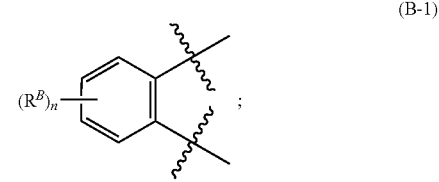

(B-1)

wherein n is 0, 1, 2 or 3.

In some embodiments, the compound is according to the following formula (I-1):

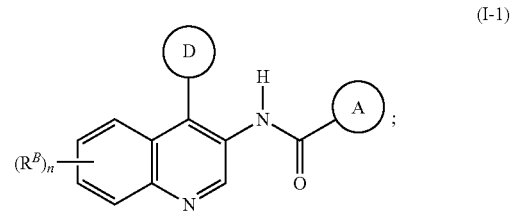

(I-1)

wherein n is 0, 1, 2 or 3.

In some such embodiments, n is 0.

In some such embodiments, n is 1.

In some embodiments, ring B is a fused 3-7 membered cycloalkyl ring optionally substituted by 1, 2 or 3 substituents independently selected from $R^B$.

In some embodiments, ring B is a fused 5-membered carbocycle optionally substituted by 1, 2 or 3 substituents independently selected from $R^B$.

In some embodiments, ring B is according to formula (B-2):

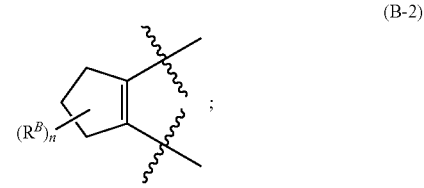

(B-2)

wherein n is 0, 1 or 2.

In some such embodiments, n is 0.

In some such embodiments, n is 1.

In some embodiments, ring B is according to formula (B-3):

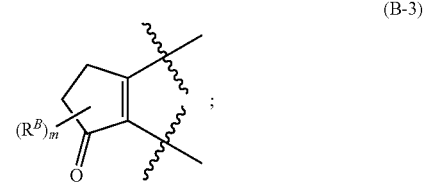

(B-3)

wherein m is 0, 1 or 2.

In some such embodiments, m is 0.

In some such embodiments, m is 1.

In some embodiments, the compound is according formula (I-2):

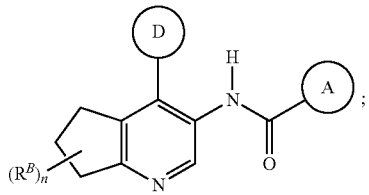

(I-2)

wherein n is 0, 1, 2 or 3.

In some such embodiments, n is 0.

In some such embodiments, n is 1.

In some embodiments, the compound is according formula (I-3):

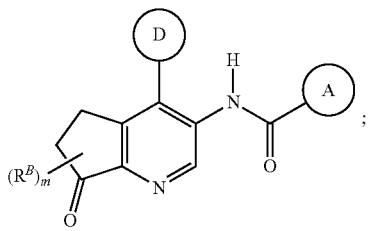

(I-3)

wherein m is 0, 1 or 2.

In some such embodiments, m is 0.

In some such embodiments, m is 1.

In some embodiments, ring B is a fused 4-7 membered heterocycle optionally substituted by 1, 2 or 3 substituents independently selected from $R^B$.

In some embodiments, ring B is a fused 5-6 membered heteroaryl ring, optionally substituted by 1, 2 or 3 substituents independently selected from $R^B$.

In some embodiments, ring B is a fused 4-7 membered heterocycloalkyl ring optionally substituted by 1, 2 or 3 substituents independently selected from $R^B$.

In some embodiments, ring B is a fused 5-membered heterocycle optionally substituted by 1, 2 or 3 substituents independently selected from $R^B$.

In some embodiments, ring B is a fused 5-membered heteroaryl optionally substituted by 1, 2 or 3 substituents independently selected from $R^B$.

In some embodiments, ring B is a fused 5-membered heterocycloalkyl optionally substituted by 1, 2 or 3 substituents independently selected from $R^B$.

In some embodiments, ring B is selected from thieno, pyrrolo, dihydrofuro and pyrazolo, each of which is optionally substituted by 1, 2 or 3 substituents independently selected from $R^B$.

In some embodiments, the compound can be according to formula (I-4):

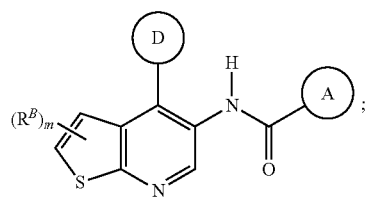

(I-4)

wherein m is 0, 1 or 2.

In some such embodiments, m is 0.

In some such embodiments, m is 1.

In some embodiments, the compound can be according to formula (I-5):

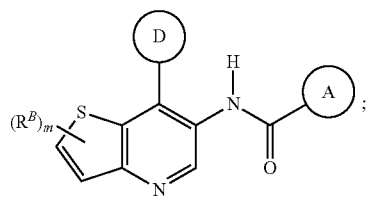

(I-5)

wherein m is 0, 1 or 2.

In some such embodiments, m is 0.

In some such embodiments, m is 1.

In some embodiments, the compound can be according to formula (I-6):

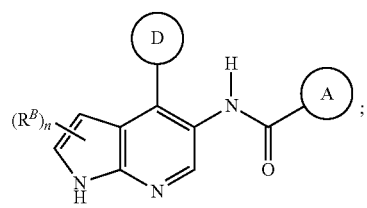

(I-6)

wherein n is 0, 1, 2 or 3, and $R^B$ can be substituted on the nitrogen of ring B.

In some such embodiments, n is 0.

In some such embodiments, n is 1.

In some embodiments, the compound can be according to formula (I-7):

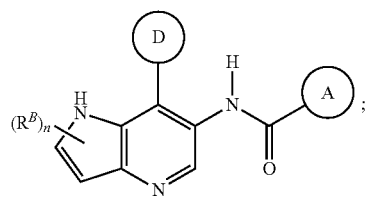

(I-7)

wherein n is 0, 1, 2 or 3, and $R^B$ can be substituted on the nitrogen of ring B.

In some such embodiments, n is 0.

In some such embodiments, n is 1.

In some embodiments, the compound can be according to formula (I-8):

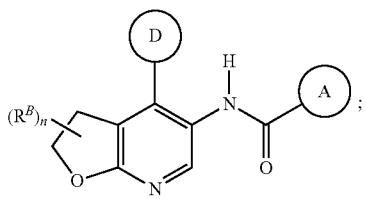

(I-8)

wherein m is 0, 1 or 2.

In some such embodiments, n is 0.

In some such embodiments, n is 1.

In some embodiments, the compound can be according to formula (I-9):

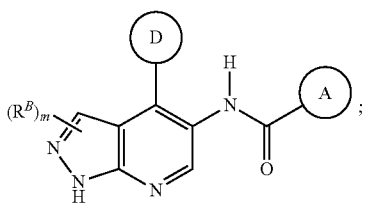

(I-9)

wherein m is 0, 1 or 2, and $R^B$ can be substituted on the nitrogen of ring.

In some such embodiments, m is 0.

In some such embodiments, m is 1.

In some embodiments, ring B is a fused 6-membered heterocycle, each optionally substituted by 1, 2 or 3 substituents independently selected from $R^B$.

In some embodiments, ring B is a fused 6-membered heteroaryl optionally substituted by 1, 2 or 3 substituents independently selected from $R^B$.

In some embodiments, ring B is a fused 6-membered heterocycloalkyl optionally substituted by 1, 2 or 3 substituents independently selected from $R^B$.

In some embodiments, ring B is according to formula (B-4):

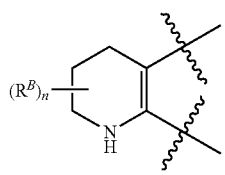

(B-4)

wherein n is 0, 1, 2 or 3 and $R^B$ can be substituted on the nitrogen atom of ring B.

In some such embodiments, n is 0.

In some such embodiments, n is 1.

In some embodiments, the compound is according to formula (I-10):

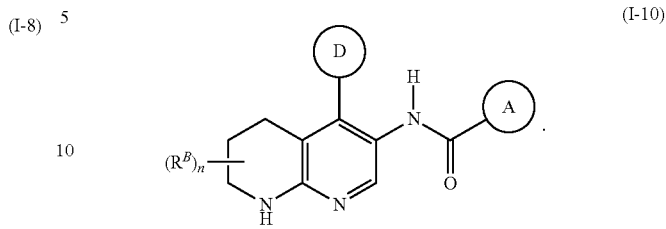

(I-10)

wherein n is 0, 1, 2 or 3 and $R^B$ can be substituted on the nitrogen atom of ring B.

In some such embodiments, n is 0.

In some such embodiments, n is 1.

In some embodiments, each $R^B$ is independently selected from halo, $C_{1-6}$ alkyl, $C_{1-6}$ haloalkyl, CN, $OR^{a1}$ and oxo.

In some embodiments, each $R^B$ is independently selected from halo, $C_{1-6}$ alkyl, $C_{1-6}$ haloalkyl, CN, $OR^{a1}$.

In some embodiments, each $R^B$ is independently selected from CN, OH, methoxy and oxo.

In some embodiments, each $R^B$ is independently selected from CN, OH and methoxy.

In some embodiments, ring B is unsubstituted or substituted by 1 substituent selected from $R^B$.

In some embodiments, ring B is unsubstituted.

In some embodiments, ring D is a $C_{3-7}$ cycloalkyl group optionally substituted by 1, 2 or 3 substituents independently selected from $R^D$.

In some embodiments, ring D is a 4-10 membered heterocycloalkyl group optionally substituted by 1, 2 or 3 substituents independently selected from $R^D$.

In some embodiments, ring D is a 5-membered or 6-membered heterocycloalkyl group optionally substituted by 1, 2 or 3 substituents independently selected from $R^D$.

In some embodiments, ring D is a pyrrolidine, piperidine or azepane ring optionally substituted by 1, 2 or 3 substituents independently selected from $R^D$.

In some embodiments, ring D is a piperidine ring optionally substituted by 1, 2 or 3 substituents independently selected from $R^D$.

In some embodiments, a nitrogen atom of ring D forms the bond to the remainder of the molecule.

In some embodiments, each $R^D$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, each $R^D$ is independently selected from $C_{1-6}$ alkyl, $OR^{a2}$, and $NR^{c2}R^{d2}$.

In some embodiments, each $R^D$ is independently selected from methyl, OH, and $NH_2$.

In some embodiments, ring D is a piperidin-1-yl ring substituted at the 3-position by an amino group. Ring D can be, e.g., 3-aminopiperidin-1-yl, 3-amino-4-hydroxypiperidinyl or 3-amino-4-hydroxy-5-methylpiperidinyl.

In some embodiments, the configuration of the carbon atom at the 3-position of the piperidin-1-yl ring forming ring D is (S) when the carbon atom at the 2-position of the piperidin-1-yl ring forming ring D has a higher Cahn-Ingold-Prelog priority than the carbon atom at the 4-position and (R) when the carbon atom at the 4-position of the piperidin-1-yl ring forming ring D has a higher Cahn-Ingold-Prelog priority than the carbon atom at the 4-position. Ring D can be, e.g., (3S)-aminopiperidin-1-yl, (3R,4R)-3-amino-4-hydroxypiperidinyl, (3R,4S)-3-amino-4-hydroxypiperidinyl, (3R,4R,5R)-3-amino-4-hydroxy-5-methylpiperidinyl, (3R,4R,5S)-3-amino-4-hydroxy-5-methylpiperidinyl, (3R,4S,5R)-3-amino-4-hydroxy-5-methylpiperidinyl or (3R,4S,5S)-3-amino-4-hydroxy-5-methylpiperidinyl.

In some embodiments, the configuration of the carbon atom at the 3-position of the piperidin-1-yl ring forming ring D is (R) when the carbon atom at the 2-position of the piperidin-1-yl ring forming ring D has a higher Cahn-Ingold-Prelog priority than the carbon atom at the 4-position and (S) when the carbon atom at the 4-position of the piperidin-1-yl ring forming ring D has a higher Cahn-Ingold-Prelog priority than the carbon atom at the 4-position. Ring D can be, e.g., (3R)-aminopiperidin-1-yl, (3S,4S)-3-amino-4-hydroxypiperidinyl, (3S,4R)-3-amino-4-hydroxypiperidinyl, (3S,4R,5R)-3-amino-4-hydroxy-5-methylpiperidinyl, (3S,4R,5S)-3-amino-4-hydroxy-5-methylpiperidinyl, (3S,4S,5R)-3-amino-4-hydroxy-5-methylpiperidinyl or (3S,4S,5S)-3-amino-4-hydroxy-5-methylpiperidinyl.

In some embodiments, ring D is a group of the following formula (D-1):

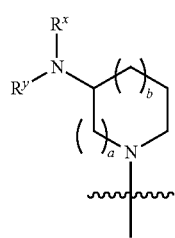

(D-1)

wherein:
$R^x$ is H, $C_{1-6}$ alkyl or $OC(=O)C_{1-6}$ alkyl;
R is H or $C_{1-6}$ alkyl;
a is 1 or 2;
b is 0, 1 or 2; and
the sum of a and b is 1, 2 or 3.

In some embodiments, ring D is a group of the following formula (D-2):

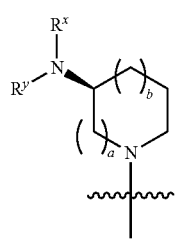

(D-2)

wherein $R^x$, $R^y$, a and b are as defined or formula (D-1).

In some embodiments, when ring D is a group of formula (D-1) or (D-2), $R^x$ is H.

In some embodiments, when ring D is a group of formula (D-1) or (D-2), $R^y$ is H.

In some embodiments, when ring D is a group of formula (D-1) or (D-2), a is 1.

In some embodiments, when ring D is a group of formula (D-1) or (D-2), b is 1.

In some embodiments, ring D is a group of formula (D-2), wherein $R^x$ is H, $C_{1-6}$ alkyl or $OC(=O)C_{1-6}$ alkyl; R is H or $C_{1-6}$ alkyl; a is 1 or 2; b is 0, 1 or 2; the sum of a and b is 1, 2 or 3; and Ring D is optionally substituted by 1 or 2 substitutents independently selected from $C_{1-6}$ alkyl, OH and $C_{1-6}$ alkoxy.

In some embodiments, ring D is a group of formula (D-2), wherein: $R^x$ is H, $C_{1-6}$ alkyl; R is H or $C_{1-6}$ alkyl; a is 1; b is 1; and Ring D is optionally substituted by 1 or 2 substitutents independently selected from $C_{1-6}$ alkyl, OH and $C_{1-6}$ alkoxy.

In some embodiments, ring D is a group selected from formula (D-3)-(D-19):

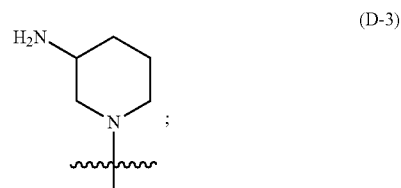

(D-3)

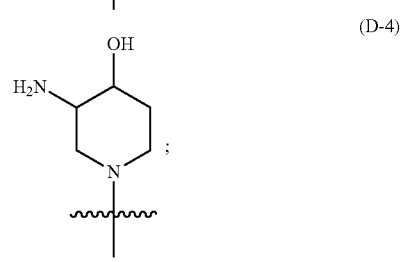

(D-4)

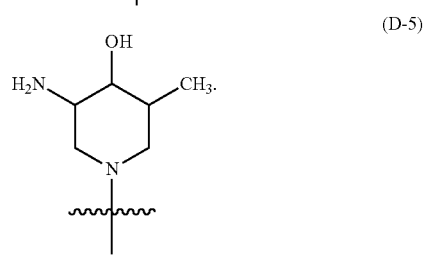

(D-5)

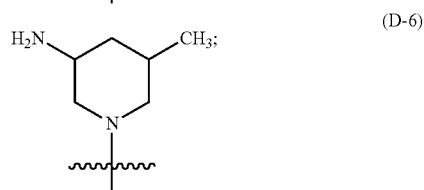

(D-6)

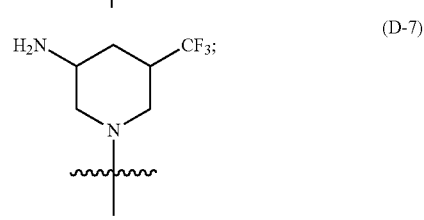

(D-7)

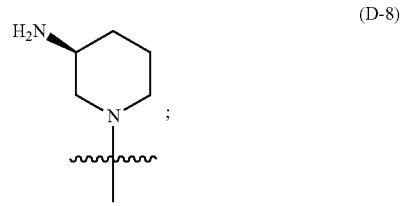

(D-8)

(D-9)
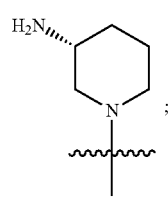
(D-10)
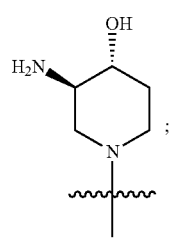
(D-11)
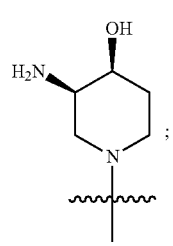
(D-12)
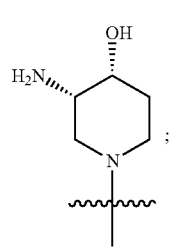
(D-13)
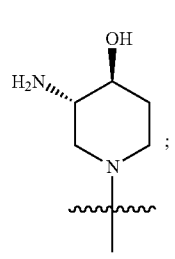
(D-14)
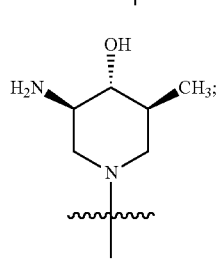
(D-15)
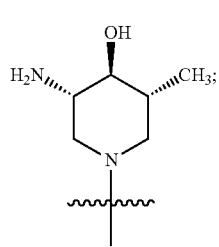
(D-16)
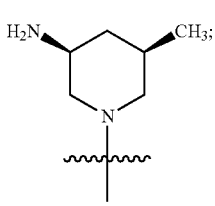
(D-17)
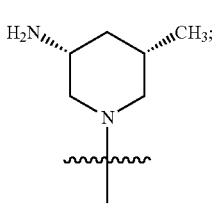
(D-18)
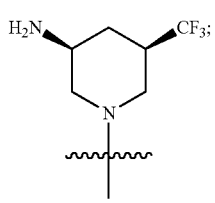
(D-19)
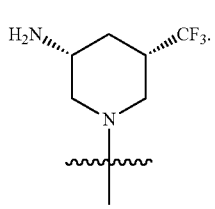
In some embodiments, ring D is a group of formula (D-3):
(D-3)
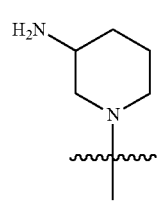
In some embodiments, ring D is a group of formula (D-4):
(D-4)
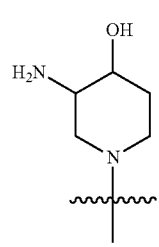

In some embodiments, ring D is a group of formula (D-5):

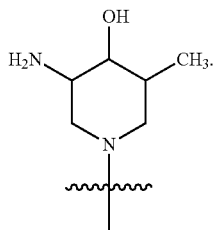
(D-5)

In some embodiments, ring A is of the formula (A-1):

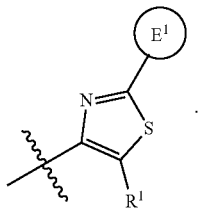
(A-1)

In some embodiments, $R^1$ is selected from H and $NH_2$.

In some embodiments, ring $E^1$ is $C_{6-10}$ aryl, which is optionally substituted by 1, 2 or 3, substituents independently selected from $R^E$.

In some embodiments, ring $E^1$ is phenyl optionally substituted by 1, 2 or 3, substituents independently selected from $R^E$.

In some embodiments, ring $E^1$ is phenyl that is 2,6-disubstituted by substituents independently selected from $R^E$.

In some embodiments, ring $E^1$ is 5-10 membered heteroaryl, which is optionally substituted by 1, 2 or 3, substituents independently selected from $R^E$.

In some embodiments, each $R^E$ is independently selected from halo, $C_{1-6}$ alkyl, $C_{1-6}$ haloalkyl, CN, $OR^{a3}$, $C(O)R^{b3}$, $C(O)NR^{c3}R^{d3}$, $C(O)OR^{a3}$, $NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, each $R^E$ is independently selected from halo.

In some embodiments, ring $E^1$ is phenyl that is 2,6-dihalosubstituted.

In some embodiments, ring $E^1$ is 2,6-difluorophenyl.

In some embodiments, ring $E^1$ is phenyl that is 2,6-dihalosubstituted and further substituted with one additional substituent, preferably at the 4-position.

In some embodiments, ring $E^1$ is phenyl that is 2,6-dihalosubstituted (e.g., 2,4-difluoro-substituted) and further substituted with one additional substituent (e.g., at the 4-position), wherein the additional substituent is, e.g., selected from $C_{1-6}$ alkoxy, $C_{1-6}$ methanesulfanyl, $C_{1-6}$ methanesulfinyl, $C_{1-6}$ methanesulfonyl, $C_{1-6}$ alkoxy-$C_{1-6}$ alkylenyl, hydroxy-$C_{1-6}$ alkylene, or tetrahydro-2H-pyran-3-yloxy, e.g., methoxy, ethoxy, methanesulfanyl, methanesulfonyl, methanesulfonyl, or methoxymethyl, or 2-hydroxypropan-2-yl.

In some embodiments, ring $E^1$ is 2,6-difluorophenyl, 2,6-difluoro-4-(2-hydroxy-2-propyl)phenyl, 2,6-difluoro-4-methanesulfanylphenyl, 2,6-difluoro-4-methanesulfinylphenyl, 2,6-difluoro-4-methanesulfonylphenyl, 2,6-difluoro-3-methoxyphenyl, 2,6-difluoro-4-methoxyphenyl, 2,6-difluoro-4-(methoxymethyl)phenyl, or 2,6-difluoro-4-(tetrahydro-2H-pyran-3-yloxy)phenyl.

In some embodiments, $G^3$ is $CR^3$.
In some embodiments, $G^3$ is N.
In some embodiments, ring A is of the formula (A-2):

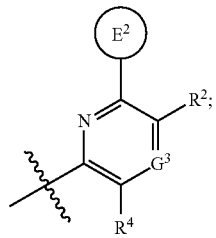
(A-2)

In some such embodiments $G^3$ is $CR^3$.
In some such embodiments, $G^3$ is N.
In some embodiments, ring A is of the formula (A-2):

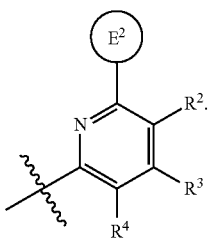
(A-2a)

In some embodiments, $R^1$ is H or halogen.
In some embodiments, $R^2$ is F.
In some embodiments, $R^3$ is H.
In some embodiments, $R^4$ is selected from H and $NH_2$.

In some embodiments, ring $E^2$ is $C_{6-10}$ aryl, which is optionally substituted by 1, 2 or 3, substituents independently selected from $R^E$.

In some embodiments, ring $E^2$ is phenyl optionally substituted by 1, 2 or 3, substituents independently selected from $R^E$.

In some embodiments, ring $E^2$ is phenyl that is 2,6-disubstituted by substituents independently selected from $R^E$.

In some embodiments, ring $E^2$ is 5-10 membered heteroaryl, which is optionally substituted by 1, 2 or 3, substituents independently selected from $R^E$.

In some embodiments, each $R^E$ is independently selected from halo, $C_{1-6}$ alkyl, $C_{1-6}$ haloalkyl, CN, $OR^{a3}$, $C(O)R^{b3}$, $C(O)NR^{c3}R^{d3}$, $C(O)OR^{a3}$, $NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, each $R^E$ is independently selected from halo.

In some embodiments, ring $E^2$ is phenyl that is 2,6-dihalosubstituted.

In some embodiments, ring $E^2$ is 2,6-difluorophenyl.

In some embodiments, ring $E^2$ is phenyl that is 2,6-dihalosubstituted and further substituted with one additional substituent, preferably at the 4-position.

In some embodiments, ring $E^2$ is phenyl that is 2,6-dihalosubstituted (e.g., 2,4-difluoro-substituted) and further substituted with one additional substituent (e.g., at the 4-position), wherein the additional substituent is, e.g., selected from $C_{1-6}$ alkoxy, $C_{1-6}$ methanesulfanyl, $C_{1-6}$ methanesulfinyl, $C_{1-6}$ methanesulfonyl, $C_{1-6}$ alkoxy-$C_{1-6}$ alkylenyl, hydroxy-$C_{1-6}$ alkylene, or tetrahydro-2H-pyran-3-yloxy, e.g., methoxy, ethoxy, methanesulfonyl, methanesulfonyl, methanesulfonyl, or methoxymethyl, or 2-hydroxypropan-2-yl.

In some embodiments, ring $E^2$ is 2,6-difluorophenyl, 2,6-difluoro-4-(2-hydroxy-2-propyl)phenyl, 2,6-difluoro-4-methanesulfanylphenyl, 2,6-difluoro-4-methanesulfinylphenyl, 2,6-difluoro-4-methanesulfonylphenyl, 2,6-difluoro-3-methoxyphenyl, 2,6-difluoro-4-methoxyphenyl, 2,6-difluoro-4-(methoxymethyl)phenyl, or 2,6-difluoro-4-(tetrahydro-2H-pyran-3-yloxy)phenyl.

In some embodiments, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$ and $R^{d3}$ are each independently H or $C_{1-6}$ alkyl.

In some embodiments, $R^{a4}$ $R^{b4}$, $R^{c4}$ and $R^{d4}$ are each independently H or $C_{1-6}$ alkyl.

In some embodiments, $R^{a5}$, $R^{b4}$, $R^{c4}$ and $R^{d4}$ are each independently H or $C_{1-6}$ alkyl.

In some embodiments, $R^{e1}$, $R^{e2}$, $R^{e3}$, $R^{e4}$ and $R^{e5}$ are each independently H or $C_{1-6}$ alkyl.

In some embodiments, $R^{e1}$, $R^{e2}$, $R^{e3}$, $R^{e4}$ and $R^{e5}$ are each H.

In some embodiments, the compound is according to the following formula (II-1):

(II-1)

wherein n is 0, 1, 2 or 3; k is 0, 1, 2 or 3, and $R^B$, $R^D$ and ring A are as defined above for the compounds of formula (I), or any of the embodiments thereof.

In some embodiments, the compound is according to the following formula (II-2):

(II-2)

wherein n is 0, 1, 2 or 3; and k is 0, 1, 2 or 3, and $R^B$, $R^D$ and ring A are as defined above for the compounds of formula (I), or any of the embodiments thereof.

In some embodiments, the compound is according to the following formula (II-3):

(II-3)

wherein m is 0 or 1; and k is 0, 1, 2 or 3, and $R^B$, $R^D$ and ring A are as defined above for the compounds of formula (I), or any of the embodiments thereof.

In some embodiments, the compound is according to the following formula (II-4):

(II-4)

wherein m is 0, 1, or 2; and k is 0, 1, 2 or 3, and $R^B$, $R^D$ and ring A as defined above for the compounds of formula (I), or any of the embodiments thereof.

In some embodiments, the compound is according to the following formula (II-5):

(II-5)

wherein m is 0, 1, or 2; and k is 0, 1, 2 or 3, and $R^B$, $R^D$ and ring A are as defined above for the compounds of formula (I), or any of the embodiments thereof.

In some embodiments, the compound is according to the following formula (II-6):

(II-6)

wherein n is 0, 1, 2 or 3; and k is 0, 1, 2 or 3, and $R^B$, $R^D$ and ring A are as defined above for the compounds of formula (I), or any of the embodiments thereof.

In some embodiments, the compound is according to the following formula (II-7):

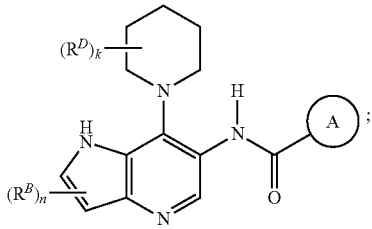

(II-7)

wherein n is 0, 1, 2 or 3; and k is 0, 1, 2 or 3, and $R^B$, $R^D$ and ring A are as defined above for the compounds of formula (I), or any of the embodiments thereof.

In some embodiments, the compound is according to the following formula (II-8):

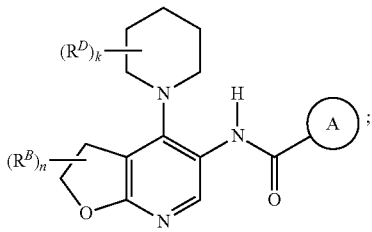

(II-8)

wherein m is 0, 1, or 2; and k is 0, 1, 2 or 3, and $R^B$, $R^D$ and ring A are as defined above for the compounds of formula (I), or any of the embodiments thereof.

In some embodiments, the compound is according to the following formula (II-9):

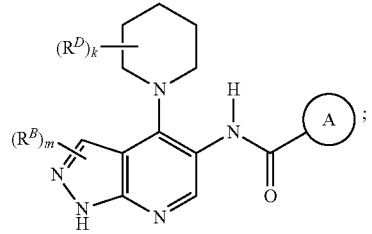

(II-9)

wherein m is 0, 1, or 2; and k is 0, 1, 2 or 3, and $R^B$, $R^D$ and ring A are as defined above for the compounds of formula (I), or any of the embodiments thereof.

In some embodiments, the compound is according to the following formula (II-10):

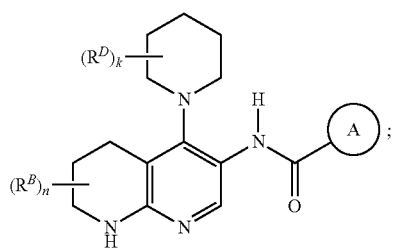

(II-10)

wherein n is 0, 1, 2 or 3; and k is 0, 1, 2 or 3, and $R^B$, $R^D$ and ring A are as defined above for the compounds of formula (I), or any of the embodiments thereof.

In some embodiments, the compound can be selected from the following compounds:
5-amino-N-{4-[3-aminopiperidin-1-yl]quinolin-3-yl}-2-(2,6-difluorophenyl)-1,3-thiazole-4-carboxamide;
N-{4-[3-aminopiperidin-1-yl]quinolin-3-yl}-2-(2,6-difluorophenyl)-1,3-thiazole-4-carboxamide;
5-amino-N-{4-[3-aminopiperidin-1-yl]thieno[2,3-b]pyridin-5-yl}-2-(2,6-difluorophenyl)-1,3-thiazole-4-carboxamide;
N-{4-[3-aminopiperidin-1-yl]thieno[2,3-b]pyridin-5-yl}-2-(2,6-difluorophenyl)-1,3-thiazole-4-carboxamide;
5-amino-N-{7-[3-aminopiperidin-1-yl]thieno[3,2-b]pyridin-6-yl}-2-(2,6-difluorophenyl)-1,3-thiazole-4-carboxamide;
N-{7-[3-aminopiperidin-1-yl]thieno[3,2-b]pyridin-6-yl}-2-(2,6-difluorophenyl)-1,3-thiazole-4-carboxamide;
5-amino-N-{4-[3-aminopiperidin-1-yl]-1H-pyrrolo[2,3-b]pyridin-5-yl}-2-(2,6-difluorophenyl)-1,3-thiazole-4-carboxamide;
N-{4-[3-aminopiperidin-1-yl]-1H-pyrrolo[2,3-b]pyridin-5-yl}-2-(2,6-difluorophenyl)-1,3-thiazole-4-carboxamide;
5-amino-N-{4-[3-aminopiperidin-1-yl]-2,3-dihydrofuro[2,3-b]pyridin-5-yl}-2-(2,6-difluorophenyl)-1,3-thiazole-4-carboxamide;
N-{4-[3-aminopiperidin-1-yl]-2,3-dihydrofuro[2,3-b]pyridin-5-yl}-2-(2,6-difluorophenyl)-1,3-thiazole-4-carboxamide;
N-{4-[3-aminopiperidin-1-yl]-2,3-dihydrofuro[2,3-b]pyridin-5-yl}-6-(2,6-difluorophenyl)-5-fluoropyridine-2-carboxamide;
3-amino-N-{4-[3-aminopiperidin-1-yl]-2,3-dihydrofuro[2,3-b]pyridin-5-yl}-6-(2,6-difluorophenyl)-5-fluoropyridine-2-carboxamide;
N-{4-[3-aminopiperidin-1-yl]-6,7-dihydro-5H-cyclopenta[b]pyridin-3-yl}-2-(2,6-difluorophenyl)-1,3-thiazole-4-carboxamide;
5-amino-N-{4-[3-aminopiperidin-1-yl]-6,7-dihydro-5H-cyclopenta[b]pyridin-3-yl}-2-(2,6-difluorophenyl)-1,3-thiazole-4-carboxamide;
5-amino-N-{4-[3-aminopiperidin-1-yl]-7-hydroxy-6,7-dihydro-5H-cyclopenta[b]pyridin-3-yl}-2-(2,6-difluorophenyl)-1,3-thiazole-4-carboxamide;
N-{4-[3-aminopiperidin-1-yl]-7-hydroxy-6,7-dihydro-5H-cyclopenta[b]pyridin-3-yl}-2-(2,6-difluorophenyl)-1,3-thiazole-4-carboxamide;
5-amino-N-{4-[3-aminopiperidin-1-yl]-7-methoxy-6,7-dihydro-5H-cyclopenta[b]pyridin-3-yl}-2-(2,6-difluorophenyl)-1,3-thiazole-4-carboxamide;

5-amino-N-{4-[3-aminopiperidin-1-yl]-7-cyano-6,7-di-hydro-5H-cyclopenta[b]pyridin-3-yl}-2-(2,6-difluoro-phenyl)-1,3-thiazole-4-carboxamide;

5-amino-N-{4-[3-aminopiperidin-1-yl]-7-hydroxy-7-methyl-6,7-dihydro-5H-cyclopenta[b]pyridin-3-yl}-2-(2,6-difluorophenyl)-1,3-thiazole-4-carboxamide;

5-amino-N-{4-[3-aminopiperidin-1-yl]-7-oxo-6,7-dihydro-5H-cyclopenta[b]pyridin-3-yl}-2-(2,6-difluorophenyl)-1,3-thiazole-4-carboxamide;

N-{4-[3-aminopiperidin-1-yl]-6,7-dihydro-5H-cyclopenta[b]pyridin-3-yl}-6-(2,6-difluorophenyl)-5-fluoropyridine-2-carboxamide;

N-{4-[3-aminopiperidin-1-yl]-7-hydroxy-6,7-dihydro-5H-cyclopenta[b]pyridin-3-yl}-6-(2,6-difluorophenyl)-5-fluoropyridine-2-carboxamide;

3-amino-N-{4-[3-aminopiperidin-1-yl]-7-hydroxy-6,7-dihydro-5H-cyclopenta[b]pyridin-3-yl}-6-(2,6-difluorophenyl)-5-fluoropyridine-2-carboxamide;

5-amino-N-{4-[3-amino-4-hydroxypiperidin-1-yl]-6,7-dihydro-5H-cyclopenta[b]pyridin-3-yl}-2-(2,6-difluorophenyl)-1,3-thiazole-4-carboxamide;

5-amino-N-{4-[3-amino-4-hydroxy-5-methylpiperidin-1-yl]-6,7-dihydro-5H-cyclopenta[b]pyridin-3-yl}-2-(2,6-difluorophenyl)-1,3-thiazole-4-carboxamide;

5-amino-N-{7-[3-amino-4-hydroxypiperidin-1-yl]thieno[3,2-b]pyridin-6-yl}-2-(2,6-difluorophenyl)-1,3-thiazole-4-carboxamide;

5-amino-N-{4-[3-aminopiperidin-1-yl]-5,6,7,8-tetrahydro-1,8-naphthyridin-3-yl}-2-(2,6-difluorophenyl)-1,3-thiazole-4-carboxamide;

3-amino-N-{4-[3-aminopiperidin-1-yl]-5,6,7,8-tetrahydro-1,8-naphthyridin-3-yl}-6-(2,6-difluorophenyl)-5-fluoropyridine-2-carboxamide;

N-{4-[3-aminopiperidin-1-yl]-5,6,7,8-tetrahydro-1,8-naphthyridin-3-yl}-6-(2,6-difluorophenyl)-5-fluoropyridine-2-carboxamide;

5-amino-N-{4-[3-aminopiperidin-1-yl]-1H-pyrazolo[3,4-b]pyridin-5-yl}-2-(2,6-difluorophenyl)-1,3-thiazole-4-carboxamide;

N-{4-[3-aminopiperidin-1-yl]-1H-pyrazolo[3,4-b]pyridin-5-yl}-2-(2,6-difluorophenyl)-1,3-thiazole-4-carboxamide;

5-amino-N-{4-[3-amino-5-methylpiperidin-1-yl]-2,3-dihydrofuro[2,3-b]pyridin-5-yl}-2-(2,6-difluorophenyl)-1,3-thiazole-4-carboxamide;

N-{4-[3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

3-amino-N-{4-[3-amino-5-methylpiperidin-1-yl]-2,3-dihydrofuro[2,3-b]pyridin-5-yl}-6-(2,6-difluorophenyl)-5-fluoropyridine-2-carboxamide;

N-{4-[3-amino-5-methylpiperidin-1-yl]-2,3-dihydrofuro[2,3-b]pyridin-5-yl}-6-(2,6-difluorophenyl)-5-fluoropyridine-2-carboxamide;

5-amino-N-{4-[3-amino-4-hydroxy-5-methylpiperidin-1-yl]-2,3-dihydrofuro[2,3-b]pyridin-5-yl}-2-(2,6-difluorophenyl)-1,3-thiazole-4-carboxamide;

N-{4-[3-amino-4-hydroxy-5-methylpiperidin-1-yl]-2,3-dihydrofuro[2,3-b]pyridin-5-yl}-6-(2,6-difluorophenyl)-5-fluoropyridine-2-carboxamide;

5-amino-N-{4-[3-amino-5-(trifluoromethyl)piperidin-1-yl]-2,3-dihydrofuro[2,3-b]pyridin-5-yl}-2-(2,6-difluorophenyl)-1,3-thiazole-4-carboxamide;

N-{4-[3-amino-5-(trifluoromethyl)piperidin-1-yl]-2,3-dihydrofuro[2,3-b]pyridin-5-yl}-6-(2,6-difluorophenyl)-5-fluoropyridine-2-carboxamide;

5-amino-N-{4-[3-amino-5-(trifluoromethyl)piperidin-1-yl]-7-hydroxy-6,7-dihydro-5H-cyclopenta[b]pyridin-3-yl}-2-(2,6-difluorophenyl)-1,3-thiazole-4-carboxamide;

N-{4-[3-amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

3-amino-N-{4-[3-amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

5-amino-N-{4-[3-amino-5-methylpiperidin-1-yl]-7-hydroxy-6,7-dihydro-5H-cyclopenta[b]pyridin-3-yl}-2-(2,6-difluorophenyl)-1,3-thiazole-4-carboxamide;

3-amino-N-{4-[3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

5-amino-N-{4-[3-amino-4-hydroxy-5-methylpiperidin-1-yl]-7-hydroxy-6,7-dihydro-5H-cyclopenta[b]pyridin-3-yl}-2-(2,6-difluorophenyl)-1,3-thiazole-4-carboxamide;

N-{4-[3-aminopiperidin-1-yl]-7-oxo-6,7-dihydro-5H-cyclopenta[b]pyridin-3-yl}-6-(2,6-difluorophenyl)-5-fluoropyridine-2-carboxamide;

N-{4-[3-amino-4-hydroxy-5-methylpiperidin-1-yl]-7-hydroxy-6,7-dihydro-5H-cyclopenta[b]pyridin-3-yl}-6-(4-ethoxy-2,6-difluorophenyl)-5-fluoropyridine-2-carboxamide;

N-{4-[3-amino-4-hydroxy-5-methylpiperidin-1-yl]-6,7-dihydro-5H-cyclopenta[b]pyridin-3-yl}-6-(2,6-difluorophenyl)-5-fluoropyridine-2-carboxamide;

5-amino-N-{4-[3-aminopiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide;

5-amino-N-{4-[3-amino-5-methylpiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide;

N-{4-[3-aminopiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide;

N-{4-[3-amino-5-methylpiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide;

5-amino-N-[4-(3-amino-3-methylpiperidin-1-yl)-6,7-dihydro-5H-cyclopenta[b]pyridin-3-yl]-2-(2,6-difluorophenyl)-1,3-thiazole-4-carboxamide;

N-{4-[3-aminopiperidin-1-yl]-7-hydroxy-6,7-dihydro-5H-cyclopenta[b]pyridin-3-yl}-6-[2,6-difluoro-4-(methylthio)phenyl]-5-fluoropyridine-2-carboxamide;

N-{4-[3-aminopiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[3-amino-5-methylpiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide; and N-{4-[3-aminopiperidin-1-yl]-7-hydroxy-6,7-dihydro-5H-cyclopenta[b]pyridin-3-yl}-6-[2,6-difluoro-4-(methylsulfonyl)phenyl]-5-fluoropyridine-2-carboxamide;

3-amino-N-{4-[3-aminopiperidin-1-yl]-7-hydroxy-6,7-dihydro-5H-cyclopenta[b]pyridin-3-yl}-6-(2,6-difluorophenyl)pyrazine-2-carboxamide;

N-{4-[3-amino-4-hydroxy-4,5-dimethylpiperidin-1-yl]-7-hydroxy-6,7-dihydro-5H-cyclopenta[b]pyridin-3-yl}-6-(2,6-difluorophenyl)-5-fluoropyridine-2-carboxamide;

N-{4-[3-amino-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[3-amino-4-hydroxy-5-methylpiperidin-1-yl]-2,3-dihydrofuro[2,3-b]pyridin-5-yl}-6-[2,6-difluoro-4-(1-hydroxy-1-methylethyl)phenyl]-5-fluoropyridine-2-carboxamide N-{4-[3-amino-4-hydroxy-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[3-amino-5-methylpiperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide N-{4-[3-amino-5-cyclopropyl-4-hydroxypiperidin-1-yl]-7-hydroxy-6,7-dihydro-5H-cyclopenta[b]pyridin-3-yl}-6-(2,6-difluorophenyl)-5-fluoropyridine-2-carboxamide N-{4-[3-amino-4-hydroxy-5-methylpiperidin-1-yl]-2,3-dihydrofuro[2,3-b]pyridin-5-yl}-6-[2,6-difluoro-4-(tetrahydro-2H-pyran-3-yloxy)phenyl]-5-fluoropyridine-2-carboxamide;

N-{4-[3-amino-5-methylpiperidin-1-yl]-7-hydroxy-6,7-dihydro-5H-cyclopenta[b]pyridin-3-yl}-6-[2,6-difluoro-4-(tetrahydro-2H-pyran-3-yloxy)phenyl]-5-fluoropyridine-2-carboxamide 3-amino-N-{4-[3-amino-4-hydroxy-5-methylpiperidin-1-yl]-2,3-dihydrofuro[2,3-b]pyridin-5-yl}-6-(2,6-difluorophenyl)-5-fluoropyridine-2-carboxamide N-{4-[3-amino-5-(trifluoromethyl)piperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[3-amino-5-methylpiperidin-1-yl]-2,3-dihydrofuro[2,3-b]pyridin-5-yl}-6-(2,6-difluoro-3-methoxyphenyl)-5-fluoropyridine-2-carboxamide;

N-{4-[3-amino-4-hydroxy-5-methylpiperidin-1-yl]-2,3-dihydrofuro[2,3-b]pyridin-5-yl}-6-(2,6-difluoro-3-methoxyphenyl)-5-fluoropyridine-2-carboxamide;

5-amino-N-{4-[3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide; and 5-amino-N-{4-[3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide.

In some embodiments, the compound can be selected from the following compounds:

5-amino-N-{4-[(3S)-3-aminopiperidin-1-yl]quinolin-3-yl}-2-(2,6-difluorophenyl)-1,3-thiazole-4-carboxamide;

N-{4-[(3S)-3-aminopiperidin-1-yl]quinolin-3-yl}-2-(2,6-difluorophenyl)-1,3-thiazole-4-carboxamide;

5-amino-N-{4-[(3S)-3-aminopiperidin-1-yl]thieno[2,3-b]pyridin-5-yl}-2-(2,6-difluorophenyl)-1,3-thiazole-4-carboxamide;

N-{4-[(3S)-3-aminopiperidin-1-yl]thieno[2,3-b]pyridin-5-yl}-2-(2,6-difluorophenyl)-1,3-thiazole-4-carboxamide;

5-amino-N-{7-[(3S)-3-aminopiperidin-1-yl]thieno[3,2-b]pyridin-6-yl}-2-(2,6-difluorophenyl)-1,3-thiazole-4-carboxamide;

N-{7-[(3S)-3-aminopiperidin-1-yl]thieno[3,2-b]pyridin-6-yl}-2-(2,6-difluorophenyl)-1,3-thiazole-4-carboxamide;

5-amino-N-{4-[(3S)-3-aminopiperidin-1-yl]-1H-pyrrolo[2,3-b]pyridin-5-yl}-2-(2,6-difluorophenyl)-1,3-thiazole-4-carboxamide;

N-{4-[(3S)-3-aminopiperidin-1-yl]-1H-pyrrolo[2,3-b]pyridin-5-yl}-2-(2,6-difluorophenyl)-1,3-thiazole-4-carboxamide;

5-amino-N-{4-[(3S)-3-aminopiperidin-1-yl]-2,3-dihydrofuro[2,3-b]pyridin-5-yl}-2-(2,6-difluorophenyl)-1,3-thiazole-4-carboxamide;

N-{4-[(3S)-3-aminopiperidin-1-yl]-2,3-dihydrofuro[2,3-b]pyridin-5-yl}-2-(2,6-difluorophenyl)-1,3-thiazole-4-carboxamide;

N-{4-[(3S)-3-aminopiperidin-1-yl]-2,3-dihydrofuro[2,3-b]pyridin-5-yl}-6-(2,6-difluorophenyl)-5-fluoropyridine-2-carboxamide;

3-amino-N-{4-[(3S)-3-aminopiperidin-1-yl]-2,3-dihydrofuro[2,3-b]pyridin-5-yl}-6-(2,6-difluorophenyl)-5-fluoropyridine-2-carboxamide;

N-{4-[(3S)-3-aminopiperidin-1-yl]-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-7-hydroxy-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7R)-7-hydroxy-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7S)-7-hydroxy-6,7-dihydro-5H-cyclopenta[b]pyridin-3-yl}-2-(2,6-difluorophenyl)-1,3-thiazole-4-carboxamide;

N-{4-[(3S)-3-aminopiperidin-1-yl]-7-hydroxy-6,7-dihydro-5H-cyclopenta[b]pyridin-3-yl}-2-(2,6-difluorophenyl)-1,3-thiazole-4-carboxamide;

N-{4-[(3S)-3-aminopiperidin-1-yl]-(7R)-7-hydroxy-6,7-dihydro-5H-cyclopenta[b]pyridin-3-yl}-2-(2,6-difluorophenyl)-1,3-thiazole-4-carboxamide;

N-{4-[(3S)-3-aminopiperidin-1-yl]-(7S)-7-hydroxy-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-7-methoxy-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7R)-7-methoxy-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7S)-7-methoxy-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-7-cyano-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7R)-7-cyano-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7S)-7-cyano-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-7-hydroxy-7-methyl-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7R)-7-hydroxy-7-methyl-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-(7S)-7-hydroxy-7-methyl-6,7-dihydro-5H-cyclopenta[b]pyridin-3-yl}-2-(2,6-difluorophenyl)-1,3-thiazole-4-carboxamide;

5-amino-N-{4-[(3S)-3-aminopiperidin-1-yl]-7-oxo-6,7-dihydro-5H-cyclopenta[b]pyridin-3-yl}-2-(2,6-difluorophenyl)-1,3-thiazole-4-carboxamide;

N-{4-[(3S)-3-aminopiperidin-1-yl]-6,7-dihydro-5H-cyclopenta[b]pyridin-3-yl}-6-(2,6-difluorophenyl)-5-fluoropyridine-2-carboxamide;

N-{4-[(3S)-3-aminopiperidin-1-yl]-7-hydroxy-6,7-dihydro-5H-cyclopenta[b]pyridin-3-yl}-6-(2,6-difluorophenyl)-5-fluoropyridine-2-carboxamide;

N-{4-[(3S)-3-aminopiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

N-{4-[(3S)-3-aminopiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S)-3-aminopiperidin-1-yl]-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S)-3-aminopiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S)-3-aminopiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

5-amino-N-{4-[(3R,4R)-3-amino-4-hydroxypiperidin-1-yl]-6,7-dihydro-5H-cyclopenta[b]pyridin-3-yl}-2-(2,6-difluorophenyl)-1,3-thiazole-4-carboxamide;

5-amino-N-{4-[(3S,4S)-3-amino-4-hydroxypiperidin-1-yl]-6,7-dihydro-5H-cyclopenta[b]pyridin-3-yl}-2-(2,6-difluorophenyl)-1,3-thiazole-4-carboxamide;

5-amino-N-{4-[(3R,4S)-3-amino-4-hydroxypiperidin-1-yl]-6,7-dihydro-5H-cyclopenta[b]pyridin-3-yl}-2-(2,6-difluorophenyl)-1,3-thiazole-4-carboxamide;

5-amino-N-{4-[(3S,4R)-3-amino-4-hydroxypiperidin-1-yl]-6,7-dihydro-5H-cyclopenta[b]pyridin-3-yl}-2-(2,6-difluorophenyl)-1,3-thiazole-4-carboxamide;

5-amino-N-{4-[(3R,4R,5S)-3-amino-4-hydroxy-5-methylpiperidin-1-yl]-6,7-dihydro-5H-cyclopenta[b]pyridin-3-yl}-2-(2,6-difluorophenyl)-1,3-thiazole-4-carboxamide;

5-amino-N-{7-[(3R,4R)-3-amino-4-hydroxypiperidin-1-yl]thieno[3,2-b]pyridin-6-yl}-2-(2,6-difluorophenyl)-1,3-thiazole-4-carboxamide;

5-amino-N-{7-[(3S,4S)-3-amino-4-hydroxypiperidin-1-yl]thieno[3,2-b]pyridin-6-yl}-2-(2,6-difluorophenyl)-1,3-thiazole-4-carboxamide;

5-amino-N-{4-[(3S)-3-aminopiperidin-1-yl]-5,6,7,8-tetrahydro-1,8-naphthyridin-3-yl}-2-(2,6-difluorophenyl)-1,3-thiazole-4-carboxamide;

3-amino-N-{4-[(3S)-3-aminopiperidin-1-yl]-5,6,7,8-tetrahydro-1,8-naphthyridin-3-yl}-6-(2,6-difluorophenyl)-5-fluoropyridine-2-carboxamide;

N-{4-[(3S)-3-aminopiperidin-1-yl]-5,6,7,8-tetrahydro-1,8-naphthyridin-3-yl}-6-(2,6-difluorophenyl)-5-fluoropyridine-2-carboxamide;

5-amino-N-{4-[(3S)-3-aminopiperidin-1-yl]-1H-pyrazolo[3,4-b]pyridin-5-yl}-2-(2,6-difluorophenyl)-1,3-thiazole-4-carboxamide;

N-{4-[(3S)-3-aminopiperidin-1-yl]-1H-pyrazolo[3,4-b]pyridin-5-yl}-2-(2,6-difluorophenyl)-1,3-thiazole-4-carboxamide;

5-amino-N-{4-[(3S,5R)-3-amino-5-methylpiperidin-1-yl]-2,3-dihydrofuro[2,3-b]pyridin-5-yl}-2-(2,6-difluorophenyl)-1,3-thiazole-4-carboxamide;

N-{4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-4-hydroxy-5-methylpiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-4-hydroxy-5-methylpiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S,5R)-3-amino-5-methylpiperidin-1-yl]-2,3-dihydrofuro[2,3-b]pyridin-5-yl}-6-(2,6-difluorophenyl)-5-fluoropyridine-2-carboxamide;

N-{4-[(3S,5R)-3-amino-5-methylpiperidin-1-yl]-2,3-dihydrofuro[2,3-b]pyridin-5-yl}-6-(2,6-difluorophenyl)-5-fluoropyridine-2-carboxamide;

5-amino-N-{4-[(3R,4R,5S)-3-amino-4-hydroxy-5-methylpiperidin-1-yl]-2,3-dihydrofuro[2,3-b]pyridin-5-yl}-2-(2,6-difluorophenyl)-1,3-thiazole-4-carboxamide;

N-{4-[(3R,4R,5S)-3-amino-4-hydroxy-5-methylpiperidin-1-yl]-2,3-dihydrofuro[2,3-b]pyridin-5-yl}-6-(2,6-difluorophenyl)-5-fluoropyridine-2-carboxamide;

5-amino-N-{4-[(3S,5R)-3-amino-5-(trifluoromethyl)piperidin-1-yl]-2,3-dihydrofuro[2,3-b]pyridin-5-yl}-2-(2,6-difluorophenyl)-1,3-thiazole-4-carboxamide;

N-{4-[(3S,5R)-3-amino-5-(trifluoromethyl)piperidin-1-yl]-2,3-dihydrofuro[2,3-b]pyridin-5-yl}-6-(2,6-difluorophenyl)-5-fluoropyridine-2-carboxamide;

5-amino-N-{4-[(3S,5R)-3-amino-5-(trifluoromethyl)piperidin-1-yl]-7-hydroxy-6,7-dihydro-5H-cyclopenta[b]pyridin-3-yl}-2-(2,6-difluorophenyl)-1,3-thiazole-4-carboxamide;

5-amino-N-{4-[(3S,5R)-3-amino-5-(trifluoromethyl)piperidin-1-yl]-(7R)-7-hydroxy-6,7-dihydro-5H-cyclopenta[b]pyridin-3-yl}-2-(2,6-difluorophenyl)-1,3-thiazole-4-carboxamide;

5-amino-N-{4-[(3S,5R)-3-amino-5-(trifluoromethyl)piperidin-1-yl]-(7S)-7-hydroxy-6,7-dihydro-5H-cyclopenta[b]pyridin-3-yl}-2-(2,6-difluorophenyl)-1,3-thiazole-4-carboxamide;

N-{4-[(3S,5R)-3-amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

N-{4-[(3S,5R)-3-amino-5-methylpiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

N-{4-[(3S,5R)-3-amino-5-methylpiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S,5R)-3-amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S,5R)-3-amino-5-methylpiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

3-amino-N-{4-[(3S,5R)-3-amino-5-methylpiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

5-amino-N-{4-[(3S,5R)-3-amino-5-methylpiperidin-1-yl]-7-hydroxy-6,7-dihydro-5H-cyclopenta[b]pyridin-3-yl}-2-(2,6-difluorophenyl)-1,3-thiazole-4-carboxamide;

5-amino-N-{4-[(3S,5R)-3-amino-5-methylpiperidin-1-yl]-(7R)-7-hydroxy-6,7-dihydro-5H-cyclopenta[b]pyridin-3-yl}-2-(2,6-difluorophenyl)-1,3-thiazole-4-carboxamide;

5-amino-N-{4-[(3S,5R)-3-amino-5-methylpiperidin-1-yl]-(7S)-7-hydroxy-6,7-dihydro-5H-cyclopenta[b]pyridin-3-yl}-2-(2,6-difluorophenyl)-1,3-thiazole-4-carboxamide;

3-amino-N-{4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide;

3-amino-N-{4-[(3R,4R,5S)-3-amino-4-hydroxy-5-methylpiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

3-amino-N-{4-[(3R,4R,5S)-3-amino-4-hydroxy-5-methylpiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

5-amino-N-{4-[(3R,4R,5S)-3-amino-4-hydroxy-5-methylpiperidin-1-yl]-7-hydroxy-6,7-dihydro-5H-cyclopenta[b]pyridin-3-yl}-2-(2,6-difluorophenyl)-1,3-thiazole-4-carboxamide;

5-amino-N-{4-[(3R,4R,5S)-3-amino-4-hydroxy-5-methylpiperidin-1-yl]-(7R)-7-hydroxy-6,7-dihydro-5H-cyclopenta[b]pyridin-3-yl}-2-(2,6-difluorophenyl)-1,3-thiazole-4-carboxamide;

5-amino-N-{4-[(3R,4R,5S)-3-amino-4-hydroxy-5-methylpiperidin-1-yl]-(7S)-7-hydroxy-6,7-dihydro-5H-cyclopenta[b]pyridin-3-yl}-2-(2,6-difluorophenyl)-1,3-thiazole-4-carboxamide;

N-{4-[(3S)-3-aminopiperidin-1-yl]-7-oxo-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-4-hydroxy-5-methylpiperidin-1-yl]-7-hydroxy-6,7-dihydro-5H-cyclopenta[b]pyridin-3-yl}-6-(4-ethoxy-2,6-difluorophenyl)-5-fluoropyridine-2-carboxamide;

N-{4-[(3R,4R,5S)-3-amino-4-hydroxy-5-methylpiperidin-1-yl]-(7R)-7-hydroxy-6,7-dihydro-5H-cyclopenta[b]pyridin-3-yl}-6-(4-ethoxy-2,6-difluorophenyl)-5-fluoropyridine-2-carboxamide;

N-{4-[(3R,4R,5S)-3-amino-4-hydroxy-5-methylpiperidin-1-yl]-(7S)-7-hydroxy-6,7-dihydro-5H-cyclopenta[b]pyridin-3-yl}-6-(4-ethoxy-2,6-difluorophenyl)-5-fluoropyridine-2-carboxamide;

N-{4-[(3R,4R,5S)-3-amino-4-hydroxy-5-methylpiperidin-1-yl]-6,7-dihydro-5H-cyclopenta[b]pyridin-3-yl}-6-(2,6-difluorophenyl)-5-fluoropyridine-2-carboxamide;

5-amino-N-{4-[(3S)-3-aminopiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide;

5-amino-N-{4-[(3S)-3-aminopiperidin-1-yl]-(7R)-7-hydroxy-6,7-dihydro-5H-cyclopenta[b]pyridin-3-yl}-2-(2,6-difluoro-3-methoxyphenyl)-1,3-thiazole-4-carboxamide;

5-amino-N-{4-[(3S)-3-aminopiperidin-1-yl]-(7S)-7-hydroxy-6,7-dihydro-5H-cyclopenta[b]pyridin-3-yl}-2-(2,6-difluoro-3-methoxyphenyl)-1,3-thiazole-4-carboxamide;

5-amino-N-{4-[(3S,5R)-3-amino-5-methylpiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide;

5-amino-N-{4-[(3S,5R)-3-amino-5-methylpiperidin-1-yl]-(7R)-7-hydroxy-6,7-dihydro-5H-cyclopenta[b]pyridin-3-yl}-2-(2,6-difluoro-3-methoxyphenyl)-1,3-thiazole-4-carboxamide;

5-amino-N-{4-[(3S,5R)-3-amino-5-methylpiperidin-1-yl]-(7S)-7-hydroxy-6,7-dihydro-5H-cyclopenta[b]pyridin-3-yl}-2-(2,6-difluoro-3-methoxyphenyl)-1,3-thiazole-4-carboxamide;

N-{4-[(3S)-3-aminopiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide;

N-{4-[(3S)-3-aminopiperidin-1-yl]-(7R)-7-hydroxy-6,7-dihydro-5H-cyclopenta[b]pyridin-3-yl}-6-(2,6-difluoro-3-methoxyphenyl)-5-fluoropyridine-2-carboxamide;

N-{4-[(3S)-3-aminopiperidin-1-yl]-(7S)-7-hydroxy-6,7-dihydro-5H-cyclopenta[b]pyridin-3-yl}-6-(2,6-difluoro-3-methoxyphenyl)-5-fluoropyridine-2-carboxamide;

N-{4-[(3S,5R)-3-amino-5-methylpiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide;

N-{4-[(3S,5R)-3-amino-5-methylpiperidin-1-yl]-(7R)-7-hydroxy-6,7-dihydro-5H-cyclopenta[b]pyridin-3-yl}-6-(2,6-difluoro-3-methoxyphenyl)-5-fluoropyridine-2-carboxamide;

N-{4-[(3S,5R)-3-amino-5-methylpiperidin-1-yl]-(7S)-7-hydroxy-6,7-dihydro-5H-cyclopenta[b]pyridin-3-yl}-6-(2,6-difluoro-3-methoxyphenyl)-5-fluoropyridine-2-carboxamide;

5-amino-N-[4-((3R)-3-amino-3-methylpiperidin-1-yl)-6,7-dihydro-5H-cyclopenta[b]pyridin-3-yl]-2-(2,6-difluorophenyl)-1,3-thiazole-4-carboxamide;

5-amino-N-[4-((3S)-3-amino-3-methylpiperidin-1-yl)-6,7-dihydro-5H-cyclopenta[b]pyridin-3-yl]-2-(2,6-difluorophenyl)-1,3-thiazole-4-carboxamide;

N-{4-[(3S)-3-aminopiperidin-1-yl]-7-hydroxy-6,7-dihydro-5H-cyclopenta[b]pyridin-3-yl}-6-[2,6-difluoro-4-(methylthio)phenyl]-5-fluoropyridine-2-carboxamide;

N-{4-[(3S)-3-aminopiperidin-1-yl]-(7R)-7-hydroxy-6,7-dihydro-5H-cyclopenta[b]pyridin-3-yl}-6-[2,6-difluoro-4-(methylthio)phenyl]-5-fluoropyridine-2-carboxamide;

N-{4-[(3S)-3-aminopiperidin-1-yl]-(7S)-7-hydroxy-6,7-dihydro-5H-cyclopenta[b]pyridin-3-yl}-6-[2,6-difluoro-4-(methylthio)phenyl]-5-fluoropyridine-2-carboxamide;

N-{4-[(3S)-3-aminopiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[(3S)-3-aminopiperidin-1-yl]-(7R)-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[(3S)-3-aminopiperidin-1-yl]-(7S)-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[(3S,5R)-3-amino-5-methylpiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[(3S,5R)-3-amino-5-methylpiperidin-1-yl]-(7R)-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[(3S,5R)-3-amino-5-methylpiperidin-1-yl]-(7S)-7-hydroxy-6,7-dihydro-5H-cyclopenta[b]pyridin-3-yl}-6-[2,6-difluoro-4-(methylsulfinyl)phenyl]-5-fluoropyridine-2-carboxamide;

N-{4-[(3S)-3-aminopiperidin-1-yl]-7-hydroxy-6,7-dihydro-5H-cyclopenta[b]pyridin-3-yl}-6-[2,6-difluoro-4-(methylsulfonyl)phenyl]-5-fluoropyridine-2-carboxamide;

N-{4-[(3S)-3-aminopiperidin-1-yl]-(7R)-7-hydroxy-6,7-dihydro-5H-cyclopenta[b]pyridin-3-yl}-6-[2,6-difluoro-4-(methylsulfonyl)phenyl]-5-fluoropyridine-2-carboxamide;

N-{4-[(3S)-3-aminopiperidin-1-yl]-(7S)-7-hydroxy-6,7-dihydro-5H-cyclopenta[b]pyridin-3-yl}-6-[2,6-difluoro-4-(methylsulfonyl)phenyl]-5-fluoropyridine-2-carboxamide;

3-amino-N-{4-[(3S)-3-aminopiperidin-1-yl]-7-hydroxy-6,7-dihydro-5H-cyclopenta[b]pyridin-3-yl}-6-(2,6-difluorophenyl)pyrazine-2-carboxamide;

3-amino-N-{4-[(3S)-3-aminopiperidin-1-yl]-(7R)-7-hydroxy-6,7-dihydro-5H-cyclopenta[b]pyridin-3-yl}-6-(2,6-difluorophenyl)pyrazine-2-carboxamide;

3-amino-N-{4-[(3S)-3-aminopiperidin-1-yl]-(7S)-7-hydroxy-6,7-dihydro-5H-cyclopenta[b]pyridin-3-yl}-6-(2,6-difluorophenyl)pyrazine-2-carboxamide;

N-{4-[(3R,5S)-3-amino-4-hydroxy-4,5-dimethylpiperidin-1-yl]-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-4-hydroxy-4,5-dimethylpiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

N-{4-[(3R,4S,5S)-3-amino-4-hydroxy-4,5-dimethylpiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-4-hydroxy-4,5-dimethylpiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

N-{4-[(3R,4S,5S)-3-amino-4-hydroxy-4,5-dimethylpiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

N-{4-[(3S,5R)-3-amino-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[(3S,5R)-3-amino-5-methylpiperidin-1-yl]-(7R)-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[(3S,5R)-3-amino-5-methylpiperidin-1-yl]-(7S)-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[(3R,4R,5S)-3-amino-4-hydroxy-5-methylpiperidin-1-yl]-2,3-dihydrofuro[2,3-b]pyridin-5-yl}-6-[2,6-difluoro-4-(1-hydroxy-1-methylethyl)phenyl]-5-fluoropyridine-2-carboxamide;

N-{4-[(3R,4R,5S)-3-amino-4-hydroxy-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[(3R,4R,5S)-3-amino-4-hydroxy-5-methylpiperidin-1-yl]-(7R)-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[(3R,4R,5S)-3-amino-4-hydroxy-5-methylpiperidin-1-yl]-(7S)-7-hydroxy-6,7-dihydro-5H-cyclopenta[b]pyridin-3-yl}-6-[2,6-difluoro-4-(methoxymethyl)phenyl]-5-fluoropyridine-2-carboxamide;

N-{4-[(3S,5R)-3-amino-5-methylpiperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[(3S,5R)-3-amino-5-methylpiperidin-1-yl]-(7R)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[(3S,5R)-3-amino-5-methylpiperidin-1-yl]-(7S)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[(3R,4R,5S)-3-amino-5-cyclopropyl-4-hydroxypiperidin-1-yl]-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-5-cyclopropyl-4-hydroxypiperidin-1-yl]-(7R)-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-5-cyclopropyl-4-hydroxypiperidin-1-yl]-(7S)-7-hydroxy-6,7-dihydro-5H-cyclopenta[b]pyridin-3-yl}-6-(2,6-difluorophenyl)-5-fluoropyridine-2-carboxamide;

N-{4-[(3R,4R,5S)-3-amino-4-hydroxy-5-methylpiperidin-1-yl]-2,3-dihydrofuro[2,3-b]pyridin-5-yl}-6-[2,6-difluoro-4-(tetrahydro-2H-pyran-3-yloxy)phenyl]-5-fluoropyridine-2-carboxamide;

N-{4-[(3S,5R)-3-amino-5-methylpiperidin-1-yl]-7-hydroxy-6,7-dihydro-5H-cyclopenta[b]pyridin-3-yl}-6-[2,6-difluoro-4-(tetrahydro-2H-pyran-3-yloxy)phenyl]-5-fluoropyridine-2-carboxamide;

N-{4-[(3S,5R)-3-amino-5-methylpiperidin-1-yl]-(7R)-7-hydroxy-6,7-dihydro-5H-cyclopenta[b]pyridin-3-yl}-6-[2,6-difluoro-4-(tetrahydro-2H-pyran-3-yloxy)phenyl]-5-fluoropyridine-2-carboxamide;

N-{4-[(3S,5R)-3-amino-5-methylpiperidin-1-yl]-(7S)-7-hydroxy-6,7-dihydro-5H-cyclopenta[b]pyridin-3-yl}-6-[2,6-difluoro-4-(tetrahydro-2H-pyran-3-yloxy)phenyl]-5-fluoropyridine-2-carboxamide;

3-amino-N-{4-[(3R,4R,5S)-3-amino-4-hydroxy-5-methylpiperidin-1-yl]-2,3-dihydrofuro[2,3-b]pyridin-5-yl}-6-(2,6-difluorophenyl)-5-fluoropyridine-2-carboxamide;

N-{4-[(3S,5R)-3-amino-5-(trifluoromethyl)piperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[(3S,5R)-3-amino-5-(trifluoromethyl)piperidin-1-yl]-(7R)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[(3S,5R)-3-amino-5-(trifluoromethyl)piperidin-1-yl]-(7S)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide;

N-{4-[(3S,5R)-3-amino-5-methylpiperidin-1-yl]-2,3-dihydrofuro[2,3-b]pyridin-5-yl}-6-(2,6-difluoro-3-methoxyphenyl)-5-fluoropyridine-2-carboxamide;

N-{4-[(3R,4R,5S)-3-amino-4-hydroxy-5-methylpiperidin-1-yl]-2,3-dihydrofuro[2,3-b]pyridin-5-yl}-6-(2,6-difluoro-3-methoxyphenyl)-5-fluoropyridine-2-carboxamide;

5-amino-N-{4-[(3R,4S,5S)-3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide; and 5-amino-N-{4-[(3R,4R,5S)-3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl, and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms, and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —NH$_2$.

The term "carbamyl" refers to a group of formula —C(=O)NH$_2$.

The term "carbonyl", employed alone or in combination with other terms, refers to a —C(=O)— group, which also may be written as C(O).

The term "carboxy" refers to a group of formula —C(=O)OH.

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

The term "heteroaryl" or "heteroaromatic", employed alone or in combination with other terms, refers to a monocyclic or polycyclic aromatic heterocycle having at least one heteroatom ring member selected from sulfur, oxygen, and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g. thieno[3,2-b]pyridine) or the like.

A five-membered heteroaryl ring is a heteroaryl group having five ring atoms wherein one or more (e.g., 1, 2 or 3) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O, and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members 4-7 ring members or 4-6 ring members. Included in heterocycloalkyl are monocyclic 4-, 5-, 6-, and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally substituted by oxo or sulfido (e.g., C(=O), S(=O), C(=S), or S(=O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azepane, azetidine, diazepan (e.g., 1,4-diazepan), dihydrobenzofuran, dihydrofuran, dihydropyran, piperazine, piperidine, pyrrolidine, pyran, morpholine, tetrahydropyran, tetrahydrofuran, 1,2,3,4-tetrahydroquinoline, thiomorpholine, and the like.

The term "carbocycle" refers to an aryl group or a cycloalkyl group.

The term "heterocycle" refers to a heteroaryl group or a heterocycloalkyl group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, e.g., 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66 (1), 1-19, and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DCM (dichloromethane); DIAD (N,N'-diisopropyl azodicarboxylate); DIC (N,N'-diisopropylcarbodiimide); DIPEA (N,N-diisopropylethylamine); DMAP (4-dimethylaminopyridine); DMF (N,N-dimethylformamide); Et (ethyl); EtOAc (ethyl acetate); EtOH (ethanol); Fmoc (9-fluorenylmethylmethoxycarbonyl); g (gram(s)); h (hour(s)); HATU (N,N, N',N'-tetramethyl-O-(7-azabenzotriazol-1-yl)uronium hexafluorophosphate); HCl (hydrochloric acid); HPLC (high performance liquid chromatography); Hz (hertz); i-Pr (isopropyl); J (coupling constant); $K_3PO_4$ (potassium phosphate); LCMS (liquid chromatography-mass spectrometry); m (multiplet); M (molar); mCPBA (3-chloroperoxybenzoic acid); Me (methyl); MeCN (acetonitrile); MeOH (methanol); mg (milligram(s)); $MgSO_4$ (magnesium sulfate); min. (minutes(s)); mL (milliliter(s)); mmol (millimole(s)); MS (Mass spectrometry); N (normal); $NaHCO_3$ (sodium bicarbonate); NaOH (sodium hydroxide); $Na_2SO_4$ (sodium sulfate); $Na_2S_2O_3$ (sodium thiosulfate); n-Bu (n-butyl); n-BuLi (n-butyllithium); $NH_4Cl$ (ammonium chloride); $NH_4OH$ (ammonium hydroxide); nM (nanomolar); NMR (nuclear magnetic resonance spectroscopy); Pd (palladium); pM (picomolar); $POCl_3$ (phosphoryl chloride); PTFE (polytetrafluoroethylene); RP-HPLC (reverse phase high performance liquid chromatography); s (singlet); t (triplet or tertiary); tert (tertiary); tt (triplet of triplets); t-Bu (tert-butyl); TFA (trifluoroacetic acid); THF (tetrahydrofuran); Tris (tris(hydroxymethyl)aminomethane); μg (microgram (s)); μL (microliter(s)); μm (micrometer); μM (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74 (11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of formula (I) can be prepared, e.g., using a process as illustrated in Scheme 1. In the process depicted in Scheme 1, a suitable aromatic amine of formula 1-1 is reacted with an acid of formula 1-2 under conditions suitable for forming an amide bond to provide the compound of formula (I). Suitable combinations for forming the amide bond include, e.g., the methods used to form amide bonds in peptides as described, e.g., in Jones, *Amino Acid and Peptide Synthesis*, 2nd Ed., Oxford University Press, 2002; and Jones, *The Chemical Synthesis of Peptides (International Series of Monographs on Chemistry)* (Oxford University Press, 1994). An example of a suitable coupling agent is HATU/DIPEA.

Scheme 1

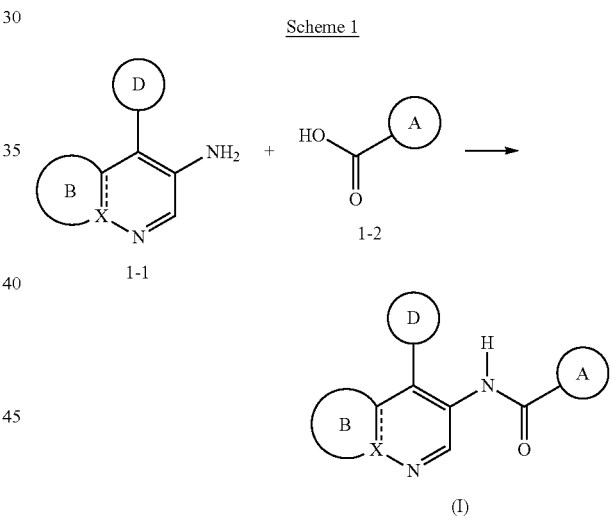

Compounds of formula (I) can be prepared, e.g., using a process as illustrated in Scheme 2.

Scheme 2

-continued

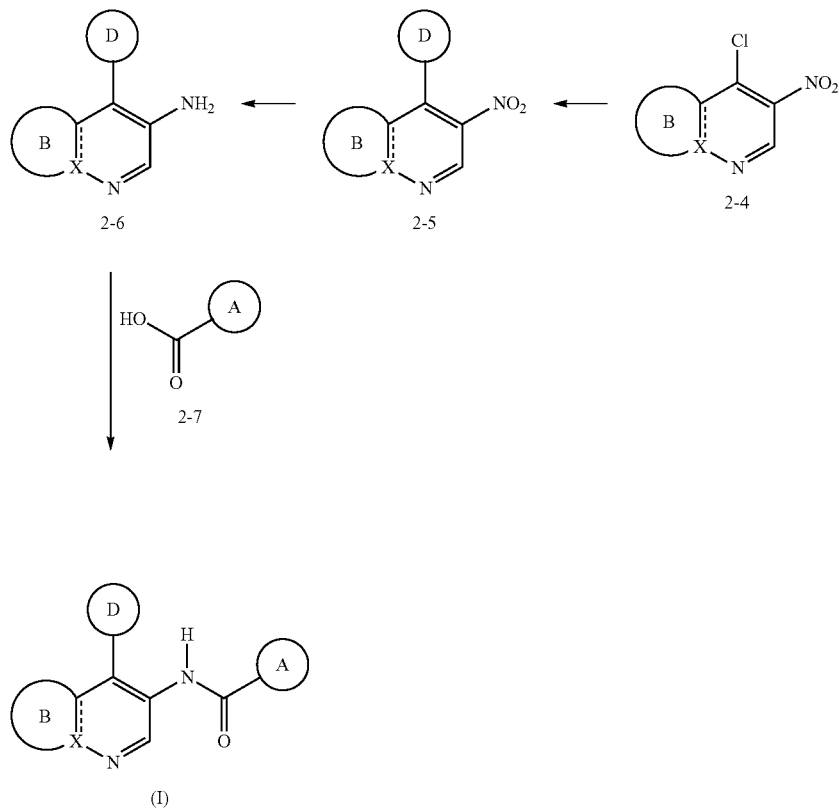

In the process depicted in Scheme 2, a suitable aromatic used aromatic compound of formula 2-1 can be oxidized to give an N-oxide 2-2. Examples of suitable oxidizing agents include peracids such as mCPBA. The N-oxide group can then be used to direct functionalization of the 4-position of the N-oxide containing ring, e.g. by reaction with a suitable electrophile or reaction with a suitable acid chloride or anhydride compound, proceeding via initial nucleophilic reaction of the N-oxide with the acid chloride or anhydride followed by nucleophilic addition to the aromatic ring. An example of a suitable acid chloride or anhydride is $POCl_3$ which can react with the N-oxide to introduce chlorine into the 4-position. Thus, the N-oxide 2-2 can be reacted with $POCl_3$ to produce the 4-chloro-substituted compound 2-3. A 4-chloro substituent provides functionalization to enable the introduction of ring D into the compound of formula (I) by suitable cross-coupling chemistry, e.g., nucleophilic substitution of the chlorine or suitable metal-catalyzed cross-coupling reactions. To introduce the amino group which forms the amide bond of formula (I), a nitro group can be introduced by electrophilic nitration at the 3-position and then reduced to the required amine group. Thus, the chloro compound 2-4 can be reacted with a suitable nitrating agent to provide the aromatic nitro compound of formula 2-5. Examples of suitable nitrating agents include nitric acid. Since the nitro group activates the chloro at the 4-position to nucleophilic coupling reactions, it may be convenient to introduce ring D by reaction of the 3-nitro-4-chloro compound, particularly when ring D is a heterocycle connected via a nitrogen atom. Thus, reaction of compound 2-4 with a suitable precursor of ring D can provide a nitro compound of formula 2-5. When ring D is a heterocycle connected via a nitrogen atom, the reaction can be carried out by nucleophilic substitution in the presence of a suitable base, e.g. sodium hydride or sodium t-butoxide. The reaction can also be carried out by suitable metal catalyzed cross-coupling reactions such as Buchwald-Hartwig cross-coupling chemistry. When ring D is not connected via nitrogen, other suitable cross-coupling reactions, e.g., Stille or Suzuki cross-coupling reactions. In other cases a suitable functional group such as nitrile can be introduced and used as a precursor for synthesis of ring D.

The nitro group of compound 2-5 can be reduced to an amino group using a suitable reducing agent. Examples of suitable reducing agents include hydrogen gas, which can be reacted with the nitro compound in the presence of a suitable catalyst, e.g., palladium, such as palladium in the form of palladium on carbon. Suitable reducing agents also include metals such as iron and zinc. Thus, reduction of nitrocompound 2-5 provides an amino-compound 2-6, which can then be subjected to amide-bond coupling with a suitable acid of formula 2-7 to provide the compound of formula (I).

Application of the general scheme described above to the preparation of a compound of formula (I) wherein the compound of formula (I) contains a dihydrocyclopentapyridine ring is illustrated in Scheme 3. As a variation of the scheme described above, instead of being nitrated directly, the chloropyridine compound 3-3 is transformed to a methoxypyridine 3-4 to take advantage of the superior efficacy of the methoxy group in activating the pyridine ring to electrophilic substitution and directing substitution to the 3-position.

Scheme 3

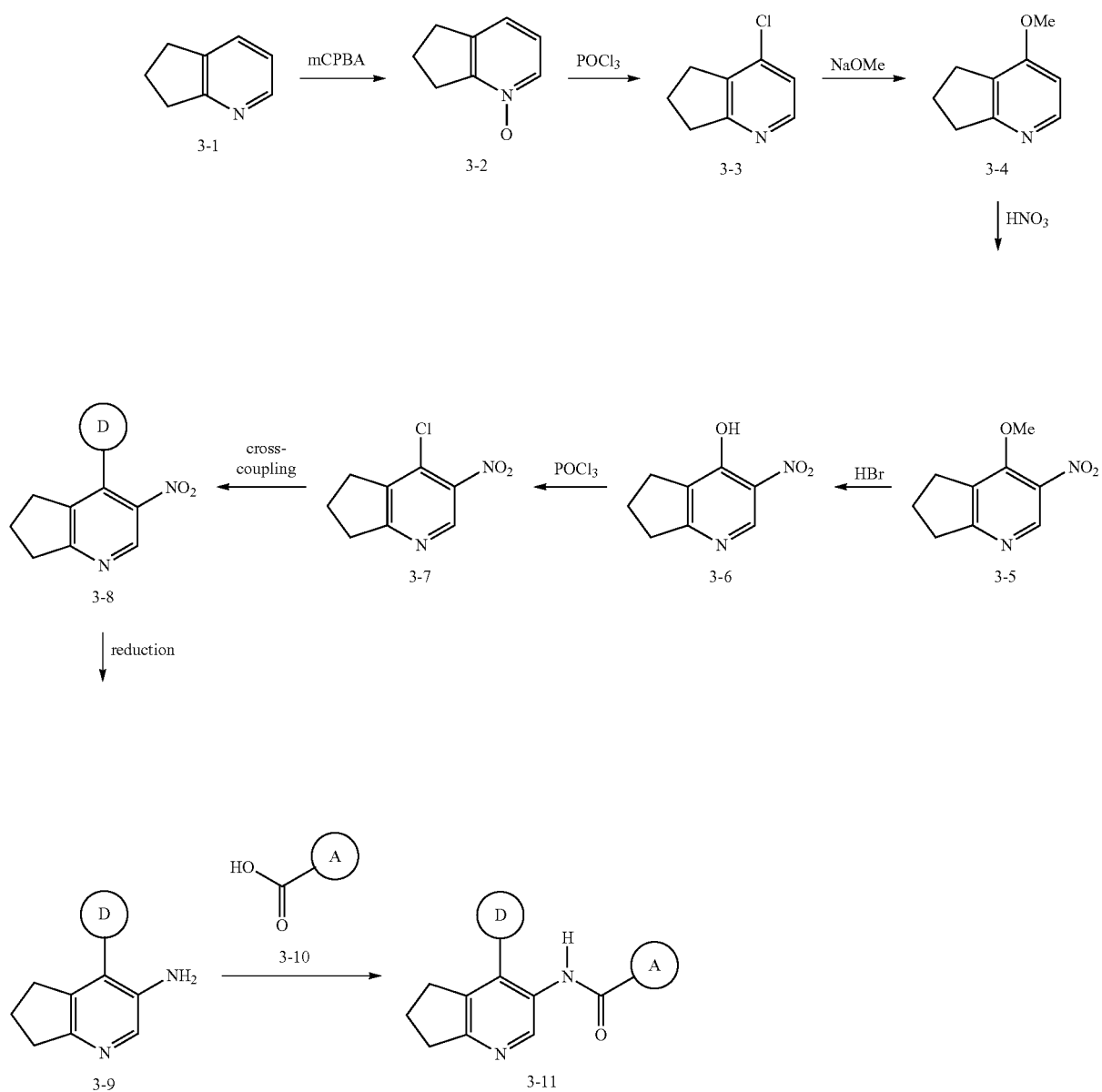

Thus, in the process illustrated by Scheme 3, commercially available cyclopentapyridine 3-1 can be oxidized with mCPBA to give corresponding N-oxide 3-2, which can be subsequently treated with POCl₃ to generate chloropyridine 3-3. Compound 3-3 can be transformed to methoxy compound 3-4 by heating with sodium methoxide. The methoxypyridine 3-4 can then be nitrated with a suitable nitrating agent. Suitable conditions for the nitration include heating with potassium nitrate and sulfuric acid. The resulting nitro compound 3-5 can be subjected to demethylation reaction to provide the hydroxypyridine 3-6. Suitable conditions for demethylation include, e.g., heating with HBr. The hydroxypyridine 3-6 can then be converted back to a chloropyridine 3-7 by reaction with a suitable acid chloride compound such as POCl₃. Then, as discussed above, the chloro compound 3-7 can be reacted to introduce ring D by a suitable procedure which will depend on the nature of ring D, such as by nucleophilic substitution, or a cross-coupling reaction such as Buchwald-Hartwig, Stille or Suzuki cross-coupling reactions. Nitro compound 3-8 can then be reduced to aminopyridine 3-9 through treatment with a suitable reducing agent such as hydrogen in the presence of a catalyst, e.g. Pd on carbon, or by reaction with iron in the presence of ammonium chloride. The resulting amino-pyridine can then be subjected to amide coupling with a carboxylic acid of formula 3-10 to provide an amide of formula 3-11, which corresponds to a compound of formula (I), wherein ring B is a fused cyclopentane ring.

A variation of the process shown in Scheme 3 to produce compounds wherein ring B is a functionalized cyclopentane ring can be carried out as shown in Scheme 4.

Scheme 4

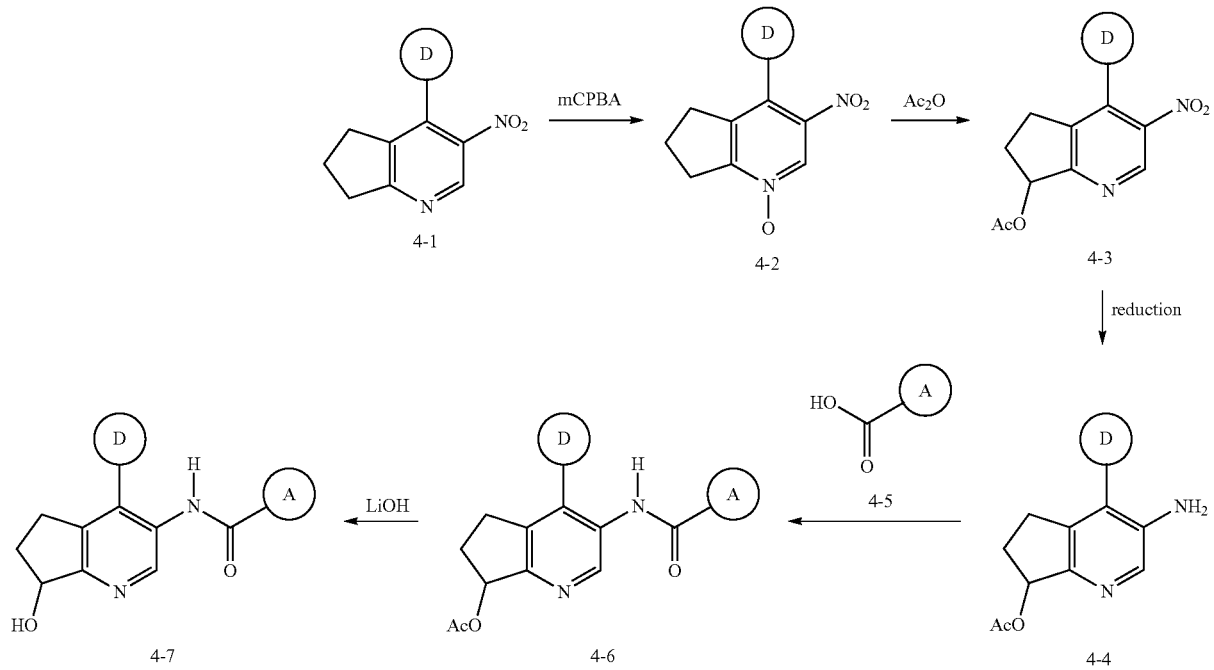

Thus, after coupling to introduce ring D, the compound 4-1 (corresponding to compound 3-8 of Scheme 3) can be oxidized to an N-oxide 4-2 with a suitable oxidizing agent such as mCPBA. Functionalization of the cyclopentane ring is then achieved by reaction of the N-oxide 4-2 with a suitable electrophilic agent such as acetic anhydride, which initially acetylates the N-oxide which then undergoes rearrangement to provide the acetate compound 4-3. Then, in the same manner as described above, the nitro compound is reduced to an amino compound 4-4 using a suitable reducing agent such as hydrogen/Pd on carbon or iron followed by amide coupling with a suitable acid of formula 4-5 to provide the amide of formula 4-6. The acetyl group of compound 4-6 can then be removed, e.g., by hydrolysis with a suitable base, e.g., potassium carbonate or lithium hydroxide. The hydroxy group of compound 4-7 can then be further transformed to other functional groups by methods known to one skilled in the art, and as illustrated in the Examples.

A modification of the general scheme described above to the synthesis of compounds wherein ring B is a fused dihydrofuran ring is shown in Scheme 5. In the process of Scheme 5, commercially available fluoroiodopyridine 5-1 can be treated with LDA followed by ethylene sulfate to provide compound 5-2 via a rearrangement reaction ("halogen dance"). Compound 5-2 can be hydrolyzed to alcohol 5-3 by treating with an acid, e.g., HCl. Cyclization of alcohol 5-3 to a dihydrofuropyridine 5-4 can then be achieved by reaction under suitable basic conditions, e.g., heating with potassium phosphate in dioxane. The dihydrofuropyridine compound 5-4 can then be nitrated with a suitable nitrating agent such as nitric acid in sulfuric acid to give the nitropyridine compound 5-5. The coupling of compound 5-5 to introduce ring D can then be achieved using the methods discussed above, such as by nucleophilic substitution, or a cross-coupling reaction such as Buchwald-Hartwig, Stille or Suzuki cross-coupling reactions. Then, analogously to the procedure described above, the resulting nitro compound 5-6 can be reduced to an aminopyridine 5-7 using a suitable reducing agent such as hydrogen/Pd on carbon or iron followed by amide coupling with a suitable acid of formula 5-8 to provide the amide of formula 5-9, which corresponds to a compound of formula (I), wherein ring B is a fused dihydrofuran ring.

Scheme 5

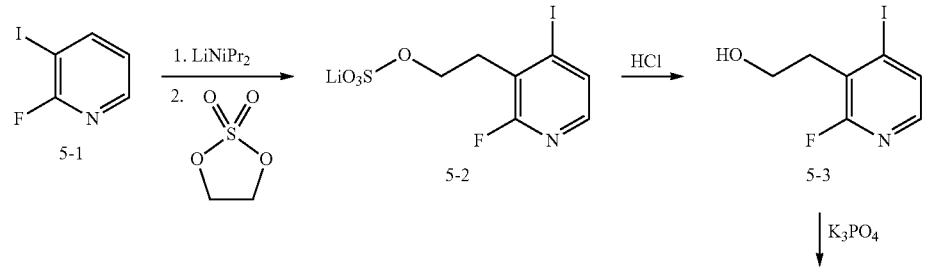

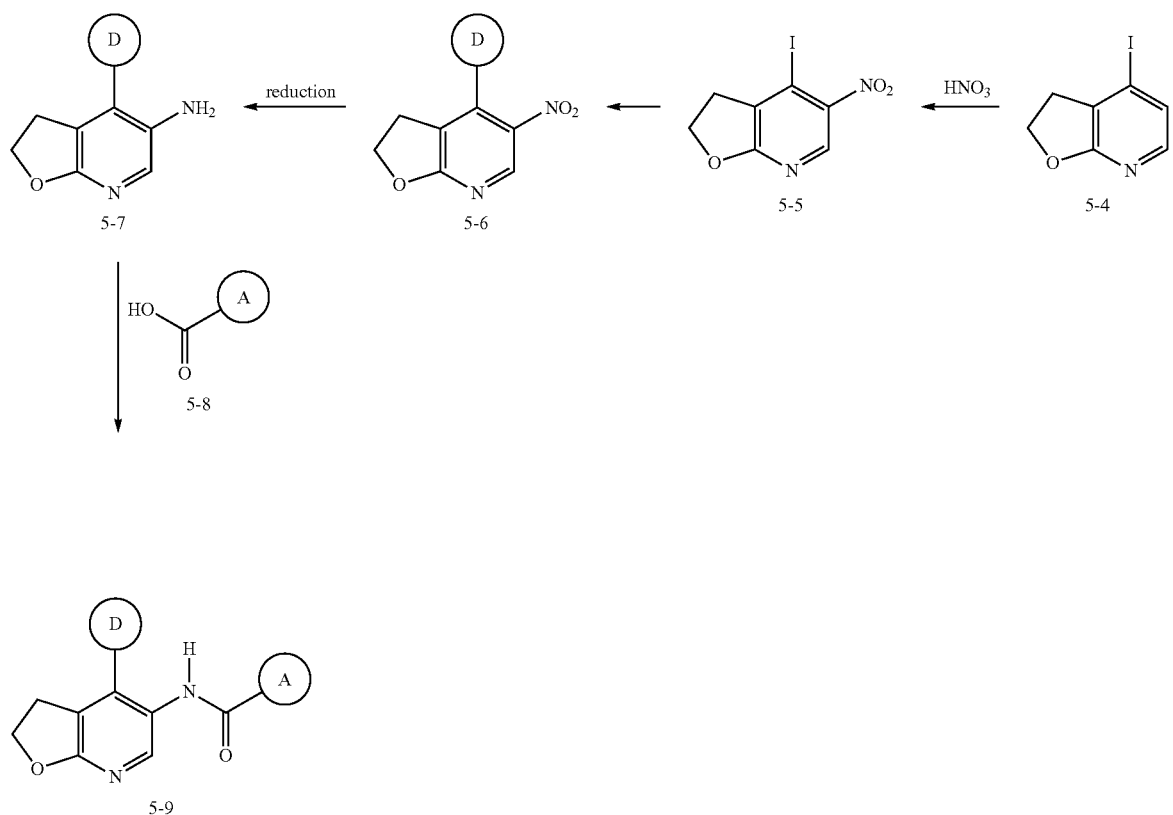

Further compounds of formula (I) can be synthesized as illustrated in Scheme 6. Commercially available N-aminophthalimide 6-1 can be treated with 2,5-dimethoxy tetrahydrofuran at elevated temperature to provide isoindolinedione compound 6-2. When treated with hydrazine monohydrate, 6-2 can be hydrolyzed to give 1-aminopyrrole 6-3. The aminopyrrole 6-3 can be transformed to 6-4 through condensation with diethyl-2-(ethoxymethylene)malonate and removal of ethanol generated. Compound 6-4 can be cyclized in a high boiling solvent such as Dowtherm A under elevated temperature to generate the pyrrolopyridazine compound 6-5. Compound 6-5 can be reacted with POCl₃ to afford the corresponding chloropyrrolopyridazine 6-6. Coupling of 6-6 with an appropriate ring D compounds can be achieved with methods known to one skilled in the art, such as direct coupling or Buchwald-Hartwig coupling when ring D is attached to pyrrolopyridazine through nitrogen; or Suzuki coupling when ring D is attached to pyrrolopyridazine through carbon. Saponification of the ester group of compound 6-7 to provide a carboxylic acid 6-8, followed by Curtius rearrangement to give a Boc-protected amino compound 6-9 and, deprotection of the Boc group can then give amino pyrrolopyridazines 6-10. Finally, amide coupling of 6-10 with a suitable ring A acid can yield desired compounds of formula 6-11. The substitutions on 6-11 can be further transformed to desired functional groups in the final product, or in any of the steps of the synthesis, using methods know to one skilled in the art.

Scheme 6

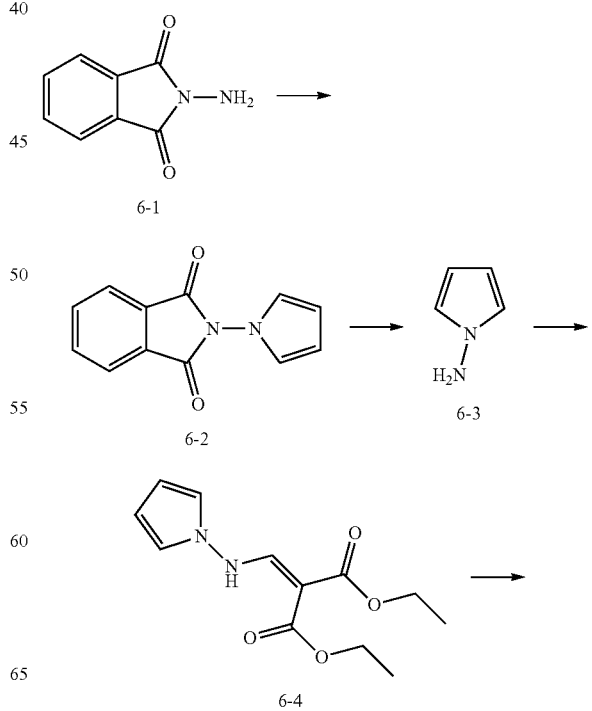

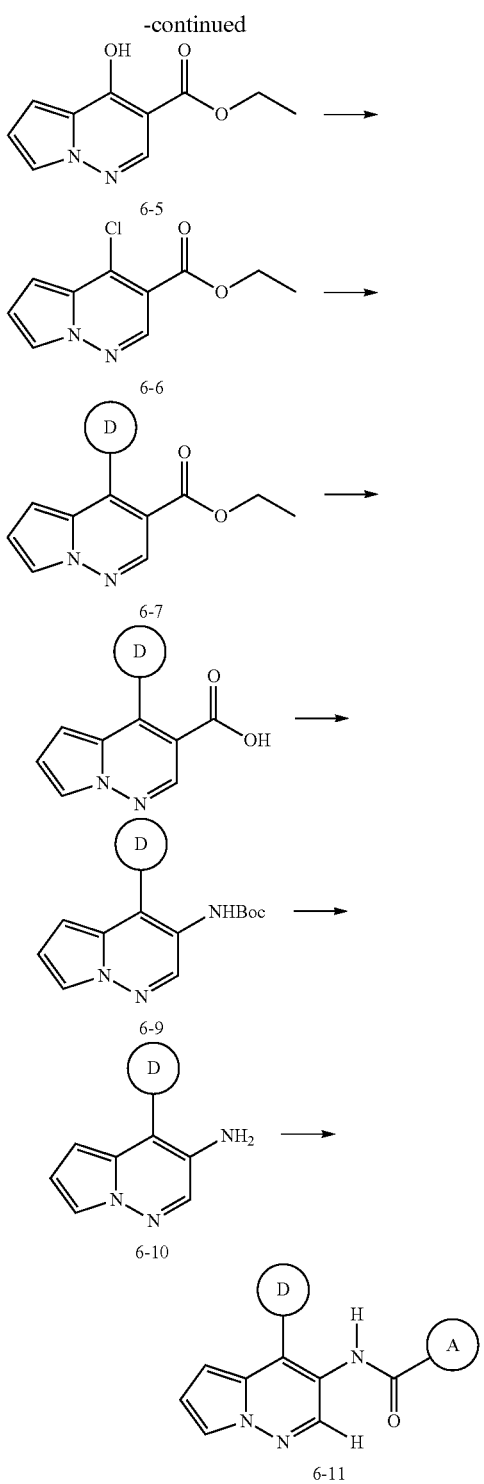

For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., March's Advanced Organic Chemistry: Reactions, Mechanisms, and Structure, $6^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of one or more members of the Pim kinase family and, thus, are useful in treating diseases and disorders associated with activity of Pim kinases. For the uses described herein, any of the compounds of the invention, including any of the embodiments thereof, may be used.

The compounds of the invention can inhibit one or more of Pim1, Pim2 and Pim3. In some embodiments the compounds are selective for one Pim kinase over another. "Selective" in this context means that the compound binds to or inhibits a Pim kinase with greater affinity or potency, respectively, compared to a reference enzyme, such as another Pim kinase. For example, the compounds can be selective for Pim1 over Pim2 and Pim3, selective for Pim2 over Pim1 and Pim3, or selective for Pim3 over Pim1 and Pim2. In some embodiments, the compounds inhibit all of the Pim family members (e.g., Pim1, Pim2 and Pim3). In some embodiments, the compounds can be selective for Pim over other kinases such as receptor and non-receptor Ser/Thr kinases such as Akt1, Akt2, Akt3, TGF-βR, PKA, PKG, PKC, CaM-kinase, phosphorylase kinase, MEKK, ERK, MAPK and mTOR; receptor Tyr kinases such as EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2; and non-receptor Tyr kinases such as Src, Fyn, Lck, Fgr, Btk, Fak, SYK, FRK, JAK or ABL. In general, selectivity can be at least about 5-fold, at least about 10-fold, at least about 20-fold, at least about 50-fold, at least about 100-fold, at least about 200-fold, at least about 500-fold or at least about 1000-fold. The method of inhibiting a Pim1, Pim2 or Pim3 kinase includes contacting the appropriate enzyme with the compound of formula (I), or any of the embodiments thereof, or a pharmaceutically acceptable salt thereof.

Thus, the present disclosure provides methods of treating a Pim kinase-associated disease or disorder in an individual (e.g., patient) by administering to the individual in need of such treatment a therapeutically effective amount or dose of a compound of formula (I), or any of the embodiments thereof, or a pharmaceutical composition thereof. The present disclosure also provides a compound of formula (I), or any of the embodiments thereof, or a pharmaceutical composition thereof, for use in treating a Pim kinase-associated disease or disorder. Also provided is the use of a compound of formula (I), or any of the embodiments thereof, or a pharmaceutical composition thereof, in the manufacture of a medicament for treating a Pim kinase-associated disease or disorder.

A Pim kinase-associated disease can include any disease, disorder or condition that is directly or indirectly linked to expression or activity of the Pim kinase, including overexpression and/or abnormal activity levels. Abnormal activity levels can be determined by comparing activity level in normal, healthy tissue or cells with activity level in diseased cells. A Pim kinase-associated disease can also include any disease, disorder or condition that can be prevented, ameliorated, inhibited or cured by modulating Pim kinase activity. In some embodiments, the disease is characterized by the abnormal activity or expression (e.g., overexpression) of one or more Pim1, Pim2 and Pim3. In some embodiments, the disease is characterized by mutant Pim1, Pim2 or Pim3. A Pim kinase associated disease can also refer to any disease, disorder or condition wherein modulating the expression or activity of one or more Pim kinases is beneficial.

Pim kinase associated diseases that can be treated using the compounds of the invention include cancer, including, in particular, cancers in which Pim kinases are upregulated or an oncogene, e.g., Myc or BCL2, is activated. Pim kinase associated diseases include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Pim kinase associated diseases also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Pim kinase associated diseases that can be treated using the compounds of the invention also include myeloproliferative disorders such as polycythemia vera (PV), essential thrombocythemia (ET), chronic myelogenous leukemia (CML) and the like. The myeloproliferative disorder can be myelofibrosis such as primary myelofibrosis (PMF), myelofibrosis with myeloid metaplasia (MMM), post-polycythemia vera/essential thrombocythemia myelofibrosis (Post-PV/ET MF), post-essential thrombocythemia myelofibrosis (Post-ET MF) or post-polycythemia vera myelofibrosis (Post-PV MF).

Pim kinase-associated diseases that can be treated with compounds according to the invention also include immune disorders such as autoimmune diseases. The immune disorders include multiple sclerosis, rheumatoid arthritis, allergy, food allergy, asthma, lupus, inflammatory bowel disease and ulcerative colitis.

Pim kinase-associated diseases that can be treated with compounds according to the invention also include atherosclerosis.

The compounds of the invention can also be used to inhibit disease processes in which Pim-kinases are involved, including angiogenesis and tumor metastasis.

Due to the fact that Pim kinases are regulated by the JAK/STAT pathway, the compounds of the invention are useful to treat diseases in which modulating JAK/STAT signaling is beneficial. Thus, other diseases that can be treated using the compounds of the invention include Crohn's disease, irritable bowel syndrome, pancreatitis, diverticulosis, Grave's disease, juvenile rheumatoid arthritis, osteoarthritis, psoriatic arthritis, ankylosing spondylitis, myasthenia gravis, vasculitis, autoimmune thyroiditis, dermatitis, psoriasis, scleroderma, systemic sclerosis, vitiligo, graft versus host disease, Sjogren's syndrome, glomerulonephritis and diabetes mellitus (type I).

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in HEK-293 cells or inhibition of the hERG potassium ion channel to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different kinase inhibitors, exhibiting different preferences in the kinases which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Accordingly, the Pim inhibitors of the present invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the Pim inhibitors of the invention can be combined with inhibitors of kinases associated with the PIK3/Akt/mTOR signaling pathway, such as PI3K, Akt (including Akt1, Akt2 and Akt3) and mTOR kinases.

The Pim inhibitors of the present invention can further be used in combination with other methods of treating cancers, for example by chemotherapy, irradiation, or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

The Pim inhibitors of the present invention can further be used in combination with one or more anti-inflammatory agents, steroids, immunosuppressants, or therapeutic antibodies.

When more than one pharmaceutical agent is administered to a patient, they can be administered simultaneously, sequentially, or in combination (e.g., for more than two agents).

IV. Formulation, Dosage Forms and Administration

When employed as pharmaceuticals, the compounds of the invention can be administered in the form of pharmaceutical compositions. Thus the present disclosure provides a composition comprising a compound of formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; and sweetening agents and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™) In some embodiments, the polyethylene oxide is polyethylene oxide WSR 1105 (e.g., Polyox WSR 1105™)

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline® (petroleum jelly) and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, including kinase signaling, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating Pim kinases in tissue samples, including human, and for identifying Pim kinase ligands by inhibition binding of a labeled compound. Accordingly, the present invention includes Pim kinase assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro Pim kinase labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$, $^{35}$S and $^{82}$Br. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a Pim-kinase by monitoring its concentration variation when contacting with the Pim kinase, through tracking of the labeling. For example, a test compound (labeled) can be evaluated for its ability to reduce binding of another compound which is known to bind to a Pim kinase (i.e., standard compound). Accordingly, the ability of a test compound to compete with the standard compound for binding to the Pim kinase directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of Pim kinase-associated diseases or disorders, such as cancer, which include one or more containers containing a pharmaceutical composition comprising a therapeutically effective amount of a compound of formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be Pim-kinase inhibitors according to at least one assay described herein.

EXAMPLES

Experimental procedures for compounds of the invention are provided below. Open Access Preparative LC-MS Purification of some of the compounds prepared was performed on Waters mass directed fractionation systems. The basic equipment setup, protocols, and control software for the operation of these systems have been described in detail in literature. See, e.g., Blom, "Two-Pump At Column Dilution Configuration for Preparative LC-MS", K. Blom, *J Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

In the cases where diastereoisomers were isolated, the HPLC retention times were obtained from analytical LCMS (Waters SunFire™ column, 2.1 mm×50 mm, 5 µm particle size, eluting with a gradient of MeOH/water containing 0.025% TFA).

Example 1

5-Amino-N-{4-[(3S)-3-aminopiperidin-1-yl]quinolin-3-yl}-2-(2,6-difluorophenyl)-1,3-thiazole-4-carboxamide

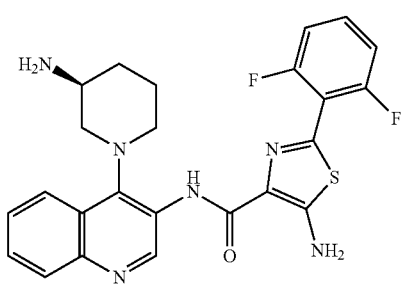 [SMILES: Nc1sc(-c2c(F)cccc2F)nc1C(=O)Nc1cnc2ccccc2c1N1CCC[C@H](N)C1]

Step 1. tert-Butyl[(3S)-1-(3-nitroquinolin-4-yl)piperidin-3-yl]carbamate

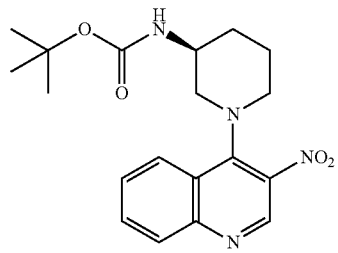 [SMILES: CC(C)(C)OC(=O)N[C@H]1CCCN(c2c(N)cnc3ccccc23)C1]

To a 5 mL microwave vial containing 4-chloro-3-nitroquinoline (Ark Pharm, 312.9 mg, 1.500 mmol) and tert-butyl (3S)-piperidin-3-ylcarbamate (Combi-Blocks, 358.9 mg, 1.792 mmol), 1-butanol (3.00 mL) was added followed by DIPEA (405.1 mg, 3.134 mmol). The reaction mixture was heated at 100° C. under microwave irradiation for 2 h. The reaction was then concentrated under reduced pressure. The resulting residue was purified by chromatography on silica gel (0-100% EtOAc in hexanes) to give the sub-title compound as a yellow oil (293.5 mg, 53%). LCMS calc. for $C_{19}H_{25}N_4O_4$ (M+H)$^+$: m/z=373.2; found 373.2.

Step 2. tert-Butyl [(3S)-1-(3-aminoquinolin-4-yl)piperidin-3-yl]carbamate

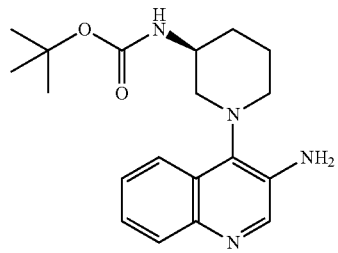

EtOH (5.00 mL) followed by water (1.00 mL) were added to vial containing tert-butyl [(3S)-1-(3-nitroquinolin-4-yl)piperidin-3-yl]carbamate (118.9 mg, 0.3193 mmol), iron powder (199.0 mg, 3.563 mmol) and NH$_4$Cl (288.9 mg, 5.401 mmol). The mixture was stirred at 80° C. for 1 h. The reaction mixture was filtered through a pad of diatomaceous earth. The pad was eluted with a 10% aq. K$_3$PO$_4$ (20 mL), and EtOAc (20 mL). The organic layer was washed with brine (20 mL), dried over Na$_2$SO$_4$, and concentrated under reduced pressure. The resulting residue was purified by chromatography on silica gel (0-100% EtOAc in hexanes) to give the sub-title compound as a pale yellow solid (36.9 mg, 34%). LCMS calc. for $C_{19}H_{27}N_4O_2$ (M+H)$^+$: m/z=343.2; found 343.2.

Step 3. Methyl 5-amino-2-bromo-1,3-thiazole-4-carboxylate

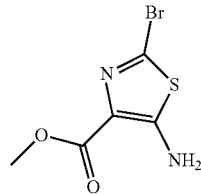

To a solution of methyl 5-amino-1,3-thiazole-4-carboxylate (J & W PharmLab, 10.0 g, 63.2 mmol) in THF (100 mL), N-bromosuccinimide (12.0 g, 67.4 mmol) was added portion-wise. After stirring at room temperature for 1 h, the mixture reaction was filtered to give a first crop of product as a pink solid (9.8 g). The filtrate was concentrated under reduced pressure. The resulting residue was triturated with EtOAc (15 mL) and filtered to give a second crop of product as a pink solid (5.0 g, total yield: 99%). LCMS calc. for $C_5H_6BrN_2O_2S$ (M+H)$^+$: m/z=236.9; found 237.0.

Step 4. Methyl 2-bromo-5-[(tert-butoxycarbonyl)amino]-1,3-thiazole-4-carboxylate

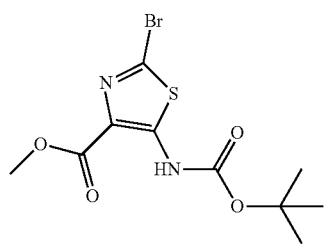 [SMILES: COC(=O)c1nc(Br)sc1NC(=O)OC(C)(C)C]

To a solution of methyl 5-amino-2-bromo-1,3-thiazole-4-carboxylate (14.8 g, 62.4 mmol) in THF (100 mL), di-tert-butyl dicarbonate (18.0 g, 82.2 mmol), DMAP (1.5 g, 13 mmol) and triethylamine (17.6 mL, 126 mmol) were added. After stirring at room temperature for 16 h, the reaction mixture was diluted with EtOAc (400 mL) and washed with water (2×250 mL). The organic layer was washed with brine (250 mL), dried over $Na_2SO_4$, and concentrated under reduced pressure. The resulting residue was purified by chromatography on silica gel (0-50% EtOAc in hexanes) to give the sub-title compound as a white solid (15.1 g, 72%). LCMS calc. for $C_{10}H_{14}BrN_2O_4S$ (M+H)$^+$: m/z=337.0; found 337.0.

Step 5. Methyl 5-[(tert-butoxycarbonyl)amino]-2-(2,6-difluorophenyl)-1,3-thiazole-4-carboxylate

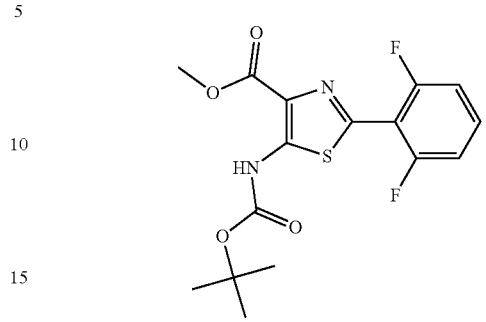

To a round bottle flask equipped with a magnetic stir bar, methyl 2-bromo-5-[(tert-butoxycarbonyl)amino]-1,3-thiazole-4-carboxylate (9.60 g, 28.5 mmol) was added, followed by 2-(2,6-difluorophenyl)-4,4,5,5-tetramethyl-1,3,2-dioxaborolane (Combi-Blocks, 8.88 g, 37.0 mmol) and bis(tri-tert-butylphosphine)palladium (2.30 g, 4.50 mmol). The flask was sealed with a rubber septum, and evacuated and backfilled with nitrogen three times. 1,4-Dioxane (40.0 mL) was added via a syringe, followed by DIPEA (9.6 mL, 55 mmol) and deoxygenated water (2.0 mL). The resulting mixture was heated at 100° C. for 1 h. After cooling to room temperature, the mixture was diluted with EtOAc (200 mL) and washed with water (100 mL) and brine (200 mL), then dried over $Na_2SO_4$, and concentrated under reduced pressure. The resulting residue was purified by chromatography on silica gel (0-100% EtOAc in hexanes) to give the sub-title compound as a white solid (9.80 g, 93%). LCMS calc. for $C_{16}H_{17}F_2N_2O_4S$ (M+H)$^+$: m/z=371.1; found 371.0.

Step 6. 5-[(tert-Butoxycarbonyl)amino]-2-(2,6-difluorophenyl)-1,3-thiazole-4-carboxylic Acid

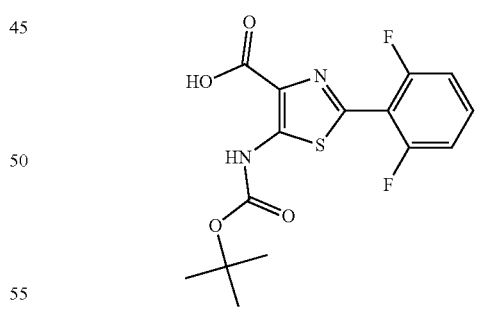

To a suspension of methyl 5-[(tert-butoxycarbonyl)amino]-2-(2,6-difluorophenyl)-1,3-thiazole-4-carboxylate (6.99 g, 18.9 mmol) in MeOH (50.0 mL), lithium hydroxide monohydrate (5.24 g, 125 mmol) was added, followed by water (50.0 mL). The mixture was heated at 60° C. for 5 h. The reaction mixture was then cooled to 0° C., and 6 M HCl was added slowly until the pH reached 2. The resulting solid was collected by filtration and the filter cake was washed with water (50 mL) and MeOH/water (1:1, 50 mL) to provide the sub-title compound as a yellow solid (6.59 g, 98%). LCMS calc. for C₁₅H₁₅F₂N₂O₄S (M+H)⁺: m/z=357.1; found 357.0.

Step 7. tert-Butyl {(3S)-1-[3-({[5-[(tert-butoxycarbonyl)amino]-2-(2,6-difluorophenyl)-1,3-thiazol-4-yl]carbonyl}amino)quinolin-4-yl]piperidin-3-yl}carbamate

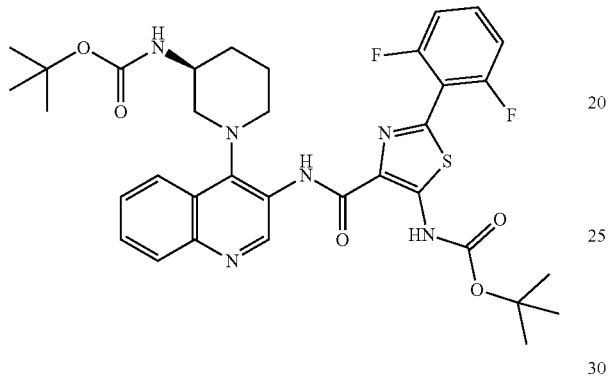

To a solution of 5-[(tert-butoxycarbonyl)amino]-2-(2,6-difluorophenyl)-1,3-thiazole-4-carboxylic acid (81.1 mg, 0.228 mmol) in THF (0.5 mL), a solution of 1-chloro-N,N,2-trimethylpropenylamine (Aldrich, 80.5 mg, 0.602 mmol) in THF (1.0 mL) was added. The mixture was stirred at room temperature for 5 h. To the above mixture was added a solution of tert-butyl [(3S)-1-(3-aminoquinolin-4-yl)piperidin-3-yl]carbamate (63.8 mg, 0.186 mmol) in THF (2.0 mL) followed by pyridine (146.4 mg, 1.851 mmol). The mixture was stirred at room temperature for 2 h, and then concentrated under reduced pressure. The resulting residue was purified by chromatography on silica gel (0-100% EtOAc in hexanes) to afford the sub-title compound as a yellow solid (115.8 mg, 91%). LCMS calc. for C₃₄H₃₉F₂N₆O₅S (M+H)⁺: m/z=681.3; found 681.3.

Step 8. 5-Amino-N-{4-[(3S)-3-aminopiperidin-1-yl]quinolin-3-yl}-2-(2,6-difluorophenyl)-1,3-thiazole-4-carboxamide To a solution of tert-butyl {(3S)-1-[3-({[5-[(tert-butoxycarbonyl)amino]-2-(2,6-difluorophenyl)-1,3-thiazol-4-yl]carbonyl}amino)quinolin-4-yl]piperidin-3-yl}carbamate (115.8 mg, 0.17 mmol) in DCM (2.0 mL) was added TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.15% NH₄OH, at flow rate of 30 mL/min.) to afford the title compound as a white solid (20.5 mg, 25%). LCMS calc. for C₂₄H₂₃F₂N₆OS (M+H)⁺: m/z=481.2; found 481.2.

Example 2

N-{4-[(3S)-3-Aminopiperidin-1-yl]quinolin-3-yl}-2-(2,6-difluorophenyl)-1,3-thiazole-4-carboxamide

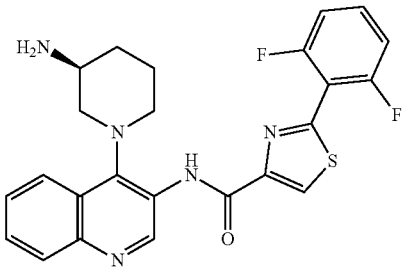 [SMILES: N[C@H]1CCCN(c2c(NC(=O)c3csc(-c4c(F)cccc4F)n3)cnc3ccccc23)C1]

Step 1. Ethyl 2-(2,6-difluorophenyl)-1,3-thiazole-4-carboxylate

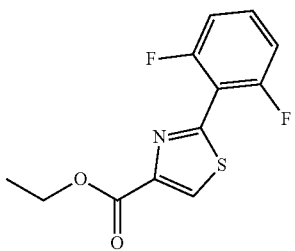 [SMILES: CCOC(=O)c1csc(-c2c(F)cccc2F)n1]

To a screw-cap vial equipped with a magnetic stir bar, ethyl 2-bromo-1,3-thiazole-4-carboxylate (Ark Pharm, 2.026 g, 8.582 mmol) was added followed by 2-(2,6-difluorophenyl)-4,4,5,5-tetramethyl-1,3,2-dioxaborolane (Combi-Blocks, 2.47 g, 10.3 mmol) and bis(tri-tert-butylphosphine)palladium (781.8 mg, 1.530 mmol). The vial was sealed with a PTFE-lined septum, and was then evacuated and backfilled with nitrogen three times. 1,4-Dioxane (10.0 mL) was added via syringe, followed by DIPEA (2.41 g, 18.6 mmol) and deoxygenated water (0.60 mL). The reaction mixture was stirred at 120° C. for 3 h. After cooling to room temperature, the mixture was filtered through a silica gel plug (eluted with EtOAc). The filtrate was concentrated under reduced pressure, and the residue was purified by chromatography on silica gel (0-100% EtOAc in hexanes) to give the title compound as a pale yellow oil (1.739 g, 75%). LCMS calc. for C₁₂H₁₀F₂NO₂S (M+H)⁺: m/z=270.0; found 270.0.

Step 2.
2-(2,6-Difluorophenyl)-1,3-thiazole-4-carboxylic Acid

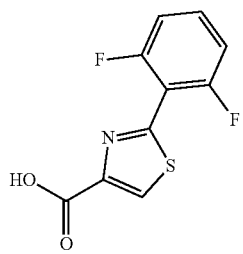 [SMILES: O=C(O)c1csc(-c2c(F)cccc2F)n1]

To a solution of ethyl 2-(2,6-difluorophenyl)-1,3-thiazole-4-carboxylate (1.72 g, 6.39 mmol) in THF (40.0 mL), lithium hydroxide monohydrate (1.51 g, 36.0 mmol) was added followed by water (10.0 mL). The mixture was stirred at 60° C. for 5 h. The reaction mixture was then cooled to 0° C., and 6 M HCl was added slowly until the pH reached 2. The mixture was diluted with EtOAc (250 mL), washed with brine (200 mL), dried over $Na_2SO_4$ and concentrated under reduced pressure. The residue was purified by chromatography on silica gel (0-30% MeOH in DCM) to give the title compound as a white solid (1.49 g, 97%). LCMS calc. for $C_{10}H_6F_2NO_2S$ (M+H)$^+$: m/z=242.0; found 242.0.

Step 3. tert-Butyl {(3S)-1-[3-({[2-(2,6-difluorophenyl)-1,3-thiazol-4-yl]carbonyl}amino)quinolin-4-yl]piperidin-3-yl}carbamate

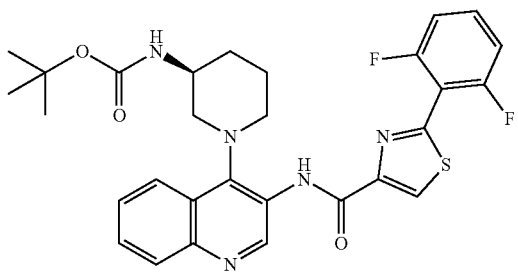 [SMILES: CC(C)(C)OC(=O)N[C@H]1CCCN(c2c(NC(=O)c3csc(-c4c(F)cccc4F)n3)cnc3ccccc23)C1]

To a suspension of 2-(2,6-difluorophenyl)-1,3-thiazole-4-carboxylic acid (28.5 mg, 0.118 mmol) in DCM (0.5 mL), a solution of 1-chloro-N,N,2-trimethylpropenylamine (45.0 mg, 0.337 mmol) in DCM (1.0 mL) was added slowly. The mixture was stirred at room temperature for 2 h. A solution of tert-butyl [(3S)-1-(3-aminoquinolin-4-yl)piperidin-3-yl]carbamate (from step 2 in Example 1, 36.9 mg, 0.108 mmol) in DCM (2.0 mL) was added, followed by pyridine (93.2 mg, 1.18 mmol). The mixture was then stirred at room temperature for a further 2 h, and then concentrated under reduced pressure. The resulting residue was purified by chromatography on silica gel (0-100% EtOAc in hexanes) to give the title compound as a pale yellow oil (57.4 mg, 94%). LCMS calc. for $C_{29}H_3F_2N_5O_3S$ (M+H)$^+$: m/z=566.2; found 566.2.

Step 4. N-{4-[(3S)-3-Aminopiperidin-1-yl]quinolin-3-yl}-2-(2,6-difluorophenyl)-1,3-thiazole-4-carboxamide TFA (2.0 mL) was added to a solution of tert-butyl {(3S)-1-[3-({[2-(2,6-difluorophenyl)-1,3-thiazol-4-yl] carbonyl}amino)quinolin-4-yl]piperidin-3-yl}carbamate (57.4 mg, 0.101 mmol) in DCM (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.15% $NH_4OH$, at flow rate of 30 mL/min.) to afford the title compound as a white solid (25.4 mg, 54%). LCMS calc. for $C_{24}H_{22}F_2N_5OS$ (M+H)$^+$: m/z=466.1; found 466.2.

Example 3

5-Amino-N-{4-[(3S)-3-aminopiperidin-1-yl]thieno[2,3-b]pyridin-5-yl}-2-(2,6-difluorophenyl)-1,3-thiazole-4-carboxamide

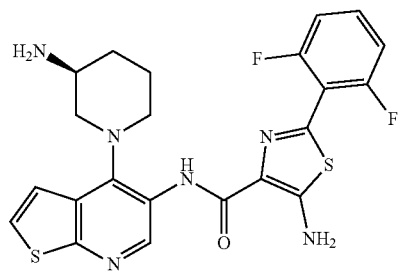 [SMILES: Nc1sc(-c2c(F)cccc2F)nc1C(=O)Nc1cnc2sccc2c1N1CCC[C@H](N)C1]

Step 1. 5-Nitrothieno[2,3-b]pyridin-4-ol

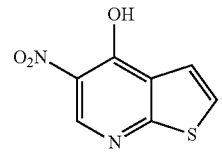 [SMILES: O=[N+]([O-])c1cnc2sccc2c1O]

To a solution of thieno[2,3-b]pyridin-4-ol (J & W PharmLab, 1.015 g, 6.714 mmol) in DCM (15 mL) at −10° C., a solution of N,N,N-tributylbutan-1-aminium nitrate (3.125 g, 10.26 mmol) in DCM (20 mL) was added. Trifluoroacetic anhydride (2.334 g, 11.11 mmol) was added dropwise. After stirring at −10° C. for 30 min., the mixture was allowed to warm to room temperature and stirred for 24 h. The reaction mixture was concentrated under reduced pressure. The resulting residue was triturated with ether (50 mL), and filtered. The filter cake was washed with water (100 mL) and ether/MeOH (1:1, 80 mL), and then dried to give the sub-title compound as a yellow solid (937.2 mg, 71%). LCMS calc. for $C_7H_5N_2O_3S$ (M+H)$^+$: m/z=197.0; found 197.0.

Step 2. 4-Chloro-5-nitrothieno[2,3-b]pyridine

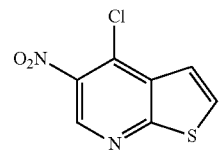 [SMILES: O=[N+]([O-])c1cnc2sccc2c1Cl]

To 5-nitrothieno[2,3-b]pyridin-4-ol (607.9 mg, 3.099 mmol), $POCl_3$ (6.00 mL) was added, then the mixture was stirred at 110° C. for 1 h. The reaction mixture was then concentrated under reduced pressure. The resulting residue was dissolved in DCM (50 mL), and a saturated aq. $NaHCO_3$ (50 mL) was added slowly. The organic layer was washed with water (50 mL) and brine (50 mL), then dried over $Na_2SO_4$ and concentrated under reduced pressure. The residue was purified by chromatography on silica gel (0 to 50% EtOAc in hexanes) to afford the sub-title compound as a pale yellow solid (605.3 mg, 91%). LCMS calc. for $C_7H_4ClN_2O_2S$ (M+H)$^+$: m/z=215.0; found 215.0.

Step 3. tert-Butyl[(3S)-1-(5-nitrothieno[2,3-b]pyridin-4-yl)piperidin-3-yl]carbamate

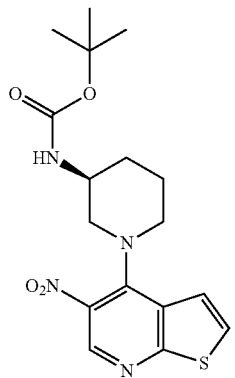 [SMILES: CC(C)(C)OC(=O)N[C@H]1CCCN(c2c([N+](=O)[O-])cnc3sccc23)C1]

To a vial containing 4-chloro-5-nitrothieno[2,3-b]pyridine (138.2 mg, 0.6439 mmol) and tert-butyl (3S)-piperidin-3-ylcarbamate (Combi-Blocks, 325.5 mg, 1.625 mmol), 1-butanol (3.00 mL) was added, followed by DIPEA (201.4 mg, 1.558 mmol), then the mixture was stirred at 110° C. for 12 h. After cooling to room temperature, the reaction mixture was concentrated under reduced pressure. The resulting residue was purified by chromatography on silica gel (0-100% EtOAc in hexanes) to give the title compound as a yellow solid (228.4 mg, 94%). LCMS calc. for $C_{17}H_{23}N_4O_4S$ (M+H)$^+$: m/z=379.1; found 379.2.

Step 4. tert-Butyl [(3S)-1-(5-aminothieno[2,3-b]pyridin-4-yl)piperidin-3-yl]carbamate

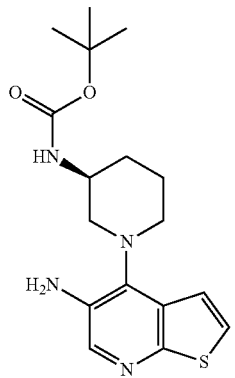 [SMILES: CC(C)(C)OC(=O)N[C@H]1CCCN(c2c(N)cnc3sccc23)C1]

To a vial containing tert-butyl [(3S)-1-(5-nitrothieno[2,3-b]pyridin-4-yl)piperidin-3-yl]carbamate (228.4 mg, 0.6035 mmol), iron powder (357.7 mg, 6.405 mmol) and $NH_4C$ (567.8 mg, 10.61 mmol), EtOH (5.00 mL) was added, followed by water (1.00 mL). The mixture was stirred at 80° C. for 1 h. The reaction mixture was then filtered through a pad of diatomaceous earth. The diatomaceous earth pad was eluted with a 10% aq. $K_3PO_4$ (30 mL), and EtOAc (30 mL). The organic layer was washed with brine (30 mL), then dried over $Na_2SO_4$, and concentrated under reduced pressure. The resulting residue (212.9 mg) was used in the next step without further purification. LCMS calc. for $C_{17}H_{25}N_4O_2S$ (M+H)$^+$: m/z=349.2; found 349.2.

Step 5. tert-Butyl {(3S)-1-[5-({[5-[(tert-butoxycarbonyl)amino]-2-(2,6-difluorophenyl)-1,3-thiazol-4-yl]carbonyl}amino)thieno[2,3-b]pyridin-4-yl]piperidin-3-yl}carbamate

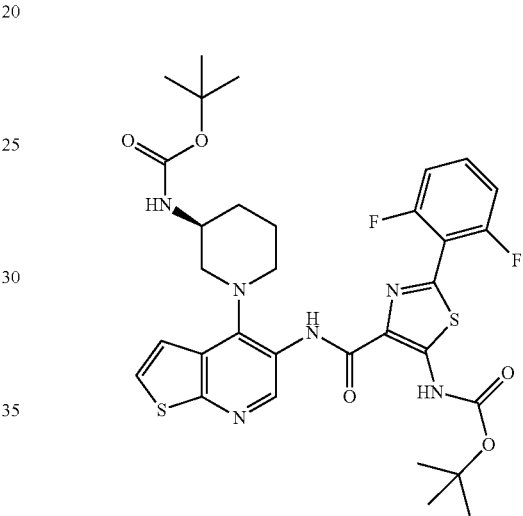

To a solution of 5-[(tert-butoxycarbonyl)amino]-2-(2,6-difluorophenyl)-1,3-thiazole-4-carboxylic acid (Example 1, step 6, 176.4 mg, 0.4950 mmol) in THF (0.5 mL), a solution of 1-chloro-N,N,2-trimethylpropenylamine (169.8 mg, 1.271 mmol) in THF (1.0 mL) was added slowly. The mixture was stirred at room temperature for 5 h. A solution of tert-butyl [(3S)-1-(5-aminothieno[2,3-b]pyridin-4-yl)piperidin-3-yl]carbamate (139.6 mg, 0.4006 mmol) in THF (2.0 mL) was then added to the resulting mixture, followed by pyridine (316.1 mg, 3.996 mmol), and the mixture was stirred at room temperature for a further 2 h. The mixture was then concentrated under reduced pressure and the resulting residue was purified by chromatography on silica gel (0-100% EtOAc in hexanes) to afford the sub-title compound as a dark semi-solid (230.7 mg, 84%). LCMS calc. for $C_{32}H_{37}F_2N_6O_5S_2$ (M+H)$^+$: m/z=687.2; found 687.2.

Step 6. 5-Amino-N-{4-[(3S)-3-aminopiperidin-1-yl]thieno[2,3-b]pyridin-5-yl}-2-(2,6-difluorophenyl)-1,3-thiazole-4-carboxamide TFA (2.0 mL) was added to a solution of tert-butyl {(3S)-1-[5-({[5-[(tert-butoxycarbonyl)amino]-2-(2,6-difluorophenyl)-1,3-thiazol-4-yl]carbonyl}amino)thieno[2,3-b]pyridin-4-yl]piperidin-3-yl}carbamate (230.7 mg, 0.3359 mmol) in DCM (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (55.3 mg, 34%). LCMS calc. for $C_{22}H_2F_2N_6OS_2$ (M+H)$^+$: m/z=487.1; found 487.1. $^1$H NMR (500 MHz, DMSO-d$_6$) δ 9.42 (s, 1H), 7.82 (d, J=6.1 Hz, 1H), 7.65 (s, 2H), 7.60 (d, J=6.2 Hz, 1H), 7.57-7.50 (m, 1H), 7.28 (t, J=8.7 Hz, 2H), 3.23-3.16 (m, 1H), 3.07-3.01 (m, 2H), 2.99-2.91 (m, 1H), 2.90-2.82 (m, 1H), 1.91-1.66 (m, 3H), 1.30-1.13 (m, 1H) ppm.

Example 4

N-{4-[(3S)-3-Aminopiperidin-1-yl]thieno[2,3-b]pyridin-5-yl}-2-(2,6-difluorophenyl)-1,3-thiazole-4-carboxamide

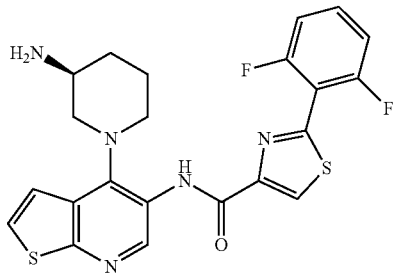 [SMILES: N[C@H]1CCCN(c2c(NC(=O)c3csc(-c4c(F)cccc4F)n3)cnc3sccc23)C1]

Step 1. tert-Butyl {(3S)-1-[5-({[2-(2,6-difluorophenyl)-1,3-thiazol-4-yl]carbonyl}amino)thieno[2,3-b]pyridin-4-yl]piperidin-3-yl}carbamate

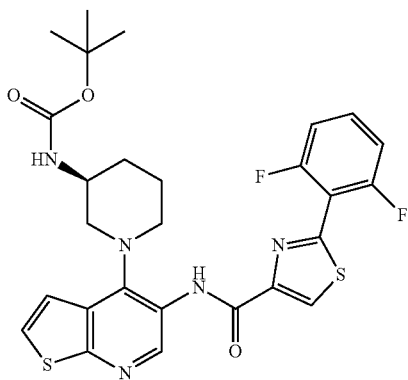 [SMILES: CC(C)(C)OC(=O)N[C@H]1CCCN(c2c(NC(=O)c3csc(-c4c(F)cccc4F)n3)cnc3sccc23)C1]

A solution of 1-chloro-N,N,2-trimethylpropenylamine (88.5 mg, 0.662 mmol) in DCM (1.0 mL) was added slowly to a suspension of 2-(2,6-difluorophenyl)-1,3-thiazole-4-carboxylic acid (from step 2 in Example 2, 56.9 mg, 0.236 mmol) in DCM (0.5 mL). The mixture was stirred at room temperature for 2 h. A solution of tert-butyl [(3S)-1-(5-aminothieno[2,3-b]pyridin-4-yl)piperidin-3-yl]carbamate (73.3 mg, 0.210 mmol) in DCM (2.0 mL), followed by pyridine (162.6 mg, 2.056 mmol) was then added and the mixture was stirred at room temperature for a further 2 h. The reaction mixture was then concentrated under reduced pressure and the resulting residue was purified by chromatography on silica gel (0-100% EtOAc in hexanes) to give the sub-title compound as a dark oil (118.2 mg, 98%). LCMS calc. for $C_{27}H_{28}F_2N_5O_3S_2$ (M+H)$^+$: m/z=572.2; found 572.2.

Step 2. N-{4-[(3S)-3-Aminopiperidin-1-yl]thieno[2,3-b]pyridin-5-yl}-2-(2,6-difluorophenyl)-1,3-thiazole-4-carboxamide TFA (2.0 mL) was added to a solution of tert-butyl {(3S)-1-[5-({[2-(2,6-difluorophenyl)-1,3-thiazol-4-yl]carbonyl}amino)thieno[2,3-b]pyridin-4-yl]piperidin-3-yl}carbamate (118.2 mg, 0.2068 mmol) in DCM (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (33.5 mg, 34%). LCMS calc. for $C_{22}H_{20}F_2N_5OS_2$ (M+H)$^+$: m/z=472.1; found 472.1.

Example 5

5-Amino-N-{7-[(3S)-3-aminopiperidin-1-yl]thieno[3,2-b]pyridin-6-yl}-2-(2,6-difluorophenyl)-1,3-thiazole-4-carboxamide

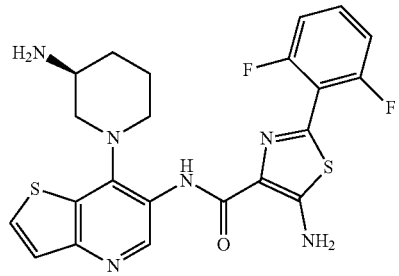 [SMILES: Nc1sc(-c2c(F)cccc2F)nc1C(=O)Nc1cnc2ccsc2c1N1CCC[C@H](N)C1]

Step 1. 6-Nitrothieno[3,2-b]pyridin-7-ol

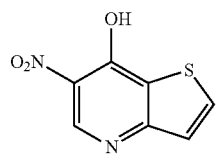 [SMILES: O=[N+]([O-])c1cnc2ccsc2c1O]

A solution of N,N,N-tributylbutan-1-aminium nitrate (4.780 g, 15.70 mmol) in DCM (20 mL) was added to a solution of thieno[3,2-b]pyridin-7-ol (Aldrich, 1.545 g, 10.22 mmol) in DCM (15 mL) at −10° C. Trifluoroacetic anhydride (3.524 g, 16.78 mmol) was then added dropwise. After stirring at −10° C. for 30 min., the mixture was allowed to warm to room temperature and stirred for 24 h. The reaction mixture was concentrated under reduced pressure. The resulting residue was triturated with ether (50 mL), and filtered. The filter cake was washed with water (100 mL) and ether/MeOH (1:1, 80 mL), and was then dried to give the sub-title compound as a yellow solid (1.56 g, 78%). LCMS calc. for $C_7H_5N_2O_3S$ (M+H)$^+$: m/z=197.0; found 197.0.

Step 2. 7-Chloro-6-nitrothieno[3,2-b]pyridine

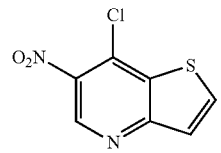 [SMILES: O=[N+]([O-])c1cnc2ccsc2c1Cl]

POCl$_3$ (20.0 mL) was added to 6-nitrothieno[3,2-b]pyridin-7-ol (1.56 g, 7.95 mmol). The mixture was stirred at 110° C. for 3 h. The reaction mixture was then concentrated under reduced pressure. The resulting residue was dissolved in DCM (150 mL), and a saturated aq. NaHCO$_3$ (150 mL) was added slowly. The organic layer was washed with water (100 mL) and brine (100 mL), then dried over Na$_2$SO$_4$ and concentrated under reduced pressure. The residue was purified by chromatography on silica gel (0 to 30% EtOAc in hexanes) to afford the sub-title compound as a pale yellow solid (1.39 g, 82%). LCMS calc. for $C_7H_4ClN_2O_2S$ (M+H)$^+$: m/z=215.0; found 215.0.

Step 3. tert-Butyl [(3S)-1-(6-nitrothieno[3,2-b]pyridin-7-yl)piperidin-3-yl]carbamate

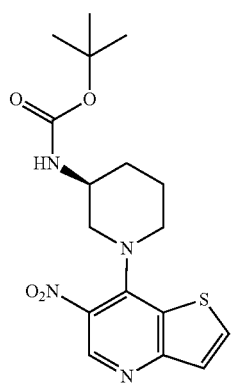 [SMILES: CC(C)(C)OC(=O)N[C@H]1CCCN(c2c([N+](=O)[O-])cnc3ccsc23)C1]

To a vial containing 7-chloro-6-nitrothieno[3,2-b]pyridine (128.7 mg, 0.5996 mmol) and tert-butyl (3S)-piperidin-3-ylcarbamate (Combi-Blocks, 297.6 mg, 1.486 mmol), 1-butanol (3.00 mL) was added, followed by DIPEA (179.9 mg, 1.392 mmol). The mixture was stirred at 110° C. for 12 h. After cooling to room temperature, the reaction mixture was concentrated under reduced pressure. The resulting residue was purified by chromatography on silica gel (0-30% EtOAc in hexanes) to give the sub-title compound as a yellow solid (210.1 mg, 93%). LCMS calc. for $C_{17}H_{23}N_4O_4S$ (M+H)$^+$: m/z=379.1; found 379.2.

Step 4. tert-Butyl [(3S)-1-(6-aminothieno[3,2-b]pyridin-7-yl)piperidin-3-yl]carbamate

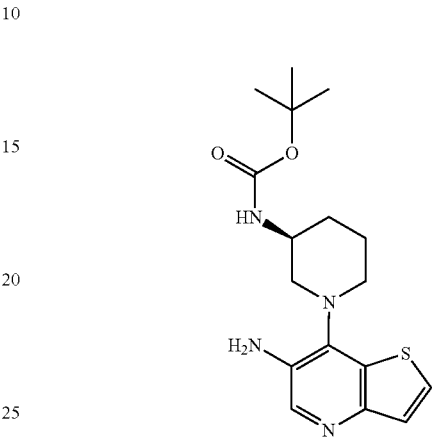

To a vial containing tert-butyl [(3S)-1-(6-nitrothieno[3,2-b]pyridin-7-yl)piperidin-3-yl]carbamate (210.1 mg, 0.5552 mmol), iron powder (306.1 mg, 5.481 mmol) and NH$_4$C (491.9 mg, 9.196 mmol), EtOH (5.00 mL) was added, followed by water (1.00 mL). The mixture was stirred at 80° C. for 2 h. The reaction mixture was then filtered through a pad of diatomaceous earth. The diatomaceous earth pad was eluted with a 10% aq. K$_3$PO$_4$ (30 mL) and EtOAc (30 mL). The organic layer was washed with brine (30 mL), then dried over Na$_2$SO$_4$, and concentrated under reduced pressure. The resulting residue (197.9 mg) of the sub-title compound was used in the next step without further purification. LCMS calc. for $C_{17}H_{25}N_4O_2S$ (M+H)$^+$: m/z=349.2; found 349.2.

Step 5. tert-Butyl {(3S)-1-[6-({[5-[(tert-butoxycarbonyl)amino]-2-(2,6-difluorophenyl)-1,3-thiazol-4-yl]carbonyl}amino)thieno[3,2-b]pyridin-7-yl]piperidin-3-yl}carbamate

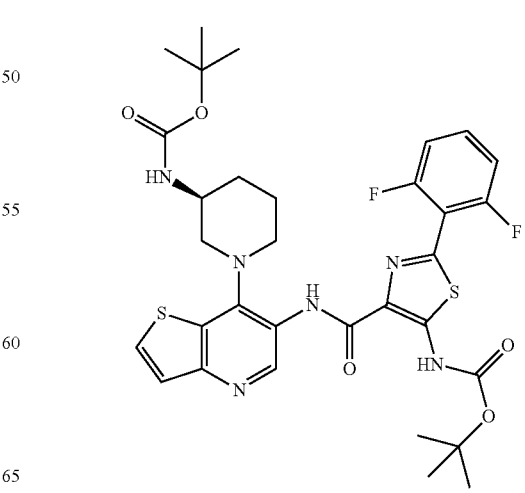

1-Chloro-N,N,2-trimethylpropenylamine (76.1 mg, 0.570 mmol) in THF (1.0 mL) was added slowly to a solution of 5-[(tert-butoxycarbonyl)amino]-2-(2,6-difluorophenyl)-1,3-thiazole-4-carboxylic acid (Example 1, step 6, 76.1 mg, 0.214 mmol) in THF (0.5 mL). The mixture was stirred at room temperature for 5 h. A solution of tert-butyl [(3S)-1-(6-aminothieno[3,2-b]pyridin-7-yl)piperidin-3-yl]carbamate (62.3 mg, 0.179 mmol) in THF (2.0 mL) was then added, followed by pyridine (135.3 mg, 1.710 mmol), and the mixture was stirred at room temperature for a further 2 h. The mixture was then concentrated under reduced pressure and the residue was purified by chromatography on silica gel (0-100% EtOAc in hexanes) to afford the sub-title compound as a dark semi-solid (78.5 mg, 64%). LCMS calc. for $C_{32}H_{37}F_2N_6O_5S_2$ (M+H)$^+$: m/z=687.2; found 687.2.

Step 6. 5-Amino-N-{7-[(3S)-3-aminopiperidin-1-yl]thieno[3,2-b]pyridin-6-yl}-2-(2,6-difluorophenyl)-1,3-thiazole-4-carboxamide TFA (2.0 mL) was added to a solution of tert-butyl {(3S)-1-[6-({[5-[(tert-butoxycarbonyl)amino]-2-(2,6-difluorophenyl)-1,3-thiazol-4-yl]carbonyl}amino)thieno[3,2-b]pyridin-7-yl]piperidin-3-yl}carbamate (78.5 mg, 0.114 mmol) in DCM (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (28.5 mg, 51%). LCMS calc. for $C_{22}H_{21}F_2N_6OS_2$ (M+H)$^+$: m/z=487.1; found 487.1. $^1$H NMR (500 MHz, DMSO-d$_6$) δ 9.56 (s, 1H), 7.95 (d, J=5.5 Hz, 1H), 7.66 (s, 2H), 7.57-7.50 (m, 1H), 7.49 (d, J=5.5 Hz, 1H), 7.28 (t, J=8.8 Hz, 2H), 3.24-3.16 (m, 1H), 3.08-3.01 (m, 1H), 3.01-2.91 (m, 2H), 2.83-2.74 (m, 1H), 1.90-1.67 (m, 3H), 1.24-1.10 (m, 1H) ppm.

Example 6

N-{7-[(3S)-3-Aminopiperidin-1-yl]thieno[3,2-b]pyridin-6-yl}-2-(2,6-difluorophenyl)-1,3-thiazole-4-carboxamide

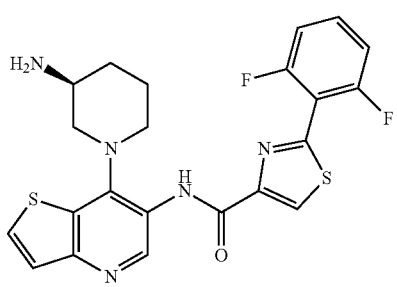 [SMILES: N[C@H]1CCCN(c2c(NC(=O)c3csc(-c4c(F)cccc4F)n3)cnc3ccsc23)C1]

Step 1. tert-Butyl {(3S)-1-[6-({[2-(2,6-difluorophenyl)-1,3-thiazol-4-yl]carbonyl}amino)thieno[3,2-b]pyridin-7-yl]piperidin-3-yl}carbamate

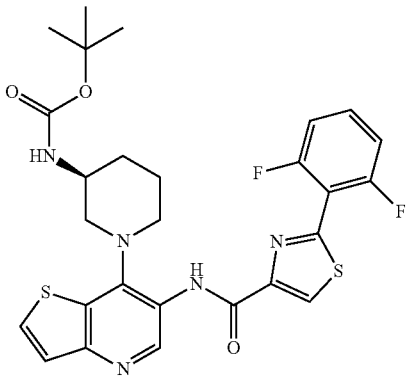 [SMILES: CC(C)(C)OC(=O)N[C@H]1CCCN(c2c(NC(=O)c3csc(-c4c(F)cccc4F)n3)cnc3ccsc23)C1]

A solution of 1-chloro-N,N,2-trimethylpropenylamine (68.8 mg, 0.515 mmol) in DCM (1.0 mL) was added slowly to a suspension of 2-(2,6-difluorophenyl)-1,3-thiazole-4-carboxylic acid (Example 2, step 2, 45.4 mg, 0.188 mmol) in DCM (0.5 mL). The mixture was stirred at room temperature for 2 h. A solution of tert-butyl [(3S)-1-(6-aminothieno[3,2-b]pyridin-7-yl)piperidin-3-yl]carbamate (58.8 mg, 0.169 mmol) in DCM (2.0 mL) was then added, followed by pyridine (123.7 mg, 1.564 mmol) and the mixture was stirred at room temperature for a further 2 h. The mixture was concentrated under reduced pressure and the resulting residue was purified by chromatography on silica gel (0-100% EtOAc in hexanes) to give the sub-title compound as a pale yellow oil (92.2 mg, 96%). LCMS calc. for $C_{27}H_{28}F_2N_5O_3S_2$ (M+H)$^+$: m/z=572.2; found 572.2.

Step 2. N-{7-[(3S)-3-aminopiperidin-1-yl]thieno[3,2-b]pyridin-6-yl}-2-(2,6-difluorophenyl)-1,3-thiazole-4-carboxamide TFA (2.0 mL) was added to a solution of tert-butyl {(3S)-1-[6-({[2-(2,6-difluorophenyl)-1,3-thiazol-4-yl]carbonyl}amino)thieno[3,2-b]pyridin-7-yl]piperidin-3-yl}carbamate (92.2 mg, 0.161 mmol) in DCM (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.15% NH$_4$OH, at flow rate of 30 mL/min.) to afford the title compound as a white solid (43.9 mg, 58%). LCMS calc. for $C_{22}H_{20}F_2N_5OS_2$ (M+H)$^+$: m/z=472.1; found 472.1.

Example 7

5-Amino-N-{4-[(3S)-3-aminopiperidin-1-yl]-1H-pyrrolo[2,3-b]pyridin-5-yl}-2-(2,6-difluorophenyl)-1,3-thiazole-4-carboxamide

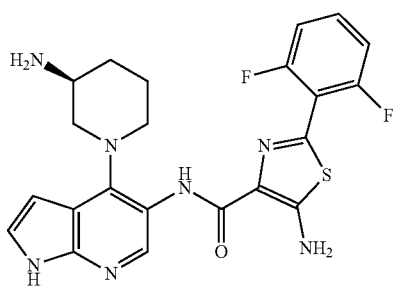 [SMILES: Nc1sc(-c2c(F)cccc2F)nc1C(=O)Nc1cnc2[nH]ccc2c1N1CCC[C@H](N)C1]

Step 1. 4-Chloro-1-(phenylsulfonyl)-1H-pyrrolo[2,3-b]pyridine

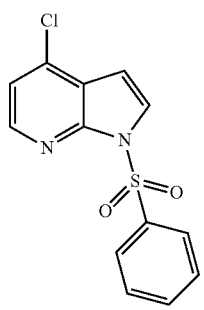 [SMILES: O=S(=O)(c1ccccc1)n1ccc2c(Cl)ccnc21]

To a solution of 4-chloro-1H-pyrrolo[2,3-b]pyridine (Ark Pharm, 5.023 g, 32.92 mmol) in DCM (150 mL), DMAP (418.1 mg, 3.422 mmol) was added, followed by triethylamine (4.984 g, 49.25 mmol) and benzenesulfonyl chloride (6.904 g, 39.09 mmol). After stirring at room temperature for 15 h, the mixture was washed with 1 M HCl (100 mL). The organic layer was washed with saturated aq. NaHCO$_3$ (100 mL) and brine (100 mL), then dried over Na$_2$SO$_4$ and concentrated under reduced pressure. The resulting residue was purified by chromatography on silica gel (0-100% EtOAc in hexanes) to give the sub-title compound as a pale yellow solid (9.39 g, 97%). LCMS calc. for C$_{13}$H$_{10}$ClN$_2$O$_2$S (M+H)$^+$: m/z=293.0; found 293.0.

Step 2. 4-Chloro-5-nitro-1-(phenylsulfonyl)-1H-pyrrolo[2,3-b]pyridine

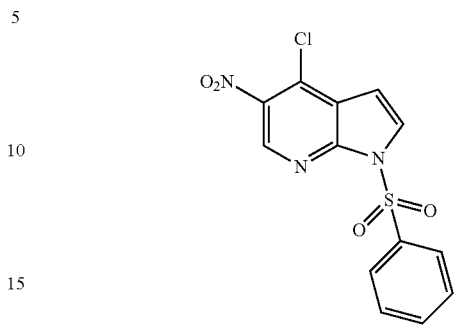

A solution of N,N,N-tributylbutan-1-aminium nitrate (4.895 g, 16.08 mmol) in DCM (20 mL) was added to a solution of 4-chloro-1-(phenylsulfonyl)-1H-pyrrolo[2,3-b]pyridine (3.038 g, 10.38 mmol) in DCM (40 mL) at −10° C. Trifluoroacetic anhydride (3.890 g, 18.52 mmol) was then added slowly. After stirring at −10° C. for 30 min., the reaction mixture was allowed to warm to room temperature and stirred for 24 h. The reaction mixture was then diluted with DCM (50 mL), washed with water (2×75 mL) and brine (75 mL), then dried with Na$_2$SO$_4$, and concentrated under reduced pressure. The resulting residue was purified by chromatography on silica gel (0-100% EtOAc in hexanes) to give the sub-title compound as a pale yellow solid (3284.5 mg, 94%). LCMS calc. for C$_{13}$H$_9$Cl N$_3$O$_4$S (M+H)$^+$: m/z=338.0; found 338.0.

Step 3. tert-Butyl {(3S)-1-[5-nitro-1-(phenylsulfonyl)-H-pyrrolo[2,3-b]pyridin-4-yl]piperidin-3-yl}carbamate

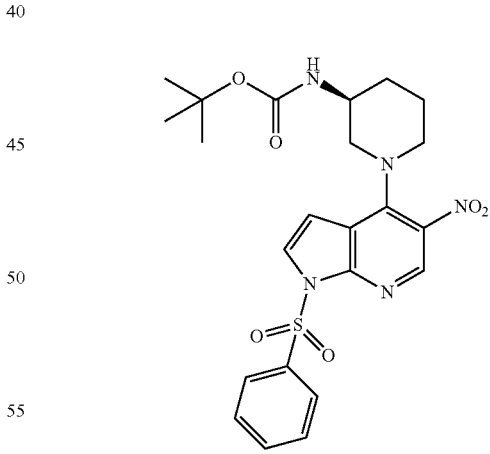

To a vial containing 4-chloro-5-nitro-1-(phenylsulfonyl)-1H-pyrrolo[2,3-b]pyridine (714.2 mg, 2.115 mmol) and tert-butyl (3S)-piperidin-3-ylcarbamate (Combi-Blocks, 645.9 mg, 3.225 mmol), 1-butanol (8.00 mL) was added followed by DIPEA (582.8 mg, 4.509 mmol). The reaction mixture was stirred at 110° C. for 12 h. After cooling to room temperature, the reaction mixture was concentrated under reduced pressure. The resulting residue was purified by chromatography on silica gel (0-50% EtOAc in hexanes) to give the sub-title compound as a yellow solid (719.5 mg, 68%). LCMS calc. for $C_{23}H_{28}N_5O_6S$ (M+H)$^+$: m/z=502.2; found 502.2.

Step 4. tert-Butyl {(3S)-1-[5-amino-1-(phenylsulfonyl)-H-pyrrolo[2,3-b]pyridin-4-yl]piperidin-3-yl}carbamate

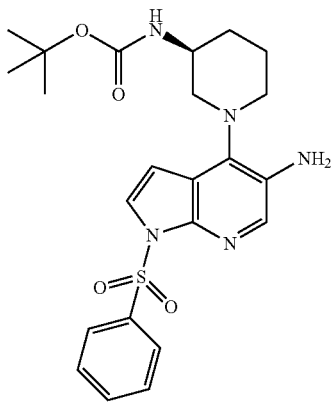 [SMILES: CC(C)(C)OC(=O)N[C@H]1CCCN(c2c(N)cnc3c2ccn3S(=O)(=O)c2ccccc2)C1]

To a vial containing tert-butyl {(3S)-1-[5-nitro-1-(phenylsulfonyl)-1H-pyrrolo[2,3-b]pyridin-4-yl]piperidin-3-yl}carbamate (719.5 mg, 1.434 mmol), iron powder (793.6 mg, 14.21 mmol) and NH$_4$Cl (1147.6 mg, 21.454 mmol), EtOH (10.00 mL) was added followed by water (2.00 mL). The mixture was stirred at 80° C. for 2 h. The reaction mixture was then filtered through a pad of diatomaceous earth. The pad was eluted with 10% aq. K$_3$PO$_4$ (50 mL) and EtOAc (50 mL). The organic layer was washed with brine (50 mL), then dried over Na$_2$SO$_4$, and concentrated under reduced pressure. The residue was purified by chromatography on silica gel (0-100% EtOAc in hexanes) to give the sub-title compound as a dark solid (491.8 mg, 73%). LCMS calc. for $C_{23}H_{30}N_5O_4S$ (M+H)$^+$: m/z=472.2; found 472.2.

Step 5. tert-Butyl {(3S)-1-[5-({[5-[(tert-butoxycarbonyl)amino]-2-(2,6-difluorophenyl)-1,3-thiazol-4-yl]carbonyl}amino)-1-(phenylsulfonyl)-1H-pyrrolo[2,3-b]pyridin-4-yl]piperidin-3-yl}carbamate

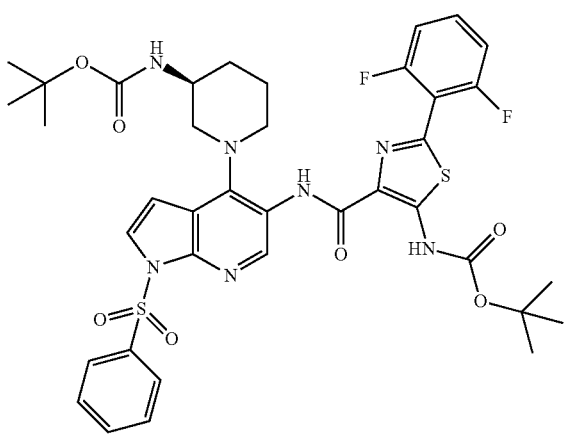 [SMILES: CC(C)(C)OC(=O)Nc1sc(-c2c(F)cccc2F)nc1C(=O)Nc1cnc2c(ccn2S(=O)(=O)c2ccccc2)c1N1CCC[C@H](NC(=O)OC(C)(C)C)C1]

A solution of 1-chloro-N,N,2-trimethylpropylamine (115.7 mg, 0.8659 mmol) in THF (1.0 mL) was added slowly to a solution of 5-[(tert-butoxycarbonyl)amino]-2-(2,6-difluorophenyl)-1,3-thiazole-4-carboxylic acid (Example 1, Step 6, 120.4 mg, 0.3379 mmol) in THF (1.0 mL). The mixture was stirred at room temperature for 5 h. A solution of tert-butyl {(3S)-1-[5-amino-1-(phenylsulfonyl)-1H-pyrrolo[2,3-b]pyridin-4-yl]piperidin-3-yl}carbamate (127.3 mg, 0.2699 mmol) in THF (2.0 mL) was then added, followed by pyridine (227.6 mg, 2.877 mmol) and the mixture was stirred at room temperature for a further 12 h. The mixture was then concentrated and the residue was purified by chromatography on silica gel (0-100% EtOAc in hexanes) to afford the sub-title compound as a yellow solid (194.4 mg, 89%). LCMS calc. for $C_{38}H_{42}F_2N_7O_7S_2$ (M+H)$^+$: m/z=810.2; found 810.2.

Step 6. 5-Amino-N-{4-[(3S)-3-aminopiperidin-1-yl]-H-pyrrolo[2,3-b]pyridin-5-yl}-2-(2,6-difluorophenyl)-1,3-thiazole-4-carboxamide To solution of tert-butyl {(3S)-1-[5-({[5-[(tert-butoxycarbonyl)amino]-2-(2,6-difluorophenyl)-1,3-thiazol-4-yl]carbonyl}amino)-1-(phenylsulfonyl)-1H-pyrrolo[2,3-b]pyridin-4-yl]piperidin-3-yl}carbamate (194.4 mg, 0.2400 mmol) in MeOH (2.0 mL), aq. NaOH (1.0 M, 2.0 mL) was added followed by THF (2.0 mL). After stirring at room temperature for 5 h, the reaction mixture was diluted with EtOAc (50 mL), washed with brine (50 mL), then dried over Na$_2$SO$_4$ and concentrated under reduced pressure. The resulting residue was dissolved in DCM (2.0 mL), and TFA (2.0 mL) was added. The mixture was stirred at room temperature for 30 min., and then concentrated under reduced pressure. The resulting residue was purified using RP-HPLC (XBridge™ C18 column, eluting with a gradient of MeCN/water containing 0.15% NH$_4$OH, at flow rate of 30 mL/min.) to afford the title compound as a white solid (46.6 mg, 41%). LCMS calc. for $C_{22}H_{22}F_2N_7OS$ (M+H)$^+$: m/z=470.1; found 470.2. $^1$H NMR (500 MHz, DMSO-d$_6$) δ 11.49 (s, 1H), 9.49 (s, 1H), 9.04 (s, 1H), 7.64-7.47 (m, 3H), 7.35 (d, J=3.3 Hz, 1H), 7.27 (t, J=8.8 Hz, 2H), 6.57 (d, J=3.4 Hz, 1H), 3.29-3.23 (m, 1H), 3.10-3.03 (m, 1H), 3.00-2.86 (m, 2H), 2.85-2.77 (m, 1H), 1.87-1.79 (m, 1H), 1.79-1.65 (m, 2H), 1.24-1.10 (m, 1H) ppm.

Example 8

N-{4-[(3S)-3-Aminopiperidin-1-yl]-1H-pyrrolo[2,3-b]pyridin-5-yl}-2-(2,6-difluorophenyl)-1,3-thiazole-4-carboxamide

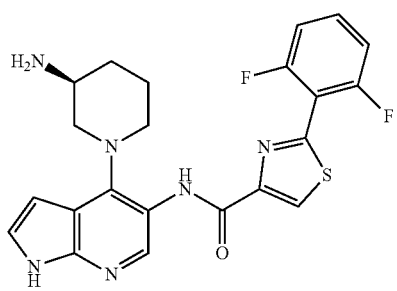 [SMILES: N[C@H]1CCCN(c2c(NC(=O)c3csc(-c4c(F)cccc4F)n3)cnc3[nH]ccc23)C1]

Step 1. tert-Butyl {(3S)-1-[5-({[2-(2,6-difluorophenyl)-1,3-thiazol-4-yl]carbonyl}amino)-1-(phenylsulfonyl)-1H-pyrrolo[2,3-b]pyridin-4-yl]piperidin-3-yl}carbamate

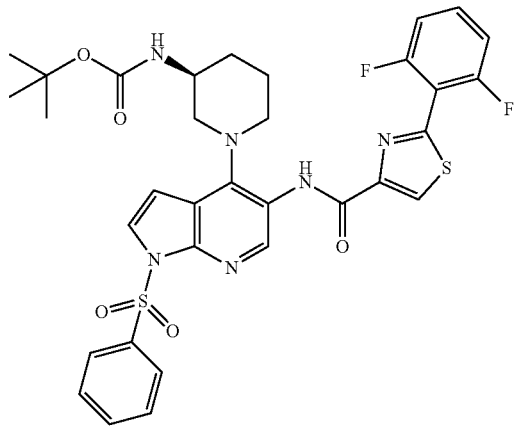 [SMILES: CC(C)(C)OC(=O)N[C@H]1CCCN(c2c(NC(=O)c3csc(-c4c(F)cccc4F)n3)cnc3c2ccn3S(=O)(=O)c2ccccc2)C1]

A solution of 1-chloro-N,N,2-trimethylpropenylamine (114.1 mg, 0.8539 mmol) in DCM (1.0 mL) was added slowly to a suspension of 2-(2,6-difluorophenyl)-1,3-thiazole-4-carboxylic acid (Example 2, Step 2, 74.2 mg, 0.308 mmol) in DCM (1.0 mL). The mixture was stirred at room temperature for 2 h. A solution of tert-butyl {(3S)-1-[5-amino-1-(phenylsulfonyl)-1H-pyrrolo[2,3-b]pyridin-4-yl]piperidin-3-yl}carbamate (125.1 mg, 0.2653 mmol) in DCM (2.0 mL) was added, followed by pyridine (217.3 mg, 2.747 mmol), and the mixture was then stirred at room temperature for 12 h. The reaction mixture was concentrated under reduced pressure and the resulting residue was purified by chromatography on silica gel (0-100% EtOAc in hexanes) to give the sub-title compound as a dark oil (175.3 mg, 95%). LCMS calc. for $C_{33}H_{33}F_2N_6O_5S_2$ (M+H)⁺: m/z=695.2; found 695.2.

Step 2. N-{4-[(3S)-3-Aminopiperidin-1-yl]-H-pyrrolo[2,3-b]pyridin-5-yl}-2-(2,6-difluorophenyl)-1,3-thiazole-4-carboxamide To a solution of tert-butyl {(3S)-1-[5-({[2-(2,6-difluorophenyl)-1,3-thiazol-4-yl]carbonyl}amino)-1-(phenylsulfonyl)-1H-pyrrolo[2,3-b]pyridin-4-yl]piperidin-3-yl}carbamate (175.3 mg, 0.2523 mmol) in MeOH (2.0 mL), aq. NaOH (1.0 M, 2.0 mL) was added, followed by THF (2.0 mL). After stirring at room temperature for 5 h, the reaction mixture was diluted with EtOAc (50 mL), washed with brine (50 mL), dried over Na₂SO₄ and concentrated under reduced pressure. The residue was dissolved in DCM (2.0 mL), and TFA (2.0 mL) was added. The mixture was stirred at room temperature for 30 min., and then concentrated under reduced pressure. The resulting residue was purified using RP-HPLC (XBridge™ C18 column, eluting with a gradient of MeCN/water containing 0.15% NH₄OH, at flow rate of 30 mL/min.) to afford the title compound as a white solid (59.1 mg, 52%). LCMS calc. for $C_{22}H_{22}F_2N_6OS$ (M+H)⁺: m/z=455.1; found 455.1.

Example 9

5-Amino-N-{4-[(3S)-3-aminopiperidin-1-yl]-2,3-dihydrofuro[2,3-b]pyridin-5-yl}-2-(2,6-difluorophenyl)-1,3-thiazole-4-carboxamide

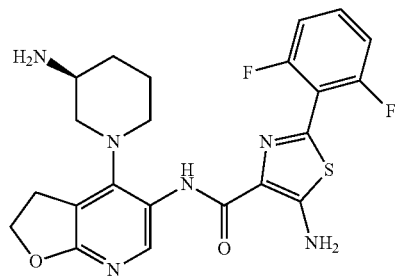 [SMILES: Nc1sc(-c2c(F)cccc2F)nc1C(=O)Nc1cnc2c(c1N1CCC[C@H](N)C1)CCO2]

Step 1. 2-(2-Fluoro-4-iodopyridin-3-yl)ethanol

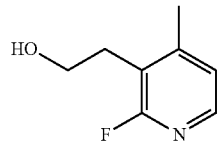

A solution of 2.0 M lithium diisopropylamide in heptane/THF/ethylbenzene (8.10 mL, 16.2 mmol) was added to a solution of 2-fluoro-3-iodopyridine (Ark Pharm, 2.989 g, 13.40 mmol) in THF (50 mL) at −78° C., then the mixture was stirred at −78° C. for 90 min. With the temperature maintained at −78° C., a solution of 1,3,2-dioxathiolane 2,2-dioxide (2.206 g, 17.77 mmol) in THF (30 mL) was added slowly over a period of 20 min., the solution was stirred at −78° C. for a further 20 min., then allowed to warm to room temperature and stirred for 2 h. The mixture was then cooled to 0° C., and 12.0 M aq. HCl (5.0 mL, 60. mmol) was added. The reaction mixture was allowed to warm to room temperature and stirred for 3 h. Saturated aq. NaHCO₃ (250 mL) was added, then the mixture was extracted with EtOAc (3×150 mL). The combined extracts were washed with brine (250 mL), dried over Na₂SO₄ and concentrated under reduced pressure. The residue was purified by chromatography on silica gel (0-100% EtOAc in hexanes) to give the sub-title compound as a white solid (3.13 g, 87%). LCMS calc. for $C_7H_8FINO$ (M+H)⁺: m/z=268.0; found 268.0.

Step 2. 4-Iodo-2,3-dihydrofuro[2,3-b]pyridine

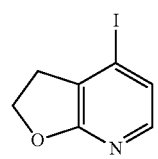

Potassium phosphate (10.0 g, 47.1 mmol) was added to a solution of 2-(2-fluoro-4-iodopyridin-3-yl)ethanol (3.13 g, 11.7 mmol) in 1,4-dioxane (100 mL). The mixture was heated under reflux for 36 h. The reaction mixture was filtered, and the filter cake was washed with EtOAc. The combined filtrates were concentrated under reduced pressure. The residue was dissolved in DCM (100 mL), washed with brine (2×100 mL), dried over $Na_2SO_4$ and concentrated under reduced. The resulting residue (2.55 g) containing the sub-title compound was used in the next step directly without further purification. LCMS calc. for $C_7H_7INO$ (M+H)⁺: m/z=247.9; found 248.0.

Step 3. 4-Iodo-5-nitro-2,3-dihydrofuro[2,3-b]pyridine

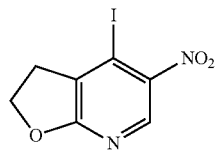 [SMILES: O=[N+]([O-])c1cnc2c(c1I)CCO2]

A solution of fuming nitric acid (15.0 mL, 358 mmol) in concentrated sulfuric acid (15.0 mL, 281 mmol) was added slowly over a period of 15 min. to a stirred solution of 4-iodo-2,3-dihydrofuro[2,3-b]pyridine (2.237 g, 9.055 mmol) in sulfuric acid (10.0 mL, 188 mmol) at −10° C. The reaction mixture was allowed to warm to room temperature, and stirred for a further 16 h. The reaction mixture was quenched by pouring onto crushed ice and was then extracted with EtOAc (6×100 mL). The organic extracts were combined and washed with saturated aq. $NaHCO_3$ (2×300 mL) and brine (300 mL), then dried over $Na_2SO_4$, and concentrated under reduced pressure. The residue was purified by chromatography on silica gel (0-100% EtOAc in hexanes) to give the sub-title compound as a pale yellow solid (2.43 g, 92%). LCMS calc. for $C_7H_6IN_2O_3$ (M+H)⁺: m/z=292.9; found 293.0.

Step 4. tert-Butyl [(3S)-1-(5-nitro-2,3-dihydrofuro[2,3-b]pyridin-4-yl)piperidin-3-yl]carbamate

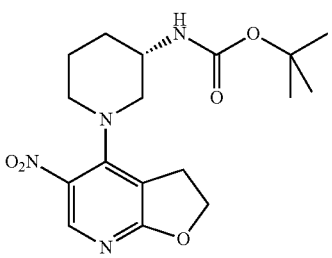

EtOH (12.00 mL) was added to a microwave vial containing 4-iodo-5-nitro-2,3-dihydrofuro[2,3-b]pyridine (2.05 g, 7.02 mmol), tert-butyl (3S)-piperidin-3-ylcarbamate (Combi-Blocks, 1.489 g, 7.435 mmol) and DIPEA (1.836 g, 14.20 mmol). The vial was sealed and the mixture was heated at 100° C. under microwave irradiation for 2 h. The reaction mixture was concentrated under reduced pressure and the resulting residue was purified by chromatography on silica gel (0-100% EtOAc in hexanes) to give the title compound as a yellow solid (2.46 g, 96%). LCMS calc. for $C_{17}H_{25}N_4O$ (M+H)⁺: m/z=365.2; found 365.1.

Step 5. tert-Butyl [(3S)-1-(5-amino-2,3-dihydrofuro[2,3-b]pyridin-4-yl)piperidin-3-yl]carbamate

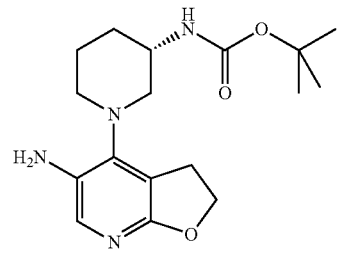 [SMILES: CC(C)(C)OC(=O)N[C@H]1CCCN(c2c([N+](=O)[O-])cnc3c2CCO3)C1]

10% Pd on carbon (108.7 mg, 0.1021 mmol) was added under a nitrogen atmosphere to a solution of tert-butyl [(3S)-1-(5-nitro-2,3-dihydrofuro[2,3-b]pyridin-4-yl)piperidin-3-yl]carbamate (411.2 mg, 1.128 mmol) in MeOH (5.00 mL). The reaction mixture was purged with hydrogen gas and was stirred under hydrogen (1 atm.) for 14 h. The reaction mixture was then filtered through a pad of diatomaceous earth. The pad was eluted with further MeOH. The filtrate was concentrated under reduced pressure to give the sub-title compound as an off-white solid (387.9 mg), which was used directly in the next step without further purification. LCMS calc. for $C_{17}H_{27}N_4O_3$ (M+H)⁺: m/z=335.2; found 335.2.

Step 6. tert-Butyl {(3S)-1-[5-({[5-[(tert-butoxycarbonyl)amino]-2-(2,6-difluorophenyl)-1,3-thiazol-4-yl]carbonyl}amino)-2,3-dihydrofuro[2,3-b]pyridin-4-yl]piperidin-3-yl}carbamate

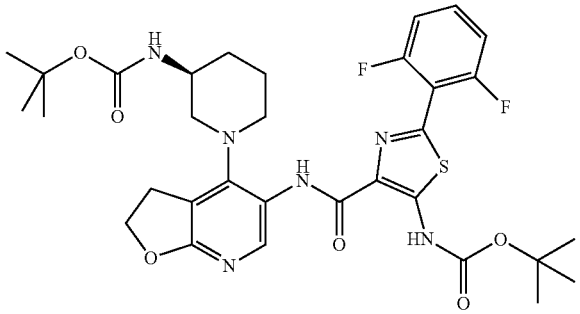 [SMILES: CC(C)(C)OC(=O)Nc1sc(-c2c(F)cccc2F)nc1C(=O)Nc1cnc2c(c1N1CCC[C@H](NC(=O)OC(C)(C)C)C1)CCO2]

To a mixture of 5-[(tert-butoxycarbonyl)amino]-2-(2,6-difluorophenyl)-1,3-thiazole-4-carboxylic acid (Example 1, Step 6, 418.2 mg, 1.174 mmol), tert-butyl [(3S)-1-(5-amino-2,3-dihydrofuro[2,3-b]pyridin-4-yl)piperidin-3-yl]carbamate (377.4 mg, 1.128 mmol) and HATU (1308 mg, 3.440 mmol), DMF (15.0 mL) was added, followed by DIPEA (1.00 mL, 5.74 mmol). The mixture was stirred at room temperature for 2 h. The reaction mixture was then diluted with EtOAc (150 mL), washed with saturated aq. $NaHCO_3$ (150 mL) and brine (2×75 mL), then dried over $Na_2SO_4$ and concentrated under reduced pressure. The residue was purified by chromatography on silica gel (0-100% EtOAc in hexanes) to give the sub-title compound as a yellow solid (720.2 mg, 95%). LCMS calc. for $C_{32}H_{39}F_2N_6O_6S$ (M+H)⁺: m/z=673.3; found 673.2.

Step 7. 5-Amino-N-{4-[(3S)-3-aminopiperidin-1-yl]-2,3-dihydrofuro[2,3-b]pyridin-5-yl}-2-(2,6-difluorophenyl)-1,3-thiazole-4-carboxamide TFA (3.0 mL) was added to a solution of tert-butyl {(3S)-1-[5-({[5-[(tert-butoxycarbonyl)amino]-2-(2,6-difluorophenyl)-1,3-thiazol-4-yl]carbonyl}amino)-2,3-dihydrofuro[2,3-b]pyridin-4-yl]piperidin-3-yl}carbamate (720.2 mg, 1.070 mmol) in DCM (3.0 mL). The mixture was stirred at room temperature for 30 min. and then concentrated under reduced pressure. The resulting residue was purified using RP-HPLC (XBridge™ C18 column, eluting with a gradient of MeCN/water containing 0.15% NH$_4$OH, at flow rate of 30 mL/min.) to give the title compound as a white solid (187.7 mg, 37%). LCMS calc. for C$_{22}$H$_{23}$F$_2$N$_6$O$_2$S (M+H)$^+$: m/z=473.1; found 473.2. $^1$H NMR (500 MHz, DMSO-d$_6$) δ 8.74 (s, 1H), 7.68-7.39 (m, 3H), 7.26 (t, J=8.8 Hz, 2H), 4.48 (t, J=8.9 Hz, 2H), 3.37 (t, J=8.5 Hz, 2H), 3.14-3.01 (m, 1H), 3.00-2.90 (m, 1H), 2.89-2.81 (m, 1H), 2.77-2.69 (m, 1H), 2.55-2.50 (m, 1H), 1.83-1.59 (m, 3H), 1.12-1.00 (m, 1H) ppm.

Example 10

N-{4-[(3S)-3-Aminopiperidin-1-yl]-2,3-dihydrofuro[2,3-b]pyridin-5-yl}-2-(2,6-difluorophenyl)-1,3-thiazole-4-carboxamide

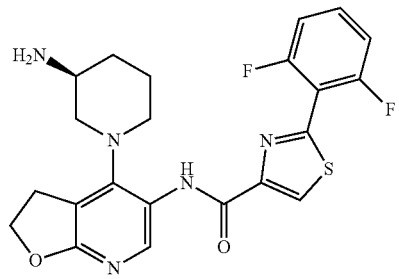 [SMILES: N[C@H]1CCCN(c2c(NC(=O)c3csc(-c4c(F)cccc4F)n3)cnc3c2CCO3)C1]

To a mixture of 2-(2,6-difluorophenyl)-1,3-thiazole-4-carboxylic acid (Example 2, Step 2, 14.5 mg, 0.0601 mmol), tert-butyl [(3S)-1-(5-amino-2,3-dihydrofuro[2,3-b]pyridin-4-yl)piperidin-3-yl]carbamate (19.2 mg, 0.0574 mmol) and HATU (72.5 mg, 0.191 mmol), DMF (1.50 mL) was added, followed by DIPEA (79.6 mg, 0.616 mmol). The reaction mixture was stirred at room temperature for 2 h, and then concentrated under reduced pressure. To the residue, DCM (2.0 mL) was added, followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.15% NH$_4$OH, at flow rate of 30 mL/min.) to afford the title compound as a white solid (5.3 mg, 20%). LCMS calc. for C$_{22}$H$_{22}$F$_2$N$_5$O$_2$S (M+H)$^+$: m/z=458.1; found 458.1.

Example 11

N-{4-[(3S)-3-Aminopiperidin-1-yl]-2,3-dihydrofuro[2,3-b]pyridin-5-yl}-6-(2,6-difluorophenyl)-5-fluoropyridine-2-carboxamide

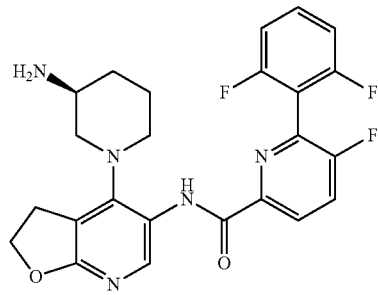 [SMILES: N[C@H]1CCCN(c2c(NC(=O)c3ccc(F)c(-c4c(F)cccc4F)n3)cnc3c2CCO3)C1]

Step 1. Methyl 6-(2,6-difluorophenyl)-5-fluoropyridine-2-carboxylate

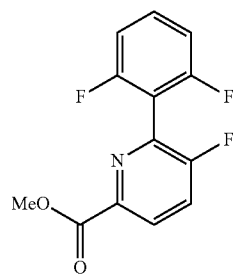 [SMILES: COC(=O)c1ccc(F)c(-c2c(F)cccc2F)n1]

To a screw-cap vial equipped with a magnetic stir bar, methyl 6-bromo-5-fluoropyridine-2-carboxylate (Frontier Scientific, 200.2 mg, 0.8555 mmol) was added followed by 2-(2,6-difluorophenyl)-4,4,5,5-tetramethyl-1,3,2-dioxaborolane (Combi-Blocks, 310.2 mg, 1.292 mmol), and bis(tri-tert-butylphosphine)palladium (87.5 mg, 0.171 mmol). The vial was sealed with a PTFE-lined septum, evacuated and backfilled with nitrogen three times. 1,4-Dioxane (3.0 mL) was added via a syringe, followed by DIPEA (0.30 mL, 1.7 mmol) and deoxygenated water (0.1 mL). The mixture was heated at 100° C. for 2 h and was then allowed to cool to room temperature. The mixture was diluted with EtOAc (40 mL), washed with water (40 mL) and brine (40 mL), then dried over Na$_2$SO$_4$, and concentrated under reduced pressure. The resulting residue was purified by chromatography on silica gel (0-50% EtOAc in hexanes) to give the sub-title compound as a white solid (210.2 mg, 92%). LCMS calc. for C$_{13}$H$_9$F$_3$NO$_2$ (M+H)$^+$: m/z=268.1; found 268.0.

Step 2. 6-(2,6-Difluorophenyl)-5-fluoropyridine-2-carboxylic Acid

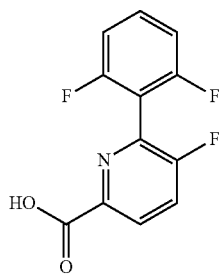

To a mixture of methyl 6-(2,6-difluorophenyl)-5-fluoropyridine-2-carboxylate (210.2 mg, 0.7867 mmol) and lithium hydroxide, monohydrate (162 mg, 3.86 mmol), THF (3.0 mL) was added followed by water (1.0 mL). The mixture was heated at 50° C. for 3 h. The reaction mixture was then cooled to 0° C., and 1 M HCl was added slowly until the pH reached 2. The reaction mixture was then diluted with water (20 mL), extracted with EtOAc (3×20 mL) and the combined organic layers were washed with brine (30 mL), dried over Na$_2$SO$_4$, and concentrated under reduced pressure to yield the sub-title compound as a white solid (162.1 mg, 81%). LCMS calc. for C$_{12}$H$_7$F$_3$NO$_2$ (M+H)$^+$: m/z=254.0; found 254.0.

Step 3. N-{4-[(3S)-3-aminopiperidin-1-yl]-2,3-dihydrofuro[2,3-b]pyridin-5-yl}-6-(2,6-difluorophenyl)-5-fluoropyridine-2-carboxamide To a mixture of 6-(2,6-difluorophenyl)-5-fluoropyridine-2-carboxylic acid (15.0 mg, 0.0592 mmol), tert-butyl [(3S)-1-(5-amino-2,3-dihydrofuro[2,3-b]pyridin-4-yl)piperidin-3-yl]carbamate (19.1 mg, 0.0571 mmol) and HATU (73.6 mg, 0.194 mmol), DMF (1.50 mL) was added, followed by DIPEA (84.8 mg, 0.656 mmol). The reaction mixture was stirred at room temperature for 2 h, and then concentrated under reduced pressure. DCM (2.0 mL) was added to the residue, followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.15% NH$_4$OH, at flow rate of 30 mL/min.) to afford the title compound as a white solid (5.9 mg, 22%). LCMS calc. for C$_{24}$H$_{23}$F$_3$N$_5$O$_2$ (M+H)$^+$: m/z=470.2; found 470.2.

Example 12

3-Amino-N-{4-[(3S)-3-aminopiperidin-1-yl]-2,3-dihydrofuro[2,3-b]pyridin-5-yl}-6-(2,6-difluorophenyl)-5-fluoropyridine-2-carboxamide

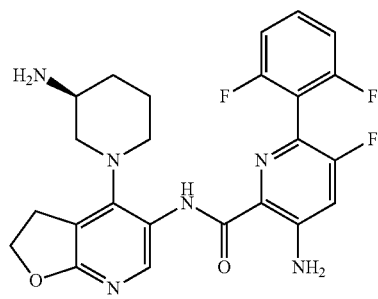 [SMILES: Nc1cc(F)c(-c2c(F)cccc2F)nc1C(=O)Nc1cnc2c(c1N1CCC[C@H](N)C1)CCO2]

Step 1. Methyl 3-amino-5-fluoropyridine-2-carboxylate

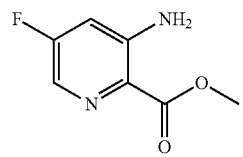

Tin dichloride (45 g, 230 mmol) was added to a solution of 5-fluoro-3-nitropyridine-2-carbonitrile (Ark Pharm, 7.2 g, 43 mmol) in EtOH (80 mL). The mixture was stirred at 90° C. for 2 h, and then concentrated under reduced pressure. Aq. HCl (10 M; 40 mL, 400 mmol) was then added and the mixture was heated under reflux for 6 h. The reaction mixture was then concentrated under reduced pressure and the resulting residue was dissolved in MeOH (120 mL). Thionyl chloride (7.2 mL, 99 mmol) was added. The solution was then stirred at 90° C. for 24 h. The reaction mixture was concentrated under reduced pressure, diluted with EtOAc (300 mL), washed with a saturated aq. NaHCO$_3$ (300 mL) and brine (200 mL), dried over Na$_2$SO$_4$ and concentrated again under reduced pressure. The resulting residue was purified by chromatography on silica gel (0-100% EtOAc in hexanes) to afford the sub-title compound (4.6 g, 63%). LCMS calc. for C$_7$H$_8$FN$_2$O$_2$ (M+H)$^+$: m/z=171.0; found 171.1.

Step 2. Methyl 3-amino-6-bromo-5-fluoropyridine-2-carboxylate

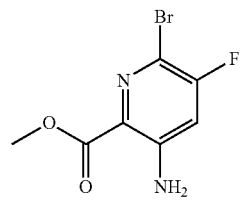

To a solution of methyl 3-amino-5-fluoropyridine-2-carboxylate (3.6 g, 21 mmol) in MeCN (60 mL), N-bromosuccinimide (4.1 g, 23 mmol) was added portionwise. After stirring at room temperature for 2 h, the reaction mixture was diluted with EtOAc (200 mL), washed with a saturated aq. NaHCO$_3$ (200 mL) and brine (200 mL), then dried over Na$_2$SO$_4$ and concentrated under reduced pressure. The resulting residue was purified by chromatography on silica gel (0-100% EtOAc in hexanes) to afford the sub-title compound as a pale yellow solid (4.0 g, 76%) LCMS calc. for C$_7$H$_7$BrFN$_2$O$_2$ (M+H)$^+$: m/z=249.0; found 249.0.

Step 3. Methyl 3-amino-6-(2,6-difluorophenyl)-5-fluoropyridine-2-carboxylate

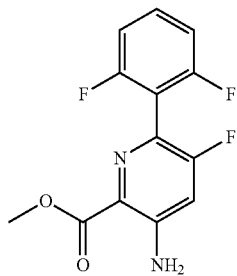 [SMILES: COC(=O)c1nc(-c2c(F)cccc2F)c(F)cc1N]

To a screw-cap vial equipped with a magnetic stir bar, methyl 3-amino-6-bromo-5-fluoropyridine-2-carboxylate (99.6 mg, 0.400 mmol) was added, followed by 2-(2,6-difluorophenyl)-4,4,5,5-tetramethyl-1,3,2-dioxaborolane (Combi-Blocks, 190 mg, 0.80 mmol), and bis(tri-tert-butylphosphine)palladium (40.9 mg, 0.080 mmol). The vial was sealed with a PTFE-lined septum, evacuated and backfilled with nitrogen three times. 1,4-Dioxane (2.0 mL) was added via a syringe, followed by DIPEA (0.14 mL, 0.80 mmol) and deoxygenated water (0.05 mL). The mixture was heated at 100° C. for 2 h. After cooling to room temperature, the mixture was diluted with EtOAc (40 mL) and washed with water (40 mL) and brine (40 mL), then dried over Na$_2$SO$_4$, and concentrated under reduced pressure. The resulting residue was purified by chromatography on silica gel (0-50% EtOAc in hexanes) to give the sub-title compound as a white solid (84.0 mg, 74%). LCMS calc. for C$_{13}$H$_{10}$F$_3$N$_2$O$_2$ (M+H)$^+$: m/z=283.1; found 283.1.

Step 4. 3-Amino-6-(2,6-difluorophenyl)-5-fluoro-pyridine-2-carboxylic Acid

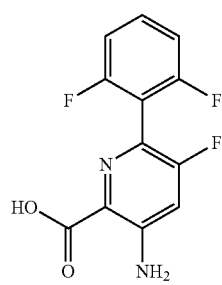

To a mixture of methyl 3-amino-6-(2,6-difluorophenyl)-5-fluoropyridine-2-carboxylate (84.0 mg, 0.298 mmol) and lithium hydroxide, monohydrate (40.2 mg, 0.958 mmol), THF (2.0 mL) was added followed by water (1.0 mL). The mixture was heated at 50° C. for 3 h. The reaction was then cooled to 0° C. for, and 1 M HCl was added slowly until the pH reached 2. The reaction mixture was then diluted with water (20 mL), extracted with EtOAc (3×20 mL), and the combined organic extract was washed with brine (30 mL), dried over Na$_2$SO$_4$, and concentrated under reduced pressure to give the sub-title compound as a white solid (68.5 mg, 86%). LCMS calc. for C$_{12}$H$_8$F$_3$N$_2$O$_2$ (M+H)$^+$: m/z=269.0; found 269.0.

Step 5. 3-Amino-N-{4-[(3S)-3-aminopiperidin-1-yl]-2,3-dihydrofuro[2,3-b]pyridin-5-yl}-6-(2,6-difluorophenyl)-5-fluoropyridine-2-carboxamide To a mixture of 3-amino-6-(2,6-difluorophenyl)-5-fluoropyridine-2-carboxylic acid (15.9 mg, 0.0592 mmol), tert-butyl [(3S)-1-(5-amino-2,3-dihydrofuro[2,3-b]pyridin-4-yl)piperidin-3-yl]carbamate (19.8 mg, 0.0592 mmol) and HATU (72.9 mg, 0.192 mmol) DMF (1.50 mL) was added, followed by DIPEA (84.1 mg, 0.651 mmol). The reaction mixture was stirred at room temperature for 2 h, and then concentrated under reduced pressure. DCM (2.0 mL) was added to the residue, followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.15% NH$_4$OH, at flow rate of 30 mL/min.) to afford the title compound as a white solid (4.9 mg, 17%). LCMS calc. for C$_{24}$H$_{24}$F$_3$N$_6$O$_2$ (M+H)$^+$: m/z=485.2; found 485.2. $^1$H NMR (500 MHz, DMSO-d$_6$) δ 10.29 (br s, 1H), 8.86 (s, 1H), 7.60 (tt, J=8.3, 6.8 Hz, 1H), 7.40 (br s, 2H), 7.26 (t, J=8.2 Hz, 2H), 7.21 (d, J=11.5 Hz, 1H), 4.47 (t, J=9.0 Hz, 2H), 3.34 (t, J=8.5 Hz, 2H), 3.04-2.93 (m, 1H), 2.88-2.78 (m, 1H), 2.69-2.57 (m, 1H), 2.54-2.46 (m, 1H), 2.46-2.37 (m, 1H), 1.50-1.17 (m, 3H), 0.95-0.78 (m, 1H) ppm.

Example 13

N-{4-[(3S)-3-Aminopiperidin-1-yl]-6,7-dihydro-5H-cyclopenta[b]pyridin-3-yl}-2-(2,6-difluorophenyl)-1,3-thiazole-4-carboxamide

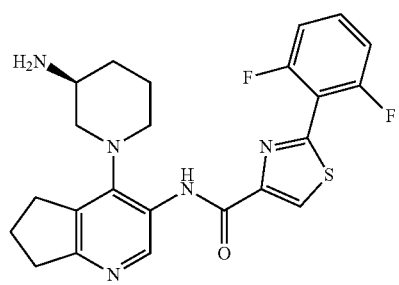 [SMILES: N[C@H]1CCCN(c2c(NC(=O)c3csc(-c4c(F)cccc4F)n3)cnc3c2CCC3)C1]

Step 1: 6,7-Dihydro-5H-cyclopenta[b]pyridine 1-oxide

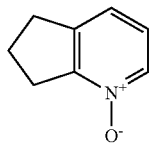

mCPBA (10.0 g, 44.6 mmol) was added slowly to a mixture of 6,7-dihydro-5H-cyclopenta[b]pyridine (from Aldrich, 5.0 g, 42 mmol) in DCM (50 mL). The reaction mixture was stirred at room temperature for 2 h. The solution was then washed with aq. $Na_2S_2O_3$ (50 mL) and 1 M NaOH (50 mL). The aqueous layer was extracted with DCM (5×70 mL). The combined organic layers were dried, filtered and concentrated under reduced pressure to give the sub-title compound (4.5 g, 79%). LCMS calc. for $C_8H_{10}NO$ $(M+H)^+$: m/z=136.1. Found: 136.2.

Step 2: 4-Chloro-6,7-dihydro-5H-cyclopenta[b]pyridine

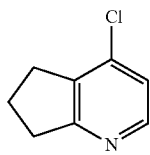

6,7-Dihydro-5H-cyclopenta[b]pyridine 1-oxide (2.5 g, 18 mmol) was mixed with $POCl_3$ (20 mL). The reaction mixture was stirred at 120° C. for 3 h. The excess $POCl_3$ was removed under reduced pressure. The residue was diluted in EtOAc (80 mL) and neutralized with aq. $Na_2CO_3$. After filtration, the aqueous layer was extracted with EtOAc twice. The combined organic layers were dried, filtered and concentrated under reduced pressure to give the sub-title compound (2.6 g, 93%). LCMS calc. for $C_8H_9ClN$ $(M+H)^+$: m/z=154.0. Found: 154.3.

Step 3: 4-Methoxy-6,7-dihydro-5H-cyclopenta[b]pyridine

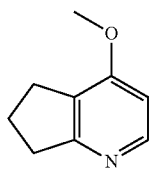

A mixture of 4-chloro-6,7-dihydro-5H-cyclopenta[b]pyridine (2.8 g, 18 mmol), MeOH (20 mL) and sodium methoxide (3.0 g, 56 mmol) was sealed in a pressurized flask and heated at 110° C. for 18 h. The mixture was diluted with EtOAc and neutralized with HCl to pH=1. The organic solvent was removed under reduced pressure. The resulting mixture was washed with ether twice, and then neutralized with $Na_2CO_3$ solution. The aqueous layer was extracted twice with EtOAc. The combined organic layers were dried, filtered and concentrated under reduced pressure to give the sub-title compound (1.20 g, 44%). LCMS calc. for $C_9H_{12}NO$ $(M+H)^+$: m/z=150.1. Found: 150.2.

Step 4: 4-Methoxy-3-nitro-6,7-dihydro-5H-cyclopenta[b]pyridine

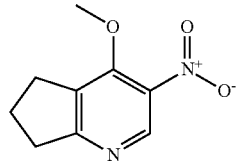

4-Methoxy-6,7-dihydro-5H-cyclopenta[b]pyridine (2.90 g, 19.4 mmol) was mixed with concentrated sulfuric acid (17.0 g, 173 mmol) at 0° C., then a mixture of potassium nitrate (5.3 g, 52 mmol) in another portion of concentrated sulfuric acid (26.5 g, 270 mmol) was added slowly. The reaction mixture was heated at 80° C. for 4 h. The crude mixture was slowly poured onto crushed ice (50 g), and neutralized carefully with 50% aq. NaOH to pH 8-9. The resulting mixture was extracted with EtOAc five times. The combined organic extracts were dried and concentrated under reduced pressure to give the crude sub-title compound as brown gum (1.56 g, 41%), which was used without further purification. LCMS calc. for $C_9H_{11}N_2O_3$ $(M+H)^+$: m/z=195.1. Found: 195.2.

Step 5: 3-Nitro-6,7-dihydro-5H-cyclopenta[b]pyridin-4-ol

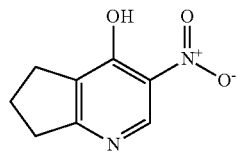 [SMILES: O=[N+]([O-])c1cnc2c(c1O)CCC2]

A mixture of 4-methoxy-3-nitro-6,7-dihydro-5H-cyclopenta[b]pyridine (1.535 g, 7.905 mmol) in AcOH (2.6 mL) was treated 48% aq. HBr (2.6 mL, 23 mmol). The flask containing the mixture was sealed and heated at 130° C. for 40 min., then allowed to cool. The resulting mixture was concentrated under reduced pressure, the residue was neutralized to pH=7-8 using 50% NaOH with cooling. After further concentrating, the residue was diluted with MeOH and THF, dried, filtered and concentrated to give the crude sub-title compound as light brown powder, which was used without further purification. LCMS calc. for $C_8H_9N_2O_3$ $(M+H)^+$: m/z=181.1. Found: 181.2.

Step 6: 4-Chloro-3-nitro-6,7-dihydro-5H-cyclopenta[b]pyridine

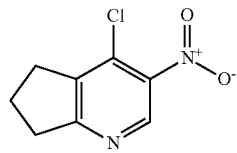 [SMILES: O=[N+]([O-])c1cnc2c(c1Cl)CCC2]

A solution of 3-nitro-6,7-dihydro-5H-cyclopenta[b]pyridin-4-ol (1.424 g, 7.904 mmol) in POCl$_3$ (11.0 mL) was heated at 110° C. in a sealed flask under N$_2$ for 2 h. The crude mixture was cooled to room temperature, and concentrated under reduced pressure. The residue was carefully quenched with ice, and neutralized with 50% NaOH to pH 7. The resulting mixture was extracted with EtOAc three times. The combined organic layers were dried, filtered and concentrated under reduced pressure to give the crude sub-title compound as a brown solid (0.82 g, 52%), which was used without further purification. LCMS calc. for C$_8$H$_8$N$_2$O$_2$ (M+H)$^+$: m/z=199.0. Found: 199.2.

Step 7: tert-Butyl [(3S)-1-(3-nitro-6,7-dihydro-5H-cyclopenta[b]pyridin-4-yl)piperidin-3-yl]carbamate

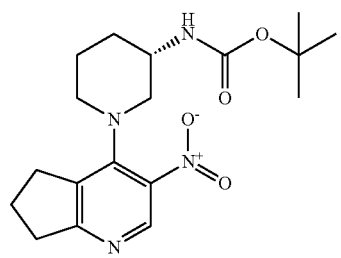 [SMILES: CC(C)(C)OC(=O)N[C@H]1CCCN(c2c([N+](=O)[O-])cnc3c2CCC3)C1]

A mixture of 4-chloro-3-nitro-6,7-dihydro-5H-cyclopenta[b]pyridine (40 mg, 0.20 mmol), tert-butyl (3S)-piperidin-3-ylcarbamate (81 mg, 0.40 mmol) and triethylamine (84 µL, 0.60 mmol) in isopropyl alcohol (0.46 mL) was stirred at 100° C. for 30 min. The reaction mixture was concentrated under reduced pressure and purified by silica gel column chromatography (eluting with 0-40% EtOAc in hexanes) to give the sub-title compound as light yellow powder (43 mg, 59%). LCMS calc. for C$_{18}$H$_{27}$N$_4$O$_4$ (M+H)$^+$: m/z=363.2. Found: 363.2.

Step 8: tert-Butyl [(3S)-1-(3-amino-6,7-dihydro-5H-cyclopenta[b]pyridin-4-yl)piperidin-3-yl]carbamate

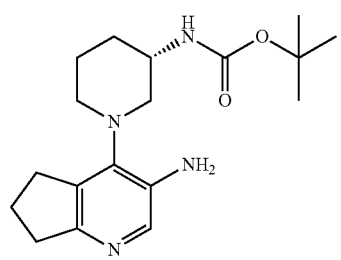 [SMILES: CC(C)(C)OC(=O)N[C@H]1CCCN(c2c(N)cnc3c2CCC3)C1]

A mixture of tert-butyl [(3S)-1-(3-nitro-6,7-dihydro-5H-cyclopenta[b]pyridin-4-yl)piperidin-3-yl]carbamate (43 mg, 0.12 mmol), iron powder (106 mg, 1.90 mmol) and NH$_4$Cl (127 mg, 2.37 mmol) in EtOH (0.69 mL) and water (0.11 mL) was heated in a sealed tube at 80° C. for 1 h. The mixture was diluted with EtOAc and the resulting solution was washed with saturated aq. Na$_2$CO$_3$, dried over Na$_2$SO$_4$, filtered and concentrated under reduced pressure to give the sub-title compound as a brown-orange powder (51 mg, 100%). LCMS calc. for C$_{18}$H$_{29}$N$_4$O$_2$ (M+H)$^+$: m/z=333.2. Found: 333.1.

Step 9: tert-Butyl {(3S)-1-[3-({[2-(2,6-difluorophenyl)-1,3-thiazol-4-yl]carbonyl}amino)-6,7-dihydro-5H-cyclopenta[b]pyridin-4-yl]piperidin-3-yl}carbamate tert-Butyl [(3S)-1-(3-amino-6,7-dihydro-5H-cyclopenta[b]pyridin-4-yl)piperidin-3-yl]carbamate (5.0 mg, 0.015 mmol) was mixed with 2-(2,6-difluorophenyl)-1,3-thiazole-4-carboxylic acid (Example 2, step 2, 4.4 mg, 0.018 mmol), HATU (14 mg, 0.038 mmol), DMF (0.035 mL) and DIPEA (5.8 mg, 0.045 mmol). The reaction mixture was stirred at room temperature for 1 h. The mixture was filtered, concentrated and purified by preparative LC-MS (XBridge™ preparative C18 5 µm 30×10 mm OBD™ column, flow rate 60 mL/min., eluting with a gradient of MeCN and water with 0.15% NH$_4$OH) to give the sub-title compound as a colorless gum (4.1 mg, 49%). LCMS calc. for C$_{28}$H$_{32}$F$_2$N$_5$O$_3$S (M+H)$^+$: m/z=556.2. Found: 556.1.

Step 10: N-{4-[(3S)-3-Aminopiperidin-1-yl]-6,7-dihydro-5H-cyclopenta[b]pyridin-3-yl}-2-(2,6-difluorophenyl)-1,3-thiazole-4-carboxamide tert-Butyl {(3S)-1-[3-({[2-(2,6-difluorophenyl)-1,3-thiazol-4-yl]carbonyl}amino)-6,7-dihydro-5H-cyclopenta[b]pyridin-4-yl]piperidin-3-yl}carbamate (4 mg, 0.007 mmol) was dissolved in DCM (0.02 mL) and then TFA (0.03 mL, 0.4 mmol) was added. The resulting reaction mixture was stirred at room temperature for 30 min. and then concentrated to give a residue, which was diluted with MeOH and neutralized with small amount of NH$_4$OH. The mixture was filtered and purified by preparative LC-MS (XBridge™ preparative C18 30×10 mm, 5 µm OBD™ column, at flow rate of 60 mL/min., eluting with a gradient of MeCN and water with 0.15% NH$_4$OH) to afford the title compound (1.9 mg, 58%). LCMS calc. for C$_{23}$H$_{24}$F$_2$N$_5$OS (M+H)$^+$: m/z=456.2. Found: 456.1.

Example 14

5-Amino-N-{4-[(3S)-3-aminopiperidin-1-yl]-6,7-dihydro-5H-cyclopenta[b]pyridin-3-yl}-2-(2,6-difluorophenyl)-1,3-thiazole-4-carboxamide

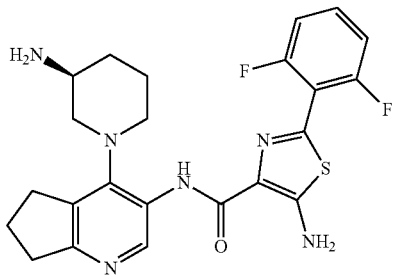 [SMILES: Nc1sc(-c2c(F)cccc2F)nc1C(=O)Nc1cnc2c(c1N1CCC[C@H](N)C1)CCC2]

A mixture of tert-butyl [(3S)-1-(3-amino-6,7-dihydro-5H-cyclopenta[b]pyridin-4-yl)piperidin-3-yl]carbamate (15 mg, 0.045 mmol), 5-[(tert-butoxycarbonyl)amino]-2-(2,6-difluorophenyl)-1,3-thiazole-4-carboxylic acid (19 mg, 0.054 mmol), HATU (43 mg, 0.11 mmol) and DIPEA (24 µL, 0.14 mmol) in dry DMF (0.11 mL) was stirred at room temperature for 16 h. The reaction mixture was concentrated under reduced pressure to give an intermediate, which was treated with TFA (0.070 mL, 0.90 mmol). The resulting reaction mixture was stirred at room temperature for 1 h then concentrated under reduced pressure. The residue was diluted with MeOH and neutralized with small amount of NH$_4$OH. The mixture was filtered and purified by preparative LC-MS (XBridge™ preparative C18 5 µm 30×10 mm OBD™ column, flow rate 60 mL/min., eluting with a gradient of MeCN and water with 1.5% NH$_4$OH) to give the title compound as a white powder (7.5 mg, 35%). LCMS calc. for C$_{23}$H$_{25}$F$_2$N$_6$OS (M+H)$^+$: m/z=471.2. Found: 471.1. $^1$H NMR (500 MHz, DMSO-d$_6$) δ 9.24 (s, 1H), 7.61 (s, 2H), 7.57-7.45 (m, 1H), 7.36-7.17 (m, 2H), 3.12-2.96 (m, 3H), 2.91 (t, J=9.8 Hz, 1H), 2.88-2.70 (m, 4H), 2.66-2.55 (m, 1H), 2.07-1.99 (m, 2H), 1.86-1.56 (m, 3H), 1.18-1.01 (m, 1H) ppm.

Example 15

5-Amino-N-{4-[(3S)-3-aminopiperidin-1-yl]-7-hydroxy-6,7-dihydro-5H-cyclopenta[b]pyridin-3-yl}-2-(2,6-difluorophenyl)-1,3-thiazole-4-carboxamide

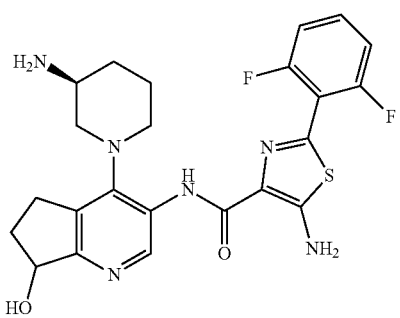 [SMILES: Nc1sc(-c2c(F)cccc2F)nc1C(=O)Nc1cnc2c(c1N1CCC[C@H](N)C1)CCC2O]

Step 1: tert-Butyl [(3S)-1-(3-nitro-1-oxido-6,7-dihydro-5H-cyclopenta[b]pyridin-4-yl)piperidin-3-yl] carbamate

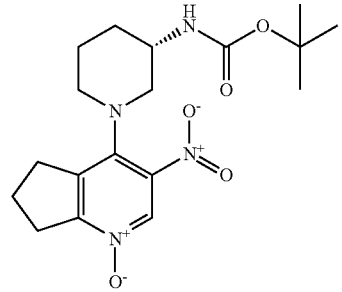 [SMILES: CC(C)(C)OC(=O)N[C@H]1CCCN(c2c([N+](=O)[O-])c[n+]([O-])c3c2CCC3)C1]

mCPBA (198 mg, 0.883 mmol) was added slowly to a solution of tert-butyl [(3S)-1-(3-nitro-6,7-dihydro-5H-cyclopenta[b]pyridin-4-yl)piperidin-3-yl]carbamate (301 mg, 0.83 mmol) in DCM (1.1 mL) at 0° C. The reaction mixture was then stirred at room temperature for 67 h. The mixture was treated with aq. Na$_2$S$_2$O$_3$ and 1 M NaOH, and then stirred for 30 min. at room temperature. The reaction mixture was extracted with DCM three times. The combined organic layers were dried over Na$_2$SO$_4$, filtered and concentrated under reduced pressure to give the sub-title compound (277 mg, 88%) as light orange powder, which was used without further purification. LCMS calc. for C$_{18}$H$_{27}$N$_4$O$_5$ (M+H)$^+$: m/z=379.2. Found: 379.2.

Step 2: 4-{(3S)-3-[(tert-Butoxycarbonyl)amino]piperidin-1-yl}-3-nitro-6,7-dihydro-5H-cyclopenta[b]pyridin-7-yl Acetate

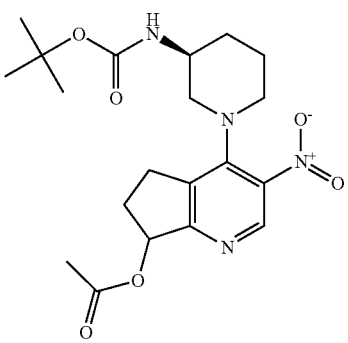 [SMILES: CC(=O)OC1CCc2c1ncc([N+](=O)[O-])c2N1CCC[C@H](NC(=O)OC(C)(C)C)C1]

A mixture of Ac$_2$O (0.90 g, 8.8 mmol) and tert-butyl [(3S)-1-(3-nitro-1-oxido-6,7-dihydro-5H-cyclopenta[b]pyridin-4-yl)piperidin-3-yl]carbamate (270 mg, 0.714 mmol) was sealed and heated at 90° C. for 1 h, then allowed to cool to room temperature. The excess Ac$_2$O was removed under reduced pressure. The residue was dissolved in DCM, and then poured into ice cold aq. Na$_2$CO$_3$. The mixture was extracted with DCM twice. The combined extracts were dried, filtered and concentrated under reduced pressure to give a crude product, which was purified by preparative LC-MS (XBridge™ preparative C18 5 µm 30×10 mm OBD™ column, flow rate 60 mL/min., eluting with a gradient of MeCN and water with 0.15% NH$_4$OH) to provide the sub-title compound as a yellow powder (65 mg, 22%). LCMS calc. for $C_{20}H_{29}N_4O_6$ (M+H)$^+$: m/z=421.2. Found: 421.3.

Step 3: 3-Amino-4-{(3S)-3-[(tert-butoxycarbonyl)amino]piperidin-1-yl}-6,7-dihydro-5H-cyclopenta[b]pyridin-7-yl Acetate

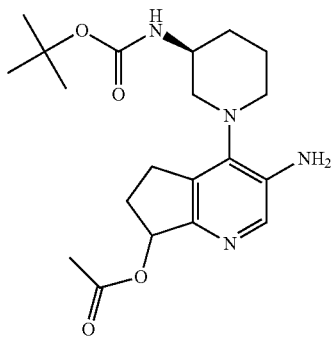 [SMILES: CC(=O)OC1CCc2c1ncc(N)c2N1CCC[C@H](NC(=O)OC(C)(C)C)C1]

A mixture of 4-{(3S)-3-[(tert-butoxycarbonyl)amino]piperidin-1-yl}-3-nitro-6,7-dihydro-5H-cyclopenta[b]pyridin-7-yl acetate (64 mg, 0.15 mmol), AcOH (0.90 mL), water (0.10 mL) and iron powder (149 mg, 2.66 mmol) was stirred at room temperature for 20 min. The mixture was diluted with EtOAc and filtered through a short silica gel plug. The filtrate was concentrated under reduced pressure, diluted with EtOAc and washed with aq. $Na_2CO_3$. The organic layer was dried, filtered and concentrated under reduced pressure to give the sub-title compound (66 mg) as a yellowish solid, which was used without further purification. LCMS calc. for $C_{20}H_{31}N_4O_4$ (M+H)$^+$: m/z=391.2. Found: 391.1.

Step 4: 3-({[5-[(tert-Butoxycarbonyl)amino]-2-(2,6-difluorophenyl)-1,3-thiazol-4-yl]carbonyl}amino)-4-{(3S)-3-[(tert-butoxycarbonyl)amino]piperidin-1-yl}-6,7-dihydro-5H-cyclopenta[b]pyridin-7-yl Acetate

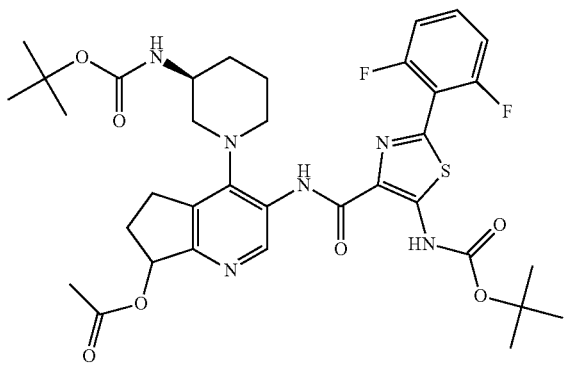 [SMILES: CC(=O)OC1CCc2c1ncc(NC(=O)c1nc(-c3c(F)cccc3F)sc1NC(=O)OC(C)(C)C)c2N1CCC[C@H](NC(=O)OC(C)(C)C)C1]

3-Amino-4-{(3S)-3-[(tert-butoxycarbonyl)amino]piperidin-1-yl}-6,7-dihydro-5H-cyclopenta[b]pyridin-7-yl acetate (20 mg, 0.051 mmol), (5-[(tert-butoxycarbonyl)amino]-2-(2,6-difluorophenyl)-1,3-thiazole-4-carboxylic acid (Example 1, step 6, 22 mg, 0.062 mmol), HATU (49 mg, 0.13 mmol), DMF (0.12 mL) and DIPEA (20 mg, 0.15 mmol) were mixed together and stirred at room temperature for 16 h. The mixture was concentrated under reduced pressure and purified by silica gel column chromatography (eluting with 0-100% EtOAc in hexanes) to give the sub-title compound as a colorless gum (30 mg, 80%). LCMS calc. for $C_{35}H_{43}F_2N_6O_7S$ (M+H)$^+$: m/z=729.3. Found: 729.1.

Step 5: 5-Amino-N-{4-[(3S)-3-aminopiperidin-1-yl]-7-hydroxy-6,7-dihydro-5H-cyclopenta[b]pyridin-3-yl}-2-(2,6-difluorophenyl)-1,3-thiazole-4-carboxamide 3-({[5-[(tert-Butoxycarbonyl)amino]-2-(2,6-difluorophenyl)-1,3-thiazol-4-yl]carbonyl}amino)-4-{(3S)-3-[(tert-butoxycarbonyl)amino]piperidin-1-yl}-6,7-dihydro-5H-cyclopenta[b]pyridin-7-yl acetate (30 mg, 0.041 mmol) in MeOH (0.59 mL) was mixed with 1.0 M NaOH (0.30 mL, 0.30 mmol) and THF (0.3 mL). The reaction mixture was stirred at room temperature for 25 min. The organic solvents were removed under reduced pressure. The aqueous layer was extracted twice with EtOAc. The combined organic layers were dried, filtered and concentrated under reduced pressure to give an intermediate (19 mg). The intermediate was treated with ice-cold TFA in DCM (4.0 M; 1.0 mL, 4.0 mmol). After stirring for 20 min. at room temperature, the reaction mixture was concentrated under reduced pressure. The residue was diluted with MeOH and neutralized with small amount of $NH_4OH$. The resulting mixture was filtered and purified by preparative LC-MS (XBridge™ preparative C18 5 μm 30×10 mm OBD™ column, flow rate 60 mL/min., eluting with a gradient of MeCN and water with 0.15% $NH_4OH$) to afford the title compound as two diastereoisomers.

Diastereoisomer 1. First peak. Retention time 1.786 min., LCMS calc. for $C_{23}H_{25}F_2N_6O_2S$ (M+H)$^+$: m/z=487.2; Found: 487.1.

Diastereoisomer 2. Second peak. Retention time 1.875 min., LCMS calc. for $C_{23}H_{25}F_2N_6O_2S$ (M+H)$^+$: m/z=487.2; Found: 487.1.

The diastereoisomers correspond to the (7R) and (7S) diastereoisomers of the title compound.

Example 16

N-{4-[(3S)-3-Aminopiperidin-1-yl]-7-hydroxy-6,7-dihydro-5H-cyclopenta[b]pyridin-3-yl}-2-(2,6-difluorophenyl)-1,3-thiazole-4-carboxamide

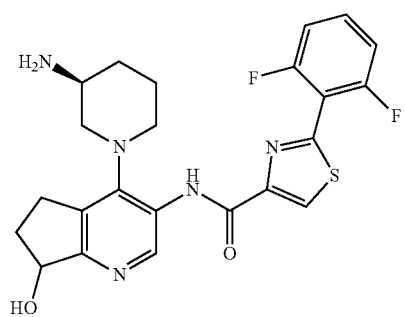 [SMILES: N[C@H]1CCCN(c2c(NC(=O)c3csc(-c4c(F)cccc4F)n3)cnc3c2CCC3O)C1]

Step 1: 4-{(3S)-3-[(tert-Butoxycarbonyl)amino]piperidin-1-yl}-3-({[2-(2,6-difluorophenyl)-1,3-thiazol-4-yl]carbonyl}amino)-6,7-dihydro-5H-cyclopenta[b]pyridin-7-yl Acetate

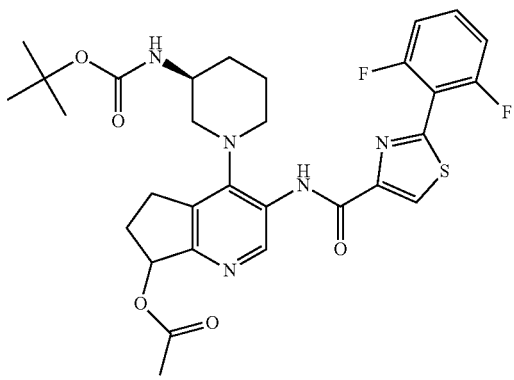 [SMILES: CC(=O)OC1CCc2c1ncc(NC(=O)c1csc(-c3c(F)cccc3F)n1)c2N1CCC[C@H](NC(=O)OC(C)(C)C)C1]

3-Amino-4-{(3S)-3-[(tert-butoxycarbonyl)amino]piperidin-1-yl}-6,7-dihydro-5H-cyclopenta[b]pyridin-7-yl acetate (7.0 mg, 0.018 mmol), 2-(2,6-difluorophenyl)-1,3-thiazole-4-carboxylic acid (5.2 mg, 0.022 mmol), HATU (17 mg, 0.045 mmol), DMF (0.042 mL) and DIPEA (7.0 mg, 0.054 mmol) were mixed together and the mixture was stirred at room temperature for 1 h. The mixture was filtered, concentrated and purified by preparative LC-MS (XBridge™ preparative C18 5 μm 30×10 mm OBD™ column, flow rate 60 mL/min., eluting with a gradient of MeCN and water with 0.15% NH$_4$OH) to give pure sub-title compound as light yellow powder (3.7 mg, 34%). LCMS calc. for C$_3$H$_{34}$F$_2$N$_5$O$_5$S (M+H)$^+$: m/z=614.2. Found: 614.1.

Step 2: N-{4-[(3S)-3-Aminopiperidin-1-yl]-7-hydroxy-6,7-dihydro-5H-cyclopenta[b]pyridin-3-yl}-2-(2,6-difluorophenyl)-1,3-thiazole-4-carboxamide 4-{(3S)-3-[(tert-Butoxycarbonyl)amino]piperidin-1-yl}-3-({[2-(2,6-difluorophenyl)-1,3-thiazol-4-yl]carbonyl}amino)-6,7-dihydro-5H-cyclopenta[b]pyridin-7-yl acetate (4.0 mg, 0.0065 mmol) was mixed with MeOH (77 μL), THF (39 μL) and 1.0 M NaOH (42 μL, 0.042 mmol). The reaction mixture was stirred at room temperature for 30 min. The organic solvents were removed under reduced pressure. The resulting aqueous solution was diluted with aq. NH$_4$Cl and extracted twice with EtOAc. The combined organic layers were dried, filtered and concentrated to give an intermediate. The intermediate was dissolved in a mixture of DCM (0.066 mL) and TFA (0.066 mL, 0.86 mmol). The resulting solution was stirred at room temperature for 30 min., then concentrated under reduced pressure. The residue was diluted with MeOH, neutralized with NH$_4$OH, filtered and purified by preparative LC-MS (XBridge™ preparative C18 5 μm 30×10 mm OBD™ column, flow rate 60 mL/min., eluting with a gradient of MeCN and water with 0.15% NH$_4$OH) to give two diastereoisomers of the title compound as white powders.

Diastereoisomer 1. First peak. Retention time 1.685 min., LCMS calc. for C$_{23}$H$_{24}$F$_2$N$_5$O$_2$S (M+H)$^+$: m/z=472.2. Found: 471.1.

Diastereoisomer 2. Second peak. Retention time 1.797 min., LCMS calc. for C$_{23}$H$_{24}$F$_2$N$_5$O$_2$S (M+H)$^+$: m/z=472.2. Found: 471.1.

The diastereoisomers correspond to the (7R) and (7S) diastereoisomers of the title compound.

Example 17

5-Amino-N-{4-[(3S)-3-aminopiperidin-1-yl]-7-methoxy-6,7-dihydro-5H-cyclopenta[b]pyridin-3-yl}-2-(2,6-difluorophenyl)-1,3-thiazole-4-carboxamide

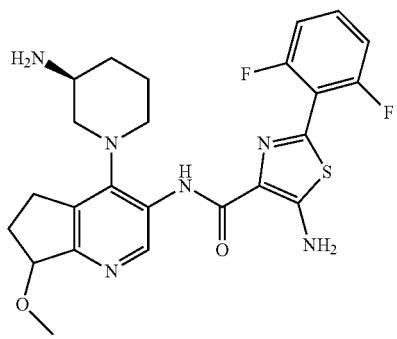 [SMILES: COC1CCc2c1ncc(NC(=O)c1nc(-c3c(F)cccc3F)sc1N)c2N1CCC[C@H](N)C1]

NaH (0.35 mg, 0.014 mmol) was added to a solution of tert-butyl {(3S)-1-[3-({[5-[(tert-butoxycarbonyl)amino]-2-(2,6-difluorophenyl)-1,3-thiazol-4-yl]carbonyl}amino)-7-hydroxy-6,7-dihydro-5H-cyclopenta[b]pyridin-4-yl]piperidin-3-yl}carbamate (4.0 mg, 0.0058 mmol) in THF (0.024 mL) at 0° C. The reaction mixture was stirred at 0° C. for 1 h and then methyl iodide (2.1 mg, 0.015 mmol) was added. The reaction mixture was stirred at 0° C. for 1 h and quenched with aq. NH$_4$Cl. The mixture was extracted with EtOAc three times. The organic layers were dried, filtered and concentrated under reduced pressure. The residue was purified by preparative LC-MS (XBridge™ preparative C18 5 μm 30×10 mm OBD™ column, flow rate 60 mL/min., eluting with a gradient of MeCN and water with 0.15% NH$_4$OH) to give the intermediate.

The intermediate was dissolved in a mixture of TFA (0.0090 mL, 0.12 mmol) in DCM (0.018 mL) and the resulting mixture was allowed to react at room temperature for 1 h. The reaction mixture was concentrated under reduced pressure, then diluted with MeOH, and neutralized with NH$_4$OH. After filtration, the crude product was purified by preparative LC-MS (XBridge™ preparative C18 5 um 30×10 mm OBD™ column, flow rate 60 mL/min., eluting with a gradient of MeCN and water with 0.15% NH$_4$OH) to give the title compound as a mixture of diastereoisomers (1.6 mg, 55%). LCMS calc. for C$_{24}$H$_{27}$F$_2$N$_6$O$_2$S (M+H)$^+$: m/z=501.2. Found: 501.1. The product is a mixture of the (7R) and (7S) diastereoisomers of the title compound.

Example 18

5-Amino-N-{4-[(3S)-3-aminopiperidin-1-yl]-7-cyano-6,7-dihydro-5H-cyclopenta[b]pyridin-3-yl}-2-(2,6-difluorophenyl)-1,3-thiazole-4-carboxamide

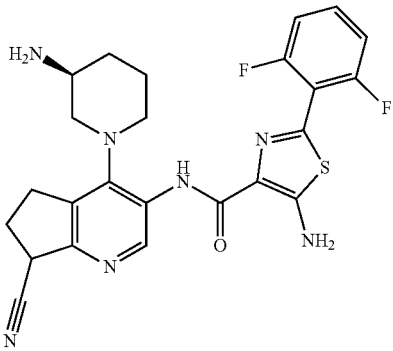 [SMILES: N#CC1CCc2c1ncc(NC(=O)c1nc(-c3c(F)cccc3F)sc1N)c2N1CCC[C@H](N)C1]

Step 1: tert-Butyl {(3S)-1-[3-({[5-[(tert-butoxycarbonyl)amino]-2-(2,6-difluorophenyl)-1,3-thiazol-4-yl]carbonyl}amino)-7-cyano-6,7-dihydro-5H-cyclopenta[b]pyridin-4-yl]piperidin-3-yl}carbamate

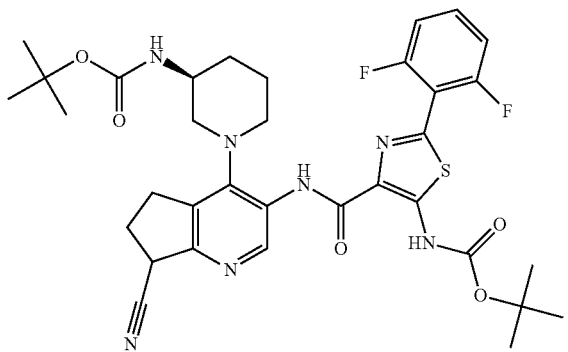 [SMILES: CC(C)(C)OC(=O)Nc1sc(-c2c(F)cccc2F)nc1C(=O)Nc1cnc2c(c1N1CCC[C@H](NC(=O)OC(C)(C)C)C1)CCC2C#N]

To a mixture of tert-butyl {(3S)-1-[3-({[5-[(tert-butoxycarbonyl)amino]-2-(2,6-difluorophenyl)-1,3-thiazol-4-yl]carbonyl}amino)-7-hydroxy-6,7-dihydro-5H-cyclopenta[b]pyridin-4-yl]piperidin-3-yl}carbamate (12.0 mg, 0.0175 mmol) and triethylamine (7.3 μL, 0.052 mmol) in DCM (0.12 mL) at 0° C., methanesulfonyl chloride (20.0 mg, 0.175 mmol) was added. The reaction mixture was allowed to warm to room temperature and stirred for 3 h, then concentrated to dryness under reduced pressure. The resulting crude mesylate was dissolved in DMF (48 μL), sodium cyanide (50 mg, 1 mmol) was added, and the mixture was stirred at room temperature for 2 h. After filtration, the crude was purified by preparative LC-MS (XBridge™ preparative C18 5 μm 30×10 mm OBD™ column, flow rate 60 mL/min., eluting with a gradient of MeCN and water with 0.15% $NH_4OH$) to give the sub-title compound as a mixture of two diastereoisomers (5 mg, 40%). LCMS calc. for $C_{34}H_{40}F_2N_7O_5S$ (M+H)$^+$: m/z=696.3. Found: 696.1.

Step 2: 5-Amino-N-{4-[(3S)-3-aminopiperidin-1-yl]-7-cyano-6,7-dihydro-5H-cyclopenta[b]pyridin-3-yl}-2-(2,6-difluorophenyl)-1,3-thiazole-4-carboxamide TFA (0.02 mL, 0.3 mmol) was added to a solution of tert-butyl {(3S)-1-[3-({[5-[(tert-butoxycarbonyl)amino]-2-(2,6-difluorophenyl)-1,3-thiazol-4-yl]carbonyl}amino)-7-cyano-6,7-dihydro-5H-cyclopenta[b]pyridin-4-yl]piperidin-3-yl}carbamate (5.0 mg, 0.0072 mmol) in DCM (0.009 mL). The reaction mixture was stirred at room temperature for 15 min., then evaporated under reduced pressure. The resulting mixture was diluted with MeOH and neutralized with small amount of $NH_4OH$. After filtration, the crude product was purified by preparative LC-MS (XBridge™ preparative C18 5 μm 30×10 mm OBD™ column, flow rate 60 mL/min., eluting with a gradient of MeCN and water with 0.15% $NH_4OH$) to give the title compound (4 mg) as a mixture of two diastereoisomers, which was further purified by chiral preparative LC (Phenomenex Lux® Cellulose-1 column, 21.2×250 mm, 5 μm particle, flow rate 18 mL/min., isocratic eluting with 45% EtOH in hexanes) to give the title compound as two separated diastereoisomers.

Diastereoisomer 1. First peak (0.5 mg). Retention time 1.579 min. LCMS calc. for $C_{24}H_{24}F_2N_7OS$ (M+H)$^+$: m/z=496.2. Found: 496.1.

Diastereoisomer 2. Second peak (0.8 mg). Retention time 1.617 min. LCMS calc. for $C_{24}H_{24}F_2N_7OS$ (M+H)$^+$: m/z=496.2. Found: 496.1.

The diastereoisomers correspond to the (7R) and (7S) diastereoisomers of the title compound.

Example 19

5-Amino-N-{4-[(3S)-3-aminopiperidin-1-yl]-7-hydroxy-7-methyl-6,7-dihydro-5H-cyclopenta[b]pyridin-3-yl}-2-(2,6-difluorophenyl)-1,3-thiazole-4-carboxamide

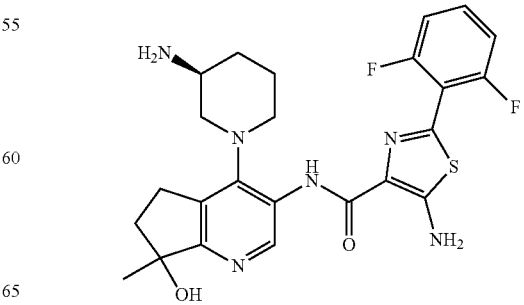

Step 1: tert-Butyl {(3S)-1-[3-({[5-[(tert-butoxycarbonyl)amino]-2-(2,6-difluorophenyl)-1,3-thiazol-4-yl]carbonyl}amino)-7-oxo-6,7-dihydro-5H-cyclopenta[b]pyridin-4-yl]piperidin-3-yl}carbamate

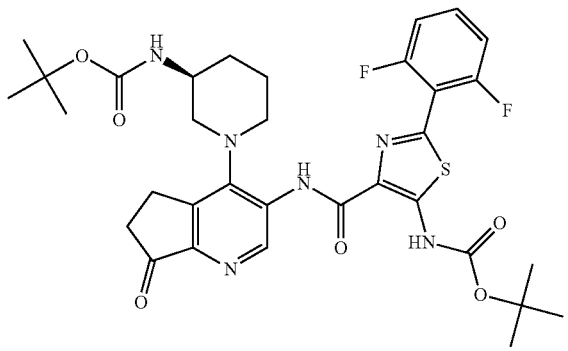 [SMILES: CC(C)(C)OC(=O)Nc1sc(-c2c(F)cccc2F)nc1C(=O)Nc1cnc2c(c1N1CCC[C@H](NC(=O)OC(C)(C)C)C1)CCC2=O]

Dess-Martin periodinane (12 mg, 0.028 mmol) was added to a solution of tert-butyl {(3S)-1-[3-({[5-[(tert-butoxycarbonyl)amino]-2-(2,6-difluorophenyl)-1,3-thiazol-4-yl]carbonyl}amino)-7-hydroxy-6,7-dihydro-5H-cyclopenta[b]pyridin-4-yl]piperidin-3-yl}carbamate (15 mg, 0.022 mmol) in DCM (0.098 mL). The reaction mixture was stirred at room temperature for 1 h. The solution was neutralized with 1 M NaOH, diluted with MeOH and filtered. The mixture was then concentrated under reduced pressure and the crude product was purified by preparative LC-MS (XBridge™ preparative C18 5 μm 30×10 mm OBD™ column, flow rate 60 mL/min., eluting with a gradient of MeCN and water with 0.15% NH$_4$OH) to give sub-title compound as off-white powder (7.5 mg, 50%). LCMS calc. for C$_{33}$H$_{39}$F$_2$N$_6$O$_6$S (M+H)$^+$: m/z=685.3. Found: 685.1.

Step 2: tert-Butyl {(3S)-1-[3-({[5-[(tert-butoxycarbonyl)amino]-2-(2,6-difluorophenyl)-1,3-thiazol-4-yl]carbonyl}amino)-7-hydroxy-7-methyl-6,7-dihydro-5H-cyclopenta[b]pyridin-4-yl]piperidin-3-yl}carbamate

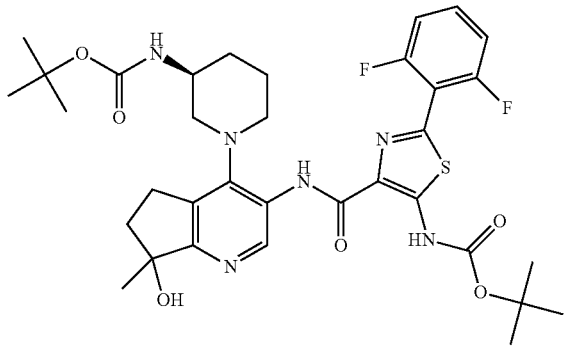 [SMILES: CC(C)(C)OC(=O)Nc1sc(-c2c(F)cccc2F)nc1C(=O)Nc1cnc2c(c1N1CCC[C@H](NC(=O)OC(C)(C)C)C1)CCC2(C)O]

Methylmagnesium bromide in THF (3.0 M, 5.8 μL, 0.018 mmol) was added to a solution of tert-butyl {(3S)-1-[3-({[5-[(tert-butoxycarbonyl)amino]-2-(2,6-difluorophenyl)-1,3-thiazol-4-yl]carbonyl}amino)-7-oxo-6,7-dihydro-5H-cyclopenta[b]pyridin-4-yl]piperidin-3-yl}carbamate (3.0 mg, 0.0044 mmol) in THF (0.068 mL), which was stirred under N$_2$ and cooled in an ice bath. The reaction mixture was slowly allowed to warmed to room temperature over a period of 1 h. EtOAc was added to the reaction mixture, then 1 M HCl was slowly added to adjust the pH to 7. The aqueous layer was extracted twice with EtOAc. The organic extracts were combined, dried over Na$_2$SO$_4$, then filtered and concentrated under reduced pressure to give the sub-title compound. LCMS calc. for C$_{34}$H$_{43}$F$_2$N$_6$O$_6$S (M+H)$^+$: m/z=701.3. Found: 701.1.

Step 3: 5-Amino-N-{4-[(3S)-3-aminopiperidin-1-yl]-7-hydroxy-7-methyl-6,7-dihydro-5H-cyclopenta[b]pyridin-3-yl}-2-(2,6-difluorophenyl)-1,3-thiazole-4-carboxamide TFA (0.02 mL, 0.2 mmol) was added to a solution of tert-butyl {(3S)-1-[3-({[5-[(tert-butoxycarbonyl)amino]-2-(2,6-difluorophenyl)-1,3-thiazol-4-yl]carbonyl}amino)-7-hydroxy-7-methyl-6,7-dihydro-5H-cyclopenta[b]pyridin-4-yl]piperidin-3-yl}carbamate (4.0 mg, 0.0044 mmol) in DCM (0.01 mL). The reaction mixture was stirred at room temperature for 30 min., and then diluted with MeOH and neutralized with NH$_4$OH. After filtration, the crude was purified by preparative LC-MS (Waters SunFire™ preparative C18 5 μm 30×10 mm column, flow rate 60 mL/min., eluting with a gradient of MeCN and water with 0.1% TFA) to give the title compound tris-trifluoroacetate salt as two diastereoisomers.

Diastereoisomer 1. First peak. Retention time 1.282 min. LCMS calc. for C$_{24}$H$_{27}$F$_2$N$_6$O$_2$S (M+H)$^+$: m/z=501.2. Found: 501.1.

Diastereoisomer 2. Second peak. Retention time 1.381 min. LCMS calc. for C$_{24}$H$_{27}$F$_2$N$_6$O$_2$S (M+H)$^+$: m/z=501.2. Found: 501.1.

The diastereoisomers correspond to the (7R) and (7S) diastereoisomers of the title compound.

Example 20

5-Amino-N-{4-[(3S)-3-aminopiperidin-1-yl]-7-oxo-6,7-dihydro-5H-cyclopenta[b]pyridin-3-yl}-2-(2,6-difluorophenyl)-1,3-thiazole-4-carboxamide

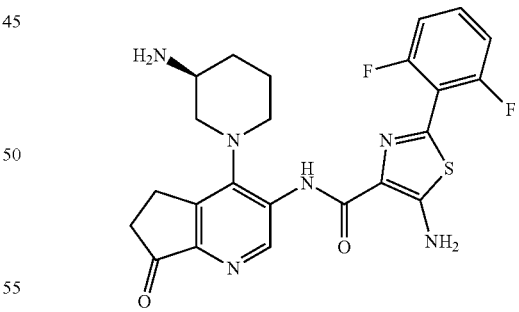

A solution of tert-butyl {(3S)-1-[3-({[5-[(tert-butoxycarbonyl)amino]-2-(2,6-difluorophenyl)-1,3-thiazol-4-yl]carbonyl}amino)-7-oxo-6,7-dihydro-5H-cyclopenta[b]pyridin-4-yl]piperidin-3-yl}carbamate (2.0 mg, 0.0029 mmol) in DCM (0.009 mL) was treated with TFA (0.01 mL, 0.1 mmol). The reaction mixture was stirred at room temperature for 1 h, concentrated and then diluted with MeOH and neutralized with NH$_4$OH. After filtration, the crude was purified by preparative LC-MS (XBridge™ preparative C18 5 μm 30×10 mm OBD™ column, flow rate 60 mL/min., eluting with a gradient of MeCN and water with 0.15% NH₄OH) to give the title compound as white powder (1.3 mg, 92%). LCMS calc. for C₂₃H₂₃F₂N₆O₂S (M+H)⁺: m/z=485.2. Found: 485.1.

Example 21

N-{4-[(3S)-3-Aminopiperidin-1-yl]-6,7-dihydro-5H-cyclopenta[b]pyridin-3-yl}-6-(2,6-difluorophenyl)-5-fluoropyridine-2-carboxamide

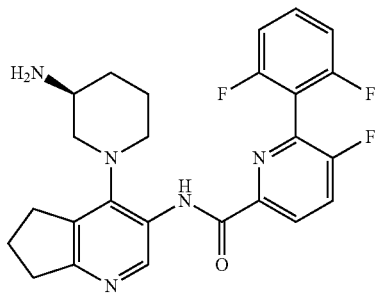 [SMILES: N[C@H]1CCCN(c2c(NC(=O)c3ccc(F)c(-c4c(F)cccc4F)n3)cnc3c2CCC3)C1]

Step 1: tert-Butyl {(3S)-1-[3-({[6-(2,6-difluorophenyl)-5-fluoropyridin-2-yl]carbonyl}amino)-6,7-dihydro-5H-cyclopenta[b]pyridin-4-yl]piperidin-3-yl}carbamate

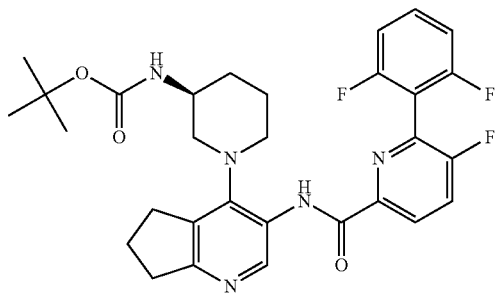 [SMILES: CC(C)(C)OC(=O)N[C@H]1CCCN(c2c(NC(=O)c3ccc(F)c(-c4c(F)cccc4F)n3)cnc3c2CCC3)C1]

tert-Butyl [(3S)-1-(3-amino-6,7-dihydro-5H-cyclopenta[b]pyridin-4-yl)piperidin-3-yl]carbamate (5.0 mg, 0.015 mmol), 6-(2,6-difluorophenyl)-5-fluoropyridine-2-carboxylic acid (4.6 mg, 0.018 mmol), HATU (14 mg, 0.038 mmol), DMF (0.035 mL) and DIPEA (5.8 mg, 0.045 mmol) were mixed together and stirred at room temperature for 1 h. The mixture was filtered, concentrated under reduced pressure and purified by preparative LC-MS (XBridge™ preparative C18 30×10 mm 5 μm OBD™ column, flow rate 60 mL/min., eluting with a gradient of MeCN and water with 0.15% NH₄OH) to give the sub-title compound as a colorless gum (4.1 mg, 48%). LCMS calc. for C₃H₃₃F₃N₅O₃ (M+H)⁺: m/z=568.3. Found: 568.1.

Step 2: N-{4-[(3S)-3-Aminopiperidin-1-yl]-6,7-dihydro-5H-cyclopenta[b]pyridin-3-yl}-6-(2,6-difluorophenyl)-5-fluoropyridine-2-carboxamide A solution of tert-butyl {(3S)-1-[3-({[6-(2,6-difluorophenyl)-5-fluoropyridin-2-yl]carbonyl}amino)-6,7-dihydro-5H-cyclopenta[b]pyridin-4-yl]piperidin-3-yl}carbamate (4.0 mg, 0.0070 mmol) in DCM (0.02 mL) was treated with TFA (0.03 mL, 0.4 mmol). The resulting reaction mixture was stirred at room temperature for 30 min. and then concentrated to give a residue, which was diluted with MeOH and neutralized with small amount of NH₄OH. After filtration, the crude was purified by preparative LC-MS (XBridge™ preparative C18 5 μm 30×10 mm OBD™ column, flow rate 60 mL/min., eluting with a gradient of MeCN and water with 0.15% NH₄OH) to afford the title compound (2.2 mg, 67%). LCMS calc. for C₂₅H₂₅F₃N₅O (M+H)⁺: m/z=468.2. Found: 468.1.

Example 22

N-{4-[(3S)-3-Aminopiperidin-1-yl]-7-hydroxy-6,7-dihydro-5H-cyclopenta[b]pyridin-3-yl}-6-(2,6-difluorophenyl)-5-fluoropyridine-2-carboxamide

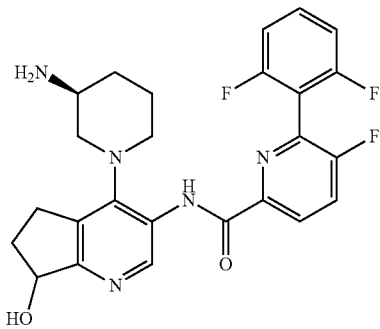 [SMILES: N[C@H]1CCCN(c2c(NC(=O)c3ccc(F)c(-c4c(F)cccc4F)n3)cnc3c2CCC3O)C1]

Step 1: 4-{(3S)-3-[(tert-Butoxycarbonyl)amino]piperidin-1-yl}-3-({[6-(2,6-difluorophenyl)-5-fluoropyridin-2-yl]carbonyl}amino)-6,7-dihydro-5H-cyclopenta[b]pyridin-7-yl Acetate

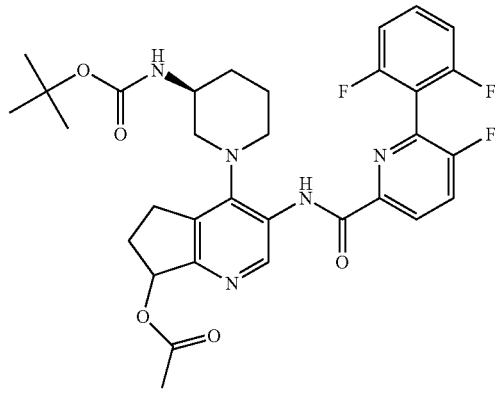 [SMILES: CC(=O)OC1CCc2c1ncc(NC(=O)c1ccc(F)c(-c3c(F)cccc3F)n1)c2N1CCC[C@H](NC(=O)OC(C)(C)C)C1]

3-Amino-4-{(3S)-3-[(tert-butoxycarbonyl)amino]piperidin-1-yl}-6,7-dihydro-5H-cyclopenta[b]pyridin-7-yl acetate (6.0 mg, 0.015 mmol), 6-(2,6-difluorophenyl)-5-fluoropyridine-2-carboxylic acid (4.7 mg, 0.018 mmol), HATU (15.0 mg, 0.038 mmol), DMF (0.036 mL) and DIPEA (6.0 mg, 0.046 mmol) were mixed together and stirred at room temperature for 1 h. The mixture was filtered, concentrated under reduced pressure, and purified by preparative LC-MS (XBridge™ preparative C18, 30×10 mm 5 μm OBD™ column, flow rate 60 mL/min., eluting with a gradient of MeCN and water with NH₄OH) to give the sub-title compound as a colorless gum (4.0 mg, 42%). LCMS calc. for $C_{32}H_{35}F_3N_5O_5$ (M+H)⁺: m/z=626.3. Found: 626.1.

Step 2: N-{4-[(3S)-3-Aminopiperidin-1-yl]-7-hydroxy-6,7-dihydro-5H-cyclopenta[b]pyridin-3-yl}-6-(2,6-difluorophenyl)-5-fluoropyridine-2-carboxamide 4-{(3S)-3-[(tert-Butoxycarbonyl)amino]piperidin-1-yl}-3-({[6-(2,6-difluorophenyl)-5-fluoropyridin-2-yl]carbonyl}amino)-6,7-dihydro-5H-cyclopenta[b]pyridin-7-yl acetate (4.0 mg, 0.0064 mmol) was mixed with MeOH (76 μL), THF (38 μL) and 1.0 M NaOH (42 μL, 0.042 mmol). The reaction mixture was stirred at room temperature for 30 min. The organic solvents were removed under reduced pressure. The aqueous layer was diluted with aq. NH₄Cl then extracted with EtOAc twice. The combined organic layers were dried, filtered and concentrated under reduced pressure to give an intermediate, which was treated with DCM (0.065 mL) and TFA (0.065 mL, 0.84 mmol). The mixture was stirred at room temperature for 30 min., then concentrated under reduced pressure. The residue was diluted with MeOH and neutralized with small amount of NH₄OH. The resulting mixture was filtered and purified by preparative LC-MS (XBridge™ preparative C18 5 μm 30×10 mm OBD™ column, flow rate 60 mL/min., eluting with a gradient of MeCN and water with 0.15% NH₄OH) to give two diastereoisomers of the title compound as white powders.

Diastereoisomer 1. First peak. Retention time 2.138 min., LCMS calc. for $C_{25}H_{25}F_3N_5O_2$ (M+H)⁺: m/z=484.2. Found: 484.0.

Diastereoisomer 2. Second peak. Retention time 2.219 min., LCMS calc. for $C_{25}H_{25}F_3N_5O_2$ (M+H)⁺: m/z=484.2. Found: 484.0. H NMR (500 MHz, CD₃CN): δ 10.80 (br, 2H), 9.52 (s, 1H), 8.39 (dd, J=8.0, 4.0 Hz, 1H), 7.93 (t, J=8.0 Hz, 1H), 4.92 (m, 1H), 3.14 (m, 1H), 3.01 (m, 2H), 2.87 (m, 1H), 2.82 (m, 2H), 2.66 (m, 1H), 2.53 (m, 2H), 2.45 (m, 2H), 1.95 (m, 1H), 1.54 (m, 1H), 1.43 (m, 1H), 0.95 (m, 1H) ppm.

The diastereoisomers correspond to the (7R) and (7S) diastereoisomers of the title compound.

Example 23

3-Amino-N-{4-[(3S)-3-aminopiperidin-1-yl]-7-hydroxy-6,7-dihydro-5H-cyclopenta[b]pyridin-3-yl}-6-(2,6-difluorophenyl)-5-fluoropyridine-2-carboxamide

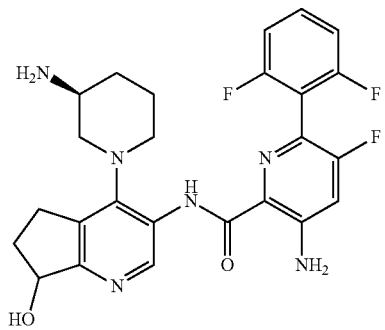 [SMILES: Nc1cc(F)c(-c2c(F)cccc2F)nc1C(=O)Nc1cnc2c(c1N1CCC[C@H](N)C1)CCC2O]

Step 1: 3-({[3-Amino-6-(2,6-difluorophenyl)-5-fluoropyridin-2-yl]carbonyl}amino)-4-{(3S)-3-[(tert-butoxycarbonyl)amino]piperidin-1-yl}-6,7-dihydro-5H-cyclopenta[b]pyridin-7-yl Acetate

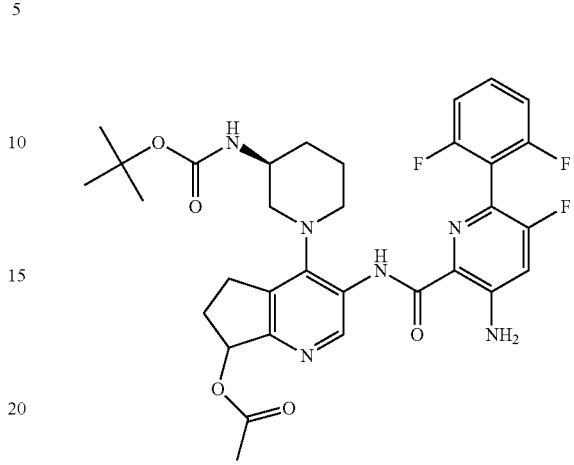

3-Amino-4-{(3S)-3-[(tert-butoxycarbonyl)amino]piperidin-1-yl}-6,7-dihydro-5H-cyclopenta[b]pyridin-7-yl acetate (6.0 mg, 0.015 mmol), 3-amino-6-(2,6-difluorophenyl)-5-fluoropyridine-2-carboxylic acid (4.9 mg, 0.018 mmol), HATU (15 mg, 0.038 mmol), DMF (0.036 mL) and DIPEA (6.0 mg, 0.046 mmol) were mixed together and stirred at room temperature for 16 h. The mixture was filtered, concentrated under reduced pressure, and purified by preparative LC-MS (XBridge™ preparative C18 5 μm 30×10 mm OBD™ column, flow rate 60 mL/min., eluting with a gradient of MeCN and water with 0.15% NH₄OH) to give the sub-title compound as a colorless gum (4 mg, 41%). LCMS calc. for $C_{32}H_{36}F_3N_6O_5$ (M+H)⁺: m/z=641.3. Found: 641.0.

Step 2: 3-Amino-N-{4-[(3S)-3-aminopiperidin-1-yl]-7-hydroxy-6,7-dihydro-5H-cyclopenta[b]pyridin-3-yl}-6-(2,6-difluorophenyl)-5-fluoropyridine-2-carboxamide 3-({[3-Amino-6-(2,6-difluorophenyl)-5-fluoropyridin-2-yl]carbonyl}amino)-4-{(3S)-3-[(tert-butoxycarbonyl)amino]piperidin-1-yl}-6,7-dihydro-5H-cyclopenta[b]pyridin-7-yl acetate (4.0 mg, 0.0062 mmol) was mixed with MeOH (74 μL), THF (37 μL) and 1.0 M NaOH (41 μL, 0.041 mmol). The reaction mixture was stirred at room temperature for 30 min. The organic solvents were removed under reduced pressure. The aqueous layer was diluted with aq. NH₄Cl, then extracted twice with EtOAc. The combined organic layers were dried, filtered and concentrated under reduced pressure to give an intermediate, which was treated with DCM (0.064 mL) and TFA (0.064 mL, 0.82 mmol). The resulting mixture was stirred at room temperature for 30 min., then concentrated under reduced pressure. The residue was diluted with MeOH and neutralized with NH₄OH. The resulting mixture was filtered and purified by preparative LC-MS (XBridge™ preparative C18 5 μm 30×10 mm OBD™ column, flow rate 60 mL/min., eluting with a gradient of MeCN and water with 0.15% NH₄OH) to give two diastereoisomers of the title compound as white powders.

Diastereoisomer 1. First peak. Retention time 1.703 min. LCMS calc. for $C_{25}H_{26}F_3N_6O_2$ (M+H)⁺: m/z=499.2. Found: 499.0.

Diastereoisomer 2. Second peak. Retention time 1.947 min. LCMS calc. for $C_{25}H_{26}F_3N_6O_2$ (M+H)$^+$: m/z=499.2. Found: 499.0. H NMR (500 MHz, DMSO-d$_6$): δ 10.58 (br, 2H), 9.37 (s, 1H), 7.56 (t, J=8.0 1H), 7.52 (br, 2H), 7.35 (m, 1H), 7.22 (s, 1H), 7.17 (s, 1H), 5.15 (s, 1H), 4.75 (m, 1H), 3.02 (m, 1H), 2.98 (m, 1H), 2.85 (m, 1H), 2.78 (m, 2H), 2.43 (m, 1H), 2.39 (m, 1H), 2.24 (m, 1H), 1.75 (m, 1H), 1.40 (m, 1H), 1.22 (m, 2H), 0.79 (m, 1H) ppm.

The diastereoisomers correspond to the (7R) and (7S) diastereoisomers of the title compound.

Example 24

5-Amino-N-{4-[3,4-trans-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 1)

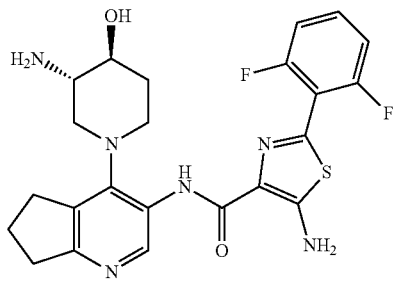 [SMILES: Nc1sc(-c2c(F)cccc2F)nc1C(=O)Nc1cnc2c(c1N1CC[C@H](O)[C@@H](N)C1)CCC2]

Step 1: Benzyl 3,6-dihydropyridine-1(2H)-carboxylate

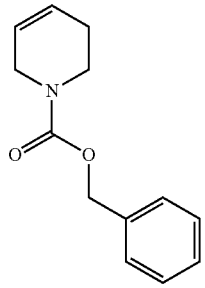 [SMILES: O=C(OCc1ccccc1)N1CC=CCC1]

1,2,3,6-Tetrahydropyridine (4.90 g, 58.9 mmol), DCM (40 mL), N-(benzyloxycarbonyloxy)succinimide (15.2 g, 61.0 mmol) and triethylamine (10.0 mL, 71.7 mmol) were mixed together and stirred at room temperature for 16 h. The reaction mixture was diluted with EtOAc and water. The organic layer was dried, filtered and concentrated under reduced pressure. The resulting residue was purified by chromatography on silica gel eluting with EtOAc in hexanes (0 to 40%) to give the sub-title compound as clear oil. LCMS calc. for $C_{13}H_{16}NO_2$ (M+H)$^+$: m/z=218.1. Found: 218.0.

Step 2: Benzyl 7-oxa-3-azabicyclo[4.1.0]heptane-3-carboxylate

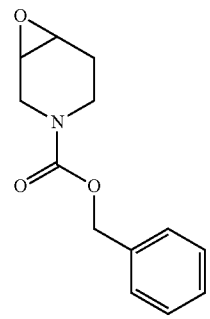 [SMILES: O=C(OCc1ccccc1)N1CCC2OC2C1]

mCPBA (14.6 g, 63.3 mmol) was added slowly to a stirred solution of benzyl 3,6-dihydropyridine-1(2H)-carboxylate (12.50 g, 57.5 mmol) in DCM (80 mL) which was cooled in an ice bath. The reaction mixture was allowed to warm to room temperature and stirred for 16 h. The reaction mixture was then quenched with aq. Na$_2$CO$_3$ and the organic layer was dried over Na$_2$SO$_4$, filtered and concentrated under reduced pressure to give the sub-title compound. LCMS calc. for $C_{13}H_{16}NO_3$ (M+H)$^+$: m/z=234.1. Found: 234.0.

Step 3: Benzyl (3R,4R)-3-[(tert-butoxycarbonyl)amino]-4-hydroxypiperidine-1-carboxylate and Benzyl (3S,4S)-3-[(tert-butoxycarbonyl)amino]-4-hydroxypiperidine-1-carboxylate

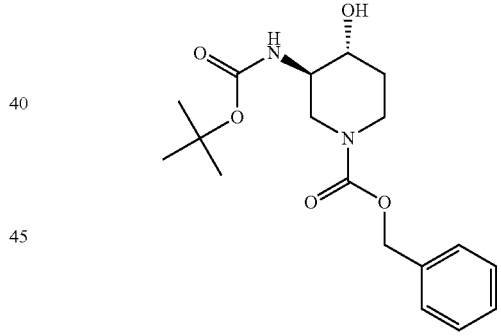

Benzyl 7-oxa-3-azabicyclo[4.1.0]heptane-3-carboxylate (13.4 g, 57.4 mmol), 14.8 M aq. NH$_4$OH (200 mL, 2.9 mol) and EtOH (200 mL) were mixed together in a sealed flask and heated at 70° C. for 5 h. The solvents were removed under reduced pressure. The residue was diluted with DCM (80 mL), then di-tert-butyl dicarbonate (12.5 g, 57.4 mmol) and triethylamine (8.0 mL, 57 mmol) were added. The reaction mixture was stirred at room temperature for 2 h. The solvent was then removed under reduced pressure and the residue was purified by silica gel column chromatography eluting with EtOAc in hexanes (0-80%) to give the sub-title compound, which was followed by chiral LC-MS separation (Phenomenex Lux® Cellulose-1 column, 21.2×250 mm, 5 micron particle, flow rate 18 mL/min., isocratic eluting with 45% EtOH in hexanes) to afford two enantiomers.

Benzyl 3,4-trans-3-[(tert-butoxycarbonyl)amino]-4-hydroxypiperidine-1-carboxylate Enantiomer 1. First peak retention time 7.163 min., LCMS calc. for $C_{18}H_{26}N_2O_5Na$ (M+Na)$^+$: m/z=373.2. Found: 373.1. (Tentatively assigned as the 3S,4S enantiomer).

Benzyl 3,4-trans-3-[(tert-butoxycarbonyl)amino]-4-hydroxypiperidine-1-carboxylate Enantiomer 2. Second peak retention time 9.247 min., LCMS calc. for $C_{18}H_{26}N_2O_5Na$ (M+Na)$^+$: m/z=373.2. Found: 373.1. (Tentatively assigned as the 3R,4R enantiomer).

LCMS calc. for $C_{18}H_{26}N_2O_5Na$ (M+Na)$^+$: m/z=373.2. Found: 373.1.

Step 4: tert-Butyl (3,4-trans-4-{[tert-butyl(dimethyl)silyl]oxy}piperidin-3-yl)carbamate (Enantiomer 1)

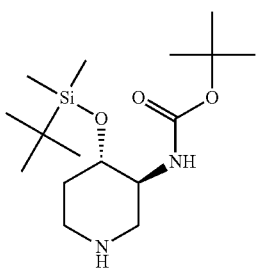 [SMILES: CC(C)(C)OC(=O)N[C@H]1CNCC[C@@H]1O[Si](C)(C)C(C)(C)C]

Benzyl 3,4-trans-3-[(tert-butoxycarbonyl)amino]-4-hydroxypiperidine-1-carboxylate (0.50 g, 1.4 mmol) (Enantiomer 1) obtained from chiral separation (step 3, peak 1) was mixed with 1H-imidazole (0.11 g, 1.6 mmol), DMAP (0.017 g, 0.14 mmol), DCM (15 mL) and tert-butyldimethylsilyl chloride (0.24 g, 1.6 mmol). The reaction mixture was stirred at room temperature for 16 h. After vacuum filtration, the filtrate was concentrated under reduced pressure, and purified by silica gel column chromatography using EtOAc in hexanes (0-30%) to give an intermediate (0.50 g). The intermediate was dissolved in EtOAc (5 mL) and MeOH (5 mL) and 10% Pd on carbon (0.10 g) was added and the reaction mixture was hydrogenated at 25 psi for 2 h. After vacuum filtration, the filtrate was concentrated under vacuum to give the sub-title compound. LCMS calc. for $C_{16}H_{35}N_2O_3Si$ (M+H)$^+$: m/z=331.2. Found: 331.3. The stereochemistry of the product was tentatively assigned as (3S,4S).

Step 5: tert-Butyl (1-(3-amino-6,7-dihydro-5H-cyclopenta[b]pyridin-4-yl)-3,4-trans-4-{[tert-butyl(dimethyl)silyl]oxy}piperidin-3-yl)carbamate (Enantiomer 1)

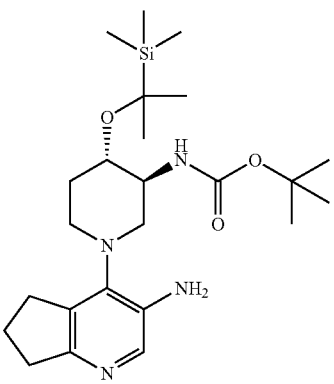 [SMILES: CC(C)(C)OC(=O)N[C@H]1CN(c2c(N)cnc3c2CCC3)CC[C@@H]1OC(C)(C)[Si](C)(C)C]

A mixture of 4-chloro-3-nitro-6,7-dihydro-5H-cyclopenta[b]pyridine (40 mg, 0.20 mmol), tert-butyl (3,4-trans-4-{[tert-butyl(dimethyl)silyl]oxy}piperidin-3-yl)carbamate (80 mg, 0.24 mmol) (Enantiomer 1) and triethylamine (0.084 mL, 0.60 mmol) in isopropyl alcohol (0.50 mL) was stirred at 70° C. for 18 h. The reaction mixture was concentrated under reduced pressure and purified by silica gel column chromatography (eluting with 0-40% EtOAc in hexanes) to give an intermediate as light yellow powder (81 mg). The intermediate was dissolved in AcOH (0.90 mL) and water (0.10 mL). Iron powder (51 mg, 0.91 mmol) was added and the reaction mixture was stirred at room temperature for 1 h. The solvent was removed under reduced pressure and the residue was diluted with EtOAc and neutralized with aq. NaHCO$_3$. The organic extract was dried over Na$_2$SO$_4$, filtered and concentrated under reduced pressure to give the sub-title compound. LCMS calc. for $C_{24}H_{43}N_4O_3Si$ (M+H)$^+$: m/z=463.3. Found: 463.1. The stereochemistry of the product was tentatively assigned as (3S,4S).

Step 6: 5-Amino-N-{4-[(3,4-trans-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 1)

A mixture containing tert-Butyl (1-(3-amino-6,7-dihydro-5H-cyclopenta[b]pyridin-4-yl)-3,4-trans-4-{[tert-butyl(dimethyl)silyl]oxy}piperidin-3-yl)carbamate (Enantiomer 1) (0.010 g, 0.022 mmol), 5-[(tert-butoxycarbonyl)amino]-2-(2,6-difluorophenyl)-1,3-thiazole-4-carboxylic acid (0.0085 g, 0.024 mmol), HATU (0.033 g, 0.086 mmol), DMF (0.15 mL) and DIPEA (0.011 g, 0.088 mmol) was stirred at room temperature for 18 h. The reaction mixture was diluted with EtOAc and washed with aq. NaOH. The organic extract concentrated under reduced pressure, and the residue was purified by silica gel column chromatography (eluting with 0-100% EtOAc in hexanes) to give an intermediate (8 mg). The intermediate was treated with HCl in dioxane (4.0 M; 2.5 mL, 10 mmol) and stirred at room temperature for 1 h then concentrated under reduced pressure. The residue was dissolved in MeOH, neutralized with aq. NH$_4$OH, and purified by preparative LC-MS (XBridge™ preparative C18 5 μm 30×10 mm OBD™ column, flow rate 60 mL/min., eluting with a gradient of MeCN and water with 0.15% NH$_4$OH) to afford the title compound. LCMS calc. for $C_{23}H_{25}F_2N_6O_2S$ (M+H)$^+$: m/z=487.2. Found: 487.1. The stereochemistry of the product was tentatively assigned as (3S,4S).

Example 25

5-Amino-N-{4-[3,4-trans-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 2)

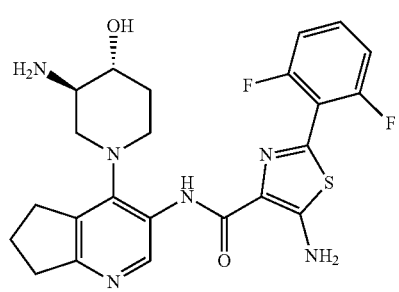 [SMILES: Nc1sc(-c2c(F)cccc2F)nc1C(=O)Nc1cnc2c(c1N1CC[C@@H](O)[C@H](N)C1)CCC2]

Step 1: tert-Butyl (3,4-trans-4-{[tert-butyl(dimethyl)silyl]oxy}piperidin-3-yl)carbamate (Enantiomer 2)

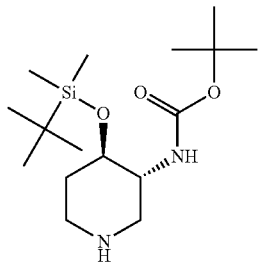 [SMILES: CC(C)(C)OC(=O)N[C@@H]1CNCC[C@H]1O[Si](C)(C)C(C)(C)C]

Benzyl 3,4-trans-3-[(tert-butoxycarbonyl)amino]-4-hydroxypiperidine-1-carboxylate (0.50 g, 1.4 mmol) (Enantiomer 2) obtained from chiral separation (Example 24, step 3, peak 2) was mixed with 1H-imidazole (0.11 g, 1.6 mmol), DMAP (0.017 g, 0.14 mmol), DCM (15 mL) and tert-butyldimethylsilyl chloride (0.24 g, 1.6 mmol). The reaction mixture was stirred at room temperature for 16 h, then filtered by vacuum filtration, and concentrated under reduced pressure. The residue was purified by silica gel column chromatography eluting with EtOAc in hexanes (0-30%) to give an intermediate (0.55 g). The intermediate was dissolved in a mixture of EtOAc (5 mL) and MeOH (5 mL), 10% Pd on carbon (0.10 g) was added, and the reaction mixture was hydrogenated at 25 psi for 2 h. The reaction mixture was then filtered by vacuum filtration through diatomaceous earth, the filtrate was concentrated under reduced pressure to give the sub-title compound. LCMS calc. for $C_{16}H_{35}N_2O_3Si$ (M+H)$^+$: m/z=331.2. Found: 331.3. The stereochemistry of the product was tentatively assigned as (3R,4R).

Step 2: tert-Butyl 1-(3-amino-6,7-dihydro-5H-cyclopenta[b]pyridin-4-yl)-3,4-trans-4-{[tert-butyl(dimethyl)silyl]oxy}piperidin-3-yl)carbamate (Enantiomer 2)

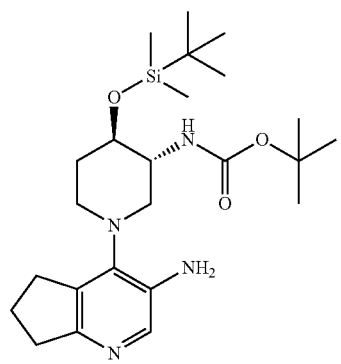 [SMILES: CC(C)(C)OC(=O)N[C@@H]1CN(c2c(N)cnc3c2CCC3)CC[C@H]1O[Si](C)(C)C(C)(C)C]

A mixture of 4-chloro-3-nitro-6,7-dihydro-5H-cyclopenta[b]pyridine (40 mg, 0.20 mmol), tert-butyl (3,4-trans-4-{[tert-butyl(dimethyl)silyl]oxy}piperidin-3-yl)carbamate (Enantiomer 2) (80 mg, 0.24 mmol) and triethylamine (0.084 mL, 0.60 mmol) in isopropyl alcohol (0.5 mL) was stirred at 70° C. for 16 h. The reaction mixture was concentrated under vacuum and purified by silica gel column chromatography (0-40% EtOAc in hexanes) to give an intermediate as light yellow powder (69.8 mg). The intermediate was dissolved in AcOH (0.90 mL) and water (0.10 mL). Iron powder was added (51 mg, 0.91 mmol) and the reaction mixture was stirred at room temperature for 1 h. The solvent was removed under vacuum and the residue was diluted with EtOAc and neutralized with aq. NaHCO$_3$. The organic layer was dried over Na$_2$SO$_4$, filtered and concentrated under reduced pressure to give the sub-title compound. LCMS calc. for $C_{24}H_{43}N_4O_3Si$ (M+H)$^+$: m/z=463.3. Found: 463.1. The stereochemistry of the product was tentatively assigned as (3R,4R).

Step 3: 5-Amino-N-{4-[3,4-trans-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 2)

A mixture containing tert-butyl 1-(3-amino-6,7-dihydro-5H-cyclopenta[b]pyridin-4-yl)-3,4-trans-4-{[tert-butyl(dimethyl)silyl]oxy}piperidin-3-yl)carbamate (Enantiomer 2) (0.010 g, 0.022 mmol), 5-[(tert-butoxycarbonyl)amino]-2-(2,6-difluorophenyl)-1,3-thiazole-4-carboxylic acid (0.0085 g, 0.024 mmol), HATU (0.033 g, 0.086 mmol), DMF (0.15 mL) and DIPEA (0.011 g, 0.088 mmol) was stirred at room temperature for 16 h. The reaction mixture was diluted with EtOAc and washed with aq. NaOH. The organic extract was concentrated under vacuum, and the residue was purified by silica gel column chromatography (eluting with 0-100% EtOAc in hexanes) to give the an intermediate (8 mg), which was treated with HCl in dioxane (4.0 M; 2.5 mL, 10 mmol). The resulting mixture was stirred at room temperature for 1 h then concentrated under reduced pressure. The residue was dissolved in MeOH, neutralized with aq. NH$_4$OH, and purified by preparative LC-MS (XBridge™ preparative C18 5 μm 30×10 mm OBD™ column, flow rate 60 mL/min., eluting with a gradient of MeCN and water with 0.15% NH$_4$OH) to provide the title compound. LCMS calc. for $C_{23}H_{25}F_2N_6O_2S$ (M+H)$^+$: m/z=487.2. Found: 487.1. $^1$H NMR (500 MHz, DMSO-d$_6$) δ 9.22 (s, 1H), 7.60 (s, 2H), 7.54-7.44 (m, 1H), 7.22 (t, J=8.7 Hz, 2H), 6.49 (s, 1H), 4.61 (d, J=2.9 Hz, 1H), 3.18-3.07 (m, 1H), 3.02 (m, 3H), 2.94-2.86 (m, 2H), 2.79 (t, J=7.7 Hz, 2H), 2.72-2.59 (m, 2H), 2.06-1.98 (m, 2H), 1.84-1.74 (m, 1H), 1.70-1.57 (m, 1H) ppm. The stereochemistry of the product was tentatively assigned as (3R,4R).

Example 26

5-Amino-N-{4-[(3,4-cis-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 1)

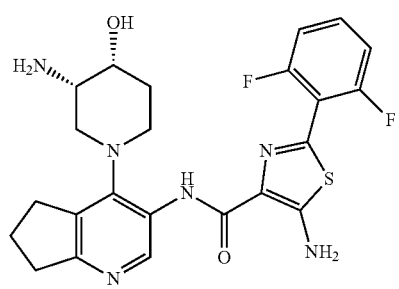 [SMILES: Nc1sc(-c2c(F)cccc2F)nc1C(=O)Nc1cnc2c(c1N1CC[C@@H](O)[C@@H](N)C1)CCC2]

Step 1: Benzyl 3,7-cis-2-oxohexahydro[1,3]oxazolo[4,5-c]pyridine-5(4H)-carboxylate (Enantiomer 1)

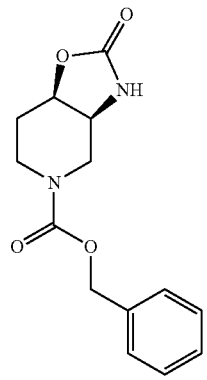 [SMILES: O=C1N[C@H]2CN(C(=O)OCc3ccccc3)CC[C@H]2O1]

Benzyl 3,4-trans-3-[(tert-butoxycarbonyl)amino]-4-hydroxypiperidine-1-carboxylate (Enantiomer 1) (0.50 g, 1.4 mmol) obtained from chiral separation (Example 24, step 3, peak 1) was mixed with DCM (12 mL), triethylamine (0.30 mL, 2.1 mmol) and methanesulfonyl chloride (0.21 g, 1.8 mmol). The reaction mixture was stirred at room temperature for 18 h and then quenched with aq. NaHCO$_3$. The aqueous layer was extracted with DCM three times. The combined organic layers were dried over Na$_2$SO$_4$, filtered and concentrated under vacuum to give the mesylate intermediate. The mesylate was then mixed with pyridine (10 mL) and heated at 120° C. for 2 h. After concentrated under vacuum, the resulting residue was purified by silica gel column chromatography (eluting with 50-100% EtOAc in hexanes) to give the sub-title compound. LCMS calc. for C$_{14}$H$_{17}$N$_2$O$_4$ (M+H)$^+$: m/z=277.1. Found: 277.1. The stereochemistry of the product was tentatively assigned as (3aS,7aR).

Step 2: tert-Butyl 3,7-cis2-oxohexahydro[1,3]oxazolo[4,5-c]pyridine-3(2H)-carboxylate (Enantiomer 1)

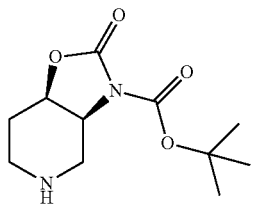 [SMILES: CC(C)(C)OC(=O)N1C(=O)O[C@@H]2CCNC[C@@H]21]

Benzyl 3,7-cis-2-oxohexahydro[1,3]oxazolo[4,5-c]pyridine-5(4H)-carboxylate (Enantiomer 1) (0.35 g, 1.3 mmol) was dissolved in DCM (6.0 mL), followed by the addition of triethylamine (0.50 mL, 3.6 mmol), DMAP (0.016 g, 0.13 mmol) and di-tert-butyl dicarbonate (0.31 g, 1.4 mmol). The reaction mixture was stirred at room temperature for 18 h then concentrated under reduced pressure. The residue was purified by silica gel column chromatography (eluting with 0-80% EtOAc in hexanes) to give an intermediate. The intermediate was mixed with EtOAc (10 mL) and MeOH (10 mL), and a mixture of 10% Pd on carbon (0.20 g). The resulting mixture was hydrogenated at 25 psi for 1 h. The catalyst was removed by vacuum filtration. The clear filtrate was concentrated under vacuum to give the sub-title compound. LCMS calc. for C$_{11}$H$_{19}$N$_2$O$_4$ (M+H)$^+$: m/z=243.1. Found: 243.1. The stereochemistry of the product was tentatively assigned as (3aS,7aR).

Step 3: tert-Butyl 3,7-cis-(3-amino-6,7-dihydro-5H-cyclopenta[b]pyridin-4-yl)-2-oxohexahydro[1,3]oxazolo[4,5-c]pyridine-3(2H)-carboxylate (Enantiomer 1)

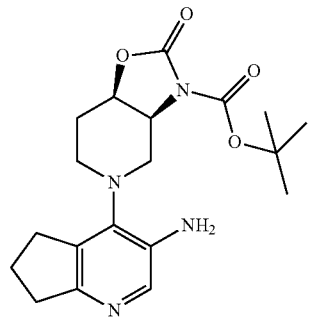 [SMILES: CC(C)(C)OC(=O)N1C(=O)O[C@@H]2CCN(c3c(N)cnc4c3CCC4)C[C@@H]21]

A mixture of 4-chloro-3-nitro-6,7-dihydro-5H-cyclopenta[b]pyridine (40 mg, 0.20 mmol), tert-butyl 3,7-cis-2-oxohexahydro[1,3]oxazolo[4,5-c]pyridine-3(2H)-carboxylate (58 mg, 0.24 mmol) (Enantiomer 1) and triethylamine (0.084 mL, 0.60 mmol) in isopropyl alcohol (0.50 mL) was stirred at 70° C. for 18 h. The mixture was concentrated and purified by silica gel column chromatography (eluting with 20-80% EtOAc in hexanes) to give an intermediate as a yellow powder (31 mg). The intermediate was dissolved in AcOH (0.90 mL, 16 mmol) and water (0.10 mL). Iron powder (51 mg, 0.91 mmol) was added, and the reaction mixture was stirred at room temperature for 1 h. The solvent was removed under vacuum and the residue was diluted with EtOAc and neutralized with aq. NaHCO$_3$. The organic extract was dried over Na$_2$SO$_4$, filtered and concentrated under reduced pressure to give the sub-title compound. LCMS calc. for C$_{19}$H$_{27}$N$_4$O$_4$ (M+H)$^+$: m/z=375.2. Found: 375.1. The stereochemistry of the product was tentatively assigned as (3aS,7aR).

Step 4: 5-Amino-N-{4-[3,4-cis-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 1)

A mixture containing tert-butyl 3,7-cis-5-(3-amino-6,7-dihydro-5H-cyclopenta[b]pyridin-4-yl)-2-oxohexahydro[1,3]oxazolo[4,5-c]pyridine-3(2H)-carboxylate (0.010 g, 0.027 mmol), 5-[(tert-butoxycarbonyl)amino]-2-(2,6-difluorophenyl)-1,3-thiazole-4-carboxylic acid (0.010 g, 0.029 mmol), HATU (0.041 g, 0.11 mmol), DMF (0.15 mL) and DIPEA (0.014 g, 0.11 mmol) was stirred at room temperature for 18 h. The reaction mixture was diluted with EtOAc and washed with aq. NaOH. The combined organic extract was concentrated under reduced pressure, and the residue was purified by silica gel column chromatography (eluting with 0-100% EtOAc in hexanes) to give an intermediate (7 mg). The intermediate was dissolved in MeOH (0.38 mL) and cesium carbonate (0.050 g, 0.15 mmol) was added. The resulting mixture was heated at 80° C. for 30 min., then filtrated and concentrated under reduced pressure. The residue was dissolved in TFA (0.50 mL, 6.5 mmol) and the reaction mixture was stirred at room temperature for 1 h. The solvent was removed under reduced pressure, and the residue was dissolved in MeOH, neutralized with aq. NH$_4$OH. The crude product was purified by preparative LC-MS (XBridge™ preparative C18 5 μm 30×10 mm OBD™ column, flow rate 60 mL/min., eluting with a gradient of MeCN and water with 0.15% NH$_4$OH) to afford the title compound. LCMS calc. for C$_{23}$H$_{25}$F$_2$N$_6$O$_2$S (M+H)$^+$: m/z=487.2. Found: 487.1. The stereochemistry of the product was tentatively assigned as (3S,4R).

Example 27

5-Amino-N-{4-[3.4-cis-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 2)

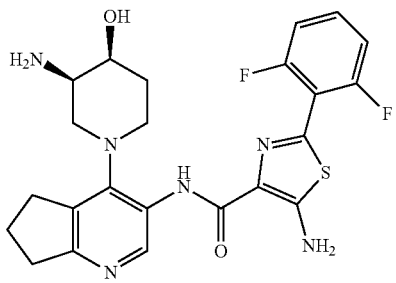 [SMILES: Nc1sc(-c2c(F)cccc2F)nc1C(=O)Nc1cnc2c(c1N1CC[C@H](O)[C@H](N)C1)CCC2]

Step 1: Benzyl 3,7-cis-2-oxohexahydro[1,3]oxazolo[4,5-c]pyridine-5(4H)-carboxylate (Enantiomer 2)

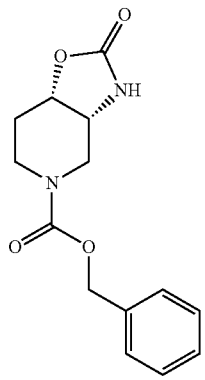 [SMILES: O=C1N[C@@H]2CN(C(=O)OCc3ccccc3)CC[C@@H]2O1]

Benzyl 3,4-trans-3-[(tert-butoxycarbonyl)amino]-4-hydroxypiperidine-1-carboxylate (0.50 g, 1.4 mmol) (Enantiomer 2) obtained from chiral separation (Example 24, step 3, peak 2) was mixed with DCM (12 mL), triethylamine (0.30 mL, 2.1 mmol) and methanesulfonyl chloride (0.21 g, 1.8 mmol) and the reaction mixture was stirred at room temperature for 18 h. The mixture was quenched with aq. NaHCO$_3$. The aqueous layer was extracted with DCM three times. The combined organic extracts were dried over Na$_2$SO$_4$, filtered and concentrated under reduced pressure to give a mesylate intermediate. The mesylate was then mixed with pyridine (10 mL, 100 mmol) and heated at 120° C. for 2 h, then the reaction mixture was concentrated reduced pressure. The residue was purified by silica gel column chromatography (eluting with 50-100% EtOAc in hexanes) to give the sub-title compound. LCMS calc. for C$_{14}$H$_{17}$N$_2$O$_4$ (M+H)$^+$: m/z=277.1. Found: 277.1. The stereochemistry of the product was tentatively assigned as (3aR,7aS).

Step 2: tert-Butyl 3,7-cis-2-oxohexahydro[1,3]oxazolo[4,5-c]pyridine-3(2H)-carboxylate (Enantiomer 2)

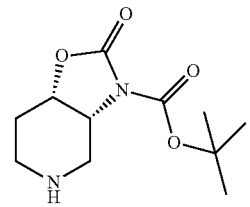 [SMILES: CC(C)(C)OC(=O)N1C(=O)O[C@H]2CCNC[C@H]21]

A mixture containing benzyl 3,7-cis-2-oxohexahydro[1,3]oxazolo[4,5-c]pyridine-5(4H)-carboxylate (0.32 g, 1.2 mmol) (Enantiomer 2), DCM (10 mL), triethylamine (0.18 mL, 1.3 mmol), DMAP (0.014 g) and di-tert-butyl dicarbonate (0.28 g, 1.3 mmol) was stirred at room temperature for 18 h, then concentrated under reduced pressure. The mixture was purified by silica gel column chromatography (eluting with 0-80% EtOAc in hexanes) to give an intermediate. The intermediate was mixed with EtOAc (10 mL) of and MeOH (10 mL), and a and 10% Pd on carbon (0.20 g). The resulting mixture was hydrogenated at 25 psi for 1 h. The catalyst was removed by vacuum filtration. The clear filtrate was concentrated under vacuum to give the sub-title compound. LCMS calc. for C$_{11}$H$_{19}$N$_2$O$_4$ (M+H)$^+$: m/z=243.1. Found: 243.1. The stereochemistry of the product was tentatively assigned as (3aR,7aS).

Step 3: tert-Butyl 3,7-cis-5-(3-amino-6,7-dihydro-5H-cyclopenta[b]pyridin-4-yl)-2-oxohexahydro[1,3]oxazolo[4,5-c]pyridine-3(2H)-carboxylate (Enantiomer 2)

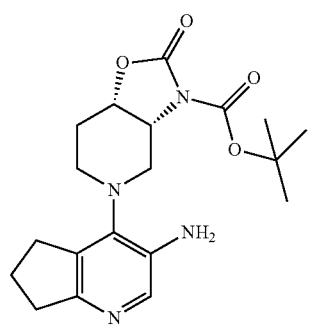 [SMILES: CC(C)(C)OC(=O)N1C(=O)O[C@H]2CCN(c3c(N)cnc4c3CCC4)C[C@H]21]

A mixture of 4-chloro-3-nitro-6,7-dihydro-5H-cyclopenta[b]pyridine (40 mg, 0.20 mmol), tert-butyl 3,7-cis-2-oxohexahydro[1,3]oxazolo[4,5-c]pyridine-3(2H)-carboxylate (58 mg, 0.24 mmol) (Enantiomer 2) and triethylamine (0.084 mL, 0.60 mmol) in isopropyl alcohol (0.50 mL) was stirred at 70° C. for 18 h. The reaction mixture was concentrated under reduced pressure and the resulting residue was purified by silica gel column chromatography (eluting with 0-80% EtOAc/hexanes) to give an intermediate as light yellow powder. The intermediate was dissolved into AcOH (0.90 mL, 16 mmol) and water (0.10 mL), and iron powder (51 mg, 0.91 mmol) was added. The reaction mixture was stirred at room temperature for 1 h. The solvent was removed under reduced pressure and the residue was diluted with EtOAc and neutralized with aq. NaHCO$_3$. The organic extract was dried over Na$_2$SO$_4$, filtered and concentrated under reduced pressure to give the sub-title compound. LCMS calc. for C$_{19}$H$_{27}$N$_4$O$_4$ (M+H)$^+$: m/z=375.2. Found: 375.1. The stereochemistry of the product was tentatively assigned as (3aR,7aS).

Step 4: 5-Amino-N-{4-[3,4-cis-3-amino-4-hydroxypiperidin-1-yl]-6,7-dihydro-5H-cyclopenta[b]pyridin-3-yl}-2-(2,6-difluorophenyl)-1,3-thiazole-4-carboxamide (Enantiomer 2)

A mixture containing tert-butyl 3,7-cis-5-(3-amino-6,7-dihydro-5H-cyclopenta[b]pyridin-4-yl)-2-oxohexahydro[1,3]oxazolo[4,5-c]pyridine-3(2H)-carboxylate (Enantiomer 2) (0.010 g, 0.027 mmol), 5-[(tert-butoxycarbonyl)amino]-2-(2,6-difluorophenyl)-1,3-thiazole-4-carboxylic acid (0.010 g, 0.029 mmol), HATU (0.041 g, 0.11 mmol), DMF (0.15 mL) and DIPEA (0.014 g, 0.11 mmol) was stirred at room temperature for 18 h. The reaction mixture was diluted with EtOAc and washed with aq. NaOH. The organic extract was concentrated under reduced pressure, and the resulting residue was purified by silica gel column chromatography (eluting with 0-100% EtOAc in hexanes) to give an intermediate (7 mg). The intermediate was dissolved in MeOH (0.38 mL) and cesium carbonate (0.050 g, 0.15 mmol) was added. The resulting mixture was heated at 80° C. for 30 min., then filtered, and concentrated under reduced pressure. The residue was dissolved in TFA (0.50 mL, 6.5 mmol) and the resulting mixture was stirred at room temperature for 1 h. The solvent was removed under reduced pressure, and the residue was dissolved in MeOH, neutralized with aq. NH$_4$OH and then purified by preparative LC-MS (XBridge™ preparative C18 5 μm 30×10 mm OBD™ column, flow rate 60 mL/min., eluting with a gradient of MeCN and water with 0.15% NH$_4$OH) to afford the title compound. LCMS calc. for C$_{23}$H$_{25}$F$_2$N$_6$O$_2$S (M+H)$^+$: m/z=487.2. Found: 487.1. The stereochemistry of the product was tentatively assigned as (3S,4R).

Example 28

5-Amino-N-{4-[(3R,4R,5S)-3-amino-4-hydroxy-5-methylpiperidin-1-yl]-6,7-dihydro-5H-cyclopenta[b]pyridin-3-yl}-2-(2,6-difluorophenyl)-1,3-thiazole-4-carboxamide

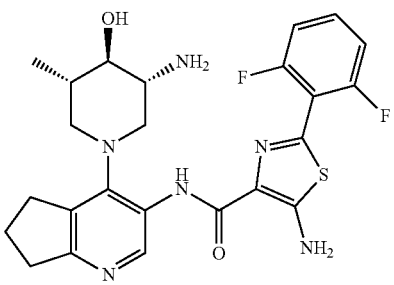 [SMILES: C[C@H]1CN(c2c(NC(=O)c3nc(-c4c(F)cccc4F)sc3N)cnc3c2CCC3)C[C@@H](N)[C@@H]1O]

Step 1. tert-Butyl (4R)-4-{(R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate

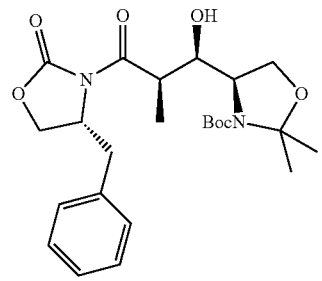 [SMILES: C[C@@H](C(=O)N1C(=O)OC[C@H]1Cc1ccccc1)[C@@H](O)[C@H]1COC(C)(C)N1C(=O)OC(C)(C)C]

To a solution of (R)-3-(1-oxopropyl)-4-benzyl-2-oxazolidinone (Aldrich, 2.0 g, 8.6 mmol) in DCM (60 mL) at −40° C., a solution of TiCl$_4$ in DCM (1.0 M, 10.0 mL, 10.0 mmol) was added. The mixture was stirred at −40° C. for 10 min., then DIPEA (3.7 mL, 21 mmol) was added. The reaction mixture was allowed to warm to 0° C. and stirred for 20 min. A solution of tert-butyl (4R)-4-formyl-2,2-dimethyl-1,3-oxazolidine-3-carboxylate (Aldrich, 2.0 g, 8.7 mmol) in DCM (20 mL) was then added dropwise and the resulting mixture was stirred for 1.5 h. The reaction was quenched by the addition of a saturated aq. NH$_4$Cl and the mixture was extracted with EtOAc. The organic extract was washed with brine, dried over MgSO$_4$, and concentrated under reduced pressure. The residue was purified by chromatography on silica gel (0-40% EtOAc in hexanes) to give the sub-title compound as the major product (5:2) in 87% yield (3.44 g). LCMS calc. for C$_{24}$H$_{34}$N$_2$NaO$_7$ (M+Na)$^+$: m/z=485.2; found 485.1.

Step 2. tert-butyl(4R)-4-((R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate

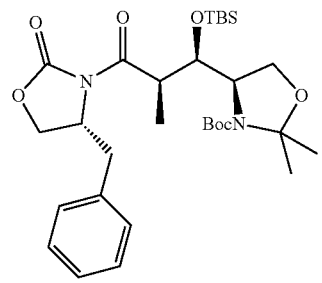 [SMILES: C[C@@H](C(=O)N1C(=O)OC[C@H]1Cc1ccccc1)[C@@H](O[Si](C)(C)C(C)(C)C)[C@H]1COC(C)(C)N1C(=O)OC(C)(C)C]

To a solution of tert-butyl (4R)-4-{(1R,2R)-3-[(4R)-4-benzyl-2-oxo-1,3-oxazolidin-3-yl]-1-hydroxy-2-methyl-3-oxopropyl}-2,2-dimethyl-1,3-oxazolidine-3-carboxylate (2.0 g, 4.3 mmol) in DCM (40 mL) at −40° C., 2,6-lutidine (0.90 mL, 7.8 mmol) was added, followed by tert-butyldimethylsilyl trifluoromethanesulfonate (1.4 mL, 6.0 mmol). The mixture was stirred at −40° C. for 2 h. The reaction mixture was diluted with EtOAc, washed with a saturated aq. NaHCO$_3$ and brine, then dried over MgSO$_4$, and concentrated under reduced pressure. The residue was purified by chromatography on silica gel (0-20% EtOAc in hexanes) to afford the sub-title compound (2.2 g, 88%). LCMS calc. for $C_3H_{49}N_2O_7Si$ (M+H)$^+$: m/z=577.3; found 577.3.

Step 3. tert-Butyl (4R)-4-((1R,2S)-1-{[tert-butyl (dimethyl)silyl]oxy}-3-hydroxy-2-methylpropyl)-2,2-dimethyl-1,3-oxazolidine-3-carboxylate

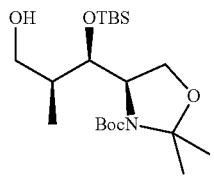 [SMILES: C[C@@H](CO)[C@@H](O[Si](C)(C)C(C)(C)C)[C@H]1COC(C)(C)N1C(=O)OC(C)(C)C]

LiBH$_4$ (0.25 g, 11 mmol) was added to a mixture of tert-butyl (4R)-4-((1R,2R)-3-[(4R)-4-benzyl-2-oxo-1,3-oxazolidin-3-yl]-1-{[tert-butyl(dimethyl)silyl]oxy}-2-methyl-3-oxopropyl)-2,2-dimethyl-1,3-oxazolidine-3-carboxylate (2.2 g, 3.8 mmol) and EtOH (0.67 mL, 11 mmol) in THF (40 mL) at −30° C. The mixture was allowed to warm to 0° C. and stirred for 3 h. The reaction mixture was then diluted with ether and 1N NaOH was added. The resulting mixture was extracted with EtOAc. The organic extract was washed with brine, dried over MgSO$_4$, and concentrated under reduced pressure. The residue was purified by chromatography on silica gel (0-20% EtOAc in hexanes) to afford the sub-title compound (1.2 g, 78%). LCMS calc. for $C_{15}H_{34}NO_3Si$ (M+H−Boc)$^+$: m/z=304.2; found 304.2.

Step 4. tert-Butyl (4R)-4-((R,2S)-3-azido-1-{[tert-butyl(dimethyl)silyl]oxy}-2-methylpropyl)-2,2-dimethyl-1,3-oxazolidine-3-carboxylate

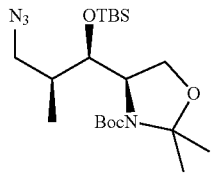 [SMILES: C[C@@H](CN=[N+]=[N-])[C@@H](O[Si](C)(C)C(C)(C)C)[C@H]1COC(C)(C)N1C(=O)OC(C)(C)C]

To a mixture of tert-butyl (4R)-4-((1R,2S)-1-{[tert-butyl (dimethyl)silyl]oxy}-3-hydroxy-2-methylpropyl)-2,2-dimethyl-1,3-oxazolidine-3-carboxylate (1.2 g, 3.0 mmol), DIAD (1.2 mL, 5.9 mmol) and PPh$_3$ (1.6 g, 5.9 mmol) in THF (20 mL), diphenylphosphonic azide (1.3 mL, 5.9 mmol) was added. The mixture was stirred at room temperature overnight. The reaction mixture was concentrated under reduced pressure. The residue was purified by chromatography on silica gel (0-15% EtOAc in hexanes) to provide the sub-title compound (1.09 g, 86%). LCMS calc. for $C_{15}H_{33}N_4O_2Si$ (M+H−Boc)$^+$: m/z=329.2; found 329.2.

Step 5. tert-Butyl [(R,2R,3S)-4-azido-2-{[tert-butyl (dimethyl)silyl]oxy}-1-(hydroxymethyl)-3-methyl-butyl]carbamate

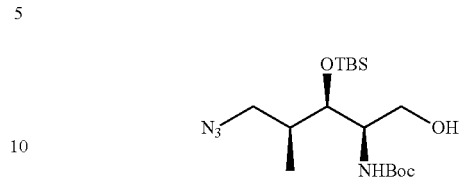

To a solution of tert-butyl (4R)-4-((1R,2S)-3-azido-1-{[tert-butyl(dimethyl)silyl]oxy}-2-methylpropyl)-2,2-dimethyl-1,3-oxazolidine-3-carboxylate (1.09 g, 2.6 mmol) in EtOH (15 mL), pyridinium p-toluenesulfonate (1.3 g, 5.2 mmol) was added. The mixture was heated under reflux for 2 days. After cooling to room temperature, the reaction mixture was concentrated under reduced pressure. The residue was dissolved in DCM (25 mL), and DIPEA (0.67 mL, 3.8 mmol) was added followed by di-tert-butyl dicarbonate (0.67 g, 3.1 mmol). The mixture was stirred at room temperature for 5 h, and then concentrated under reduced pressure. The residue was purified by chromatography on silica gel (0-25% EtOAc in hexanes) to afford the sub-title compound (0.56 g, 56%). LCMS calc. for $C_{12}H_{29}N_4O_2Si$ (M+H−Boc)$^+$: m/z=289.2; found 289.2.

Step 6. (2R,3R,4S)-5-Azido-2-[(tert-butoxycarbonyl)amino]-3-{[tert-butyl(dimethyl)silyl]oxy}-4-methylpentyl methanesulfonate

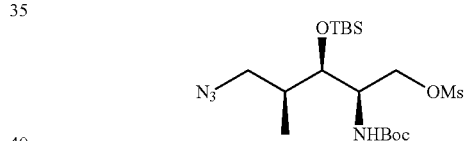

To a solution of tert-butyl [(1R,2R,3S)-4-azido-2-{[tert-butyl(dimethyl)silyl]oxy}-1-(hydroxymethyl)-3-methyl-butyl]carbamate (0.56 g, 1.4 mmol) in pyridine (7.3 mL) at 0° C., methanesulfonyl chloride (0.14 mL, 1.9 mmol) was added followed by DMAP (0.04 g, 0.3 mmol). After stirring at 0° C. for 1 h, the mixture was diluted with EtOAc, washed with saturated aq. NaHCO$_3$ and brine, then dried over MgSO$_4$ and concentrated under reduced pressure. The residue was purified by chromatography on silica gel (0-25% EtOAc in hexanes) to afford the sub-title compound (0.59 g, 88%). LCMS calc. for $C_{13}H_{31}N_4O_4SSi$ (M+H−Boc)$^+$: m/z=367.2; found 367.2.

Step 7. tert-butyl ((3R,4R,5S)-4-{[tert-butyl(dimethyl)silyl]oxy}-5-methylpiperidin-3-yl)carbamate

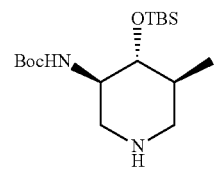 [SMILES: C[C@H]1CNC[C@@H](NC(=O)OC(C)(C)C)[C@@H]1O[Si](C)(C)C(C)(C)C]

A solution of (2R,3R,4S)-5-azido-2-[(tert-butoxycarbonyl)amino]-3-{[tert-butyl(dimethyl)silyl]oxy}-4-methylpentyl methanesulfonate (0.59 g, 1.3 mmol) in MeOH (10 mL) was deoxygenated with $N_2$ for 20 min. DIPEA (0.55 mL, 3.2 mmol) was added, followed by 10 wt % Pd on carbon (0.1 g, 0.1 mmol). The mixture was hydrogenated at 1 atm. for 2 h, and then filtered. The filtrate was concentrated to afford the sub-title compound (0.43 g, 98%). LCMS calc. for $C_{17}H_{37}N_2O_3Si$ $(M+H)^+$: m/z=345.3; found 345.2. $^1H$ NMR (500 MHz, CDCl$_3$) δ 4.35 (bs, 1H), 3.32 (dt, J=13.1, 6.3 Hz, 1H), 3.25 (d, J=12.3 Hz, 1H), 3.04 (t, J=8.8 Hz, 1H), 2.94 (ddd, J=13.1, 4.1, 1.5 Hz, 1H), 2.33 (dd, J=12.6, 10.5 Hz, 1H), 2.24 (dd, J=13.1, 10.9 Hz, 1H), 1.76 (bs, 1H), 1.55 (tdd, J=8.9, 6.7, 4.2 Hz, 1H), 1.41 (s, 9H), 0.92 (d, J=6.6 Hz, 3H), 0.87 (s, 9H), 0.07 (d, J=10.3 Hz, 6H) ppm.

Step 8: tert-Butyl ((3R,4R,5S)-1-(3-amino-6,7-dihydro-5H-cyclopenta[b]pyridin-4-yl)-4-{[tert-butyl(dimethyl)silyl]oxy}-5-methylpiperidin-3-yl)carbamate

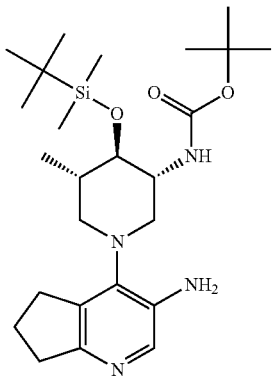 [SMILES: C[C@H]1CN(c2c(N)cnc3c2CCC3)C[C@@H](NC(=O)OC(C)(C)C)[C@@H]1O[Si](C)(C)C(C)(C)C]

A mixture of 4-chloro-3-nitro-6,7-dihydro-5H-cyclopenta[b]pyridine (40 mg, 0.20 mmol), tert-butyl ((3R,4R,5S)-4-{[tert-butyl(dimethyl)silyl]oxy}-5-methylpiperidin-3-yl)carbamate (83 mg, 0.24 mmol) and triethylamine (0.084 mL, 0.60 mmol) in isopropyl alcohol (0.50 mL) was stirred at 70° C. for 18 h. The reaction mixture was concentrated under reduced pressure and purified by silica gel column chromatography (eluting with 20-80% EtOAc in hexanes) to give an intermediate as a yellow powder (43 mg). The intermediate was dissolved in EtOH (1.0 mL) and water (0.10 mL). Iron powder (51 mg, 0.91 mmol) and $NH_4Cl$ (54 mg, 1.0 mmol) were added and the reaction mixture was stirred at 80° C. for 1 h. The solvent was removed under reduced pressure and the residue was diluted with EtOAc and DCM. After vacuum filtration, the clear filtrate was concentrated under reduced pressure to give the sub-sub-title compound. LCMS calc. for $C_{25}H_{45}N_4O_3Si$ $(M+H)^+$: m/z=477.3. Found: 477.1.

Step 9: 5-Amino-N-{4-[(3R,4R,5S)-3-amino-4-hydroxy-5-methylpiperidin-1-yl]-6,7-dihydro-5H-cyclopenta[b]pyridin-3-yl}-2-(2,6-difluorophenyl)-1,3-thiazole-4-carboxamide A mixture containing tert-butyl ((3R,4R,5S)-1-(3-amino-6,7-dihydro-5H-cyclopenta[b]pyridin-4-yl)-4-{[tert-butyl(dimethyl)silyl]oxy}-5-methylpiperidin-3-yl)carbamate (0.020 g, 0.042 mmol), 5-[(tert-butoxycarbonyl)amino]-2-(2,6-difluorophenyl)-1,3-thiazole-4-carboxylic acid (0.016 g, 0.046 mmol), HATU (0.064 g, 0.17 mmol), DMF (0.29 mL) and DIPEA (0.022 g, 0.17 mmol) was stirred at room temperature for 18 h. The reaction mixture was diluted with EtOAc and washed with NaOH solution. The combined organic extract was concentrated under reduced pressure, and the residue was purified by silica gel column chromatography (eluting with 0-100% EtOAc in hexanes) to give an intermediate (8 mg). The intermediate was treated with HCl in dioxane (4.0 M; 4.8 mL, 19 mmol) at room temperature for 1 h. The reaction mixture was concentrated under reduced pressure and the residue was dissolved in MeOH, neutralized with $NH_4OH$ solution, and purified by preparative LC-MS (XBridge™ preparative C18 5 μm 30×10 mm OBD™ column, flow rate 60 mL/min., eluting with a gradient of MeCN and water with 0.15% $NH_4OH$) to give the title compound. LCMS calc. for $C_{24}H_{27}F_2N_6O_2S$ $(M+H)^+$: m/z=501.2. Found: 501.1.

Example 29

5-Amino-N-{7-[3,4-trans-3-amino-4-hydroxypiperidin-1-yl]thieno[3,2-b]pyridin-6-yl}-2-(2,6-difluorophenyl)-1,3-thiazole-4-carboxamide (Enantiomer 2)

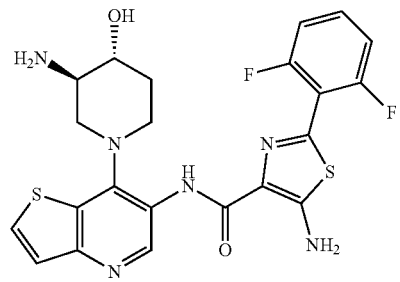 [SMILES: Nc1sc(-c2c(F)cccc2F)nc1C(=O)Nc1cnc2ccsc2c1N1CC[C@@H](O)[C@H](N)C1]

Step 1: tert-Butyl (1-(6-aminothieno[3,2-b]pyridin-7-yl)-3,4-trans-4-{[tert-butyl(dimethyl)silyl]oxy}piperidin-3-yl)carbamate (Enantiomer 2)

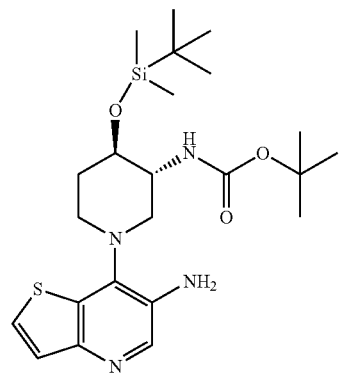 [SMILES: CC(C)(C)OC(=O)N[C@@H]1CN(c2c(N)cnc3ccsc23)CC[C@H]1O[Si](C)(C)C(C)(C)C]

A mixture of 7-chloro-6-nitrothieno[3,2-b]pyridine (Example 5, step 2, 43 mg, 0.20 mmol), tert-butyl ((3R,4R)-4-{[tert-butyl(dimethyl)silyl]oxy}piperidin-3-yl)carbamate (Enantiomer 2) (Example 25, step 1, 80 mg, 0.24 mmol) and triethylamine (0.084 mL, 0.60 mmol) in isopropyl alcohol (0.50 mL) was stirred at 70° C. for 18 h. The reaction mixture was concentrated and purified by silica gel column chromatography (eluting with 20-40% EtOAc in hexanes) to give an intermediate as light yellow powder. The intermediate was dissolved in AcOH (0.90 mL, 16 mmol) and water (0.10 mL). Iron powder (51 mg, 0.91 mmol) was added and the reaction mixture was stirred at room temperature for 1 h. The solvent was removed under reduced pressure and the residue was diluted with EtOAc and neutralized with aq. NaHCO$_3$. The organic extract was dried over Na$_2$SO$_4$, filtered and concentrated under reduced pressure to give the sub-title compound. LCMS calc. for C$_{23}$H$_{39}$N$_4$O$_3$SSi (M+H)$^+$: m/z=479.2. Found: 479.1. The stereochemistry of the product was tentatively assigned as (3R,4R).

Step 2: 5-Amino-N-{7-[3,4-trans-3-amino-4-hydroxypiperidin-1-yl]thieno[3,2-b]pyridin-6-yl}-2-(2,6-difluorophenyl)-1,3-thiazole-4-carboxamide (Enantiomer 2)

A mixture containing tert-butyl ((3R,4R)-1-(6-aminothieno[3,2-b]pyridin-7-yl)-4-{[tert-butyl(dimethyl)silyl]oxy}piperidin-3-yl)carbamate (Enantiomer 2) (0.010 g, 0.022 mmol), 5-[(tert-butoxycarbonyl)amino]-2-(2,6-difluorophenyl)-1,3-thiazole-4-carboxylic acid (0.0085 g, 0.024 mmol), HATU (0.033 g, 0.086 mmol), DMF (0.15 mL) and DIPEA (0.011 g, 0.088 mmol) was stirred at room temperature for 18 h. The reaction mixture was diluted with EtOAc and washed with aq. NaOH. The combined organic extract was concentrated under reduced pressure, and the residue was purified by silica gel column chromatography (eluting with 0-100% EtOAc in hexanes) to give an intermediate (8 mg). The intermediate was treated with HCl in dioxane (4.0 M; 2.5 mL, 10 mmol) and stirred at room temperature for 1 h. The solution was evaporated under reduced pressure, the residue was dissolved in MeOH, neutralized with aq. NH$_4$OH, and purified by preparative LC-MS (XBridge™ preparative C18 5 μm 30×10 mm OBD™ column, flow rate 60 mL/min., eluting with a gradient of MeCN and water with 0.15% NH$_4$OH) to afford the title compound. LCMS calc. for C$_{22}$H$_{21}$F$_2$N$_6$O$_2$S$_2$ (M+H)$^+$: m/z=503.1. Found: 503.1. The stereochemistry was tentatively assigned as (3R,4R).

Example 30

5-Amino-N-{7-[3,4-cis-3-amino-4-hydroxypiperidin-1-yl]thieno[3,2-b]pyridin-6-yl}-2-(2,6-difluorophenyl)-1,3-thiazole-4-carboxamide (Enantiomer 2)

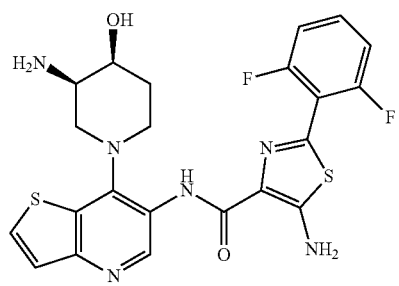 [SMILES: Nc1sc(-c2c(F)cccc2F)nc1C(=O)Nc1cnc2ccsc2c1N1CC[C@H](O)[C@H](N)C1]

Step 1: tert-Butyl 3,7-cis-5-(6-aminothieno[3,2-b]pyridin-7-yl)-2-oxohexahydro[1,3]oxazolo[4,5-c]pyridine-3(2H)-carboxylate (Enantiomer 2)

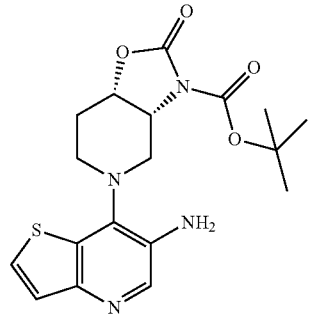 [SMILES: CC(C)(C)OC(=O)N1C(=O)O[C@H]2CCN(c3c(N)cnc4ccsc34)C[C@H]21]

A mixture of 7-chloro-6-nitrothieno[3,2-b]pyridine (43.2 mg, 0.201 mmol), tert-butyl 3,7-cis-2-oxohexahydro[1,3]oxazolo[4,5-c]pyridine-3(2H)-carboxylate (Enantiomer 2) (Example 27 step 2, 58 mg, 0.24 mmol) and triethylamine (0.084 mL, 0.60 mmol) in isopropyl alcohol (0.50 mL) was stirred at 70° C. for 18 h. The reaction mixture was concentrated under reduced pressure and purified by silica gel column chromatography (eluting with 0-80% EtOAc in hexanes) to give an intermediate as light yellow powder (81 mg). The intermediate was dissolved in AcOH (0.90 mL, 16 mmol) and water (0.10 mL). Iron powder (51 mg, 0.91 mmol) was added and the reaction mixture was stirred at room temperature for 1 h. The solvent was removed under reduced pressure and the residue was diluted with EtOAc, then neutralized with aq. NaHCO$_3$. The organic extract was dried over Na$_2$SO$_4$, filtered and concentrated under reduced pressure to give the sub-title compound. LCMS calc. for C$_{18}$H$_{23}$N$_4$O$_4$S (M+H)$^+$: m/z=391.1. Found: 391.1. The stereochemistry of the product was tentatively assigned as (3aR,7aS).

Step 2: 5-Amino-N-{7-[(3R,4S)-3-amino-4-hydroxypiperidin-1-yl]thieno[3,2-b]pyridin-6-yl}-2-(2,6-difluorophenyl)-1,3-thiazole-4-carboxamide (Enantiomer 2)

A mixture containing tert-butyl (3aR,7aS)-5-(6-aminothieno[3,2-b]pyridin-7-yl)-2-oxohexahydro[1,3]oxazolo[4,5-c]pyridine-3(2H)-carboxylate (Enantiomer 2) (0.010 g, 0.027 mmol), 5-[(tert-butoxycarbonyl)amino]-2-(2,6-difluorophenyl)-1,3-thiazole-4-carboxylic acid (0.010 g, 0.029 mmol), HATU (0.041 g, 0.11 mmol), DMF (0.15 mL) and DIPEA (0.014 g, 0.11 mmol) was stirred at room temperature for 18 h. The reaction mixture was diluted with EtOAc and washed with aq. NaOH. The combined organic extract was concentrated under reduced pressure, and the residue was purified by silica gel column chromatography (eluting with 0-100% EtOAc in hexanes) to give an intermediate (8 mg). The intermediate was dissolved in MeOH (0.38 mL) and cesium carbonate (0.050 g, 0.15 mmol) was added. The resulting mixture was heated at 80° C. for 30 min., then filtered and concentrated under reduced pressure. The residue was dissolved in TFA (0.50 mL, 6.5 mmol) and the resulting mixture was stirred at room temperature for 1 h. The solvent was removed under reduced pressure, and the residue was dissolved in MeOH, neutralized with NH$_4$OH solution and then purified by preparative LC-MS (XBridge™ preparative C18 5 μm 30×10 mm OBD™ column, flow rate 60 mL/min., eluting with a gradient of MeCN and water with 0.15% NH₄OH) to give the title compound. LCMS calc. for $C_{26}H_{21}F_2N_6O_2S_2(M+H)^+$: m/z=503.1. Found: 503.1. The stereochemistry of the product was tentatively assigned as (3R,4S).

Example 31

5-Amino-N-{4-[(3S)-3-aminopiperidin-1-yl]-5,6,7,8-tetrahydro-1,8-naphthyridin-3-yl}-2-(2,6-difluorophenyl)-1,3-thiazole-4-carboxamide

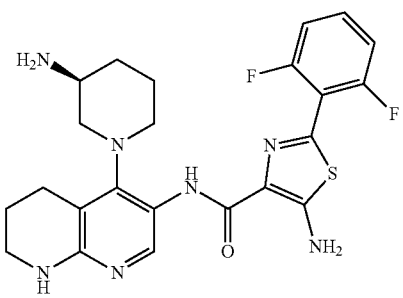 [SMILES: Nc1sc(-c2c(F)cccc2F)nc1C(=O)Nc1cnc2c(c1N1CCC[C@H](N)C1)CCCN2]

Step 1. 3-(3-Chloropropyl)-2-fluoro-4-iodopyridine

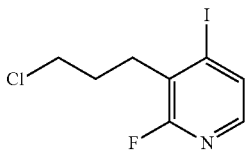 [SMILES: Fc1nccc(I)c1CCCCl]

Lithium diisopropylamide in THF (2.0 M; 12 mL, 24 mmol) was added to a mixture of 2-fluoro-3-iodopyridine (Alfa Aesar, 5.0 g, 22 mmol) in THF (50 mL) at −78° C. The solution was stirred at −78° C. for 1 h, then a solution of 1-chloro-3-iodo-propane, (5.0 g, 24 mmol) in 15 mL THF was added dropwise. The reaction mixture was stirred at −78° C. for 30 min., then allowed to warm to room temperature. The reaction mixture was quenched with aq. NH₄Cl and extracted with EtOAc. The combined organic extract was dried over Na₂SO₄ and concentrated under reduced pressure. The residue was purified by column chromatography on silica gel using CombiFlash® apparatus, eluting with 0 to 50% EtOAc/hexanes, to give the sub-title compound (6.2 g, 92%). LCMS calc. for $C_8H_9ClFIN$ (M+H)⁺: m/z=299.9. Found: 300.1.

Step 2. 5-Iodo-1,2,3,4-tetrahydro-1,8-naphthyridine

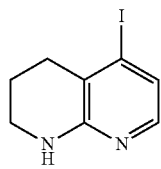 [SMILES: Ic1ccnc2c1CCCN2]

A mixture of 3-(3-chloropropyl)-2-fluoro-4-iodopyridine (5.0 g, 17 mmol), NH₄OH (100 mL, 800 mmol), ammonium acetate (18 g, 230 mmol), potassium iodide (5.5 g, 33 mmol), potassium carbonate (12 g, 87 mmol) and DMF (26 mL) was heated at 60° C. for 8 h. The mixture allowed to cool, and diluted with EtOAc. The layers were separated and the organic layer was washed with brine, dried with MgSO₄, then concentrated under reduced pressure. The residue was purified by column chromatography on silica gel using CombiFlash® apparatus, eluting with 0 to 50% EtOAc in hexanes, to give the sub-title compound (3.0 g, 69% yield). LCMS calc. for $C_8H_{10}IN_2$ (M+H)⁺: m/z=261.0; Found: 261.1.

Step 3. 5-Iodo-6-nitro-1,2,3,4-tetrahydro-1,8-naphthyridine

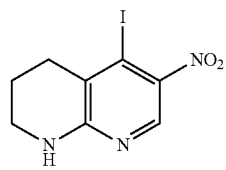 [SMILES: O=[N+]([O-])c1cnc2c(c1I)CCCN2]

Fuming nitric acid (0.5 mL, 10 mmol) was added a mixture of 5-iodo-1,2,3,4-tetrahydro-1,8-naphthyridine (1.0 g, 3.8 mmol) in sulfuric acid (10 mL) at 0° C. The reaction was allowed to warm to room temperature and stirred for 30 min. The mixture was poured into ice-water and neutralized with 3 M aq. NaOH. The resulting solid precipitate was collected by filtration, washed with water and dried to give the sub-title compound (0.50 g, 43%). LCMS calc. for $C_8H_9IN_3O_2$ (M+H)⁺: m/z=306.0; Found: 306.1.

Step 4. tert-Butyl [(3S)-1-(3-nitro-5,6,7,8-tetrahydro-1,8-naphthyridin-4-yl)piperidin-3-yl]carbamate

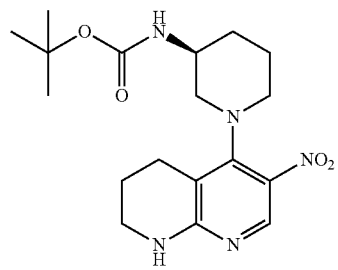 [SMILES: CC(C)(C)OC(=O)N[C@H]1CCCN(c2c([N+](=O)[O-])cnc3c2CCCN3)C1]

A mixture of 5-iodo-6-nitro-1,2,3,4-tetrahydro-1,8-naphthyridine (0.50 g, 1.6 mmol), tert-butyl (3S)-piperidin-3-ylcarbamate (0.39 g, 2.0 mmol), DIPEA (0.64 g, 5.0 mmol)

and 1-butanol (6 mL) was heated at 140° C. for 14 h, then allowed to cool. The solvent was removed under reduced pressure, then the residue was diluted with EtOAc and washed with aq. Na₂CO₃ solution. The organic layer was washed with water and brine, dried and concentrated under reduced pressure. The residue was purified by column chromatography on silica gel using CombiFlash® apparatus, eluting with 10 to 90% EtOAc in hexanes, to give the sub-title compound (0.55 g, 89%). LCMS calc. for $C_{18}H_{28}N_5O_4$ (M+H)⁺: m/z=378.2; Found: 378.1.

Step 5. tert-Butyl 5-{(3S)-3-[(tert-butoxycarbonyl)amino]piperidin-1-yl}-6-nitro-3,4-dihydro-1,8-naphthyridine-1(2H)-carboxylate

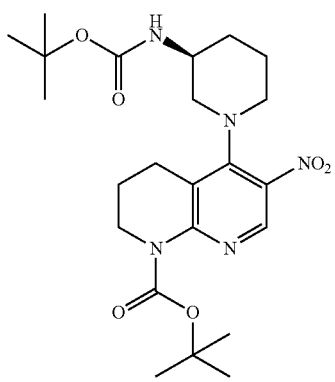

A mixture of tert-butyl [(3S)-1-(3-nitro-5,6,7,8-tetrahydro-1,8-naphthyridin-4-yl)piperidin-3-yl]carbamate (0.55 g, 1.4 mmol), di-tert-butyl dicarbonate (0.35 g, 1.6 mmol), DMAP (0.18 g, 1.4 mmol) and MeCN (10 mL) was stirred at room temperature for 2 h. The reaction mixture was concentrated under reduced pressure. The residue was purified by column chromatography on silica gel using CombiFlash® apparatus, eluting with 20-100% EtOAc in hexanes, to give 0.60 g (86%) of sub-title compound as a white solid. LCMS calc. for $C_{23}H_{36}N_5O_6$ (M+H)⁺: m/z=478.3; Found: 478.1.

Step 6. tert-Butyl 6-amino-5-{(3S)-3-[(tert-butoxycarbonyl)amino]piperidin-1-yl}-3,4-dihydro-1,8-naphthyridine-1(2H)-carboxylate

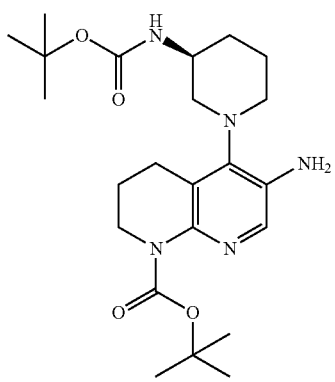 [SMILES: CC(C)(C)OC(=O)N[C@H]1CCCN(c2c([N+](=O)[O-])cnc3c2CCCN3C(=O)OC(C)(C)C)C1]

Iron powder (0.26 g, 4.6 mmol) was added to a mixture containing tert-butyl 5-{(3S)-3-[(tert-butoxycarbonyl)amino]piperidin-1-yl}-6-nitro-3,4-dihydro-1,8-naphthyridine-1(2H)-carboxylate (0.60 g, 1.2 mmol), AcOH (9 mL), and water (1 mL). The reaction mixture was stirred at room temperature for 2 h. The solution was filtered and the filtrate was concentrated under reduced pressure. The residue was diluted with EtOAc (50 mL) and filtered. The filtrate was neutralized with saturated aq. NaHCO₃. The organic layer was washed with brine, dried with Na₂SO₄ and concentrated under reduced pressure to give the sub-title compound (0.51 g, 90%). LCMS calc. for $C_{23}H_{38}N_5O_4$ (M+H)⁺: m/z=448.3; Found: 448.1.

Step 7. 5-Amino-N-{4-[(3S)-3-aminopiperidin-1-yl]-5,6,7,8-tetrahydro-1,8-naphthyridin-3-yl}-2-(2,6-difluorophenyl)-1,3-thiazole-4-carboxamide

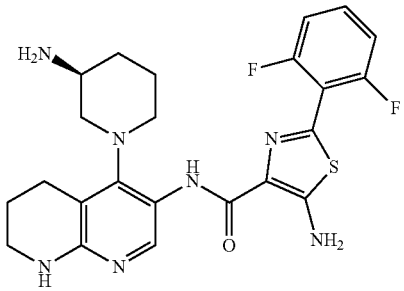 [SMILES: Nc1sc(-c2c(F)cccc2F)nc1C(=O)Nc1cnc2c(c1N1CCC[C@H](N)C1)CCCN2]

A mixture of tert-butyl 6-amino-5-{(3S)-3-[(tert-butoxycarbonyl)amino]piperidin-1-yl}-3,4-dihydro-1,8-naphthyridine-1(2H)-carboxylate (0.049 g, 0.11 mmol), 5-[(tert-butoxycarbonyl)amino]-2-(2,6-difluorophenyl)-1,3-thiazole-4-carboxylic acid (0.039 g, 0.11 mmol) and HATU (0.063 g, 0.16 mmol) in DMF (2 mL), and DIPEA (0.021 g, 0.16 mmol) was stirred at 50° C. for 2 h. The reaction mixture was diluted with EtOAc and washed with aq. NaHCO₃, water and brine. The organic extract was dried with Na₂SO₄, concentrated and the resulting residue was purified by preparative LC-MS (XBridge™ preparative C18 5 μm 30×10 mm OBD™ column, flow rate 60 mL/min., eluting with a gradient of MeCN and water with 0.1% TFA) to give a Boc-protected intermediate, LCMS (M+1): 786.1. The intermediate was treated with 50% TFA in DCM (2 mL) and the resulting mixture stirred at room temperature for 1 h. The solvent was removed under reduced pressure. The residue was purified by preparative LC-MS (XBridge™ preparative C18 5 μm 30×10 mm OBD™ column, flow rate 60 mL/min., eluting with a gradient of MeCN and water with 0.15%

NH₄OH) to afford the title compound (5 mg, 10%). LCMS calc. for $C_{23}H_{26}F_2N_7OS$ (M+H)⁺: m/z=486.2; Found: 486.1. ¹H NMR (DMSO-d₆, 300 MHz): δ 9.24 (s, 1H), 7.99 (s, 3H), 7.56 (m, 3H), 7.28 (t, J=8.4 Hz, 2H), 6.63 (br s, 1H), 3.35-3.65 (m, 5H), 3.20 (m, 4H), 2.70 (m, 2H), 2.00 (m, 1H), 1.78 (m, 3H), 1.42 (m, 1H) ppm.

Example 32

3-Amino-N-{4-[(3S)-3-aminopiperidin-1-yl]-5,6,7,8-tetrahydro-1,8-naphthyridin-3-yl}-6-(2,6-difluorophenyl)-5-fluoropyridine-2-carboxamide

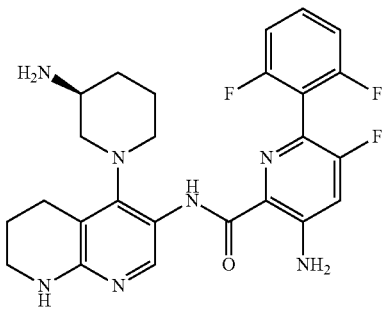 [SMILES: Nc1cc(F)c(-c2c(F)cccc2F)nc1C(=O)Nc1cnc2c(c1N1CCC[C@H](N)C1)CCCN2]

A mixture containing tert-butyl 6-amino-5-{(3S)-3-[(tert-butoxycarbonyl)amino]piperidin-1-yl}-3,4-dihydro-1,8-naphthyridine-1(2H)-carboxylate (0.030 g, 0.067 mmol), 3-[(tert-butoxycarbonyl)amino]-6-(2,6-difluorophenyl)-5-fluoropyridine-2-carboxylic acid (0.022 g, 0.060 mmol), HATU (0.04 g, 0.1 mmol), DMF (2 mL), and DIPEA (0.021 g, 0.16 mmol) was stirred at 50° C. for 2 h. The reaction mixture was diluted with EtOAc and washed with aq. NaHCO₃, water and brine. The organic extract was dried with Na₂SO₄ then concentrated under reduced pressure. The resulting residue was purified by preparative LC-MS (XBridge™ preparative C18 5 μm 30×10 mm OBD™ column, flow rate 60 mL/min., eluting with a gradient of MeCN and water with 0.1% TFA) to give a Boc-protected intermediate, LCMS (M+H): 798.1. The intermediate was treated with 50% TFA in DCM (2 mL) and stirred at room temperature for 1 h. The solvent was removed under reduced pressure. The resulting residue was purified using preparative LC-MS (XBridge™ preparative C18 5 μm 30×10 mm OBD™ column, flow rate 60 mL/min., eluting with a gradient of MeCN and water with 0.15% NH₄OH) to afford the title compound (4 mg, 13%). LCMS calc. for $C_{25}H_{27}F_3N_7O$ (M+H)⁺: m/z=498.2; Found: 498.2. ¹H NMR (DMSO-d₆, 300 MHz): δ 10.31 (s, 1H), 8.80 (s, 1H), 7.60 (m, 1H), 7.35 (br s, 2H), 7.20 (m, 2H), 6.23 (s, 1H), 3.33 (s, 3H), 3.09 (m, 2H), 2.82 (m, 2H), 2.62 (m, 2H), 1.66 (m, 2H), 1.17 (m, 2H), 1.05 (m, 1H), 0.80 (m, 1H) ppm.

Example 33

N-{4-[(3S)-3-Aminopiperidin-1-yl]-5,6,7,8-tetrahydro-1,8-naphthyridin-3-yl}-6-(2,6-difluorophenyl)-5-fluoropyridine-2-carboxamide

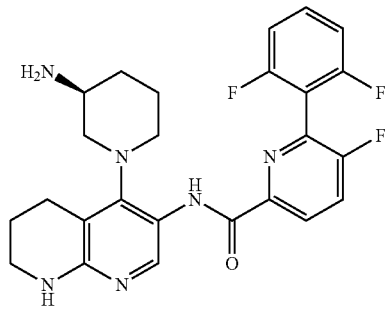 [SMILES: N[C@H]1CCCN(c2c(NC(=O)c3ccc(F)c(-c4c(F)cccc4F)n3)cnc3c2CCCN3)C1]

A mixture containing tert-butyl 6-amino-5-{(3S)-3-[(tert-butoxycarbonyl)amino]piperidin-1-yl}-3,4-dihydro-1,8-naphthyridine-1(2H)-carboxylate (0.049 g, 0.11 mmol), 6-(2,6-difluorophenyl)-5-fluoropyridine-2-carboxylic acid (0.028 g, 0.11 mmol) and HATU (0.063 g, 0.16 mmol) DIPEA (0.021 g, 0.16 mmol) and DMF (2 mL), was stirred at 50° C. for 2 h. The reaction mixture was diluted with EtOAc and washed with aq. NaHCO₃, water and brine. The organic extract was dried with Na₂SO₄ and concentrated under reduced pressure. The resulting residue was purified by preparative LC-MS (XBridge™ preparative C18 5 μm 30×10 mm OBD™ column, flow rate 60 mL/min., eluting with a gradient of MeCN and water with 0.1% TFA) to give a Boc-protected intermediate, LCMS (M+H): 782.1. The intermediate was treated with 50% TFA in DCM (2 mL) and stirred at room temperature for 1 h. The solvent was removed under reduced pressure. The resulting residue was purified using preparative LC-MS (XBridge™ preparative C18 5 μm 30×10 mm OBD™ column, flow rate 60 mL/min., eluting with a gradient of MeCN and water with 0.15% NH₄OH) to afford the title compound (5 mg, 10%). LCMS calc. for $C_{25}H_{26}F_3N_6O$ (M+H)⁺: m/z=483.2; Found: 483.1. ¹H NMR (DMSO-d₆, 300 MHz): δ 10.23 (s, 1H), 8.35 (m, 1H), 8.23 (t, J=9.0 Hz, 1H), 8.06 (br s, 4H), 7.70 (m, 1H), 7.37 (m, 2H), 3.33 (s, 3H), 2.90-3.10 (m, 4H), 2.67 (m, 2H), 1.77 (m, 3H), 1.54 (m, 2H), 1.29 (m, 1H) ppm.

Example 34

5-Amino-N-{4-[(3S)-3-aminopiperidin-1-yl]-1H-pyrazolo[3,4-b]pyridin-5-yl}-2-(2,6-difluorophenyl)-1,3-thiazole-4-carboxamide

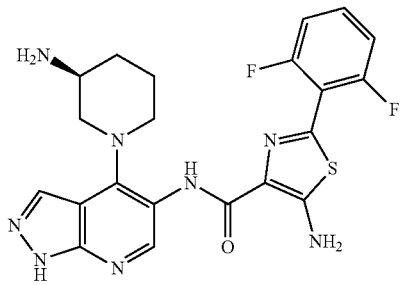 [SMILES: Nc1sc(-c2c(F)cccc2F)nc1C(=O)Nc1cnc2[nH]ncc2c1N1CCC[C@H](N)C1]

Step 1. 1-(4Methoxybenzyl)-1H-pyrazol-5-amine

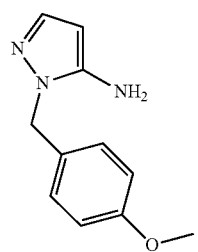

Hydrazine (10 mL, 320 mmol) was added over 10 min. to a vigorously stirred solution of 2-propenenitrile (22.3 mL, 339 mmol) in EtOH (100 mL), which was cooled in an ice-water bath to below 20° C. After stirring for 20 h, the reaction mixture was cooled in an ice-water bath, and 4-methoxybenzaldehyde (41.1 mL, 338 mmol) was added slowly. The reaction mixture was stirred at room temperature for 60 h. The solution was concentrated under reduced pressure and the residue was dissolved in isopropyl alcohol (100 mL). NaOH (7 g, 200 mmol) was added and the resulting mixture was heated at 120° C. for 2 h. The solution was concentrated under reduced pressure and the residue was diluted with water and EtOAc. The layers were separated and the aqueous layer was then extracted with further EtOAc. The combined organic extract was washed with 1 M HCl. The HCl layers were combined and the pH was adjusted to 14 using NaOH. The resulting slurry was extracted with DCM. The DCM layers were dried over $Na_2SO_4$, filtered and concentrated under reduced pressure to afford 21 g of the sub-title compound (30%). LCMS calc. for $C_{11}H_{14}N_3O$ $(M+H)^+$: m/z=204.1; Found: 204.2.

Step 2. Ethyl 4-hydroxy-1-(4-methoxybenzyl)-H-pyrazolo[3,4-b]pyridine-5-carboxylate

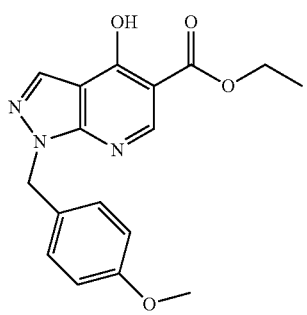 [SMILES: CCOC(=O)c1cnc2c(cnn2Cc2ccc(OC)cc2)c1O]

A mixture of 1-(4-methoxybenzyl)-1H-pyrazol-5-amine (3 g, 10 mmol) and (ethoxymethylene)propanedioic acid, diethyl ester (3.8 g, 18 mmol) was heated at 120° C. for 1.5 h, then allowed to cool. After cooling, the mixture was concentrated and the resulting residue was purified with CombiFlash® eluting with 0-30% EtOAc in hexanes to give an intermediate, LCMS (M+H): 374.1. The intermediate was dissolved in diphenyl ether (5 mL). The resulted solution was heated at 240° C. in microwave reactor for 1 h 20 min. After cooling, the solid crashed out was filtered and washed with hexanes to afford 4.0 g (80%) of the sub-title compound. LCMS calc. for $C_{17}H_{18}N_3O_4$ $(M+H)^+$: m/z=328.1; Found: 328.1.

Step 3. Ethyl 4-chloro-1-(4-methoxybenzyl)-1H-pyrazolo[3,4-b]pyridine-5-carboxylate

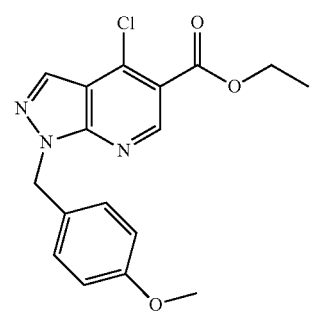 [SMILES: CCOC(=O)c1cnc2c(cnn2Cc2ccc(OC)cc2)c1Cl]

To a solution of ethyl 1-(4-methoxybenzyl)-4-oxo-4,7-dihydro-1H-pyrazolo[3,4-b]pyridine-5-carboxylate (4.0 g, 13 mmol) in 1,2-dichloroethane (9.8 mL) was added $POCl_3$ (2.4 mL, 26 mmol). The resulting mixture was heated at 90° C. for 3 h. After cooling, the most volatile were removed by vacuum, and the residue was diluted with EtOAc and washed with aq. $Na_2CO_3$ solution. The organic layer was washed water and brine, dried and concentrated under reduced pressure. The residue was purified by column chromatography on silica gel using CombiFlash® apparatus, eluting with 10 to 60% EtOAc in hexanes, to give the sub-title compound (3.9 g, 95%). LCMS calc. for $C_{17}H_{17}ClN_3O_3$ $(M+H)^+$: m/z=346.1; Found: 346.1.

Step 4. Ethyl 4-{(3S)-3-[(tert-butoxycarbonyl)amino]piperidin-1-yl}-1-(4-methoxybenzyl)-1H-pyrazolo[3,4-b]pyridine-5-carboxylate

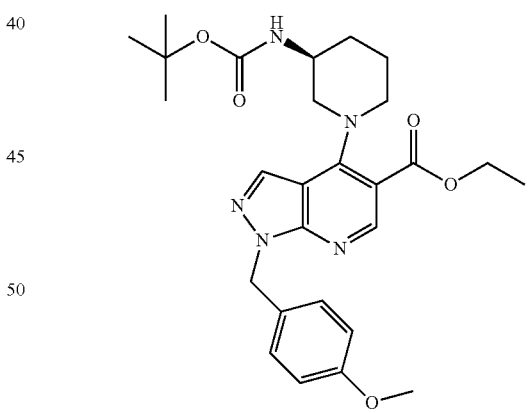

A mixture of ethyl 4-chloro-1-(4-methoxybenzyl-1H-pyrazolo[3,4-b]pyridine-5-carboxylate (1.5 g, 4.3 mmol), tert-butyl (3S)-piperidin-3-ylcarbamate (1.0 g, 5.0 mmol) and DIPEA (0.84 g, 6.5 mmol) in 1-butanol (10 mL) was heated to 140° C. for 14 h, then allowed to cool. The mixture was concentrated under reduced pressure, and the resulting residue was diluted with EtOAc and washed with aq. $NaHCO_3$. The organic extract was washed with water and brine, dried and concentrated under reduced pressure. The residue was purified by column chromatography on silica gel using CombiFlash® apparatus, eluting with 20-100%

EtOAc in hexanes, to give the sub-title compound (1.9 g, 86%). LCMS calc. for C$_{27}$H$_{36}$N$_5$O$_5$ (M+H)$^+$: m/z=510.3; Found: 510.2.

Step 5. 4-{(3S)-3-[(tert-Butoxycarbonyl)amino]piperidin-1-yl}-1-(4-methoxybenzyl)-1H-pyrazolo[3,4-b]pyridine-5-carboxylic Acid

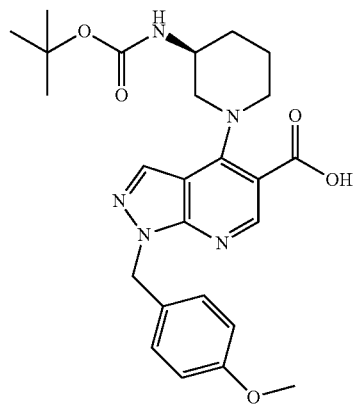 [SMILES: COc1ccc(Cn2ncc3c(N4CCC[C@H](NC(=O)OC(C)(C)C)C4)c(C(=O)O)cnc32)cc1]

Water (5 mL) and lithium hydroxide (1.5 g, 63 mmol) were added to a solution of ethyl 4-{(3S)-3-[(tert-butoxycarbonyl)amino]piperidin-1-yl}-1-(4-methoxybenzyl)-1H-pyrazolo[3,4-b]pyridine-5-carboxylate (1.9 g, 3.7 mmol) in MeOH (5 mL) and THF (5 mL). The mixture heated at 50° C. with stirring for 2 h. The mixture was allowed to cool to room and concentrated under reduced pressure. The residue was neutralized with 2N HCl and extracted twice with EtOAc. The organic extract was dried with Na$_2$SO$_4$ and concentrated under reduced pressure to give the sub-title compound (1.6 g (89%). LCMS calc. for C$_{25}$H$_{32}$N$_5$O$_5$ (M+H)$^+$: m/z=482.2; Found: 482.1.

Step 6. tert-Butyl {(3S)-1-[5-[(tert-butoxycarbonyl)amino]-1-(4-methoxybenzyl)-H-pyrazolo[3,4-b]pyridin-4-yl]piperidin-3-yl}carbamate

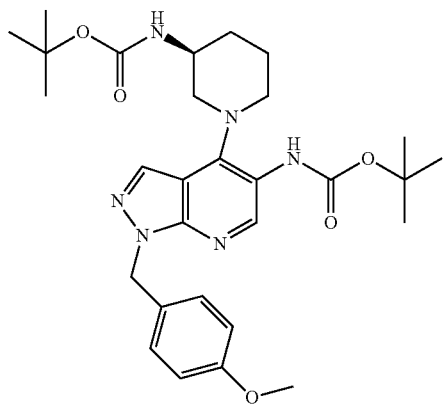 [SMILES: COc1ccc(Cn2ncc3c(N4CCC[C@H](NC(=O)OC(C)(C)C)C4)c(NC(=O)OC(C)(C)C)cnc32)cc1]

A mixture of 4-{(3S)-3-[tert-butoxycarbonyl)amino]piperidin-1-yl}-1-(4-methoxybenzyl)-1H-pyrazolo[3,4-b]pyridine-5-carboxylic acid (1.0 g, 2.1 mmol), diphenylphosphonic azide (0.58 mL, 2.7 mmol) and DIPEA (0.72 mL, 4.2 mmol) in tert-butyl alcohol (20 mL) heated under reflux overnight. The solution was then evaporated under reduced pressure. The resulting residue was dissolved in DCM, washed with 1 M aq. NaOH and brine, then dried over Na$_2$SO$_4$ and evaporated under reduced pressure. The residue was purified by column chromatography on silica gel using CombiFlash® apparatus, eluting with 0 to 50% EtOAc/hexanes, to give the sub-title compound as a brown oil (0.50 g, 44%). LCMS calc. for C$_{29}$H$_{41}$N$_6$O$_5$ (M+H)$^+$: m/z=553.3; Found: 553.2.

Step 7. tert-Butyl {(3S)-1-[5-amino-1-(4-methoxybenzyl)-H-pyrazolo[3,4-b]pyridin-4-yl]piperidin-3-yl}carbamate

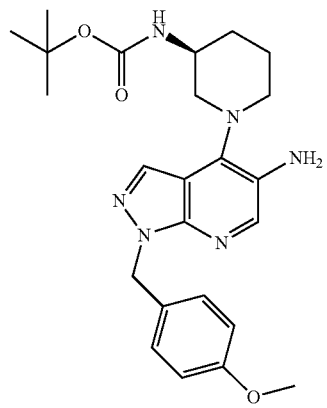 [SMILES: COc1ccc(Cn2ncc3c(N4CCC[C@H](NC(=O)OC(C)(C)C)C4)c(N)cnc32)cc1]

A mixture of tert-butyl {(3S)-1-[5-[(tert-butoxycarbonyl)amino]-1-(4-methoxybenzyl)-1H-pyrazolo[3,4-b]pyridin-4-yl]piperidin-3-yl}carbamate (0.50 g, 0.90 mmol) and HCl in dioxane (4.0 M; 10 mL, 40 mmol) was stirred at room temperature for 2 h. The solution was then evaporated under reduced pressure. The resulting residue was dissolved in THF (10 mL), and di-tert-butyl dicarbonate (0.20 g, 0.92 mmol) in THF (5 mL) and triethylamine (0.37 g, 3.6 mmol) were added. The mixture was stirred at room temperature for 3 h. The reaction mixture was then diluted with EtOAc and the resulting solution was washed with aq. NaHCO$_3$ and brine. The organic layer was then dried over Na$_2$SO$_4$ and concentrated under reduced pressure. The residue was purified by column chromatography on silica gel using CombiFlash® apparatus, eluting with 20 to 100% EtOAc in hexanes, to give 0.30 g (73%) of the sub-title compound. LCMS calc. for C$_{24}$H$_{33}$N$_6$O$_3$ (M+H)$^+$: m/z=453.3; Found: 453.1.

Step 8. 5-Amino-N-{4-[(3S)-3-aminopiperidin-1-yl]-H-pyrazolo[3,4-b]pyridin-5-yl}-2-(2,6-difluorophenyl)-1,3-thiazole-4-carboxamide A mixture containing tert-butyl {(3S)-1-[5-amino-1-(4-methoxybenzyl)-1H-pyrazolo[3,4-b]pyridin-4-yl]piperidin-3-yl}carbamate (0.050 g, 0.11 mmol), 5-[(tert-butoxycarbonyl)amino]-2-(2,6-difluorophenyl)-1,3-thiazole-4-carboxylic acid (0.043 g, 0.12 mmol), HATU (0.063 g, 0.16 mmol), DIPEA (0.021 g, 0.16 mmol) and DMF (2 mL) was stirred at 50° C. for 2 h, then allowed to cool. The reaction mixture was diluted with EtOAc and the resulting solution was washed with aq. NaHCO$_3$, water and brine, then dried with Na$_2$SO$_4$, and concentrated under reduced pressure. The residue was purified by preparative LC-MS (XBridge™ preparative C18 5 μm 30×10 mm OBD™ column, flow rate 60 mL/min., eluting with a gradient of MeCN and water with 0.1% TFA) to give a Boc-protected intermediate (15 mg), LCMS (M+H): 791.1. The intermediate was treated with 50% TFA in DCM (2 mL) and stirred at room temperature for 1 h. The solvent was removed under reduced pressure. The residue was purified by preparative LC-MS (XBridge™ preparative C18 5 μm 30×10 mm OBD™ column, flow rate 60 mL/min., eluting with a gradient of MeCN and water with 0.15% NH$_4$OH) to afford the title compound (5 mg, 10%). LCMS calc. for $C_{21}H_{21}F_2N_8OS$ (M+H)$^+$: m/z=471.1; Found: 471.1.

Example 35

N-{4-[(3S)-3-aminopiperidin-1-yl]-1H-pyrazolo[3,4-b]pyridin-5-yl}-2-(2,6-difluorophenyl)-1,3-thiazole-4-carboxamide

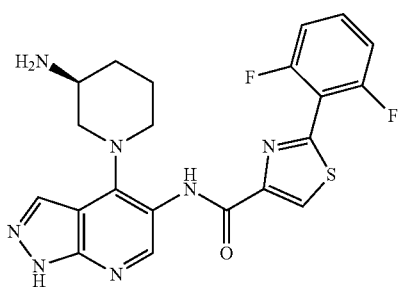 [SMILES: N[C@H]1CCCN(c2c(NC(=O)c3csc(-c4c(F)cccc4F)n3)cnc3[nH]ncc23)C1]

A mixture containing tert-butyl {(3S)-1-[5-amino-1-(4-methoxybenzyl)-1H-pyrazolo[3,4-b]pyridin-4-yl]piperidin-3-yl}carbamate (0.050 g, 0.11 mmol), 2-(2,6-difluorophenyl)-1,3-thiazole-4-carboxylic acid (0.029 g, 0.12 mmol), HATU (0.063 g, 0.16 mmol), DIPEA (0.021 g, 0.16 mmol) and DMF (2 mL) was stirred at 50° C. for 2 h. The reaction mixture was diluted with EtOAc and the resulting solution was washed with aq. NaHCO$_3$, water and brine, then dried with Na$_2$SO$_4$, and concentrated under reduced pressure. The resulting residue was purified by preparative LC-MS (XBridge™ preparative C18 5 μm 30×10 mm OBD™ column, flow rate 60 mL/min., eluting with a gradient of MeCN and water with 0.1% TFA) to give a Boc-protected intermediate (10 mg), LCMS (M+H): 676.1. The intermediate was treated with TFA (2 mL) and stirred at 50° C. for 2 h. The solvent was then evaporated under reduced pressure and the resulting residue was purified by preparative LC-MS (XBridge™ preparative C18 5 μm 30×10 mm OBD™ column, flow rate 60 mL/min., eluting with a gradient of MeCN and water with 0.15% NH$_4$OH) to afford the title compound (4 mg, 10%). LCMS calc. for $C_{21}H_{20}F_2N_7OS$ (M+H)$^+$: m/z=456.1; Found: 456.1. $^1$H NMR (DMSO-d$_6$, 300 MHz): δ 8.67 (s, 1H), 8.57 (s, 1H), 8.14 (s, 1H), 7.62 (m, 1H), 7.32 (m, 2H), 3.53 (d, J=8.2 Hz, 1H), 3.40 (m, 2H), 3.27 (m, 2H), 3.00 (t, J=9.3 Hz, 1H), 2.85 (m, 2H), 1.76 (d, J=9.3 Hz, 1H), 1.56 (m, 2H), 1.14 (m, 1H) ppm.

Example 36

5-Amino-N-{4-[(3S,5R)-3-amino-5-methylpiperidin-1-yl]-2,3-dihydrofuro[2,3-b]pyridin-5-yl}-2-(2,6-difluorophenyl)-1,3-thiazole-4-carboxamide

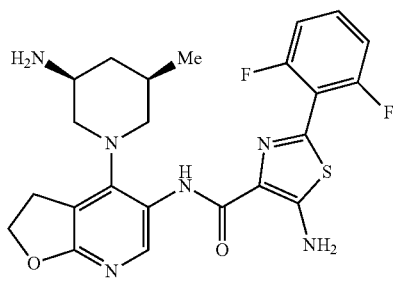 [SMILES: C[C@@H]1C[C@H](N)CN(c2c(NC(=O)c3nc(-c4c(F)cccc4F)sc3N)cnc3c2CCO3)C1]

Step 1. 1-tert-Butyl 2-methyl (2S)-5-oxopyrrolidine-1,2-dicarboxylate

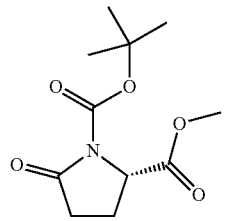 [SMILES: COC(=O)[C@@H]1CCC(=O)N1C(=O)OC(C)(C)C]

Thionyl chloride (5.6 mL, 77 mmol) was added dropwise over 10 min. to a solution of (2S)-5-oxopyrrolidine-2-carboxylic acid (Aldrich, 5.0 g, 39 mmol) in MeOH (30.0 mL) at 0° C. The mixture was allowed to warm to room temperature and stirred for 2 h. The reaction was concentrated under reduced pressure and the resulting residue was dissolved in EtOAc (25 mL). After slow addition of triethylamine (5.4 mL, 39 mmol), the mixture was filtered. DMAP (0.48 g, 3.9 mmol) was added to the filtrate, followed by di-tert-butyl dicarbonate (8.4 g, 39 mmol) and the mixture was stirred at room temperature for 2 h. The reaction mixture was then diluted with EtOAc (25 mL) and cooled to 0° C. 1N HCl (50 mL) was added slowly. The organic layer was separated, washed with a saturated aq. NaHCO$_3$ (50 mL) and brine (50 mL), then dried over Na$_2$SO$_4$ and concentrated to give the sub-title compound as a white solid (8.08 g, 86%). LCMS calc. for $C_{11}H_{17}NNaO_5$ (M+Na)$^+$: m/z=266.1; found 266.1.

Step 2. 1-tert-Butyl 2-methyl (2S,4R)-4-methyl-5-oxopyrrolidine-1,2-dicarboxylate

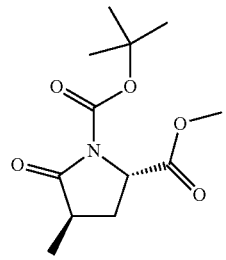 [SMILES: COC(=O)[C@@H]1C[C@@H](C)C(=O)N1C(=O)OC(C)(C)C]

This compound is prepared as described by Gu et al, *Tetrahedron Lett.*, 2003, 44, 3203-3205. Lithium hexamethyldisilazide in THF (1.0 M; 8.47 mL, 8.47 mmol) was added dropwise over 30 min. to a solution of 1-tert-butyl 2-methyl (2S)-5-oxopyrrolidine-1,2-dicarboxylate (2.0 g, 8.2 mmol) in THF (20 mL) at −78° C. The resulting mixture was stirred at −78° C. for 1 h. Methyl iodide (1.30 mL, 20.9 mmol) was then added dropwise over 10 min. After stirring at −78° C. for 2 h, the reaction mixture was allowed to warm to room temperature and stirred for 14 h. The reaction was then quenched by the addition of AcOH (1.00 mL, 17.6 mmol), and the reaction mixture was concentrated under reduced pressure. The residue was diluted with EtOAc (100 mL), washed with brine (100 mL), dried over $Na_2SO_4$, and concentrated under reduced pressure. The resulting residue was purified by chromatography on silica gel (0-50% EtOAc in hexanes) to give the sub-title compound (0.47 g, 22%). LCMS calc. for $C_{12}H_{19}NNaO_5$ (M+Na)$^+$: m/z=280.1; found 280.1. $^1$H NMR (CDCl$_3$, 400 MHz) δ 4.57 (1H, dd, J=1.6 and 9.6 Hz), 3.77 (3H, s), 2.68 (1H, m), 2.27 (1H, m), 1.93 (1H, m), 1.49 (9H, s), 1.21 (3H, d, J=6.8 Hz) ppm.

Step 3. tert-Butyl [(1S,3R)-4-hydroxy-1-(hydroxymethyl)-3-methylbutyl]carbamate

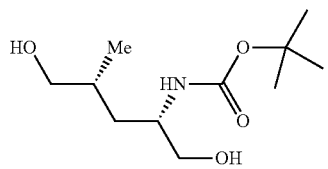

To a solution of 1-tert-butyl 2-methyl (2S,4R)-4-methyl-5-oxopyrrolidine-1,2-dicarboxylate (0.47 g, 1.8 mmol) in THF (4.0 mL) at −10° C., NaBH$_4$ (0.207 g, 5.48 mmol) was added followed by EtOH (1.0 mL). After stirring at −10° C. for 1 h, the mixture was allowed to warm to room temperature and stirred for 15 h. The reaction mixture was then diluted with EtOAc (50 mL), washed with water (25 mL) and brine (30 mL), then dried over Na$_2$SO$_4$ and concentrated under reduced pressure. The resulting crude product (0.39 g, 92%) was used directly in the next step without further purification. LCMS calc. for $C_{11}H_{24}NO_4$ (M+H)$^+$: m/z=234.2; found no ionization.

Step 4. tert-Butyl [(3S,5R)-1-benzyl-5-methylpiperidin-3-yl]carbamate

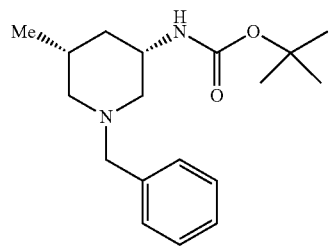 [SMILES: C[C@@H]1C[C@H](NC(=O)OC(C)(C)C)CN(Cc2ccccc2)C1]

Triethylamine (0.932 mL, 6.69 mmol) was added to a solution of tert-butyl [(1S,3R)-4-hydroxy-1-(hydroxymethyl)-3-methylbutyl]carbamate (0.39 g, 1.7 mmol) in DCM (7.5 mL) at 0° C. Methanesulfonyl chloride (0.388 mL, 5.01 mmol) was then added dropwise to the resulting solution. After stirring at 0° C. for 1 h, the mixture was diluted with DCM (50 mL), washed with saturated aq. NaHCO$_3$ (50 mL), dried over Na$_2$SO$_4$ and concentrated under reduced pressure. Benzylamine (3.65 mL, 33.4 mmol) was added to the resulting residue and mixture was stirred at 70° C. for 18 h, then cooled to room temperature. The reaction mixture was diluted with EtOAc (100 mL), washed with a 10% aq. K$_3$PO$_4$ (50 mL) and brine (50 mL), dried over Na$_2$SO$_4$, and concentrated under reduced pressure. The residue was purified by chromatography on silica gel (0-30% EtOAc in hexanes) to give the title compound as a white solid (0.34 g, 67%). LCMS calc. for $C_{18}H_{29}N_2O_2$ (M+H)$^+$: m/z=305.2; found 305.2.

Step 5. tert-Butyl [(3S,5R)-5-methylpiperidin-3-yl]carbamate

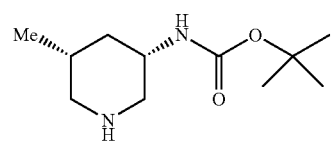

10 wt % Pd on carbon (120 mg, 0.11 mmol) was added to a solution of tert-butyl [(3S,5R)-1-benzyl-5-methylpiperidin-3-yl]carbamate (0.34 g, 1.1 mmol) in MeOH (15.0 mL). The mixture was stirred at room temperature under a hydrogen atmosphere (1 atm.) for 15 h. The reaction was filtered through a pad of diatomaceous earth (eluted with MeOH), and then concentrated under reduced pressure. The resulting crude product was used directly in the next step residue without further purification (0.21 g, 88%). LCMS calc. for $C_{11}H_{23}N_2O_2$ (M+H)$^+$: m/z=215.2; found 215.2. $^1$H NMR (CDCl$_3$, 400 MHz) δ 4.33 (1H, m), 3.46 (1H, m), 3.25 (1H, m), 2.94 (1H, dd, J=3.6 and 12.8 Hz), 2.18-2.02 (3H, m), 1.60 (1H, m), 1.43 (9H, s), 0.85 (3H, d, J=6.8 Hz) ppm.

Step 6. tert-Butyl [(3S,5R)-5-methyl-1-(5-nitro-2,3-dihydrofuro[2,3-b]pyridin-4-yl)piperidin-3-yl]carbamate

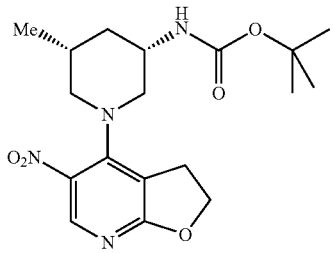 [SMILES: C[C@@H]1C[C@H](NC(=O)OC(C)(C)C)CN(c2c([N+](=O)[O-])cnc3c2CCO3)C1]

To a microwave vial containing 4-iodo-5-nitro-2,3-dihydrofuro[2,3-b]pyridine (from Example 9, step 3) (47.8 mg, 0.164 mmol) and tert-butyl [(3S,5R)-5-methylpiperidin-3-yl]carbamate (33.7 mg, 0.157 mmol), EtOH (1.00 mL) was added, followed by DIPEA (41.5 mg, 0.321 mmol). The mixture was heated under microwave irradiation at 100° C. for 2 h. After cooling to room temperature, the reaction mixture was concentrated under reduced pressure. The resulting residue was purified by chromatography on silica gel (0-100% EtOAc in hexanes) to give the title compound as a yellow solid (44.5 mg, 75%). LCMS calc. for $C_{18}H_{27}N_4O_5$ $(M+H)^+$: m/z=379.2; found 379.2.

Step 7. tert-Butyl [(3S,5R)-1-(5-amino-2,3-dihydrofuro[2,3-b]pyridin-4-yl)-5-methylpiperidin-3-yl]carbamate

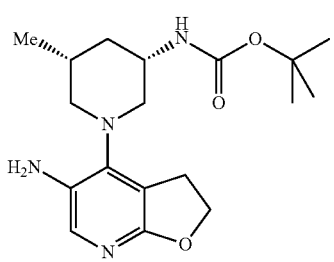

To a solution of tert-butyl [(3S,5R)-5-methyl-1-(5-nitro-2,3-dihydrofuro[2,3-b]pyridin-4-yl)piperidin-3-yl]carbamate (44.5 mg, 0.118 mmol) in MeOH (2.00 mL), 10 wt % Pd on carbon (9.3 mg, 0.0087 mmol) was added under a nitrogen atmosphere. The mixture was then hydrogenated (1 atm.) for 4 h. The reaction mixture was then filtered through a pad of diatomaceous earth (eluted with MeOH). The filtrate was concentrated under reduced pressure to give the crude product as a red semi-solid (41.0 mg). The crude product was used directly in the next step without further purification. LCMS calc. for $C_{18}H_{29}N_4O_3$ $(M+H)^+$: m/z=349.2; found 349.2.

Step 8. 5-Amino-N-{4-[(3S,5R)-3-amino-5-methylpiperidin-1-yl]-2,3-dihydrofuro[2,3-b]pyridin-5-yl}-2-(2,6-difluorophenyl)-1,3-thiazole-4-carboxamide

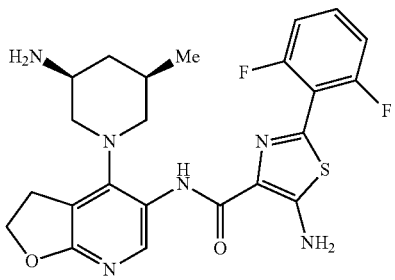 [SMILES: C[C@@H]1C[C@H](N)CN(c2c(NC(=O)c3nc(-c4c(F)cccc4F)sc3N)cnc3c2CCO3)C1]

To a mixture of 5-[(tert-butoxycarbonyl)amino]-2-(2,6-difluorophenyl)-1,3-thiazole-4-carboxylic acid (Example 1, step 6) (47.3 mg, 0.133 mmol), tert-butyl [(3S,5R)-1-(5-amino-2,3-dihydrofuro[2,3-b]pyridin-4-yl)-5-methylpiperidin-3-yl]carbamate (41.0 mg, 0.118 mmol) and HATU (142.3 mg, 0.3742 mmol), DMF (2.0 mL) was added followed by DIPEA (115.8 mg, 0.8960 mmol). The reaction mixture was stirred at room temperature for 2 h, and then concentrated under reduced pressure. DCM (2.0 mL) was added to the residue followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (25.2 mg, 44%). LCMS calc. for $C_{23}H_{25}F_2N_6O_2S$ $(M+H)^+$: m/z=487.2; found 487.2.

Example 37

N-{4-[(3R,4R,5S)-3-Amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide

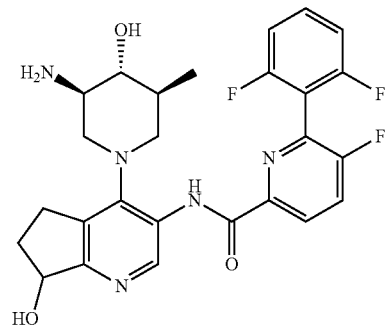 [SMILES: C[C@H]1CN(c2c(NC(=O)c3ccc(F)c(-c4c(F)cccc4F)n3)cnc3c2CCC3O)C[C@@H](N)[C@@H]1O]

Step 1: tert-Butyl [(3R, 4R, 5S)-4-hydroxy-5-methyl-1-(3-nitro-6,7-dihydro-5H-cyclopenta[b]pyridin-4-yl)piperidin-3-yl]carbamate

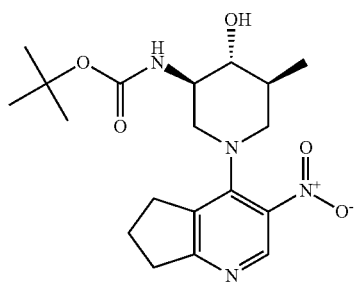 [SMILES: C[C@H]1CN(c2c([N+](=O)[O-])cnc3c2CCC3)C[C@@H](NC(=O)OC(C)(C)C)[C@@H]1O]

A mixture containing 4-chloro-3-nitro-6,7-dihydro-5H-cyclopenta[b]pyridine (410 mg, 2.1 mmol), tert-butyl [(3R,4R,5S)-4-hydroxy-5-methylpiperidin-3-yl]carbamate (240 mg, 1.0 mmol) and triethylamine (0.5 mL, 4 mmol) in isopropyl alcohol (3.0 mL) was stirred at 100° C. for 2 h. The reaction mixture was concentrated under reduced pressure and the resulting residue was purified by column chromatography on silica gel using a CombiFlash® apparatus (eluting with 0 to 80% EtOAc in hexanes) to give the sub-title compound as pale yellow powder (200 mg, 50%). LCMS calc. for $C_{19}H_{29}N_4O_5$ $(M+H)^+$: m/z=393.2. Found: 393.2.

Step 2: tert-Butyl [(3R,4R,5S)-4-hydroxy-5-methyl-1-(3-nitro-1-oxido-6,7-dihydro-5H-cyclopenta[b]pyridin-4-yl)piperidin-3-yl]carbamate

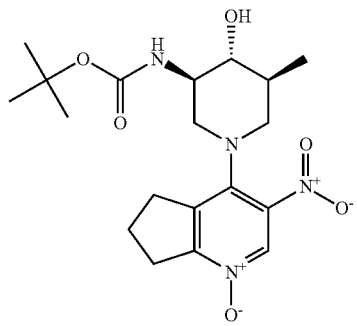 [SMILES: C[C@H]1CN(c2c([N+](=O)[O-])c[n+]([O-])c3c2CCC3)C[C@@H](NC(=O)OC(C)(C)C)[C@@H]1O]

mCPBA (0.420 g, 1.87 mmol) was slowly added to a solution of tert-butyl [(3R,4R,5S)-4-hydroxy-5-methyl-1-(3-nitro-6,7-dihydro-5H-cyclopenta[b]pyridin-4-yl)piperidin-3-yl]carbamate (0.200 g, 0.510 mmol) in DCM (3.0 mL) at room temperature. The reaction mixture was stirred at room temperature for 1 h. The mixture was then washed with aq. $Na_2S_2O_3$, followed by 1 M NaOH. The organic layer was separated, dried and concentrated under reduced pressure. The resulting residue was further purified by silica gel column chromatography (eluting with 0-30% MeOH in EtOAc) to give the sub-title compound (90 mg, 43%) as a light orange powder. LCMS calc. for $C_{19}H_{29}N_4O_6$ $(M+H)^+$: m/z=409.2. Found: 409.2.

Step 3: 4-{(3R,4R,5S)-4-(Acetyloxy)-3-[(tert-butoxycarbonyl)amino]-5-methylpiperidin-1-yl}-3-nitro-6,7-dihydro-5H-cyclopenta[b]pyridin-7-yl Acetate

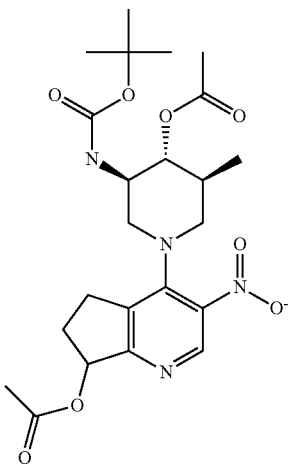

Ac₂O (2.0 mL, 21 mmol) was added to tert-butyl [(3R, 4R,5S)-4-hydroxy-5-methyl-1-(3-nitro-1-oxido-6,7-dihydro-5H-cyclopenta[b]pyridin-4-yl)piperidin-3-yl]carbamate (0.090 g, 0.22 mmol) in a tube that was then sealed. The reaction mixture was heated in the sealed tube with stirring in an oil bath at 90° C. oil bath. The reaction mixture was allowed to cool to room temperature and acetyl chloride (0.10 mL) and DIPEA (0.2 mL) were then added. The resulting mixture was stirred at room temperature for 15 min. After removal of the solvents under reduced pressure, the resulting residue was diluted with EtOAc and aq. $Na_2CO_3$ and stirred at room temperature for 30 min. The organic layer was separated, dried and concentrated under reduced pressure. The resulting residue was purified by silica gel column chromatography (eluting with 0-70% EtOAc in hexanes) to give the sub-title compound (86 mg, 79%) as a foamy brown powder. LCMS calc. for $C_{23}H_{33}N_4O_8$ $(M+1)^+$: m/z=493.2. Found: 493.2.

Step 4: (3R,4R,5S)-1-[7-(Acetyloxy)-3-amino-6,7-dihydro-5H-cyclopenta[b]pyridin-4-yl]-3-[(tert-butoxycarbonyl)amino]-5-methylpiperidin-4-yl Acetate

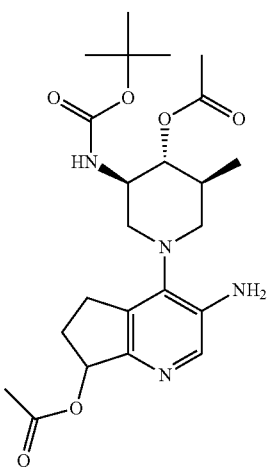 [SMILES: CC(=O)OC1CCc2c1ncc(N)c2N1C[C@H](C)[C@@H](OC(C)=O)[C@H](NC(=O)OC(C)(C)C)C1]

A mixture of 4-{(3R,4R,5S)-4-(acetyloxy)-3-[(tert-butoxycarbonyl)amino]-5-methylpiperidin-1-yl}-3-nitro-6,7-dihydro-5H-cyclopenta[b]pyridin-7-yl acetate (0.086 g, 0.17 mmol), water (0.10 mL), AcOH (3.0 mL) and iron powder (0.200 g, 3.58 mmol) was stirred at room temperature for 3 h. The reaction mixture was diluted with EtOAc (10 mL), then filtered. The filtrate was concentrated under reduced pressure. EtOAc (20 mL) and aq. $Na_2CO_3$ (10 mL) were added to the residue and the mixture was stirred at room temperature for 30 min. The organic layer was separated, dried over $Na_2SO_4$, then filtered and concentrated under reduced pressure to give the sub-title compound (80 mg, 92%) as a brown foamy powder. LCMS calc. for $C_{23}H_{35}N_4O_6$ $(M+H)^+$: m/z=463.3. Found: 463.3.

Step 5: tert-Butyl {(3R,4R,5S)-1-[3-({[6-(2,6-difluorophenyl)-5-fluoropyridin-2-yl]carbonyl}amino)-7-hydroxy-6,7-dihydro-5H-cyclopenta[b]pyridin-4-yl]-4-hydroxy-5-methylpiperidin-3-yl}carbamate

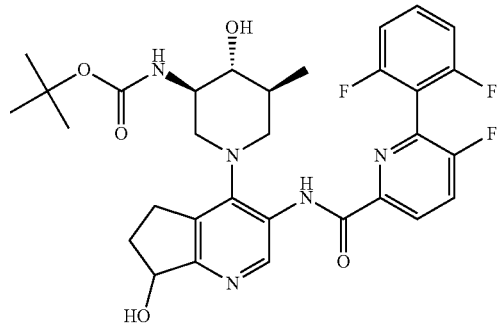 [SMILES: C[C@H]1CN(c2c(NC(=O)c3ccc(F)c(-c4c(F)cccc4F)n3)cnc3c2CCC3O)C[C@@H](NC(=O)OC(C)(C)C)[C@@H]1O]

A mixture of (3R,4R,5S)-1-[7-(acetyloxy)-3-amino-6,7-dihydro-5H-cyclopenta[b]pyridin-4-yl]-3-[(tert-butoxycarbonyl)amino]-5-methylpiperidin-4-yl acetate (11 mg, 0.024 mmol), 6-(2,6-difluorophenyl)-5-fluoropyridine-2-carboxylic acid (9.0 mg, 0.036 mmol), HATU (33 mg, 0.086 mmol), DMF (0.090 mL) and DIPEA (23 mg, 0.18 mmol) was stirred at room temperature for 16 h. The reaction mixture was diluted with 1 M NaOH (1.0 mL) and MeOH (1.0 mL) and the mixture was stirred at room temperature for a further 1 h, and then concentrated under reduced pressure. After concentrating under reduced pressure, the aqueous layer was extracted with DCM three times. The combined organic extract was dried, filtered and concentrated under reduced pressure to give a crude product, which was further purified by preparative LCMS (pH=10 method; XBridge preparative C18 5 μm OBD™ column, 30×10 mm, 60 mL/min., eluting with a gradient of MeCN and water with 0.15% $NH_4OH$) to give the sub-title compound as a colorless gum. LCMS calc. for $C_{31}H_{35}F_3N_5O_5$ $(M+H)^+$: m/z=614.3. Found: 614.2.

Step 6: N-{4-[(3R,4R,5S)-3-Amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide A mixture of tert-butyl {(3R,4R,5S)-1-[3-({[6-(2,6-difluorophenyl)-5-fluoropyridin-2-yl]carbonyl}amino)-7-hydroxy-6,7-dihydro-5H-cyclopenta[b]pyridin-4-yl]-4-hydroxy-5-methylpiperidin-3-yl}carbamate (6 mg, 0.01 mmol) and TFA in DCM (4.0 M; 2.0 mL, 8.0 mmol) was stirred at room temperature for 1 h. After removal of the solvent, the residue was then diluted with MeOH (4 mL) and $NH_4OH$ solution (0.5 mL) and filtered. The filtrate was purified by preparative LCMS (pH=10 method; XBridge™ preparative C18 5 μm OBD™ column, 30×10 mm, 60 mL/min., eluting with a gradient of MeCN and water with 0.15% $NH_4OH$) to give two diastereoisomers of the title compound as a white powders.

Diastereoisomer 1. First peak. Retention time 1.223 min., LCMS calc. for $C_{26}H_{27}F_3N_5O_3$ $(M+H)^+$: m/z=514.2; Found: 514.2. $^1H$ NMR (DMSO-$d_6$, 500 MHz) δ 10.47 (1H, s), 9.31 (1H, s), 8.38 (1H, dd, J=8.5 and 4.0 Hz), 8.20 (1H, dd, J=8.5 and 8.5 Hz), 7.64 (1H, m), 7.29 (2H, dd, J=8.5 and 8.5 Hz), 5.24 (1H, d, J=5.0 Hz), 4.84 (1H, m), 4.40 (1H, d, J=4.0 Hz), 3.06 (1H, m), 2.94 (1H, m), 2.85 (2H, m), 2.72 (1H, m), 2.63 (1H, m), 2.58 (1H, m), 2.46 (1H, m), 2.31 (1H, m), 1.80 (1H, m), 1.49 (1H, m), 1.41 (1H, m), 0.71 (3H, d, J=6.5 Hz) ppm.

Diastereoisomer 2. Second peak. Retention time 1.288 min., LCMS calc. for $C_{26}H_{27}F_3N_5O_3$ $(M+H)^+$: m/z=514.2. Found: 514.2. $^1H$ NMR (DMSO-$d_6$, 500 MHz) δ 10.49 (1H, s), 9.31 (1H, s), 8.39 (1H, dd, J=8.5 and 4.0 Hz), 8.21 (1H, dd, J=8.5 and 8.5 Hz), 7.65 (1H, m), 7.29 (2H, dd, J=8.5 and 8.5 Hz), 5.24 (1H, d, J=5.5 Hz), 4.82 (1H, m), 4.39 (1H, d, J=4.0 Hz), 3.06 (1H, m), 2.96 (1H, m), 2.85 (2H, m), 2.72 (1H, m), 2.63 (1H, m), 2.59 (1H, m), 2.48 (1H, m), 2.29 (1H, m), 1.82 (1H, m), 1.48 (1H, m), 1.41 (1H, m), 0.71 (3H, d, J=6.5 Hz) ppm.

The diastereoisomers correspond to the (7R) and (7S) diastereoisomers of the title compound.

Example 38

3-Amino-N-{4-[(3S,5R)-3-amino-5-methylpiperidin-1-yl]-2,3-dihydrofuro[2,3-b]pyridin-5-yl}-6-(2,6-difluorophenyl)-5-fluoropyridine-2-carboxamide

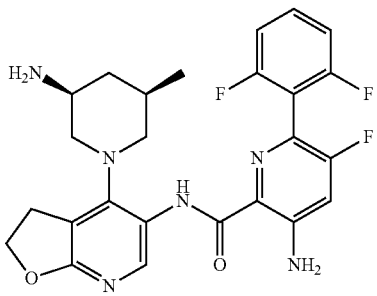 [SMILES: C[C@@H]1C[C@H](N)CN(c2c(NC(=O)c3nc(-c4c(F)cccc4F)c(F)cc3N)cnc3c2CCO3)C1]

To a mixture of 3-[(tert-butoxycarbonyl)amino]-6-(2,6-difluorophenyl)-5-fluoropyridine-2-carboxylic acid (16.1 mg, 0.0437 mmol), tert-butyl [(3S,5R)-1-(5-amino-2,3-dihydrofuro[2,3-b]pyridin-4-yl)-5-methylpiperidin-3-yl]carbamate (14.0 mg, 0.0402 mmol) and HATU (53.1 mg, 0.140 mmol), DMF (1.0 mL) was added followed by DIPEA (70.1 µL, 0.402 mmol). The reaction mixture was stirred at room temperature for 2 h, and then concentrated under reduced pressure. To the resulting residue, DCM (2.0 mL) was added, followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (5.9 mg, 29%). LCMS calc. for C$_{25}$H$_{26}$F$_3$N$_6$O$_2$ (M+H)$^+$: m/z=499.2; found 499.2.

Example 39

N-{4-[(3S,5R)-3-Amino-5-methylpiperidin-1-yl]-2,3-dihydrofuro[2,3-b]pyridin-5-yl}-6-(2,6-difluorophenyl)-5-fluoropyridine-2-carboxamide

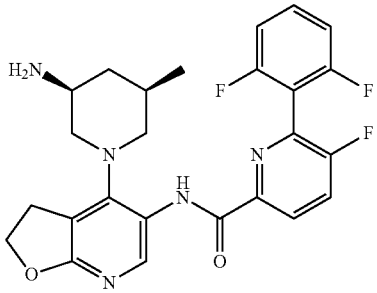 [SMILES: C[C@@H]1C[C@H](N)CN(c2c(NC(=O)c3ccc(F)c(-c4c(F)cccc4F)n3)cnc3c2CCO3)C1]

To a mixture of 6-(2,6-difluorophenyl)-5-fluoropyridine-2-carboxylic acid (13.7 mg, 0.0541 mmol), tert-butyl [(3S,5R)-1-(5-amino-2,3-dihydrofuro[2,3-b]pyridin-4-yl)-5-methylpiperidin-3-yl]carbamate (15.9 mg, 0.0456 mmol), and HATU (59.1 mg, 0.155 mmol), DMF (1.0 mL) was added followed by DIPEA (70.1 µL, 0.402 mmol). The reaction mixture was stirred at room temperature for 2 h, and then concentrated under reduced pressure. To the resulting residue, DCM (2.0 mL) was added followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (8.5 mg, 38%). LCMS calc. for C$_{25}$H$_{25}$F$_3$N$_5$O$_2$ (M+H)$^+$: m/z=484.2; found 484.2.

Example 40

5-Amino-N-{4-[(3R,4R,5S)-3-amino-4-hydroxy-5-methylpiperidin-1-yl]-2,3-dihydrofuro[2,3-b]pyridin-5-yl}-2-(2,6-difluorophenyl)-1,3-thiazole-4-carboxamide

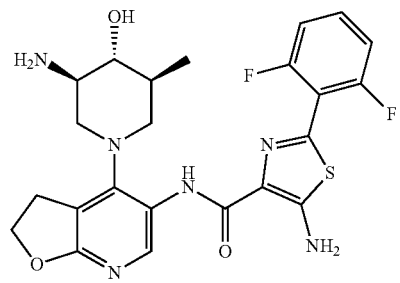 [SMILES: C[C@H]1CN(c2c(NC(=O)c3nc(-c4c(F)cccc4F)sc3N)cnc3c2CCO3)C[C@@H](N)[C@@H]1O]

Step 1. tert-Butyl [(3R,4R,5S)-4-{[tert-butyl(dimethyl)silyl]oxy}-5-methyl-1-(5-nitro-2,3-dihydrofuro[2,3-b]pyridin-4-yl)piperidin-3-yl]carbamate

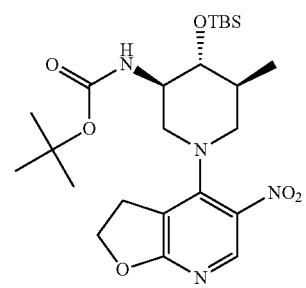 [SMILES: C[C@H]1CN(c2c([N+](=O)[O-])cnc3c2CCO3)C[C@@H](NC(=O)OC(C)(C)C)[C@@H]1O[Si](C)(C)C(C)(C)C]

To a mixture of 4-iodo-5-nitro-2,3-dihydrofuro[2,3-b]pyridine (110.4 mg, 0.3780 mmol) and tert-butyl ((3R,4R,5S)-4-{[tert-butyl(dimethyl)silyl]oxy}-5-methylpiperidin-3-yl)carbamate (from Example 28, Step 7, 100.0 mg, 0.2902 mmol) was added EtOH (2.0 mL) followed by DIPEA (163.8 mg, 1.267 mmol). The reaction mixture was heated at 100° C. for 15 h, and then concentrated under reduced pressure. The residue was purified by chromatography on silica gel (0-50% EtOAc in hexanes) to afford the sub-title compound as a yellow solid (118.2 mg, 80%). LCMS calc. for C$_{24}$H$_4$N$_4$O$_6$Si (M+H)$^+$: m/z=509.3; found 509.3.

Step 2. tert-Butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate

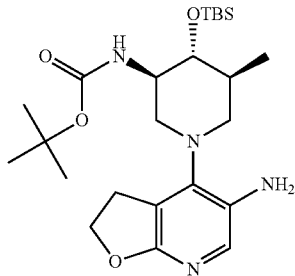 [SMILES: C[C@H]1CN(c2c(N)cnc3c2CCO3)C[C@@H](NC(=O)OC(C)(C)C)[C@@H]1O[Si](C)(C)C(C)(C)C]

To a mixture of tert-butyl [(3R,4R,5S)-4-{[tert-butyl(dimethyl)silyl]oxy}-5-methyl-1-(5-nitro-2,3-dihydrofuro[2,3-b]pyridin-4-yl)piperidin-3-yl]carbamate (73.4 mg, 0.144 mmol), iron powder (89.0 mg, 1.59 mmol), and ammonium chloride (151.4 mg, 2.830 mmol) was added EtOH (2.0 mL) followed by water (0.50 mL, 28 mmol). The mixture was stirred at 80° C. for 1 h. The reaction mixture was filtered through a pad of diatomaceous earth. The diatomaceous earth pad was eluted with a 10% aqueous solution of $K_3PO_4$ (20 mL), and EtOAc (20 mL). The organic layers were washed with brine (20 mL), dried over $Na_2SO_4$, and concentrated to give the crude sub-title compound (67.8 mg). The crude product was used directly in the next step without further purification. LCMS calc. for $C_{24}H_{43}N_4O_4Si$ (M+H)$^+$: m/z=479.3; found 479.3.

Step 3. tert-Butyl[4-({[4-((3R,4R,5S)-3-[(tert-butoxycarbonyl)amino]-4-{[tert-butyl(dimethyl)silyl]oxy}-5-methylpiperidin-1-yl)-2,3-dihydrofuro[2,3-b]pyridin-5-yl]amino}carbonyl)-2-(2,6-difluorophenyl)-1,3-thiazol-5-yl]carbamate

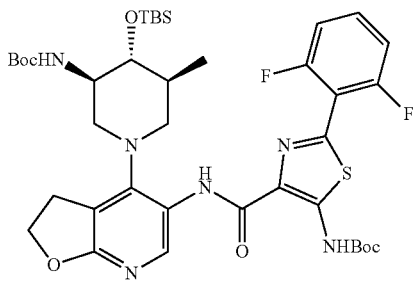 [SMILES: C[C@H]1CN(c2c(NC(=O)c3nc(-c4c(F)cccc4F)sc3NC(=O)OC(C)(C)C)cnc3c2CCO3)C[C@@H](NC(=O)OC(C)(C)C)[C@@H]1O[Si](C)(C)C(C)(C)C]

To a mixture of tert-butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate (67.8 mg, 0.142 mmol), 5-[(tert-butoxycarbonyl)amino]-2-(2,6-difluorophenyl)-1,3-thiazole-4-carboxylic acid (65.4 mg, 0.184 mmol) and HATU (168.1 mg, 0.4421 mmol) was added DMF (2.0 mL) followed by DIPEA (144.5 mg, 1.118 mmol). The reaction mixture was stirred at room temperature for 3 h, and then concentrated under reduced pressure. The residue was purified by chromatography on silica gel (0-50% EtOAc in hexanes) to afford the sub-title compound as a brown solid (29.2 mg, 25%). LCMS calc. for $C_{39}H_{55}F_2N_6O_7SSi$ (M+H)$^+$: m/z=817.4; found 817.3.

Step 4. 5-Amino-N-{4-[(3R,4R,5S)-3-amino-4-hydroxy-5-methylpiperidin-1-yl]-2,3-dihydrofuro[2,3-b]pyridin-5-yl}-2-(2,6-difluorophenyl)-1,3-thiazole-4-carboxamide To a solution of tert-butyl [4-({[4-((3R,4R,5S)-3-[(tert-butoxycarbonyl)amino]-4-{[tert-butyl(dimethyl)silyl]oxy}-5-methylpiperidin-1-yl)-2,3-dihydrofuro[2,3-b]pyridin-5-yl]amino}carbonyl)-2-(2,6-difluorophenyl)-1,3-thiazol-5-yl]carbamate (29.2 mg, 0.0357 mmol) in MeCN (2.0 mL) was added a 1.7 M dihydrogen hexafluorosilicate solution in water (0.5 mL, 0.8 mmol). The mixture was stirred at 50° C. for 2 h. After cooling to room temperature, the reaction mixture was neutralized with a 14.8 M NH$_4$OH solution in water (300 µL, 4.44 mmol), and was purified using RP-HPLC (XBridge™ C18 column, eluting with a gradient of MeCN/water containing 0.1% NH$_4$OH, at flow rate of 30 mL/min.) to afford the title compound as a white solid (6.0 mg, 33%). LCMS calc. for $C_{23}H_{25}F_2N_6O_3S$ (M+H)$^+$: m/z=503.2; found 503.2.

Example 41

N-{4-[(3R,4R,5S)-3-Amino-4-hydroxy-5-methylpiperidin-1-yl]-2,3-dihydrofuro[2,3-b]pyridin-5-yl}-6-(2,6-difluorophenyl)-5-fluoropyridine-2-carboxamide

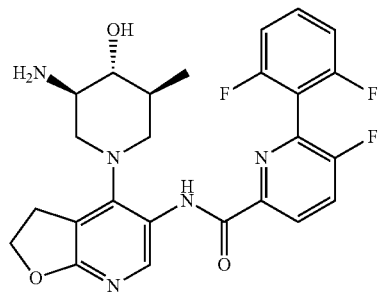 [SMILES: C[C@H]1CN(c2c(NC(=O)c3ccc(F)c(-c4c(F)cccc4F)n3)cnc3c2CCO3)C[C@@H](N)[C@@H]1O]

Step 1. tert-Butyl {(3R,4R,5S)-4-{[tert-butyl(dimethyl)silyl]oxy}-1-[5-({[6-(2,6-difluorophenyl)-5-fluoropyridin-2-yl]carbonyl}amino)-2,3-dihydrofuro[2,3-b]pyridin-4-yl]-5-methylpiperidin-3-yl}carbamate

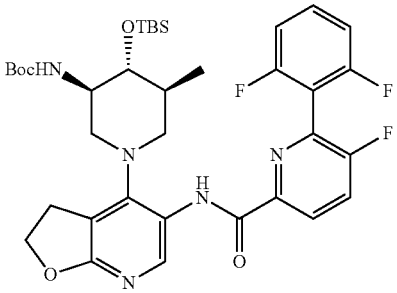 [SMILES: C[C@H]1CN(c2c(NC(=O)c3ccc(F)c(-c4c(F)cccc4F)n3)cnc3c2CCO3)C[C@@H](NC(=O)OC(C)(C)C)[C@@H]1O[Si](C)(C)C(C)(C)C]

To a mixture of 6-(2,6-difluorophenyl)-5-fluoropyridine-2-carboxylic acid (13.3 mg, 0.0525 mmol), tert-butyl ((3R,4R,5S)-1-(5-amino-2,3-dihydrofuro[2,3-b]pyridin-4-yl)-4-{

[tert-butyl(dimethyl)silyl]oxy}-5-methylpiperidin-3-yl)carbamate (16.7 mg, 0.0349 mmol) and HATU (46.2 mg, 0.122 mmol) was added DMF (2.0 mL) followed by DIPEA (70.0 µL, 0.402 mmol). The reaction mixture was stirred at room temperature for 3 h, and then concentrated under reduced pressure. The residue was purified by chromatography on silica gel (0-100% EtOAc in hexanes) to afford the sub-title compound as a brown solid (24.9 mg). LCMS calc. for $C_{36}H_{47}F_3N_5O_5Si$ (M+H)$^+$: m/z=714.3; found 714.3.

Step 2. N-{4-[(3R,4R,5S)-3-amino-4-hydroxy-5-methylpiperidin-1-yl]-2,3-dihydrofuro[2,3-b]pyridin-5-yl}-6-(2,6-difluorophenyl)-5-fluoropyridine-2-carboxamide To a solution of tert-butyl {(3R,4R,5S)-4-{[tert-butyl(dimethyl)silyl]oxy}-1-[5-({[6-(2,6-difluorophenyl)-5-fluoropyridin-2-yl]carbonyl}amino)-2,3-dihydrofuro[2,3-b]pyridin-4-yl]-5-methylpiperidin-3-yl}carbamate (24.9 mg, 0.0349 mmol) in MeCN (2.0 mL) was added a 1.7 M dihydrogen hexafluorosilicate solution in water (200 µL, 0.340 mmol). The mixture was stirred at 50° C. for 2 h. After cooling to room temperature, the reaction mixture was neutralized with a 14.8 M NH$_4$OH solution in water (200 µL, 2.96 mmol), and was purified using RP-HPLC (XBridge™ C18 column, eluting with a gradient of MeCN/water containing 0.1% NH$_4$OH, at flow rate of 30 mL/min.) to afford the title compound as a white solid (2.8 mg, 16%). LCMS calc. for $C_{25}H_{25}F_3N_5O_3$ (M+H)$^+$: m/z=500.2; found 500.1.

Example 42

5-Amino-N-{4-[(3S,5R)-3-amino-5-(trifluoromethyl)piperidin-1-yl]-2,3-dihydrofuro[2,3-b]pyridin-5-yl}-2-(2,6-difluorophenyl)-1,3-thiazole-4-carboxamide

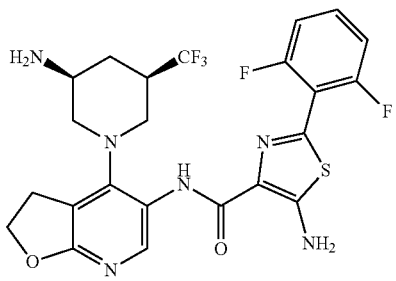

Step 1. tert-Butyl [(3S,5R)-1-(5-nitro-2,3-dihydrofuro[2,3-b]pyridin-4-yl)-5-(trifluoromethyl)piperidin-3-yl]carbamate

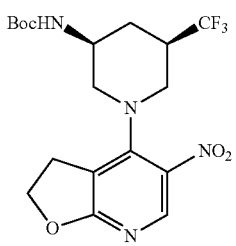 [SMILES: CC(C)(C)OC(=O)N[C@H]1C[C@@H](C(F)(F)F)CN(c2c([N+](=O)[O-])cnc3c2CCO3)C1]

To a mixture of 4-iodo-5-nitro-2,3-dihydrofuro[2,3-b]pyridine (238.2 mg, 0.8157 mmol) and tert-butyl [(3S,5R)-5-(trifluoromethyl)piperidin-3-yl]carbamate (from MolBridge, 203.9 mg, 0.7600 mmol) was added EtOH (3.0 mL), followed by DIPEA (539.5 mg, 4.174 mmol). The mixture was stirred at 120° C. for 18 h. After cooling to room temperature, the reaction was concentrated under reduced pressure. The residue was purified by chromatography on silica gel (0-50% EtOAc in hexanes) to afford the sub-title compound as a yellow solid (227.1 mg, 69%). LCMS calc. for $C_{18}H_{24}F_3N_4O_5$ (M+H)$^+$: m/z=433.2; found 433.2.

Step 2. tert-Butyl [(3S,5R)-1-(5-amino-2,3-dihydrofuro[2,3-b]pyridin-4-yl)-5-(trifluoromethyl)piperidin-3-yl]carbamate

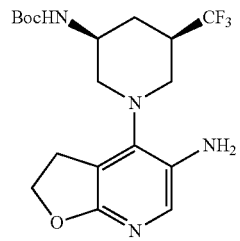

To a mixture of tert-butyl [(3S,5R)-1-(5-nitro-2,3-dihydrofuro[2,3-b]pyridin-4-yl)-5-(trifluoromethyl)piperidin-3-yl]carbamate (227.1 mg, 0.5252 mmol), iron powder (289.6 mg, 5.186 mmol) and ammonium chloride (462.4 mg, 8.644 mmol) was added EtOH (5.0 mL) followed by water (2.5 mL). The mixture was stirred at 80° C. for 1 h. The reaction mixture was filtered through a pad of diatomaceous earth. The diatomaceous earth pad was eluted with a 10% aqueous solution of K$_3$PO$_4$ (50 mL), and EtOAc (50 mL). The separated organic layer was washed with brine (50 mL), dried over Na$_2$SO$_4$, and concentrated to give the crude sub-title compound (211.5 mg). The crude product was used directly in the next step without further purification. LCMS calc. for $C_{18}H_{26}F_3N_4O_3$ (M+H)$^+$: m/z=403.2; found 403.2.

Step 3. 5-Amino-N-{4-[(3S,5R)-3-amino-5-(trifluoromethyl)piperidin-1-yl]-2,3-dihydrofuro[2,3-b]pyridin-5-yl}-2-(2,6-difluorophenyl)-1,3-thiazole-4-carboxamide To a mixture of 5-[(tert-butoxycarbonyl)amino]-2-(2,6-difluorophenyl)-1,3-thiazole-4-carboxylic acid (58.2 mg, 0.163 mmol), tert-butyl [(3S,5R)-1-(5-amino-2,3-dihydrofuro[2,3-b]pyridin-4-yl)-5-(trifluoromethyl)piperidin-3-yl]carbamate (55.3 mg, 0.137 mmol) and HATU (180.9 mg, 0.4758 mmol) was added DMF (2.0 mL) followed by DIPEA (162.2 mg, 1.255 mmol). The reaction mixture was stirred at room temperature for 3 h, and then concentrated under reduced pressure. To the resulting residue was added DCM (2.0 mL), followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (9.7 mg, 13%). LCMS calc. for $C_{23}H_{22}F_5N_6O_2S$ (M+H)$^+$: m/z=541.1; found 541.1.

Example 43

N-{4-[(3S,5R)-3-amino-5-(trifluoromethyl)piperidin-1-yl]-2,3-dihydrofuro[2,3-b]pyridin-5-yl}-6-(2,6-difluorophenyl)-5-fluoropyridine-2-carboxamide

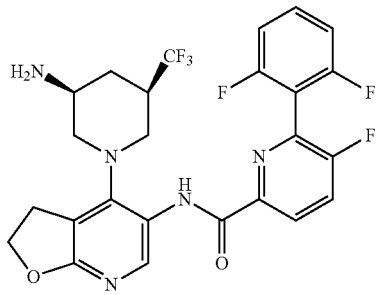 [SMILES: N[C@H]1C[C@@H](C(F)(F)F)CN(c2c(NC(=O)c3ccc(F)c(-c4c(F)cccc4F)n3)cnc3c2CCO3)C1]

To a mixture of 6-(2,6-difluorophenyl)-5-fluoropyridine-2-carboxylic acid (38.7 mg, 0.153 mmol), tert-butyl [(3S,5R)-1-(5-amino-2,3-dihydrofuro[2,3-b]pyridin-4-yl)-5-(trifluoromethyl)piperidin-3-yl]carbamate (51.4 mg, 0.128 mmol) and HATU (178.7 mg, 0.4700 mmol) was added DMF (2.0 mL) followed by DIPEA (159.5 mg, 1.234 mmol). The reaction mixture was stirred at room temperature for 3 h, and then concentrated under reduced pressure. To the resulting residue was added DCM (2.0 mL), followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (13.5 mg, 20%). LCMS calc. for C$_{25}$H$_{22}$F$_6$N$_5$O$_2$ (M+H)$^+$: m/z=538.2; found 538.2.

Example 44

5-Amino-N-{4-[(3S,5R)-3-amino-5-(trifluoromethyl)piperidin-1-yl]-7-hydroxy-6,7-dihydro-5H-cyclopenta[b]pyridin-3-yl}-2-(2,6-difluorophenyl)-1,3-thiazole-4-carboxamide

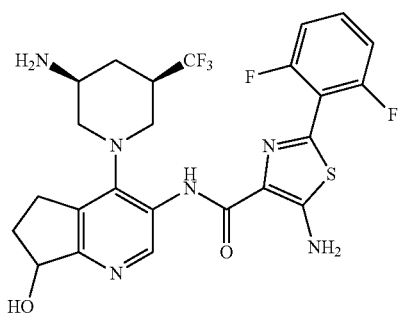 [SMILES: Nc1sc(-c2c(F)cccc2F)nc1C(=O)Nc1cnc2c(c1N1C[C@@H](N)C[C@@H](C(F)(F)F)C1)CCC2O]

Step 1. tert-Butyl [(3S,5R)-1-(3-nitro-6,7-dihydro-5H-cyclopenta[b]pyridin-4-yl)-5-(trifluoromethyl)piperidin-3-yl]carbamate

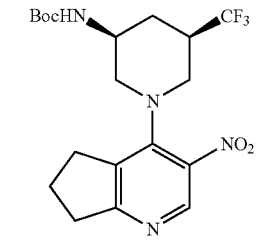 [SMILES: CC(C)(C)OC(=O)N[C@H]1C[C@@H](C(F)(F)F)CN(c2c([N+](=O)[O-])cnc3c2CCC3)C1]

To a mixture of 4-chloro-3-nitro-6,7-dihydro-5H-cyclopenta[b]pyridine (144.2 mg, 0.7260 mmol) and tert-butyl [(3S,5R)-5-(trifluoromethyl)piperidin-3-yl]carbamate (from MolBridge, 179.9 mg, 0.6706 mmol) was added 1-butanol (3.0 mL) followed by DIPEA (493.7 mg, 3.820 mmol). The mixture was stirred at 150° C. for 6 h. After cooling to room temperature, the reaction mixture was concentrated under reduced pressure. The residue was purified by chromatography on silica gel (0-50% EtOAc in hexanes) to afford the sub-title compound as a pale yellow solid (179.2 mg, 62%). LCMS calc. for C$_{19}$H$_{26}$F$_3$N$_4$O$_4$ (M+H)$^+$: m/z=431.2; found 431.2.

Step 2. tert-Butyl[(3S,5R)-1-(3-nitro-1-oxido-6,7-dihydro-5H-cyclopenta[b]pyridin-4-yl)-5-(trifluoromethyl)piperidin-3-yl]carbamate

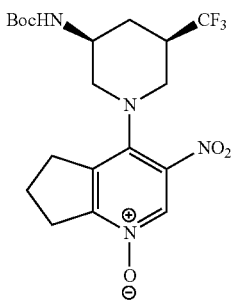 [SMILES: CC(C)(C)OC(=O)N[C@H]1C[C@@H](C(F)(F)F)CN(c2c([N+](=O)[O-])c[n+]([O-])c3c2CCC3)C1]

To a mixture of tert-butyl [(3S,5R)-1-(3-nitro-6,7-dihydro-5H-cyclopenta[b]pyridin-4-yl)-5-(trifluoromethyl)piperidin-3-yl]carbamate (179.2 mg, 0.4163 mmol) and mCPBA (210.6 mg, 0.9397 mmol) was added DCM (2.00 mL). The reaction mixture was stirred at room temperature for 13 h. The mixture was diluted with DCM (30 mL), washed with 1 M NaOH aqueous solution. The separated aqueous layer was extracted with DCM (3×30 mL). The combined organic layers were washed with brine (100 mL), dried over Na$_2$SO$_4$, and concentrated under reduced pressure. The resulting residue was purified by chromatography on silica gel (0-30% MeOH in DCM) to give the sub-title compound (114.7 mg, 62%). LCMS calc. for C$_{19}$H$_{26}$F$_3$N$_4$O$_5$ (M+H)$^+$: m/z=447.2; found 447.2.

Step 3. 4-[(3S,5R)-3-[(tert-Butoxycarbonyl)amino]-5-(trifluoromethyl)piperidin-1-yl]-3-nitro-6,7-dihydro-5H-cyclopenta[b]pyridin-7-yl Acetate

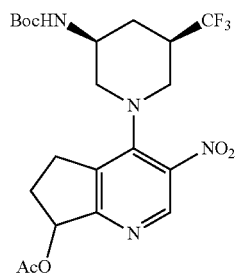 [SMILES: CC(=O)OC1CCc2c1ncc([N+](=O)[O-])c2N1C[C@@H](NC(=O)OC(C)(C)C)C[C@@H](C(F)(F)F)C1]

To tert-butyl [(3S,5R)-1-(3-nitro-1-oxido-6,7-dihydro-5H-cyclopenta[b]pyridin-4-yl)-5-(trifluoromethyl)piperidin-3-yl]carbamate (114.7 mg, 0.2569 mmol) was added Ac$_2$O (2.0 mL, 21 mmol). The reaction mixture was heated at 90° C. for 1 h. After cooling to room temperature, the reaction mixture was concentrated under reduced pressure. The residue was diluted with DCM, and poured into a saturated aqueous solution of Na$_2$CO$_3$ at 0° C. The separated aqueous layer was further extracted with DCM (3 times). The combined organic layers were washed with brine, dried over Na$_2$SO$_4$, and concentrated under reduced pressure. The resulting residue was purified by chromatography on silica gel (0-100% EtOAc in hexanes) to give the sub-title compound as a brown foamy solid (92.3 mg, 74%). LCMS calc. for C$_{21}$H$_{28}$F$_3$N$_4$O$_6$ (M+H)$^+$: m/z=489.2; found 489.2.

Step 4. 3-Amino-4-[(3S,5R)-3-[(tert-butoxycarbonyl)amino]-5-(trifluoromethyl)piperidin-1-yl]-6,7-dihydro-5H-cyclopenta[b]pyridin-7-yl Acetate

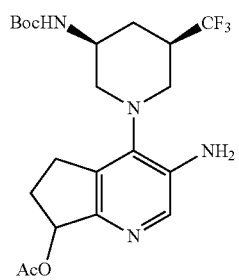

To a mixture of 4-[(3S,5R)-3-[(tert-butoxycarbonyl)amino]-5-(trifluoromethyl)piperidin-1-yl]-3-nitro-6,7-dihydro-5H-cyclopenta[b]pyridin-7-yl acetate (92.3 mg, 0.189 mmol) and iron powder (295.6 mg, 5.293 mmol) was added AcOH (2.0 mL). The mixture was stirred at room temperature for 3 h. The reaction mixture was diluted with EtOAc, filtered through a pad of diatomaceous earth (eluted with EtOAc). The filtrate was washed with a saturated aqueous solution of Na$_2$CO$_3$, dried over Na$_2$SO$_4$, and concentrated to give the crude sub-title compound as dark semi-solid (86.6 mg). The crude product was used directly in the next step without further purification. LCMS calc. for C$_{21}$H$_{30}$F$_3$N$_4$O$_4$ (M+H)$^+$: m/z=459.2; found 459.2.

Step 5. 3-({[5-[(tert-Butoxycarbonyl)amino]-2-(2,6-difluorophenyl)-1,3-thiazol-4-yl]carbonyl}amino)-4-[(3S,5R)-3-[(tert-butoxycarbonyl)amino]-5-(trifluoromethyl)piperidin-1-yl]-6,7-dihydro-5H-cyclopenta[b]pyridin-7-yl Acetate

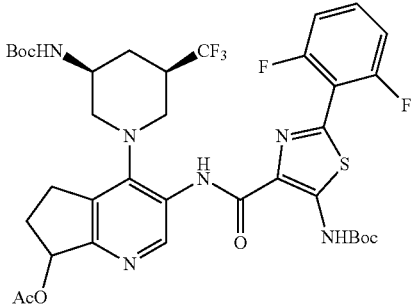 [SMILES: CC(=O)OC1CCc2c1ncc(NC(=O)c1nc(-c3c(F)cccc3F)sc1NC(=O)OC(C)(C)C)c2N1C[C@@H](NC(=O)OC(C)(C)C)C[C@@H](C(F)(F)F)C1]

To a mixture of 3-amino-4-[(3S,5R)-3-[(tert-butoxycarbonyl)amino]-5-(trifluoromethyl)piperidin-1-yl]-6,7-dihydro-5H-cyclopenta[b]pyridin-7-yl acetate (86.6 mg, 0.189 mmol), 5-[(tert-butoxycarbonyl)amino]-2-(2,6-difluorophenyl)-1,3-thiazole-4-carboxylic acid (89.5 mg, 0.251 mmol), and HATU (221.8 mg, 0.5833 mmol) was added DMF (2.0 mL) followed by DIPEA (164.3 mg, 1.271 mmol). The reaction mixture was stirred at 45° C. for 14 h, and then concentrated under reduced pressure. The resulting residue was purified by chromatography on silica gel (0-100% EtOAc in hexanes) to give the sub-title compound as a dark semi-oil (110.3 mg, 73%). LCMS calc. for C$_{36}$H$_{42}$F$_5$N$_6$O$_7$S (M+H)$^+$: m/z=797.3; found 797.3.

Step 6. 5-Amino-N-{4-[(3S,5R)-3-amino-5-(trifluoromethyl)piperidin-1-yl]-7-hydroxy-6,7-dihydro-5H-cyclopenta[b]pyridin-3-yl}-2-(2,6-difluorophenyl)-1,3-thiazole-4-carboxamide To a solution of 3-({[5-[(tert-butoxycarbonyl)amino]-2-(2,6-difluorophenyl)-1,3-thiazol-4-yl]carbonyl}amino)-4-[(3S,5R)-3-[(tert-butoxycarbonyl)amino]-5-(trifluoromethyl)piperidin-1-yl]-6,7-dihydro-5H-cyclopenta[b]pyridin-7-yl acetate (110.3 mg, 0.1384 mmol) in THF (1.0 mL) was added a 1.0 M NaOH solution in water (1.00 mL, 1.00 mmol) followed by MeOH (2.0 mL). The reaction mixture was stirred at room temperature for 1 h, and then concentrated under reduced pressure. To the resulting residue was added DCM (2.0 mL), followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford both diastereoisomers of the title compound as white solids (9.3 mg for each, total yield 24%).

Diastereoisomer 1. First peak. Retention time 2.044 min., LCMS calc. for C$_{24}$H$_{24}$F$_5$N$_6$O$_2$S (M+H)$^+$: m/z=555.2; found 555.0.

Diastereoisomer 2. Second peak. Retention time 2.163 min., LCMS calc. for C$_{24}$H$_{24}$F$_5$N$_6$O$_2$S (M+H)$^+$: m/z=555.2; found 555.0.

The diastereoisomers correspond to the (7R) and (7S) diastereoisomers of the title compound.

Example 45

N-{4-[(3S,5R)-3-Amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide

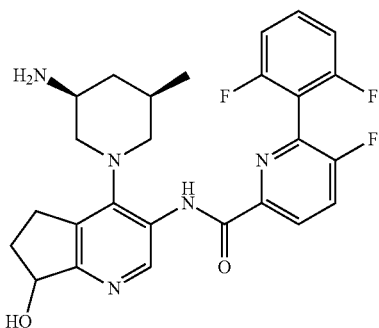 [SMILES: C[C@@H]1C[C@H](N)CN(c2c(NC(=O)c3ccc(F)c(-c4c(F)cccc4F)n3)cnc3c2CCC3O)C1]

Step 1: tert-Butyl [(3S,5R)-5-methyl-1-(3-nitro-6,7-dihydro-5H-cyclopenta[b]pyridin-4-yl)piperidin-3-yl]carbamate

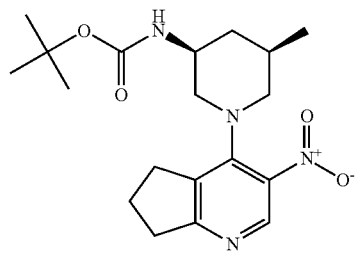 [SMILES: C[C@@H]1C[C@H](NC(=O)OC(C)(C)C)CN(c2c([N+](=O)[O-])cnc3c2CCC3)C1]

A mixture of 4-chloro-3-nitro-6,7-dihydro-5H-cyclopenta[b]pyridine (19.4 mg, 0.10 mmol), tert-butyl [(3S,5R)-5-methylpiperidin-3-yl]carbamate (22.0 mg, 0.10 mmol) and triethylamine (40.9 µL, 0.29 mmol) in isopropyl alcohol (0.224 mL) was stirred at 100° C. for 40 min. The reaction mixture was concentrated under vacuum and the residue was purified by silica gel column chromatography using CombiFlash® (0 to 50% EtOAc in hexanes) to give the sub-title compound as pale yellow powder (36.8 mg, 100%). LCMS calc. for $C_{19}H_{29}N_4O_4$ (M+H)$^+$: m/z=377.1. Found: 377.1.

Step 2: tert-Butyl [(3S,5R)-5-methyl-1-(3-nitro-1-oxido-6,7-dihydro-5H-cyclopenta[b]pyridin-4-yl)piperidin-3-yl]carbamate

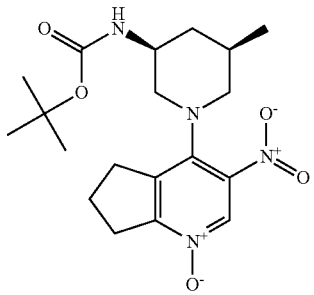 [SMILES: C[C@@H]1C[C@H](NC(=O)OC(C)(C)C)CN(c2c([N+](=O)[O-])c[n+]([O-])c3c2CCC3)C1]

To a solution of tert-butyl [(3S,5R)-5-methyl-1-(3-nitro-6,7-dihydro-5H-cyclopenta[b]pyridin-4-yl)piperidin-3-yl]carbamate (32.3 mg, 0.086 mmol) in DCM (0.50 mL) at 0° C. was added mCPBA (25.0 mg, 0.112 mmol). The reaction mixture was stirred at room temperature for 1 h. The mixture was treated with $Na_2S_2O_3$ solution, followed by 1N NaOH, and stirred for 30 min. at room temperature. The organic layer was separated, dried, filtered and concentrated under vacuum to give the crude N-oxide product. The crude product was purified by preparative LC-MS (XBridge™ preparative C18 5 µm OBD™ column, 30×10 mm, 60 mL/min., eluting with a gradient of MeCN and water with 0.1% $NH_4OH$) to afford the sub-title compound (20 mg, 40%). LCMS calc. for $C_{19}H_{29}N_4O_5$ (M+H)$^+$: m/z=393.2. Found: 393.1.

Step 3: 4-{(3S,5R)-3-[(tert-Butoxycarbonyl)amino]-5-methylpiperidin-1-yl}-3-nitro-6,7-dihydro-5H-cyclopenta[b]pyridin-7-yl Acetate

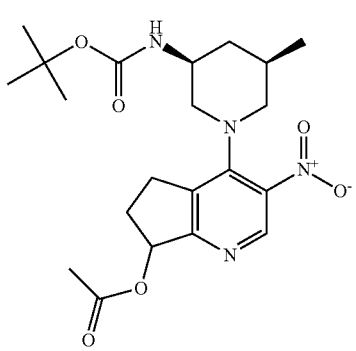 [SMILES: CC(=O)OC1CCc2c1ncc([N+](=O)[O-])c2N1C[C@H](C)C[C@H](NC(=O)OC(C)(C)C)C1]

$Ac_2O$ (15.6 mg, 0.153 mmol) was added to the N-oxide tert-butyl [(3S,5R)-5-methyl-1-(3-nitro-1-oxido-6,7-dihydro-5H-cyclopenta[b]pyridin-4-yl)piperidin-3-yl]carbamate (10.0 mg, 0.026 mmol) in a sealed tube. The reaction mixture was heated at 90° C. for 30 min. and the solution was then concentrated under reduced pressure. The residue was then dissolved in DCM, then poured into ice cold $Na_2CO_3$ solution. The aqueous layer was extracted with DCM twice. The combined organic layers were dried, filtered and concentrated under reduced pressure to give the sub-title compound as off-white powder (11.2 mg, 95%). LCMS calc. for $C_{21}H_{31}N_4O_6$ (M+H)$^+$: m/z=435.2. Found: 435.1.

Step 4: 3-Amino-4-{(3S,5R)-3-[(tert-butoxycarbonyl)amino]-5-methylpiperidin-1-yl}-6,7-dihydro-5H-cyclopenta[b]pyridin-7-yl Acetate

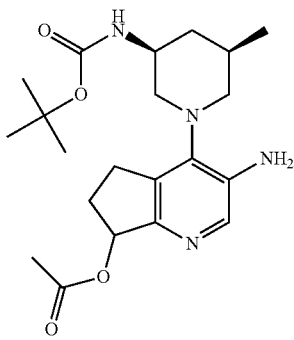 [SMILES: CC(=O)OC1CCc2c1ncc(N)c2N1C[C@H](C)C[C@H](NC(=O)OC(C)(C)C)C1]

A mixture of 4-{(3S,5R)-3-[(tert-butoxycarbonyl)amino]-5-methylpiperidin-1-yl}-3-nitro-6,7-dihydro-5H-cyclopenta[b]pyridin-7-yl acetate (11.2 mg, 0.026 mmol), AcOH (73.3 µL) and iron powder (14.4 mg, 0.26 mmol) was stirred at room temperature for 3 h. The reaction mixture was diluted with EtOAc, filtered and washed with more EtOAc. The filtrate was concentrated under vacuum, and the residue was diluted with EtOAc and neutralized with $Na_2CO_3$ solution. The mixture was stirred at room temperature for 30 min. The organic layer was separated, dried over $Na_2SO_4$, filtered and concentrated under vacuum to give the sub-title compound as a yellowish solid (10.0 mg, 96%). LCMS calc. for $C_{21}H_{33}N_4O_4$ (M+H)⁺: m/z=405.2. Found: 405.1.

Step 5: 4-{(3S,5R)-3-[(tert-Butoxycarbonyl)amino]-5-methylpiperidin-1-yl}-3-({[6-(2,6-difluorophenyl)-5-fluoropyridin-2-yl]carbonyl}amino)-6,7-dihydro-5H-cyclopenta[b]pyridin-7-yl Acetate

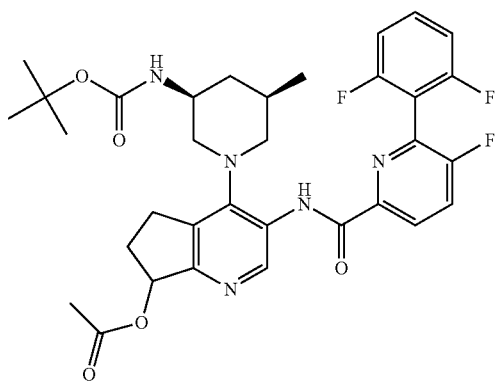 [SMILES: CC(=O)OC1CCc2c1ncc(NC(=O)c1ccc(F)c(-c3c(F)cccc3F)n1)c2N1C[C@H](C)C[C@H](NC(=O)OC(C)(C)C)C1]

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (12.0 mg, 0.030 mmol), 6-(2,6-difluorophenyl)-5-fluoropyridine-2-carboxylic acid (9.0 mg, 0.036 mmol), HATU (28.2 mg, 0.074 mmol) in DMF (0.07 mL) and DIPEA (11.5 mg, 0.089 mmol) was stirred at room temperature for 2 h. The reaction mixture was filtered, concentrated and purified by preparative LC-MS (XBridge™ preparative C18 5 µm OBD™ column, 30×10 mm, 60 mL/min., eluting with a gradient of MeCN and water with 0.1% $NH_4OH$) to afford the sub-title compound (11 mg, 58%). LCMS calc. for $C_{33}H_{37}F_3N_5O_5$ (M+H)⁺: m/z=640.3. Found: 640.1.

Step 6: N-{4-[(3S,5R)-3-Amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide A mixture of 4-{(3S,5R)-3-[(tert-butoxycarbonyl)amino]-5-methylpiperidin-1-yl}-3-({[6-(2,6-difluorophenyl)-5-fluoropyridin-2-yl]carbonyl}amino)-6,7-dihydro-5H-cyclopenta[b]pyridin-7-yl acetate (10.2 mg, 0.0159 mmol), MeOH (0.2 mL), THF (0.1 mL) and 1.0 M aq. NaOH (0.10 mL, 0.10 mmol) was stirred at room temperature for 30 min., then evaporated under reduced pressure.

The resulting crude intermediate was dissolved in DCM (0.2 mL), and TFA (0.16 mL, 2.1 mmol) was added. The reaction mixture was stirred at room temperature for 30 min. The solvent was removed under reduced pressure. The residue was diluted with 4 mL of MeOH, filtered and purified by preparative LC-MS (XBridge™ preparative C18 5 µm OBD™ column, 30×10 mm, 60 mL/min., eluting with a gradient of MeCN and water with 0.1% $NH_4OH$) to give both diastereoisomers of the title compound as white powders. On analytical HPLC (Waters SunFire™ C18, 2.1×50 mm, 5 µm; flow rate 3 m/min.; injection volume 2 µL; gradient from 2 to 80% B in 3 minutes (A=water with 0.025% TFA, B=MeCN)) the diastereoisomers had the following properties: Diastereoisomer 1. First peak. Retention time 1.805 min., LCMS calc. for $C_{26}H_{27}F_3N_5O_2$ (M+H)⁺: m/z=498.2. Found: 498.1.

Diastereoisomer 2. Second peak. Retention time 1.942 min., LCMS calc. for $C_{26}H_{27}F_3N_5O_2$ (M+H)⁺: m/z=498.2. Found: 498.1.

Example 46

3-Amino-N-{4-[(3S,5R)-3-amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide

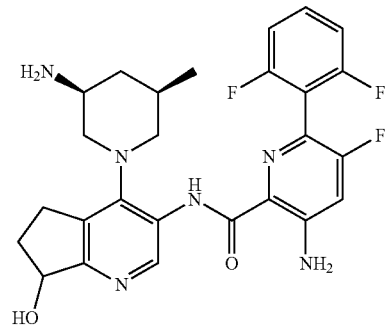 [SMILES: C[C@@H]1C[C@H](N)CN(c2c(NC(=O)c3nc(-c4c(F)cccc4F)c(F)cc3N)cnc3c2CCC3O)C1]

Step 1: 3-({[3-[(tert-Butoxycarbonyl)amino]-6-(2,6-difluorophenyl)-5-fluoropyridin-2-yl]carbonyl}amino)-4-{(3S,5R)-3-[(tert-butoxycarbonyl)amino]-5-methylpiperidin-1-yl}-6,7-dihydro-5H-cyclopenta[b]pyridin-7-yl Acetate

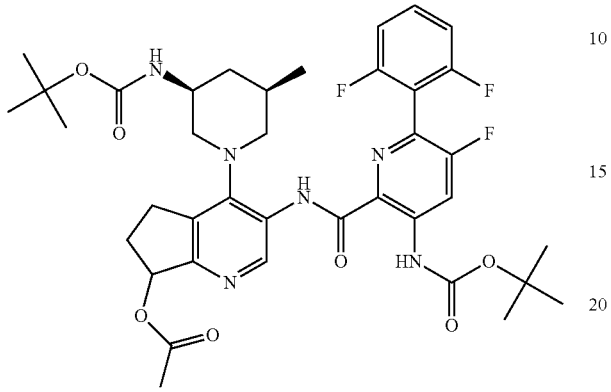

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (13.0 mg, 0.032 mmol), 3-[(tert-butoxycarbonyl)amino]-6-(2,6-difluorophenyl)-5-fluoropyridine-2-carboxylic acid (14.2 mg, 0.039 mmol), HATU (30.5 mg, 0.080 mmol) in DMF (0.09 mL) and DIPEA (0.019 mL, 0.096 mmol) was stirred at room temperature for 16 h. The reaction mixture was diluted with MeOH and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a white powder (14.2 mg, 59%). LCMS calc. for $C_{38}H_{46}F_3N_6O_7$ (M+H)$^+$: m/z=755.3. Found: 755.1.

Step 2: 3-Amino-N-{4-[(3S,5R)-3-amino-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide A mixture of 3-({[3-[(tert-butoxycarbonyl)amino]-6-(2,6-difluorophenyl)-5-fluoropyridin-2-yl]carbonyl}amino)-4-{(3S,5R)-3-[(tert-butoxycarbonyl)amino]-5-methylpiperidin-1-yl}-6,7-dihydro-5H-cyclopenta[b]pyridin-7-yl acetate (14.2 mg, 0.019 mmol), MeOH (0.22 mL), THF (0.12 mL) and 1.0 M aq. NaOH (0.12 mL, 0.12 mmol) was stirred at room temperature for 20 min. The solvent was then evaporated under reduced pressure.

The crude intermediate was dissolved in DCM (0.19 mL), and TFA (0.19 mL, 2.5 mmol) was added. The reaction mixture was stirred at room temperature for 20 min. then evaporated under reduced pressure. The residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give both diastereoisomers of the title compound as white powders. On analytical HPLC (Waters SunFire™ C18, 2.1×50 mm, 5 μm; Flow rate 3 mL/min.; injection volume 2 μL; gradient from 2 to 80% B in 3 minutes (A=water with 0.025% TFA, B=MeCN)) the diastereoisomers had the following properties:

Diastereoisomer 1. First peak. Retention time 1.775 min., LCMS calc. for $C_{26}H_{28}F_3N_6O_2$ (M+H)$^+$: m/z=513.2. Found: 513.1.

Diastereoisomer 2. Second peak. Retention time 1.853 min., LCMS calc. for $C_{26}H_{28}F_3N_6O_2$ (M+H)$^+$: m/z=513.2. Found: 513.1.

The diastereoisomers correspond to the (7R) and (7S) diastereoisomers of the title compound.

Example 47

5-Amino-N-{4-[(3S,5R)-3-amino-5-methylpiperidin-1-yl]-7-hydroxy-6,7-dihydro-5H-cyclopenta[b]pyridin-3-yl}-2-(2,6-difluorophenyl)-1,3-thiazole-4-carboxamide

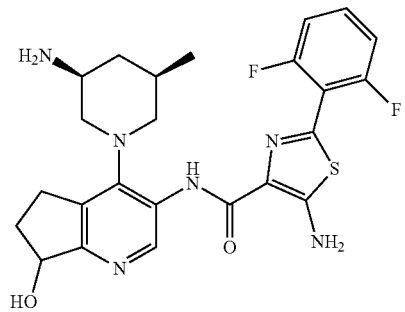 [SMILES: C[C@@H]1C[C@H](N)CN(c2c(NC(=O)c3nc(-c4c(F)cccc4F)sc3N)cnc3c2CCC3O)C1]

Step 1: 3-({[5-[(tert-Butoxycarbonyl)amino]-2-(2,6-difluorophenyl)-1,3-thiazol-4-yl]carbonyl}amino)-4-{(3S,5R)-3-[(tert-butoxycarbonyl)amino]-5-methylpiperidin-1-yl}-6,7-dihydro-5H-cyclopenta[b]pyridin-7-yl Acetate

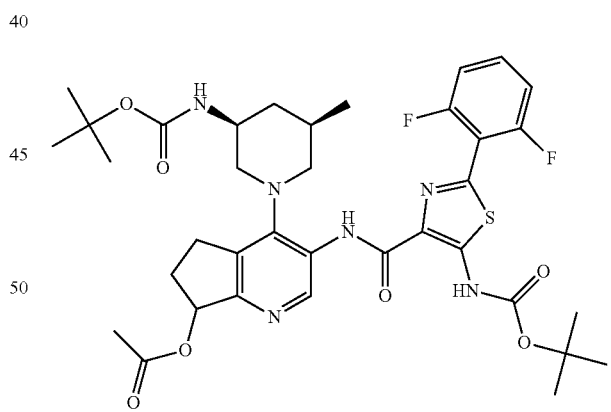

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (13.0 mg, 0.032 mmol), 5-[(tert-butoxycarbonyl)amino]-2-(2,6-difluorophenyl)-1,3-thiazole-4-carboxylic acid (13.7 mg, 0.040 mmol), HATU (30.5 mg, 0.080 mmol) in DMF (0.09 mL) and DIPEA (12.5 mg, 0.096 mmol) was stirred at room temperature for 16 h. The reaction mixture was diluted with MeOH and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a white powder (12.4 mg, 52%). LCMS calc. for $C_{36}H_{45}F_2N_6O_7S$ (M+H)$^+$: m/z=743.3. Found: 743.3.

Step 2: 5-Amino-N-{4-[(3S,5R)-3-amino-5-methylpiperidin-1-yl]-7-hydroxy-6,7-dihydro-5H-cyclopenta[b]pyridin-3-yl}-2-(2,6-difluorophenyl)-1,3-thiazole-4-carboxamide A mixture of 3-({[5-[(tert-butoxycarbonyl)amino]-2-(2,6-difluorophenyl)-1,3-thiazol-4-yl]carbonyl}amino)-4-{(3S,5R)-3-[(tert-butoxycarbonyl)amino]-5-methylpiperidin-1-yl}-6,7-dihydro-5H-cyclopenta[b]pyridin-7-yl acetate (12.4 mg, 0.0167 mmol), MeOH (0.2 mL), THF (0.1 mL) and 1.0 M aq. NaOH (0.11 mL, 0.11 mmol) was stirred at room temperature for 20 min. The organic solvents and water were removed under reduced pressure to give a crude intermediate, which was dissolved in DCM (0.2 mL), followed by the addition of TFA (0.17 mL, 2.2 mmol). The reaction mixture was stirred at room temperature for 20 min. After removal of the solvent under reduced pressure, the residue was diluted with MeOH, filtered and purified by preparative LC-MS (XBridge™ preparative C18 5 µm OBD™ column, 30×10 mm, 60 mL/min., eluting with a gradient of MeCN and water with 0.1% NH$_4$OH) to give both diastereoisomers of the title compound as white powders. On analytical HPLC (Waters SunFire™ C18, 2.1×50 mm, 5 µm; Flow rate 3 mL/min.; injection volume 2 µL; gradient from 2 to 80% B in 3 minutes (A=water with 0.025% TFA, B=MeCN)) the diastereoisomers had the following properties:

Diastereoisomer 1. First peak. Retention time 1.693 min., LCMS calc. for $C_{24}H_{27}F_2N_6O_2S$ (M+H)$^+$: m/z=501.2. Found: 501.1.

Diastereoisomer 2. Second peak. Retention time 1.824 min., LCMS calc. for $C_{24}H_{27}F_2N_6O_2S$ (M+H)$^+$: m/z=501.2. Found: 501.1.

The diastereoisomers correspond to the (7R) and (7S) diastereoisomers of the title compound.

Example 48

3-Amino-N-{4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide

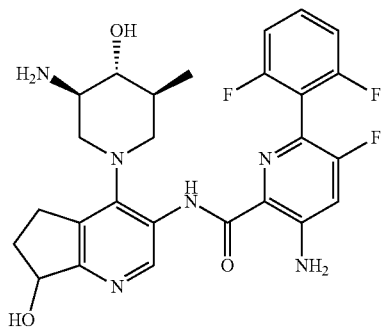 [SMILES: C[C@H]1CN(c2c(NC(=O)c3nc(-c4c(F)cccc4F)c(F)cc3N)cnc3c2CCC3O)C[C@@H](N)[C@@H]1O]

Step 1: tert-Butyl {(3R,4R,5S)-1-[3-({[3-[(tert-butoxycarbonyl)amino]-6-(2,6-difluorophenyl)-5-fluoropyridin-2-yl]carbonyl}amino)-7-hydroxy-6,7-dihydro-5H-cyclopenta[b]pyridin-4-yl]-4-hydroxy-5-methylpiperidin-3-yl}carbamate

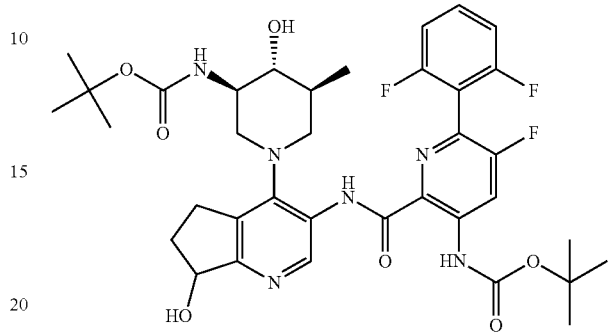

A mixture of (3R,4R,5S)-1-[7-(acetyloxy)-3-amino-6,7-dihydro-5H-cyclopenta[b]pyridin-4-yl]-3-[(tert-butoxycarbonyl)amino]-5-methylpiperidin-4-yl acetate (11.0 mg, 0.024 mmol), 3-[(tert-butoxycarbonyl)amino]-6-(2,6-difluorophenyl)-5-fluoropyridine-2-carboxylic acid (12 mg, 0.03 mmol), HATU (33 mg, 0.09 mmol) in DMF (0.09 mL) and DIPEA (23 mg, 0.18 mmol) was stirred at room temperature for 16 h. The reaction mixture was diluted with 1N NaOH solution (0.5 mL) and MeOH (0.5 mL). The reaction mixture was stirred at room temperature for 1 h. After concentration under vacuum, the aqueous layer was extracted with DCM three times. The combined organic layers were dried, filtered and concentrated under reduced pressure to give the crude product, which was purified by preparative LC-MS (XBridge™ preparative C18 5 µm OBD™ column, 30×10 mm, 60 mL/min., eluting with a gradient of MeCN and water with 0.1% NH$_4$OH) to give the sub-title compound as a white powder. LCMS calc. for $C_{36}H_{44}F_3N_6O_7$ (M+H)$^+$: m/z=729.3; Found: 729.4.

Step 2: 3-Amino-N-{4-[(3R,4R,5S)-3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide A mixture of tert-butyl {(3R,4R,5S)-1-[3-({[3-[(tert-butoxycarbonyl)amino]-6-(2,6-difluorophenyl)-5-fluoropyridin-2-yl]carbonyl}amino)-7-hydroxy-6,7-dihydro-5H-cyclopenta[b]pyridin-4-yl]-4-hydroxy-5-methylpiperidin-3-yl}carbamate (7.0 mg, 0.01 mmol) and 4.0 M TFA in DCM (2.0 mL) was stirred at room temperature for 1 h. After removal of the solvent under reduced pressure, the residue was diluted with MeOH, filtered and purified by preparative LC-MS (XBridge™ preparative C18 5 µm OBD™ column, 30×10 mm, 60 mL/min., eluting with a gradient of MeCN and water with 0.1% NH$_4$OH) to give both diastereoisomers of the title compound as white powders. On analytical HPLC (Waters SunFire™ C18, 2.1×50 mm, 5 µm; flow rate 3 mL/min.; injection volume 2 µL; gradient from 2 to 80% B in 3 minutes (A=water with 0.025% TFA, B=MeCN)), the diastereoisomers had the following properties:

Diastereoisomer 1. First peak. Retention time 1.450 min., LCMS calc. for $C_{26}H_{28}F_3N_6O_3$ (M+H)$^+$: m/z=529.2. Found: 529.2.

Diastereoisomer 2. Second peak. Retention time 1.506 min., LCMS calc. for $C_{26}H_{28}F_3N_6O_3$ (M+H)$^+$: m/z=529.2. Found: 529.2.

The diastereoisomers correspond to the (7R) and (7S) diastereoisomers of the title compound.

Example 49

5-Amino-N-{4-[(3R,4R,5S)-3-amino-4-hydroxy-5-methylpiperidin-1-yl]-7-hydroxy-6,7-dihydro-5H-cyclopenta[b]pyridin-3-yl}-2-(2,6-difluorophenyl)-1,3-thiazole-4-carboxamide

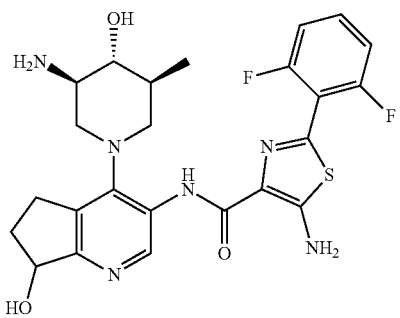 [SMILES: C[C@H]1CN(c2c(NC(=O)c3nc(-c4c(F)cccc4F)sc3N)cnc3c2CCC3O)C[C@@H](N)[C@@H]1O]

Step 1: tert-Butyl {(3R,4R,5S)-1-[3-({[5-[(tert-butoxycarbonyl)amino]-2-(2,6-difluorophenyl)-1,3-thiazol-4-yl]carbonyl}amino)-7-hydroxy-6,7-dihydro-5H-cyclopenta[b]pyridin-4-yl]-4-hydroxy-5-methylpiperidin-3-yl}carbamate

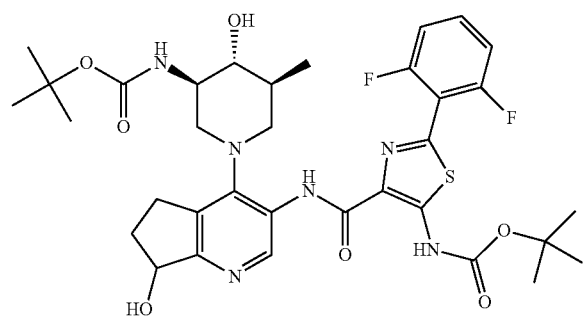 [SMILES: C[C@H]1CN(c2c(NC(=O)c3nc(-c4c(F)cccc4F)sc3NC(=O)OC(C)(C)C)cnc3c2CCC3O)C[C@@H](NC(=O)OC(C)(C)C)[C@@H]1O]

A mixture of (3,4R,5S)-1-[7-(acetyloxy)-3-amino-6,7-dihydro-5H-cyclopenta[b]pyridin-4-yl]-3-[(tert-butoxycarbonyl)amino]-5-methylpiperidin-4-yl acetate (11.0 mg, 0.024 mmol), 5-[(tert-butoxycarbonyl)amino]-2-(2,6-difluorophenyl)-1,3-thiazole-4-carboxylic acid (12 mg, 0.032 mmol), HATU (33 mg, 0.09 mmol) in DMF (0.09 mL) and DIPEA (23 mg, 0.18 mmol) was stirred at room temperature for 16 h. The reaction mixture was diluted with 1 M NaOH solution (0.5 mL) and MeOH (0.5 mL). The reaction mixture was stirred at room temperature for 1 h, and was then concentrated under reduced pressure. The resulting aqueous layer was extracted with DCM three times. The combined organic layers were dried, filtered and concentrated under reduced pressure to give the crude product, which was purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a white powder. LCMS calc. for $C_{34}H_{43}F_2N_6O_7S$ (M+H)$^+$: m/z=717.3. Found: 717.3.

Step 2: 5-Amino-N-{4-[(3R,4R,5S)-3-amino-4-hydroxy-5-methylpiperidin-1-yl]-7-hydroxy-6,7-dihydro-5H-cyclopenta[b]pyridin-3-yl}-2-(2,6-difluorophenyl)-1,3-thiazole-4-carboxamide A mixture of tert-butyl {(3R,4R,5S)-1-[3-({[5-[(tert-butoxycarbonyl)amino]-2-(2,6-difluorophenyl)-1,3-thiazol-4-yl]carbonyl}amino)-7-hydroxy-6,7-dihydro-5H-cyclopenta[b]pyridin-4-yl]-4-hydroxy-5-methylpiperidin-3-yl}carbamate (7.0 mg, 0.01 mmol) and 4.0 M TFA in DCM (2.0 mL) was stirred at room temperature for 1 h. After removal of the solvent under reduced pressure, the residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give both diastereoisomers of the title compound as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)), the diastereoisomers had the following properties:

Diastereoisomer 1. First peak. Retention time 1.325 min., LCMS calc. for $C_{24}H_{27}F_2N_6O_3S$ (M+H)$^+$: m/z=517.2. Found: 517.2.

Diastereoisomer 2. Second peak. Retention time 1.378 min., LCMS calc. for $C_{24}H_{27}F_2N_6O_3S$ (M+H)$^+$: m/z=517.2. Found: 517.2.

The diastereoisomers correspond to the (7R) and (7S) diastereoisomers of the title compound.

Example 50

N-{4-[(3S)-3-Aminopiperidin-1-yl]-7-oxo-6,7-dihydro-5H-cyclopenta[b]pyridin-3-yl}-6-(2,6-difluorophenyl)-5-fluoropyridine-2-carboxamide

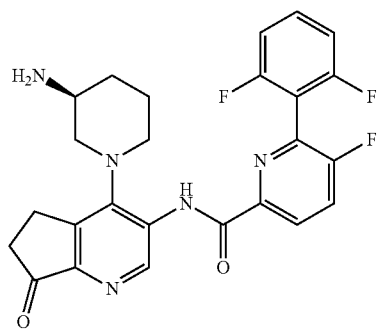 [SMILES: N[C@H]1CCCN(c2c(NC(=O)c3ccc(F)c(-c4c(F)cccc4F)n3)cnc3c2CCC3=O)C1]

165

Step 1: tert-Butyl {(3S)-1-[3-({[6-(2,6-difluorophenyl)-5-fluoropyridin-2-yl]carbonyl}amino)-7-hydroxy-6,7-dihydro-5H-cyclopenta[b]pyridin-4-yl]piperidin-3-yl}carbamate

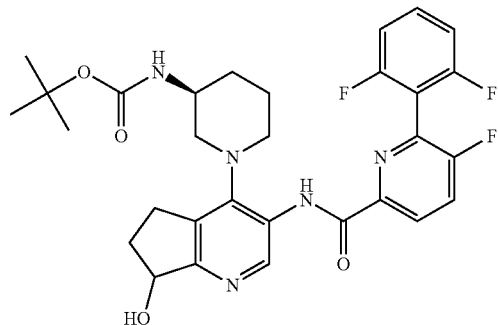 [SMILES: CC(C)(C)OC(=O)N[C@H]1CCCN(c2c(NC(=O)c3ccc(F)c(-c4c(F)cccc4F)n3)cnc3c2CCC3O)C1]

A mixture of 4-{(3S)-3-[(tert-butoxycarbonyl)amino]piperidin-1-yl}-3-({[6-(2,6-difluorophenyl)-5-fluoropyridin-2-yl]carbonyl}amino)-6,7-dihydro-5H-cyclopenta[b]pyridin-7-yl acetate (174 mg, 0.28 mmol), MeOH (0.7 mL), THF (0.7 mL) and 1.0 M aq. NaOH (1.1 mL, 1.1 mmol) was stirred at room temperature for 20 min. The organic solvents were removed under reduced pressure. The aqueous layer was diluted with EtOAc and NH$_4$Cl (aq.), extracted with EtOAc twice. The combined organic layers were dried, filtered and concentrated under reduced pressure to give the sub-title compound (151 mg, 93%). LCMS calc. for C$_{30}$H$_{33}$F$_3$N$_5$O$_4$ (M+H)$^+$: m/z=584.2. Found: 584.2.

Step 2: tert-Butyl {(3S)-1-[3-({[6-(2,6-difluorophenyl)-5-fluoropyridin-2-yl]carbonyl}amino)-7-oxo-6,7-dihydro-5H-cyclopenta[b]pyridin-4-yl]piperidin-3-yl}carbamate

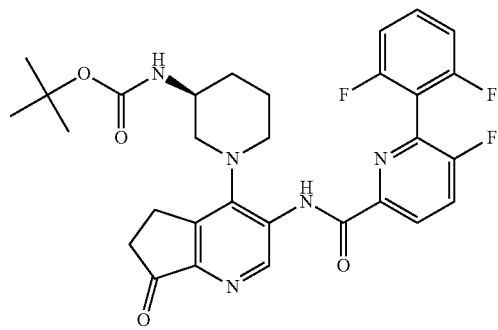 [SMILES: CC(C)(C)OC(=O)N[C@H]1CCCN(c2c(NC(=O)c3ccc(F)c(-c4c(F)cccc4F)n3)cnc3c2CCC3=O)C1]

To a solution of tert-butyl {(3S)-1-[3-({[6-(2,6-difluorophenyl)-5-fluoropyridin-2-yl]carbonyl}amino)-7-hydroxy-6,7-dihydro-5H-cyclopenta[b]pyridin-4-yl]piperidin-3-yl}carbamate (100 mg, 0.17 mmol) in DCM (0.8 mL), Dess-Martin periodinane (95 mg, 0.22 mmol) was slowly added. The reaction mixture was stirred at room temperature for 40 min. The reaction mixture was neutralized with 1 M NaOH, diluted with MeOH, filtered and concentrated under vacuum. The crude product was purified by silica gel column chromatography using CombiFlash® (0 to 100% EtOAc in hexanes) to give light brown powder as the sub-title compound (41 mg, 41%). LCMS calc. for C$_3$H$_{31}$F$_3$N$_5$O$_4$ (M+H)$^+$: m/z=582.2. Found: 582.2.

166

Step 3: N-{4-[(3S)-3-Aminopiperidin-1-yl]-7-oxo-6,7-dihydro-5H-cyclopenta[b]pyridin-3-yl}-6-(2,6-difluorophenyl)-5-fluoropyridine-2-carboxamide A mixture of tert-butyl {(3S)-1-[3-({[6-(2,6-difluorophenyl)-5-fluoropyridin-2-yl]carbonyl}amino)-7-oxo-6,7-dihydro-5H-cyclopenta[b]pyridin-4-yl]piperidin-3-yl}carbamate (6.0 mg, 0.010 mmol) in DCM (0.05 mL) and TFA (0.052 mL, 0.68 mmol) was stirred at room temperature for 20 min. The solution was then concentrated under reduced pressure. The residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give the title compound as a white powder (2.2 mg, 44%). LCMS calc. for C$_{25}$H$_{23}$F$_3$N$_5$O$_2$ (M+H)$^+$: m/z=482.2; Found: 482.3.

Example 51

N-{4-[(3R,4R,5S)-3-Amino-4-hydroxy-5-methylpiperidin-1-yl]-7-hydroxy-6,7-dihydro-5H-cyclopenta[b]pyridin-3-yl}-6-(4-ethoxy-2,6-difluorophenyl)-5-fluoropyridine-2-carboxamide

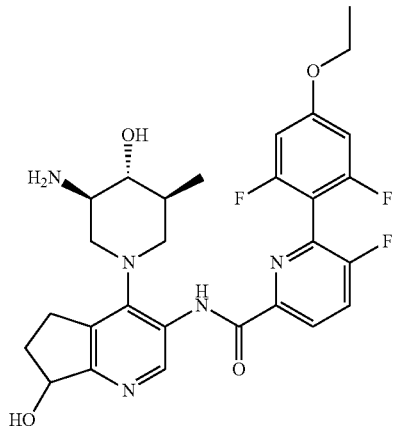 [SMILES: CCOc1cc(F)c(-c2nc(C(=O)Nc3cnc4c(c3N3C[C@@H](N)[C@H](O)[C@@H](C)C3)CCC4O)ccc2F)c(F)c1]

Step 1: 6-(4-Ethoxy-2,6-difluorophenyl)-5-fluoropyridine-2-carboxylic Acid

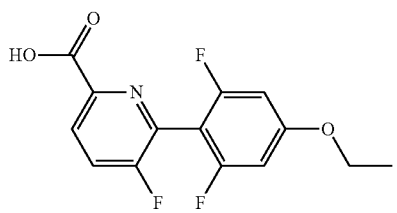 [SMILES: CCOc1cc(F)c(-c2nc(C(=O)O)ccc2F)c(F)c1]

A mixture of (4-ethoxy-2,6-difluorophenyl)boronic acid (0.11 g, 0.54 mmol), methyl 6-bromo-5-fluoropyridine-2-carboxylate (0.14 g, 0.60 mmol), 1,4-dioxane (1.3 mL), DIPEA (0.19 mL, 1.1 mmol) and water (0.03 mL) was flushed with nitrogen for 5 min. and then bis(tri-tert-butylphosphine)palladium (0.056 g, 0.11 mmol) was added. The reaction mixture was heated at 130° C. for 2 h. The mixture was filtered and concentrated under vacuum, and the residue was purified by silica gel column chromatography using CombiFlash® (0-50% EtOAc in hexanes) to give the desired ester (0.27 g, 60%). This ester was dissolved in THF (1.0 mL) and MeOH (1.0 mL), followed by the addition of 1.0 M aq. NaOH (2.0 mL, 2.0 mmol). The reaction mixture was stirred at room temperature for 1 h, After removal of the organic solvent under reduced pressure, the residue was neutralized with HCl. The aqueous layer was extracted with EtOAc twice. The combined organic layers were dried over $Na_2SO_4$, filtered and concentrated under vacuum to give the sub-title compound. LCMS calc. for $C_{14}H_{11}F_3NO_3$ $(M+H)^+$: m/z=298.1. Found: 298.1.

Step 2: tert-Butyl {(3R,4R,5S)-1-[3-({[6-(4-ethoxy-2,6-difluorophenyl)-5-fluoropyridin-2-yl]carbonyl}amino)-7-hydroxy-6,7-dihydro-5H-cyclopenta[b]pyridin-4-yl]-4-hydroxy-5-methylpiperidin-3-yl}carbamate

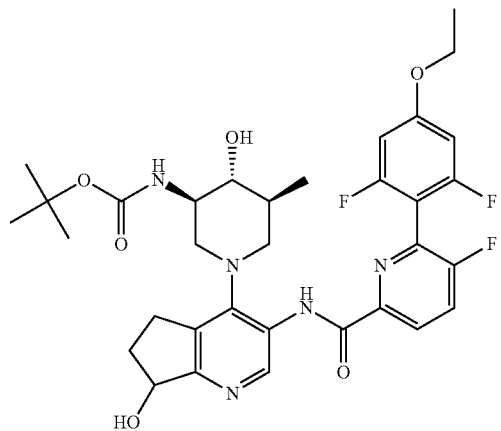 [SMILES: CCOc1cc(F)c(-c2nc(C(=O)Nc3cnc4c(c3N3C[C@H](C)[C@@H](O)[C@H](NC(=O)OC(C)(C)C)C3)CCC4O)ccc2F)c(F)c1]

A mixture of (3R,4R,5S)-1-[7-(acetyloxy)-3-amino-6,7-dihydro-5H-cyclopenta[b]pyridin-4-yl]-3-[(tert-butoxycarbonyl)amino]-5-methylpiperidin-4-yl acetate (12.4 mg, 0.027 mmol), 6-(4-ethoxy-2,6-difluorophenyl)-5-fluoropyridine-2-carboxylic acid (8.0 mg, 0.027 mmol), HATU (37 mg, 0.098 mmol) in DMF (0.1 mL) and DIPEA (26 mg, 0.20 mmol) was stirred at room temperature for 16 h. The reaction mixture was diluted with 1 M NaOH solution (0.5 mL) and MeOH (0.5 mL). The reaction mixture was stirred at room temperature for 1 h. After concentration under reduced pressure, the aqueous layer was extracted with DCM three times. The combined organic layers were dried, filtered and concentrated under vacuum to give the crude product, which was purified by preparative LC-MS (XBridge™ preparative C18 5 μm OBD™ column, 30×10 mm, 60 mL/min., eluting with a gradient of MeCN and water with 0.1% $NH_4OH$) to give the sub-title compound as a white powder. LCMS calc. for $C_{33}H_{39}F_3N_5O_6$ $(M+H)^+$: m/z=658.3. Found: 658.3.

Step 3: N-{4-[(3R,4R,5S)-3-Amino-4-hydroxy-5-methylpiperidin-1-yl]-7-hydroxy-6,7-dihydro-5H-cyclopenta[b]pyridin-3-yl}-6-(4-ethoxy-2,6-difluorophenyl)-5-fluoropyridine-2-carboxamide A mixture of tert-butyl {(3R,4R,5S)-1-[3-({[6-(4-ethoxy-2,6-difluorophenyl)-5-fluoropyridin-2-yl]carbonyl}amino)-7-hydroxy-6,7-dihydro-5H-cyclopenta[b]pyridin-4-yl]-4-hydroxy-5-methylpiperidin-3-yl}carbamate (6 mg, 0.01 mmol) and 4.0 M TFA in DCM (2.0 mL) was stirred at room temperature for 1 h. After removal of the solvent under reduced pressure, the residue was diluted with MeOH, filtered and purified by preparative LC-MS (XBridge™ preparative C18 5 μm OBD™ column, 30×10 mm, 60 mL/min., eluting with a gradient of MeCN and water with 0.1% $NH_4OH$) to give both diastereoisomers as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)), the diastereoisomers had the following properties:

Diastereoisomer 1. First peak. Retention time 1.551 min., LCMS calc. for $C_{28}H_{31}F_3N_5O_4$ $(M+H)^+$: m/z=558.2. Found: 558.2.

Diastereoisomer 2. Second peak. Retention time 1.608 min., LCMS calc. for $C_{28}H_3F_3N_5O_4$ $(M+H)^+$: m/z=558.2. Found: 558.2.

The diastereoisomers correspond to the (7R) and (7S) diastereoisomers of the title compound.

Example 52

N-{4-[(3R,4R,5S)-3-Amino-4-hydroxy-5-methylpiperidin-1-yl]-6,7-dihydro-5H-cyclopenta[b]pyridin-3-yl}-6-(2,6-difluorophenyl)-5-fluoropyridine-2-carboxamide

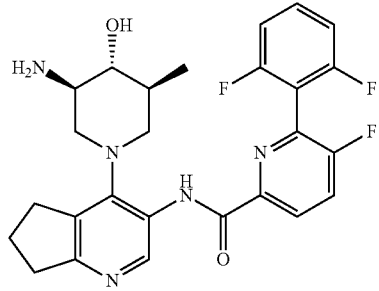 [SMILES: C[C@H]1CN(c2c(NC(=O)c3ccc(F)c(-c4c(F)cccc4F)n3)cnc3c2CCC3)C[C@@H](N)[C@@H]1O]

Step 1: tert-Butyl {(3R,4R,5S)-1-[3-({[6-(2,6-difluorophenyl)-5-fluoropyridin-2-yl]carbonyl}amino)-6,7-dihydro-5H-cyclopenta[b]pyridin-4-yl]-4-hydroxy-5-methylpiperidin-3-yl}carbamate

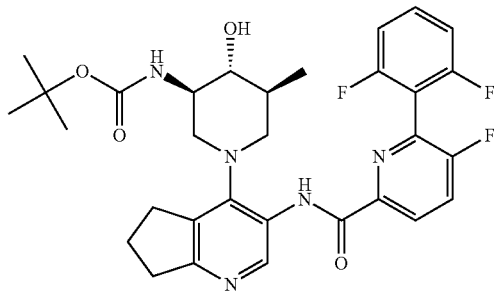 [SMILES: C[C@H]1CN(c2c(NC(=O)c3ccc(F)c(-c4c(F)cccc4F)n3)cnc3c2CCC3)C[C@@H](NC(=O)OC(C)(C)C)[C@@H]1O]

A mixture of tert-butyl [(3R,4R,5S)-1-(3-amino-6,7-dihydro-5H-cyclopenta[b]pyridin-4-yl)-4-hydroxy-5-methylpiperidin-3-yl]carbamate (6.0 mg, 0.017 mmol), 6-(2,6-difluorophenyl)-5-fluoropyridine-2-carboxylic acid (5.0 mg, 0.02 mmol), HATU (15.7 mg, 0.041 mmol) in DMF (0.05 mL) and DIPEA (0.01 mL, 0.05 mmol) was stirred at room temperature for 1 h. The reaction mixture was diluted with EtOAc and Na$_2$CO$_3$ (aq.). The aqueous layer was extracted with EtOAc twice. The combined organic layers were dried, filtered and concentrated under vacuum. The resulting crude product was used directly in the next step. LCMS calc. for C$_{31}$H$_{35}$F$_3$N$_5$O$_4$ (M+H)$^+$: m/z=598.3. Found: 598.2.

Step 2: N-{4-[(3R,4R,5S)-3-Amino-4-hydroxy-5-methylpiperidin-1-yl]-6,7-dihydro-5H-cyclopenta[b]pyridin-3-yl}-6-(2,6-difluorophenyl)-5-fluoropyridine-2-carboxamide A mixture of tert-butyl {(3R,4R,5S)-1-[3-({[6-(2,6-difluorophenyl)-5-fluoropyridin-2-yl]carbonyl}amino)-6,7-dihydro-5H-cyclopenta[b]pyridin-4-yl]-4-hydroxy-5-methylpiperidin-3-yl}carbamate (6.0 mg, 0.010 mmol), DCM (0.09 mL) and TFA (0.085 mL, 1.1 mmol) was stirred at room temperature for 20 min. After concentration, the residue was diluted with MeOH, filtered and purified by preparative LC-MS (XBridge™ preparative C18 μm OBD™ column, 30×10 mm, 60 mL/min., eluting with a gradient of MeCN and water with 0.1% NH$_4$OH) to give the title compound as a white powder (4.6 mg, 92%). LCMS calc. for C$_{26}$H$_{27}$F$_3$N$_5$O$_2$ (M+H)$^+$: m/z=498.2. Found: 498.3.

Example 53

5-Amino-N-{4-[(3S)-3-aminopiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide

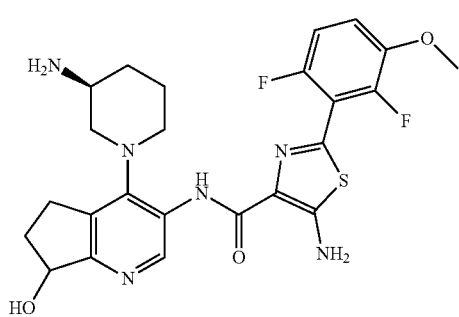 [SMILES: COc1ccc(F)c(-c2nc(C(=O)Nc3cnc4c(c3N3CCC[C@H](N)C3)CCC4O)c(N)s2)c1F]

Step 1. Methyl 5-[(tert-butoxycarbonyl)amino]-2-(2,6-difluoro-3-methoxyphenyl)-1,3-thiazole-4-carboxylate

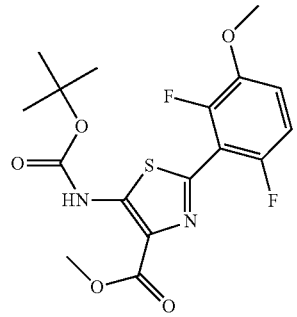 [SMILES: COC(=O)c1nc(-c2c(F)ccc(OC)c2F)sc1NC(=O)OC(C)(C)C]

To a vial, methyl 2-bromo-5-[(tert-butoxycarbonyl)amino]-1,3-thiazole-4-carboxylate (from Example 1 step 3, 104 mg, 0.309 mmol), (2,6-difluoro-3-methoxyphenyl)boronic acid (from Aldrich, 207 mg, 1.10 mmol), dicyclohexyl(2',4',6'-triisopropylbiphenyl-2-yl)phosphine-(2'-aminobiphenyl-2-yl)(chloro)palladium (1:1) (37.5 mg, 0.0477 mmol), and potassium phosphate (276 mg, 1.30 mmol) were added. The vial was sealed with a PTFE screw-cap then purged with nitrogen three times. 1,4-Dioxane (4.0 mL) was added, followed by deoxygenated water (2.0 mL). The mixture was heated at 40° C. for 1 h. The reaction mixture was allowed to cool to room temperature. Additional (2,6-difluoro-3-methoxyphenyl)boronic acid (262 mg, 1.39 mmol) and dicyclohexyl(2',4',6'-triisopropylbiphenyl-2-yl)phosphine-(2'-aminobiphenyl-2-yl)(chloro)palladium (1:1) (40.2 mg, 0.0511 mmol) were added. The mixture was stirred at room temperature for 15 h. The mixture was filtered through a pad of diatomaceous earth (eluted with EtOAc) and concentrated. The residue was purified on silica gel (eluting with 0-50% EtOAc in hexanes) to give the sub-title compound as a white solid (48.5 mg, 39%). LCMS calc. for C$_{17}$H$_{19}$F$_2$N$_2$O$_5$S (M+H)$^+$: m/z=401.1; Found: 401.1.

Step 2. 5-[(tert-Butoxycarbonyl)amino]-2-(2,6-difluoro-3-methoxyphenyl)-1,3-thiazole-4-carboxylic Acid

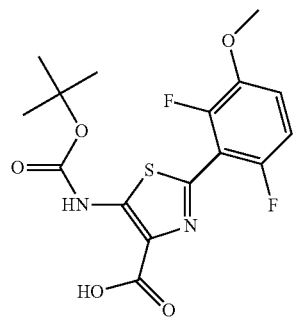 [SMILES: COc1ccc(F)c(-c2nc(C(=O)O)c(NC(=O)OC(C)(C)C)s2)c1F]

To a mixture of methyl 5-[(tert-butoxycarbonyl)amino]-2-(2,6-difluoro-3-methoxyphenyl)-1,3-thiazole-4-carboxylate (48.5 mg, 0.121 mmol) and lithium hydroxide, monohydrate (37 mg, 0.89 mmol) was added MeOH (1.5 mL), followed by water (1.5 mL). The reaction mixture was stirred at 60° C. for 3.5 h. The reaction mixture was allowed to cool to room temperature and 4.0 M hydrogen chloride in water (0.25 mL, 0.99 mmol) was added to adjust the pH to 1-2. The mixture was diluted with EtOAc (50 mL) and brine (50 mL). The aqueous layer was further extracted with EtOAc (2×50 mL). The combined organic extracts were dried over $Na_2SO_4$ and concentrated under reduced pressure to give the sub-title compound as a white solid which was used directly in the next step without further purification (52.2 mg). LCMS calc. for $C_{16}H_{17}F_2N_2O_5S$ (M+H)$^+$: m/z=387.1. Found: 387.1.

Step 3: 3-({[5-[(tert-Butoxycarbonyl)amino]-2-(2,6-difluoro-3-methoxyphenyl)-1,3-thiazol-4-yl]carbonyl}amino)-4-{(3S)-3-[(tert-butoxycarbonyl)amino]piperidin-1-yl}-6,7-dihydro-5H-cyclopenta[b]pyridin-7-yl Acetate

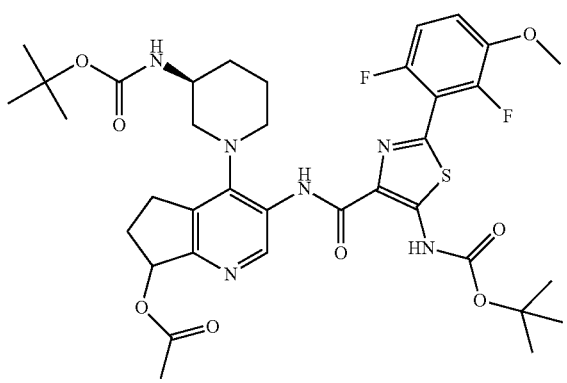 [SMILES: COc1ccc(F)c(-c2nc(C(=O)Nc3cnc4c(c3N3CCC[C@H](NC(=O)OC(C)(C)C)C3)CCC4OC(C)=O)c(NC(=O)OC(C)(C)C)s2)c1F]

A mixture of 3-amino-4-{(3S)-3-[(tert-butoxycarbonyl)amino]piperidin-1-yl}-6,7-dihydro-5H-cyclopenta[b]pyridin-7-yl acetate (10.0 mg, 0.0256 mmol), 5-[(tert-butoxycarbonyl)amino]-2-(2,6-difluoro-3-methoxyphenyl)-1,3-thiazole-4-carboxylic acid (9.9 mg, 0.026 mmol) and HATU (24.3 mg, 0.064 mmol) in DMF (0.06 mL) and DIPEA (0.014 mL, 0.077 mmol) was stirred at room temperature for 4 h. The mixture was diluted with MeOH and purified by preparative LC-MS (XBridge™ preparative C18 5 µm OBD™ column, 30×10 mm, 60 mL/min., eluting with a gradient of MeCN and water with 0.1% $NH_4OH$) to give the sub-title compound as a white powder (3.2 mg, 16%). LCMS calc. for $C_{36}H_{45}F_2N_6O_8S$ (M+H)$^+$: m/z=759.3. Found: 759.3.

Step 4: 5-Amino-N-{4-[(3S)-3-aminopiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide A mixture of 3-({[5-[(tert-butoxycarbonyl)amino]-2-(2,6-difluoro-3-methoxyphenyl)-1,3-thiazol-4-yl]carbonyl}amino)-4-{(3S)-3-[(tert-butoxycarbonyl)amino]piperidin-1-yl}-6,7-dihydro-5H-cyclopenta[b]pyridin-7-yl acetate (3.2 mg, 0.0042 mmol), MeOH (50 µL), THF (25 µL) and 1.0 M aq. NaOH (27 µL, 0.027 mmol) was stirred at room temperature for 20 min. The organic solvents were removed under reduced pressure to give a crude intermediate, which was dissolved in DCM (0.04 mL), and then TFA (0.043 mL, 0.56 mmol) was added. The reaction mixture was stirred at room temperature for 20 min. After concentration under reduced pressure, the residue was diluted with MeOH, filtered and purified by preparative LC-MS (XBridge™ preparative C18 5 µm OBD™ column, 30×10 mm, 60 mL/min., eluting with a gradient of MeCN and water with 0.1% $NH_4OH$) to give both diastereoisomers of the title compound as white powders. On analytical HPLC (Waters SunFire™ C18, 2.1×50 mm, 5 µm; flow rate 3 mL/min.; injection volume 2 µL; gradient from 2 to 80% B in 3 minutes (A=water with 0.025% TFA, B=MeCN)) the diastereoisomers had the following properties:

Diastereoisomer 1. First peak. Retention time 1.855 min., LCMS calc. for $C_{24}H_{27}F_2N_6O_3S$ (M+H)$^+$: m/z=517.2. Found: 517.2.

Diastereoisomer 2. Second peak. Retention time 1.841 min., LCMS calc. for $C_{24}H_{27}F_2N_6O_3S$ (M+H)$^+$: m/z=517.2. Found: 517.2.

The diastereoisomers correspond to the (7R) and (7S) diastereoisomers of the title compound.

Example 54

5-Amino-N-{4-[(3S,5R)-3-amino-5-methylpiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide

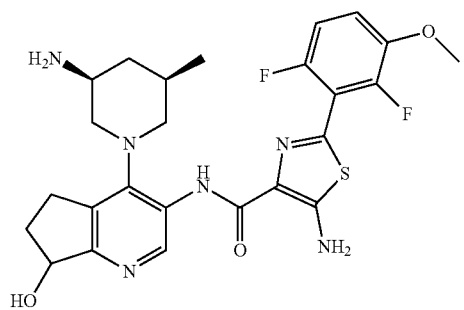 [SMILES: COc1ccc(F)c(-c2nc(C(=O)Nc3cnc4c(c3N3C[C@H](C)C[C@H](N)C3)CCC4O)c(N)s2)c1F]

Step 1: 3-({[5-[(tert-Butoxycarbonyl)amino]-2-(2,6-difluoro-3-methoxyphenyl)-1,3-thiazol-4-yl]carbonyl}amino)-4-{(3S,5R)-3-[(tert-butoxycarbonyl)amino]-5-methylpiperidin-1-yl}-6,7-dihydro-5H-cyclopenta[b]pyridin-7-yl Acetate

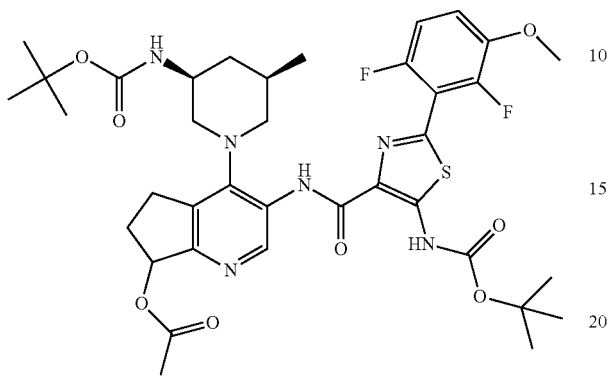

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (10.0 mg, 0.025 mmol), 5-[(tert-butoxycarbonyl)amino]-2-(2,6-difluoro-3-methoxyphenyl)-1,3-thiazole-4-carboxylic acid (9.6 mg, 0.025 mmol), HATU (23.5 mg, 0.062 mmol) in DMF (0.06 mL) and DIPEA (0.013 mL, 0.074 mmol) was stirred at room temperature for 3 h. The mixture was diluted with MeOH and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a white powder (5.5 mg, 29%). LCMS calc. for $C_{37}H_{47}F_2N_6O_8S$ (M+H)$^+$: m/z=773.3. Found: 773.3.

Step 2: 5-Amino-N-{4-[(3S,5R)-3-Amino-5-methylpiperidin-1-yl]-7-hydroxy-6,7-dihydro-5H-cyclopenta[b]pyridin-3-yl}-2-(2,6-difluoro-3-methoxyphenyl)-1,3-thiazole-4-carboxamide A mixture of 3-({[5-[(tert-butoxycarbonyl)amino]-2-(2,6-difluoro-3-methoxyphenyl)-1,3-thiazol-4-yl]carbonyl}amino)-4-{(3S,5R)-3-[(tert-butoxycarbonyl)amino]-5-methylpiperidin-1-yl}-6,7-dihydro-5H-cyclopenta[b]pyridin-7-yl acetate (5.5 mg, 0.007 mmol), MeOH (84 μL), THF (42 μL) and 1.0 M aq. NaOH (46 μL, 0.046 mmol) was stirred at room temperature for 20 min. The solvents were removed under reduced pressure to give a crude intermediate, which was dissolved in DCM (0.07 mL), and TFA (0.072 mL, 0.94 mmol) was then added. The reaction mixture was stirred at room temperature for 20 min. The solution was then concentrated under reduced pressure and the residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give both diastereoisomers as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)) the diastereoisomers had the following properties:

Diastereoisomer 1. First peak. Retention time 2.140 min., LCMS calc. for $C_{25}H_{29}F_2N_6O_3S$ (M+H)$^+$: m/z=531.2. Found: 531.2.

Diastereoisomer 2. Second peak. Retention time 2.267 min., LCMS calc. for $C_{25}H_{29}F_2N_6O_3S$ (M+H)$^+$: m/z=531.2. Found: 531.2.

Example 55

N-{4-[(3S)-3-Aminopiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide

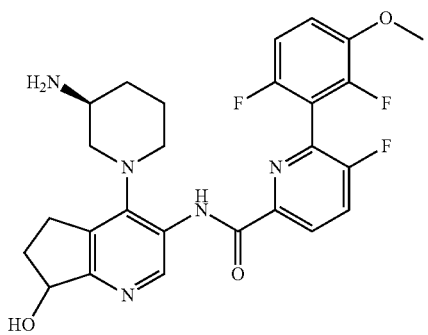 [SMILES: COc1ccc(F)c(-c2nc(C(=O)Nc3cnc4c(c3N3CCC[C@H](N)C3)CCC4O)ccc2F)c1F]

Step 1: Methyl 6-(2,6-difluoro-3-methoxyphenyl)-5-fluoropyridine-2-carboxylate

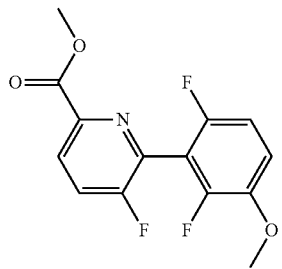 [SMILES: COC(=O)c1ccc(F)c(-c2c(F)ccc(OC)c2F)n1]

In a sealed tube to a mixture of methyl 6-bromo-5-fluoropyridine-2-carboxylate (374 mg, 1.60 mmol) and (2,6-difluoro-3-methoxyphenyl)boronic acid (150 mg, 0.798 mmol) in THF (6.0 mL) and water (0.6 mL) was added potassium fluoride (153 mg, 2.64 mmol). The reaction mixture was purged with N$_2$ for 5 min., then tris(dibenzylideneacetone)dipalladium (0) (180 mg, 0.20 mmol) and tri-tert-butylphosphine (81 mg, 0.40 mmol) were added subsequently. The reaction mixture was then heated at 100° C. for 30 min. After filtration and concentration of the solution under reduced pressure, the residue was purified by silica gel column chromatography using CombiFlash® (0 to 40% EtOAc in hexanes) to give the sub-title compound as a white powder (83.3 mg, 35%). LCMS calc. for $C_{14}H_{11}F_3NO_3$ (M+H)$^+$: m/z=298.1. Found: 298.2.

Step 2: 6-(2,6-Difluoro-3-methoxyphenyl)-5-fluoro-pyridine-2-carboxylic Acid

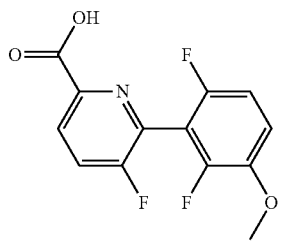 [SMILES: COc1ccc(F)c(-c2nc(C(=O)O)ccc2F)c1F]

To a mixture of methyl 6-(2,6-difluoro-3-methoxyphenyl)-5-fluoropyridine-2-carboxylate (82.9 mg, 0.279 mmol) in THF (0.3 mL) and MeOH (0.3 mL) was added 1.0 M aq. NaOH (1.39 mL, 1.39 mmol). The reaction mixture was stirred at room temperature for 40 min., neutralized with HCl (12 M) to pH=7 and concentrated under reduced pressure to remove the solvents. The residue was dissolved in THF, dried, filtered and concentrated under reduced pressure to give the sub-title compound as a white powder (53.4 mg, 68%). LCMS calc. for $C_{13}H_9F_3NO_3$ $(M+H)^+$: m/z=284.1. Found: 284.2.

Step 3: 4-{(3S)-3-[(tert-Butoxycarbonyl)amino]piperidin-1-yl}-3-({[6-(2,6-difluoro-3-methoxyphenyl)-5-fluoropyridin-2-yl]carbonyl}amino)-6,7-dihydro-5H-cyclopenta[b]pyridin-7-yl Acetate

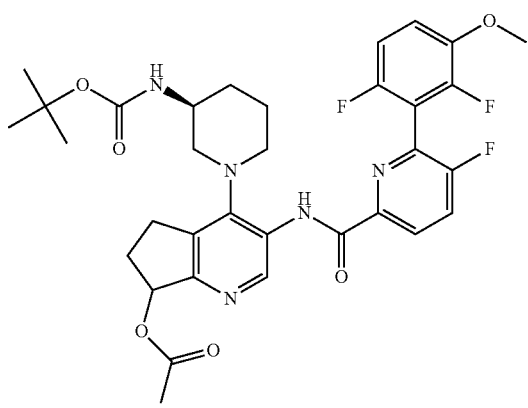 [SMILES: COc1ccc(F)c(-c2nc(C(=O)Nc3cnc4c(c3N3CCC[C@H](NC(=O)OC(C)(C)C)C3)CCC4OC(C)=O)ccc2F)c1F]

A mixture of 3-amino-4-{(3S)-3-[(tert-butoxycarbonyl)amino]piperidin-1-yl}-6,7-dihydro-5H-cyclopenta[b]pyridin-7-yl acetate (13.6 mg, 0.035 mmol), 6-(2,6-difluoro-3-methoxyphenyl)-5-fluoropyridine-2-carboxylic acid (9.0 mg, 0.032 mmol), HATU (30.2 mg, 0.080 mmol) in DMF (0.07 mL) and DIPEA (0.017 mL, 0.095 mmol) was stirred at room temperature for 16 h. The mixture was diluted with MeOH and purified by preparative LC-MS (XBridge™ preparative C18 5 μm OBD™ column, 30×10 mm, 60 mL/min., eluting with a gradient of MeCN and water with 0.1% NH₄OH) to give the sub-title compound as a white powder (5.0 mg, 24%). LCMS calc. for $C_{33}H_{37}F_3N_5O_6$ $(M+H)^+$: m/z=656.3. Found: 656.3.

Step 4: N-{4-[(3S)-3-Aminopiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide A mixture of 4-{(3S)-3-[(tert-butoxycarbonyl)amino]piperidin-1-yl}-3-({[6-(2,6-difluoro-3-methoxyphenyl)-5-fluoropyridin-2-yl]carbonyl}amino)-6,7-dihydro-5H-cyclopenta[b]pyridin-7-yl acetate (5.0 mg, 0.008 mmol), MeOH (90 μL), THF (45 μL) and 1.0 M aq. NaOH (50 μL, 0.050 mmol) was stirred at room temperature for 20 min. The solvents were removed under reduced pressure to give the crude intermediate, which was dissolved in DCM (0.08 mL), followed by the addition of TFA (0.078 mL, 1.0 mmol). The reaction mixture was stirred at room temperature for 20 min. After concentrating the solution under reduced pressure, the residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH₄OH) to give both diastereoisomers of the title compound as white powders.

Diastereoisomer 1. First peak. Retention time 1.908 min., LCMS calc. for $C_{26}H_{27}F_3N_5O_3$ $(M+H)^+$: m/z=514.2; Found: 514.2.

Diastereoisomer 2. Second peak. Retention time 1.962 min., LCMS calc. for $C_{26}H_{27}F_3N_5O_3$ $(M+H)^+$: m/z=514.2; Found: 514.2.

The diastereoisomers correspond to the (7R) and (7S) diastereoisomers of the title compound.

Example 56

N-{4-[(3S,5R)-3-Amino-5-methylpiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide

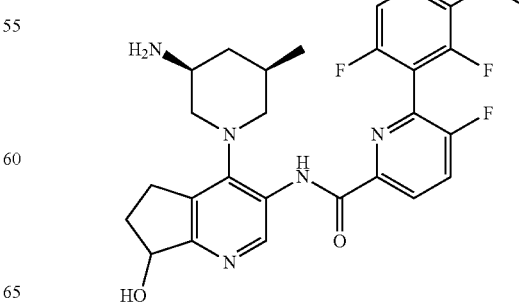

Step 1: 4-{(3S,5R)-3-[(tert-Butoxycarbonyl)amino]-5-methylpiperidin-1-yl}-3-({[6-(2,6-difluoro-3-methoxyphenyl)-5-fluoropyridin-2-yl]carbonyl}amino)-6,7-dihydro-5H-cyclopenta[b]pyridin-7-yl Acetate

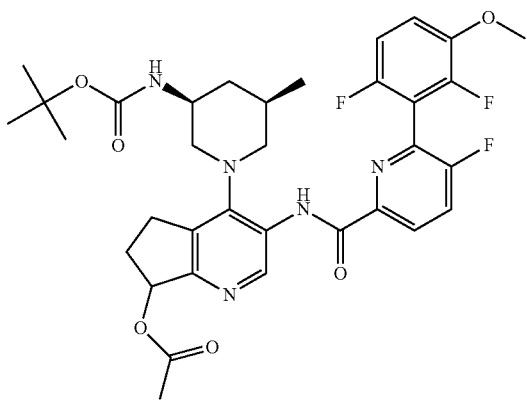 [SMILES: COc1ccc(F)c(-c2nc(C(=O)Nc3cnc4c(c3N3C[C@H](C)C[C@H](NC(=O)OC(C)(C)C)C3)CCC4OC(C)=O)ccc2F)c1F]

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (14.1 mg, 0.035 mmol), 6-(2,6-difluoro-3-methoxyphenyl)-5-fluoropyridine-2-carboxylic acid (9.0 mg, 0.032 mmol), HATU (30.2 mg, 0.08 mmol) in DMF (0.07 mL) and DIPEA (0.017 mL, 0.095 mmol) was stirred at room temperature for 16 h. The mixture was diluted with MeOH and purified by preparative LC-MS (XBridge™ preparative C18 5 μm OBD™ column, 30×10 mm, 60 mL/min., eluting with a gradient of MeCN and water with 0.1% NH₄OH) to give the sub-title compound as a white powder (8.0 mg, 38%). LCMS calc. for $C_{34}H_{39}F_3N_5O_6$ (M+H)⁺: m/z=670.3. Found: 670.3.

Step 2: N-{4-[(3S,5R)-3-Amino-5-methylpiperidin-1-yl]-7-hydroxy-6,7-dihydro-5H-cyclopenta[b]pyridin-3-yl}-6-(2,6-difluoro-3-methoxyphenyl)-5-fluoropyridine-2-carboxamide A mixture of 4-{(3S,5R)-3-[(tert-butoxycarbonyl)amino]-5-methylpiperidin-1-yl}-3-({[6-(2,6-difluoro-3-methoxyphenyl)-5-fluoropyridin-2-yl]carbonyl}amino)-6,7-dihydro-5H-cyclopenta[b]pyridin-7-yl acetate (8.0 mg, 0.012 mmol), MeOH (140 μL), THF (71 μL) and 1.0 M aq. NaOH (78 μL, 0.078 mmol) was stirred at room temperature for 20 min. The organic solvents were removed under vacuum and dried to give the crude intermediate, which was dissolved in DCM (0.1 mL), followed by the addition of TFA (0.12 mL, 1.6 mmol). The reaction mixture was stirred at room temperature for 20 min. The solution was then concentrated under reduced pressure and the residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH₄OH) to give both diastereoisomers of the title compound as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)) the diastereoisomers had the following properties:

Diastereoisomer 1. First peak. Retention time 1.969 min., LCMS calc. for $C_{27}H_{29}F_3N_5O_3$ (M+H)⁺: m/z=528.2. Found: 528.2.

Diastereoisomer 2. Second peak. Retention time 2.079 min., LCMS calc. for $C_{27}H_{29}F_3N_5O_3$ (M+H)⁺: m/z=528.2. Found: 528.2.

The diastereoisomers correspond to the (7R) and (7S) diastereoisomers of the title compound.

Example 57

5-Amino-N-[4-(3-amino-3-methylpiperidin-1-yl)-6,7-dihydro-5H-cyclopenta[b]pyridin-3-yl]-2-(2,6-difluorophenyl)-1,3-thiazole-4-carboxamide

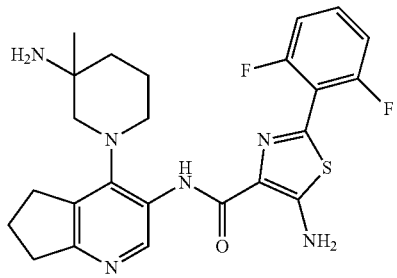 [SMILES: CC1(N)CCCN(c2c(NC(=O)c3nc(-c4c(F)cccc4F)sc3N)cnc3c2CCC3)C1]

Step 1: tert-Butyl [3-methyl-1-(3-nitro-6,7-dihydro-5H-cyclopenta[b]pyridin-4-yl)piperidin-3-yl]carbamate

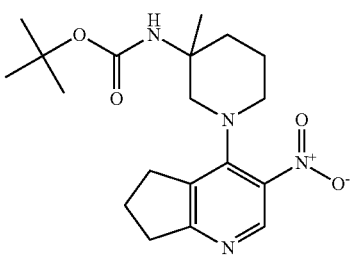 [SMILES: CC1(NC(=O)OC(C)(C)C)CCCN(c2c([N+](=O)[O-])cnc3c2CCC3)C1]

A mixture of 4-chloro-3-nitro-6,7-dihydro-5H-cyclopenta[b]pyridine (200 mg, 1.01 mmol), tert-butyl (3-methylpiperidin-3-yl)carbamate (227 mg, 1.06 mmol) and triethylamine (281 μL, 2.01 mmol) in isopropyl alcohol (1.2 mL) was stirred at 100° C. for 20 min. After cooling, the sub-title compound precipitated out and was collected by vacuum filtration, followed by washing with cold ether to give the sub-title compound as light yellow powder. LCMS calc. for $C_{19}H_{29}N_4O_4$ (M+H)⁺: m/z=377.2. Found: 377.2.

Step 2: tert-Butyl [1-(3-amino-6,7-dihydro-5H-cyclopenta[b]pyridin-4-yl)-3-methylpiperidin-3-yl]carbamate

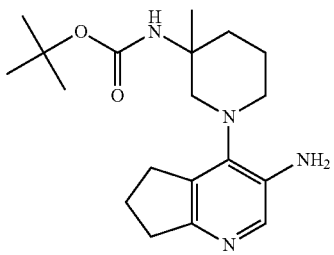 [SMILES: CC1(NC(=O)OC(C)(C)C)CCCN(c2c(N)cnc3c2CCC3)C1]

A mixture of tert-butyl [3-methyl-1-(3-nitro-6,7-dihydro-5H-cyclopenta[b]pyridin-4-yl)piperidin-3-yl]carbamate (100.0 mg, 0.27 mmol), AcOH (1.44 mL) and iron powder (222 mg, 3.98 mmol) was stirred at room temperature for 1 h. The reaction mixture was diluted with EtOAc, filtered through a short silica gel plug. The residue was rinsed with fresh EtOAc and filtered. The filtrate was concentrated under reduced pressure, diluted with EtOAc and neutralized with $Na_2CO_3$ solution. After vacuum filtration to remove insoluble impurities, the aqueous layer was extracted with EtOAc three times. The combined organic layers were dried, filtered and concentrated under reduced pressure to give the sub-title compound as off-white powder (80 mg, 90%). LCMS calc. for $C_{19}H_{31}N_4O_2$ (M+H)$^+$: m/z=347.2. Found: 347.2.

Step 3: tert-Butyl {i-[3-({[5-[(tert-butoxycarbonyl)amino]-2-(2,6-difluorophenyl)-1,3-thiazol-4-yl]carbonyl}amino)-6,7-dihydro-5H-cyclopenta[b]pyridin-4-yl]-3-methylpiperidin-3-yl}carbamate

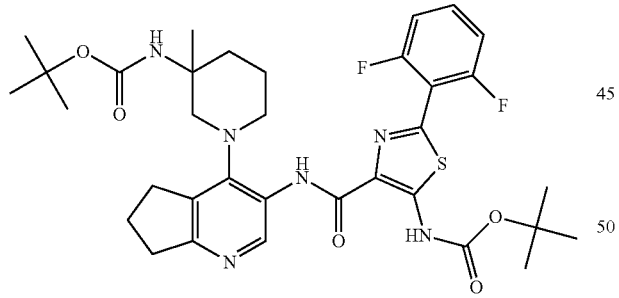

A mixture of tert-butyl [1-(3-amino-6,7-dihydro-5H-cyclopenta[b]pyridin-4-yl)-3-methylpiperidin-3-yl]carbamate (8.0 mg, 0.023 mmol), 5-[(tert-butoxycarbonyl)amino]-2-(2,6-difluorophenyl)-1,3-thiazole-4-carboxylic acid (9.1 mg, 0.025 mmol), HATU (21.9 mg, 0.058 mmol) in DMF (0.05 mL) and DIPEA (0.012 mL, 0.069 mmol) was stirred at room temperature for 2 h. The reaction mixture was diluted with MeOH and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a white powder (8.4 mg, 53%). LCMS calc. for $C_{34}H_{43}F_2N_6O_5S$ (M+H)$^+$: m/z=685.3. Found: 685.3.

Step 4: 5-Amino-N-[4-(3-amino-3-methylpiperidin-1-yl)-6,7-dihydro-5H-cyclopenta[b]pyridin-3-yl]-2-(2,6-difluorophenyl)-1,3-thiazole-4-carboxamide A mixture of tert-butyl {1-[3-({[5-[(tert-butoxycarbonyl)amino]-2-(2,6-difluorophenyl)-1,3-thiazol-4-yl]carbonyl}amino)-6,7-dihydro-5H-cyclopenta[b]pyridin-4-yl]-3-methylpiperidin-3-yl}carbamate (8.4 mg, 0.012 mmol), DCM (0.12 mL) and TFA (0.12 mL, 1.6 mmol) was stirred at room temperature for 30 min. The solution was then concentrated under reduced pressure and the residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give the title compound as a white powder (3.5 mg, 59%). LCMS calc. for $C_{24}H_{27}F_2N_6OS$ (M+H)$^+$: m/z=485.2. Found: 485.2.

Example 58

N-{4-[(3S)-3-Aminopiperidin-1-yl]-7-hydroxy-6,7-dihydro-5H-cyclopenta[b]pyridin-3-yl}-6-[2,6-difluoro-4-(methylthio)phenyl]-5-fluoropyridine-2-carboxamide

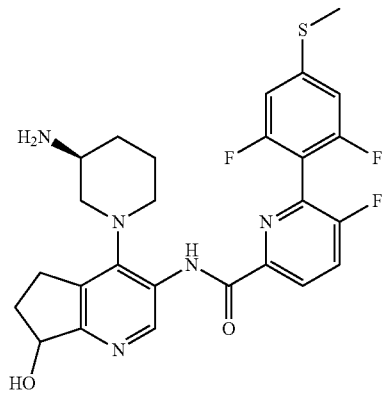 [SMILES: CSc1cc(F)c(-c2nc(C(=O)Nc3cnc4c(c3N3CCC[C@H](N)C3)CCC4O)ccc2F)c(F)c1]

Step 1: 1,3-Difluoro-5-(methylthio)benzene

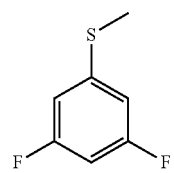

Methyl iodide (2.91 g, 20.5 mmol) was added dropwise to a stirred mixture of 3,5-difluorobenzenethiol (2.00 g, 13.7 mmol) and potassium carbonate (5.67 g, 41.0 mmol) in dry MeCN (24 mL) at room temperature. The reaction mixture was stirred at 80° C. for 2 h. After cooling, the mixture was filtered under vacuum, washed with MeCN and concentrated under reduced pressure to give the sub-title compound, which was used directly in the next step without further purification (1.74 g, 80%).

Step 2: 2-[2,6-Difluoro-4-(methylthio)phenyl]-4,4,5,5-tetramethyl-1,3,2-dioxaborolane

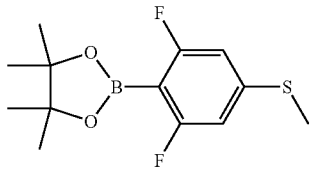

To a solution of 1,3-difluoro-5-(methylthio)benzene (0.800 g, 4.99 mmol) in dry THF (25 mL) under nitrogen at −78° C., n-BuLi in THF (1.6 M; 3.28 mL, 5.24 mmol) was added slowly while keeping the internal temperature below −65° C. The reaction mixture was stirred at −78° C. for 2 h. 2-isopropoxy-4,4,5,5-tetramethyl-1,3,2-dioxaborolane (1.07 g, 5.74 mmol) was then added. The reaction mixture was allowed to warm to room temperature for 2 h, and then quenched with aq. NaHCO$_3$ and extracted with EtOAc. The organic extracts were washed with brine, dried, filtered and concentrated under reduced pressure to yield the crude sub-title compound (1.42 g, 99%) as a viscous liquid.

Step 3: Methyl 6-[2,6-difluoro-4-(methylthio)phenyl]-5-fluoropyridine-2-carboxylate

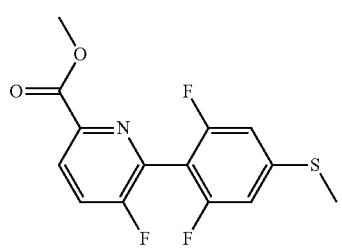 [SMILES: COC(=O)c1ccc(F)c(-c2c(F)cc(SC)cc2F)n1]

In a sealed tube, a mixture of 2-[2,6-difluoro-4-(methylthio)phenyl]-4,4,5,5-tetramethyl-1,3,2-dioxaborolane (1.00 g, 3.49 mmol), methyl 6-bromo-5-fluoropyridine-2-carboxylate (1.23 g, 5.24 mmol) and DIPEA (1.83 mL, 10.5 mmol) in a mixed solvent of 1,4-dioxane (15 mL) and water (0.51 mL) was stirred and flushed with nitrogen bubbles for 5 min. before bis(tri-tert-butylphosphine)palladium (360 mg, 0.70 mmol) was added. The reaction mixture was heated at 120° C. for 30 min. After cooling, the reaction mixture was filtered, and the filter was washed with THF. The filtrate was concentrated and then purified by silica gel column chromatography using CombiFlash® (0 to 20% EtOAc in hexanes) to give the sub-title compound as powder (442 mg, 40%). LCMS calc. for $C_{14}H_{11}F_3NO_2S$ (M+H)$^+$: m/z=314.1. Found: 314.2.

Step 4: 6-[2,6-Difluoro-4-(methylthio)phenyl]-5-fluoropyridine-2-carboxylic acid Methyl 6-[2,6-difluoro-4-(methylthio)phenyl]-5-fluoropyridine-2-carboxylate (80.0 mg, 0.255 mmol) was dissolved in THF (0.3 mL) and MeOH (0.3 mL), then 1.0 M aq. NaOH (1.28 mL, 1.28 mmol) was added. The reaction mixture was stirred at room temperature for 50 min., then neutralized with HCl (12 M) to pH=7 and concentrated under reduced pressure to remove all the solvents. The residue was dissolved in THF, dried, filtered and concentrated under vacuum to give the sub-title compound as a white powder (42 mg, 55%). LCMS calc. for $C_{13}H_9F_3NO_2S$ (M+H)$^+$: m/z=300.0. Found: 300.2.

Step 5: 4-{(3S)-3-[(tert-Butoxycarbonyl)amino]piperidin-1-yl}-3-[({6-[2,6-difluoro-4-(methylthio)phenyl]-5-fluoropyridin-2-yl}carbonyl)amino]-6,7-dihydro-5H-cyclopenta[b]pyridin-7-yl Acetate

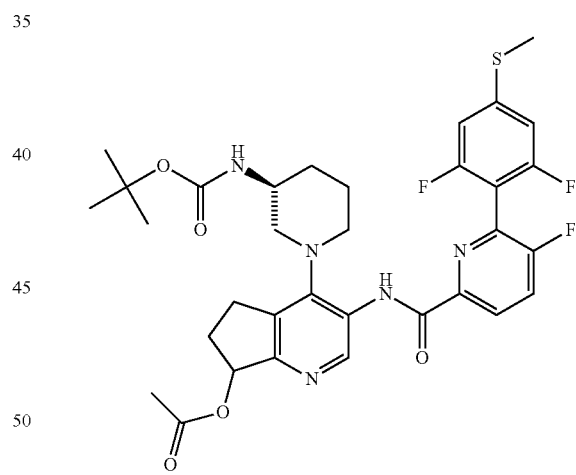

A mixture of 3-amino-4-{(3S)-3-[(tert-butoxycarbonyl)amino]piperidin-1-yl}-6,7-dihydro-5H-cyclopenta[b]pyridin-7-yl acetate (12.0 mg, 0.031 mmol), 6-[2,6-difluoro-4-(methylthio)phenyl]-5-fluoropyridine-2-carboxylic acid (11.0 mg, 0.037 mmol), HATU (29.2 mg, 0.077 mmol) in DMF (0.07 mL) and DIPEA (11.9 mg, 0.092 mmol) was stirred at room temperature for 16 h. The reaction mixture was filtered, concentrated and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a colorless gum (6.3 mg, 30%). LCMS calc. for $C_{33}H_{37}F_3N_5O_5S$ (M+H)$^+$: m/z=672.2. Found: 672.2.

Step 6: N-{4-[(3S)-3-Aminopiperidin-1-yl]-7-hydroxy-6,7-dihydro-5H-cyclopenta[b]pyridin-3-yl}-6-[2,6-difluoro-4-(methylthio)phenyl]-5-fluoropyridine-2-carboxamide 4-{(3S)-3-[(tert-Butoxycarbonyl)amino]piperidin-1-yl}-3-[({6-[2,6-difluoro-4-(methylthio)phenyl]-5-fluoropyridin-2-yl}carbonyl)amino]-6,7-dihydro-5H-cyclopenta[b]pyridin-7-yl acetate (6.3 mg, 0.009 mmol) was dissolved in MeOH (0.1 mL) and THF (0.06 mL), then 1.0 M aq. NaOH (0.038 mL, 0.038 mmol) was added. The reaction mixture was stirred at room temperature for 20 min. The organic solvents and trace of water were removed under reduced pressure to give a crude intermediate. The residue was dissolved in DCM (0.1 mL) and then TFA (0.095 mL, 1.2 mmol) was added. The reaction mixture was stirred at room temperature for 20 min., then the solution was evaporated under reduced pressure. The residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give both diastereoisomers of the title compound as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)), the diastereoisomers of the product had the following properties:

Diastereoisomer 1. First peak. Retention time 2.471 min., LCMS calc. for $C_{26}H_{27}F_3N_5O_2S$ (M+H)$^+$: m/z=530.2. Found: 530.2.

Diastereoisomer 2. Second peak. Retention time 2.551 min., LCMS calc. for $C_{26}H_{27}F_3N_5O_2S$ (M+H)$^+$: m/z=530.2. Found: 530.2.

The diastereoisomers correspond to the (7R) and (7S) diastereoisomers of the title compound.

Example 59

N-{4-[(3S)-3-Aminopiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide

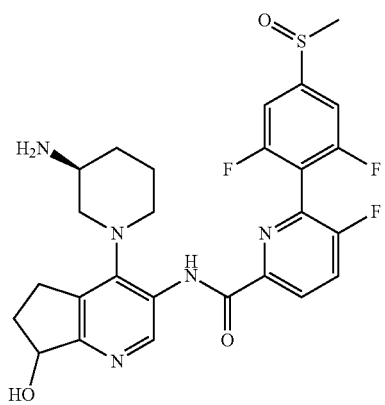 [SMILES: CS(=O)c1cc(F)c(-c2nc(C(=O)Nc3cnc4c(c3N3CCC[C@H](N)C3)CCC4O)ccc2F)c(F)c1]

Step 1: Methyl 6-[2,6-difluoro-4-(methylsulfinyl)phenyl]-5-fluoropyridine-2-carboxylate

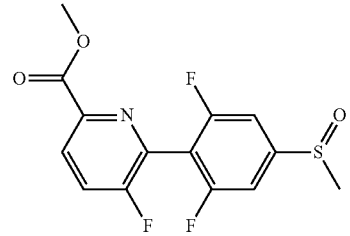 [SMILES: COC(=O)c1ccc(F)c(-c2c(F)cc(S(C)=O)cc2F)n1]

To a solution of methyl 6-[2,6-difluoro-4-(methylthio)phenyl]-5-fluoropyridine-2-carboxylate (150 mg, 0.479 mmol) in DCM (3.0 mL) was added potassium peroxymonosulfate (147 mg, 0.958 mmol) at room temperature. The reaction mixture was stirred at room temperature for 2 h. The solution was partitioned between EtOAc and water. The organic layer was dried, filtered. The filtrate was concentrated and then purified by silica gel column chromatography using CombiFlash® (0 to 100% EtOAc in hexanes) to give the sub-title compound as a white powder (37 mg, 23%). LCMS calc. for $C_4H_{11}F_3NO_3S$ (M+H)$^+$: m/z=330.0. Found: 330.2.

Step 2: 6-[2,6-Difluoro-4-(methylsulfinyl)phenyl]-5-fluoropyridine-2-carboxylic acid

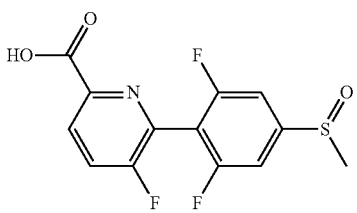 [SMILES: CS(=O)c1cc(F)c(-c2nc(C(=O)O)ccc2F)c(F)c1]

Methyl 6-[2,6-difluoro-4-(methylsulfinyl)phenyl]-5-fluoropyridine-2-carboxylate (37.0 mg, 0.112 mmol) was dissolved in THF (0.12 mL) and MeOH (0.12 mL), and 1.0 M aq. NaOH (0.56 mL, 0.56 mmol) was then added. The reaction mixture was stirred at room temperature for 50 min. The mixture was then neutralized with HCl (12 M) to pH=7 and concentrated under reduced pressure to remove all the solvents. The residue was dissolved in THF, dried, filtered and concentrated under reduced pressure to give the sub-title compound as a white powder. LCMS calc. for $C_{13}H_9F_3NO_3S$ (M+H)$^+$: m/z=316.0. Found: 316.2.

Step 3: 4-{(3S)-3-[(tert-Butoxycarbonyl)amino]piperidin-1-yl}-3-[({6-[2,6-difluoro-4-(methylsulfinyl)phenyl]-5-fluoropyridin-2-yl}carbonyl)amino]-6,7-dihydro-5H-cyclopenta[b]pyridin-7-yl Acetate

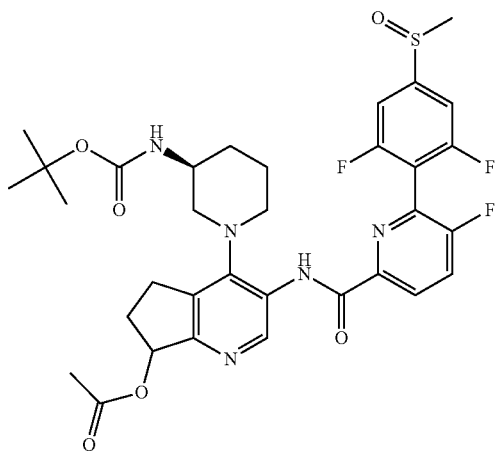 [SMILES: CC(=O)OC1CCc2c1ncc(NC(=O)c1ccc(F)c(-c3c(F)cc(S(C)=O)cc3F)n1)c2N1CCC[C@H](NC(=O)OC(C)(C)C)C1]

A mixture of 3-amino-4-{(3S)-3-[(tert-butoxycarbonyl)amino]piperidin-1-yl}-6,7-dihydro-5H-cyclopenta[b]pyridin-7-yl acetate (12.0 mg, 0.031 mmol), 6-[2,6-difluoro-4-(methylsulfinyl)phenyl]-5-fluoropyridine-2-carboxylic acid (11.6 mg, 0.037 mmol), HATU (29.2 mg, 0.077 mmol) in DMF (0.07 mL) and DIPEA (11.9 mg, 0.092 mmol) was stirred at room temperature for 16 h. The reaction mixture was filtered, concentrated under reduced pressure and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a colorless gum (3.0 mg, 14%). LCMS calc. for C$_{33}$H$_{37}$F$_3$N$_5$O$_6$S (M+H)$^+$: m/z=688.2. Found: 688.2.

Step 4: N-{4-[(3S)-3-Aminopiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide

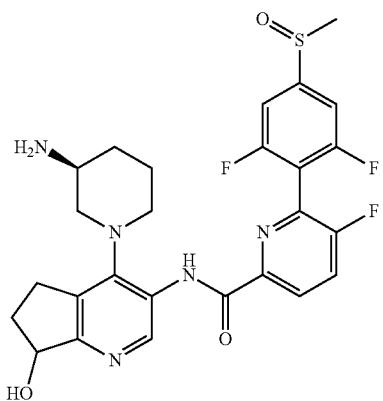 [SMILES: CS(=O)c1cc(F)c(-c2nc(C(=O)Nc3cnc4c(c3N3CCC[C@H](N)C3)CCC4O)ccc2F)c(F)c1]

4-{(3S)-3-[(tert-Butoxycarbonyl)amino]piperidin-1-yl}-3-[({6-[2,6-difluoro-4-(methylsulfinyl)phenyl]-5-fluoropyridin-2-yl}carbonyl)amino]-6,7-dihydro-5H-cyclopenta[b]pyridin-7-yl acetate (3.0 mg, 0.0044 mmol) was dissolved in MeOH (0.01 mL) and THF (0.05 mL), and 1.0 M aq. NaOH (0.017 mL, 0.017 mmol) was then added. The reaction mixture was stirred at room temperature for 60 min. The organic solvents and trace of water were removed under reduced pressure to give a crude intermediate. The residue was dissolved in DCM (0.04 mL), then TFA (0.044 mL, 0.58 mmol) was added. The reaction mixture was stirred at room temperature for 16 h. The solution was then concentrated again under reduced pressure. The residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH$_4$OH) to give two mixtures of diastereoisomers of the title compound as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)) the diastereoisomers had the following properties:

Diastereoisomer 1. First peak. Retention time 1.371 min., LCMS calc. for C$_{26}$H$_{27}$F$_3$N$_5$O$_3$S (M+H)$^+$: m/z=546.2. Found: 546.2.

Diastereoisomer 2. Second peak. Retention time 1.440 min., LCMS calc. for C$_{26}$H$_{27}$F$_3$N$_5$O$_3$S (M+H)$^+$: m/z=546.2. Found: 546.2.

The diastereoisomers are tentatively assigned as the separated (7R) and (7S) diastereoisomers of the title compound, each being a mixture of diastereoisomers having (R) and (S) configuration of the sulfoxide sulfur atom.

Example 60

N-{4-[(3S,5R)-3-Amino-5-methylpiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide

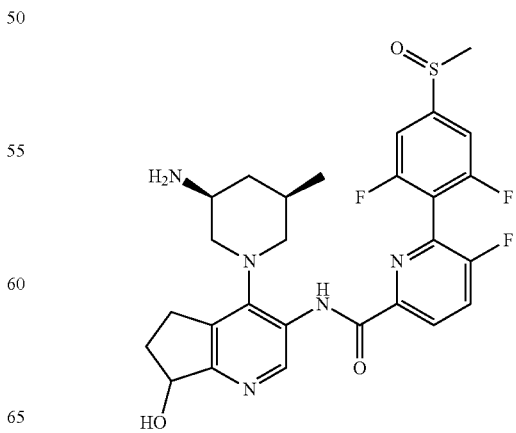

Step 1: 4-{(3S,5R)-3-[(tert-Butoxycarbonyl)amino]-5-methylpiperidin-1-yl}-3-[({6-[2,6-difluoro-4-(methylsulfinyl)phenyl]-5-fluoropyridin-2-yl}carbonyl)amino]-6,7-dihydro-5H-cyclopenta[b]pyridin-7-yl Acetate

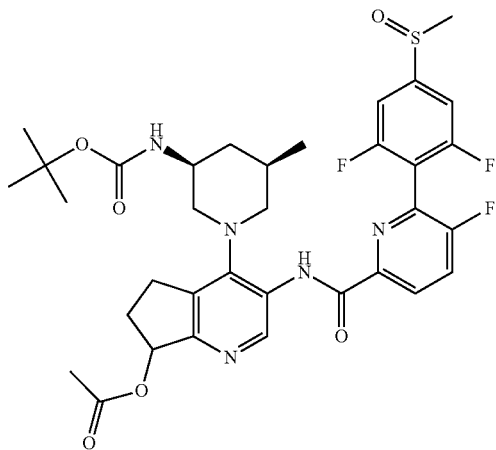 [SMILES: CC(=O)OC1CCc2c1ncc(NC(=O)c1ccc(F)c(-c3c(F)cc(S(C)=O)cc3F)n1)c2N1C[C@H](C)C[C@H](NC(=O)OC(C)(C)C)C1]

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (10.0 mg, 0.025 mmol), 6-[2,6-difluoro-4-(methylsulfinyl)phenyl]-5-fluoropyridine-2-carboxylic acid (9.4 mg, 0.03 mmol), HATU (23.5 mg, 0.062 mmol) in DMF (0.06 mL) and DIPEA (9.6 mg, 0.074 mmol) was stirred at room temperature for 16 h. The mixture was filtered, concentrated and purified by preparative LC-MS (XBridge™ preparative C18 5 μm OBD™ column, 30×10 mm, 60 mL/min., eluting with a gradient of MeCN and water with 0.1% NH$_4$OH) to give the sub-title compound as a colorless gum (3.0 mg, 17%). LCMS calc. for C$_{34}$H$_{39}$F$_3$N$_5$O$_6$S (M+H)$^+$: m/z=702.3. Found: 702.2.

Step 2: N-{4-[(3S,5R)-3-Amino-5-methylpiperidin-1-yl]-7-hydroxy-6,7-dihydro-5H-cyclopenta[b]pyridin-3-yl}-6-[2,6-difluoro-4-(methylsulfinyl)phenyl]-5-fluoropyridine-2-carboxamide 4-{(3S,5R)-3-[(tert-Butoxycarbonyl)amino]-5-methylpiperidin-1-yl}-3-[({6-[2,6-difluoro-4-(methylsulfinyl)phenyl]-5-fluoropyridin-2-yl}carbonyl)amino]-6,7-dihydro-5H-cyclopenta[b]pyridin-7-yl acetate (3.0 mg, 0.0043 mmol) was dissolved in MeOH (0.02 mL) and THF (0.08 mL), followed by the addition of 1.0 M aq. NaOH (0.017 mL, 0.017 mmol). The reaction mixture was stirred at room temperature for 20 min. The organic solvents and trace of water were removed under vacuum to give the crude intermediate, which was dissolved in DCM (0.044 mL), followed by the addition of TFA (0.044 mL, 0.56 mmol). The reaction mixture was stirred at room temperature for 20 min. After concentration, the residue was diluted with MeOH, filtered and purified by preparative LC-MS(XBridge™ preparative C18 5 μm OBD™ column, 30×10 mm, 60 mL/min., eluting with a gradient of MeCN and water with 0.1% NH$_4$OH) to give two mixtures of diastereoisomers of the title compound as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)) the diastereoisomers had the following properties:

Diastereoisomer 1. First peak. Retention time 1.858 min., LCMS calc. for C$_{27}$H$_{29}$F$_3$N$_5$O$_3$S (M+H)$^+$: m/z=560.2. Found: 560.2.

Diastereoisomer 2. Second peak. Retention time 1.975 min., LCMS calc. for C$_{27}$H$_{29}$F$_3$N$_5$O$_3$S (M+H)$^+$: m/z=560.2. Found: 560.2.

The diastereoisomers are tentatively assigned as the separated (7R) and (7S) diastereoisomers of the title compound, each being a mixture of diastereoisomers having (R) and (S) configuration of the sulfoxide sulfur atom.

Example 61

N-{4-[(3S)-3-Aminopiperidin-1-yl]-7-hydroxy-6,7-dihydro-5H-cyclopenta[b]pyridin-3-yl}-6-[2,6-difluoro-4-(methylsulfonyl)phenyl]-5-fluoropyridine-2-carboxamide

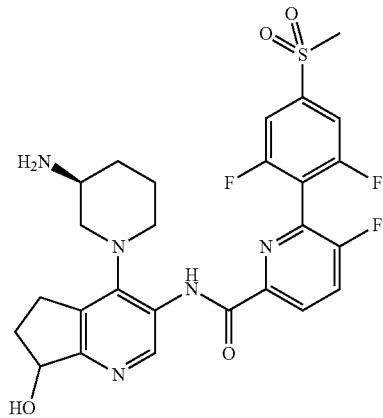 [SMILES: CS(=O)(=O)c1cc(F)c(-c2nc(C(=O)Nc3cnc4c(c3N3CCC[C@H](N)C3)CCC4O)ccc2F)c(F)c1]

Step 1: Methyl 6-[2,6-difluoro-4-(methylsulfonyl)phenyl]-5-fluoropyridine-2-carboxylate

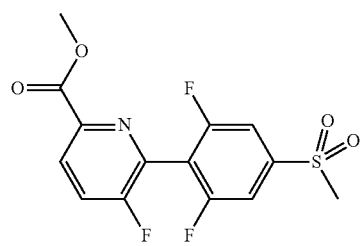 [SMILES: COC(=O)c1ccc(F)c(-c2c(F)cc(S(C)(=O)=O)cc2F)n1]

To a solution of methyl 6-[2,6-difluoro-4-(methylthio)phenyl]-5-fluoropyridine-2-carboxylate (81.0 mg, 0.258 mmol) in DCM (1.2 mL) at 0° C. was added mCPBA (185 mg, 0.827 mmol). The reaction mixture was stirred at 0° C. for 2 h, followed by the addition of Na$_2$S$_2$O$_3$ solution and then 1 M NaOH. The reaction mixture was stirred for 20 min. at room temperature, then extracted with DCM three times. The combined organic layers were dried over Na$_2$SO$_4$, filtered and concentrated under reduced pressure to give the sub-title compound (78 mg, 87%). LCMS calc. for C$_{14}$H$_{11}$F$_3$NO$_4$S (M+H)$^+$: m/z=346.0; Found: 346.2.

Step 2: 6-[2,6-Difluoro-4-(methylsulfonyl)phenyl]-5-fluoropyridine-2-carboxylic Acid

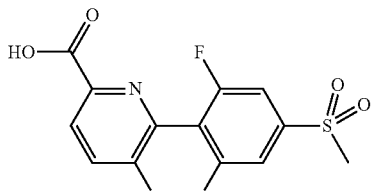

Methyl 6-[2,6-difluoro-4-(methylsulfonyl)phenyl]-5-fluoropyridine-2-carboxylate (78.0 mg, 0.226 mmol) was dissolved in THF (0.2 mL) and MeOH (0.2 mL), and 1.0 M aq. NaOH (0.90 mL, 0.90 mmol) was then added. The reaction mixture was stirred at room temperature for 40 min. The solution was then neutralized with HCl (12 M) to pH=7 and concentrated under reduced pressure to remove all the solvents. The residue was dissolved in THF and MeOH, dried, filtered and concentrated under reduced pressure to give the sub-title compound as a white powder. LCMS calc. for $C_{13}H_9F_3NO_4S$ $(M+H)^+$: m/z=332.0. Found: 332.2.

Step 3: 4-{(3S)-3-[(tert-Butoxycarbonyl)amino]piperidin-1-yl}-3-[({6-[2,6-difluoro-4-(methylsulfonyl)phenyl]-5-fluoropyridin-2-yl}carbonyl)amino]-6,7-dihydro-5H-cyclopenta[b]pyridin-7-yl Acetate

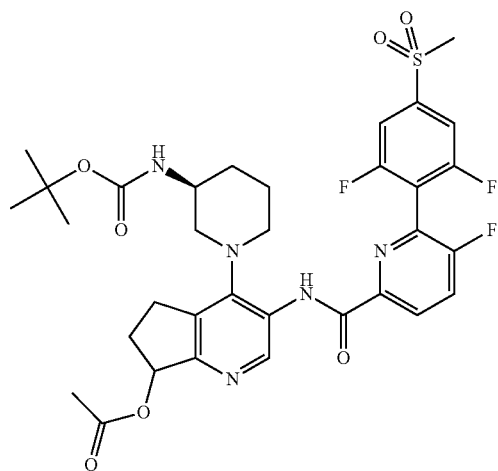 [SMILES: CC(=O)OC1CCc2c1ncc(NC(=O)c1ccc(F)c(-c3c(F)cc(S(C)(=O)=O)cc3F)n1)c2N1CCC[C@H](NC(=O)OC(C)(C)C)C1]

A mixture of 3-amino-4-{(3S)-3-[(tert-butoxycarbonyl)amino]piperidin-1-yl}-6,7-dihydro-5H-cyclopenta[b]pyridin-7-yl acetate (15.0 mg, 0.0384 mmol), 6-[2,6-difluoro-4-(methylsulfonyl)phenyl]-5-fluoropyridine-2-carboxylic acid (15.3 mg, 0.0461 mmol), HATU (36.5 mg, 0.0960 mmol) in DMF (0.09 mL) and DIPEA (14.9 mg, 0.115 mmol) was stirred at room temperature for 16 h. The mixture was filtered, concentrated under reduced pressure and purified by preparative LC-MS (method: XBridge™ preparative C18 5 μm OBD™ column, 30×10 mm, 60 mL/min., eluting with a gradient of MeCN and water with 0.1% NH₄OH) to give the sub-title compound as a colorless gum (11.0 mg, 41%). LCMS calc. for $C_{33}H_{37}F_3N_5O_7S$ $(M+H)^+$: m/z=704.2. Found: 704.2.

Step 4: N-{4-[(3S)-3-Aminopiperidin-1-yl]-7-hydroxy-6,7-dihydro-5H-cyclopenta[b]pyridin-3-yl}-6-[2,6-difluoro-4-(methylsulfonyl)phenyl]-5-fluoropyridine-2-carboxamide 4-{(3S)-3-[(tert-Butoxycarbonyl)amino]piperidin-1-yl}-3-[({6-[2,6-difluoro-4-(methylsulfonyl)phenyl]-5-fluoropyridin-2-yl}carbonyl)amino]-6,7-dihydro-5H-cyclopenta[b]pyridin-7-yl acetate (11.0 mg, 0.0156 mmol) was dissolved in MeOH (0.04 mL) and THF (0.20 mL), then 1.0 M aq. NaOH (0.062 mL, 0.062 mmol) was added. The reaction mixture was stirred at room temperature for 30 min. The organic solvents and trace of water were removed under vacuum to give a crude intermediate. The intermediate was dissolved in DCM (0.16 mL) and TFA (0.16 mL, 2.1 mmol) was then added. The reaction mixture was stirred at room temperature for 30 min. The solution was concentrated under reduced pressure and the residue was diluted with MeOH, filtered and purified by preparative LC-MS (XBridge™ preparative C18 5 μm OBD™ column, 30×10 mm, 60 mL/min., eluting with a gradient of MeCN and water with 0.1% NH₄OH) to give both diastereoisomers of the title compound as white powders. On analytical HPLC (Waters SunFire™ C18, 2.1×50 mm, 5 μm; flow rate 3 mL/min.; injection volume 2 μL; gradient from 2 to 80% B in 3 minutes (A=water with 0.025% TFA, B=MeCN)), the diastereoisomers had the following properties:

Diastereoisomer 1. First peak. Retention time 1.542 min., LCMS calc. for $C_{26}H_{27}F_3N_5O_4S$ $(M+H)^+$: m/z=562.2. Found: 562.2.

Diastereoisomer 2. Second peak. Retention time 1.611 min., LCMS calc. for $C_{26}H_{27}F_3N_5O_4S$ $(M+H)^+$: m/z=562.2. Found: 562.2.

The diastereoisomers correspond to the (7R) and (7S) diastereoisomers of the title compound.

Example 62

3-Amino-N-{4-[(3S)-3-aminopiperidin-1-yl]-7-hydroxy-6,7-dihydro-5H-cyclopenta[b]pyridin-3-yl}-6-(2,6-difluorophenyl)pyrazine-2-carboxamide

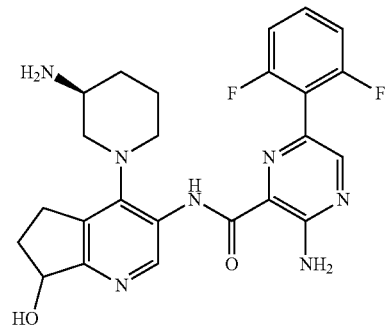 [SMILES: Nc1ncc(-c2c(F)cccc2F)nc1C(=O)Nc1cnc2c(c1N1CCC[C@H](N)C1)CCC2O]

Step 1. Methyl 3-amino-6-(2,6-difluorophenyl)pyrazine-2-carboxylate

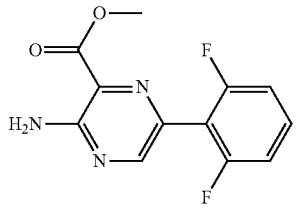 [SMILES: COC(=O)c1nc(-c2c(F)cccc2F)cnc1N]

A solution of (2,6-difluorophenyl)boronic acid (270 mg, 1.7 mmol), methyl 3-amino-6-bromopyrazine-2-carboxylate (from Ark Pharm, 250 mg, 1.1 mmol), bis(tri-tert-butylphosphine) palladium (82 mg, 0.16 mmol), and DIPEA (370 μL, 2.1 mmol) in 1,4-dioxane (4 mL) and water (320 μL) in a vial was deoxygenated and purged with nitrogen several times. The vial was sealed and the reaction mixture was heated at 100° C. in the sealed vial for 14 h. The crude reaction mixture was filtered through a pad of diatomaceous earth and the inorganics were washed thoroughly with EtOAc. The filtrate was concentrated under reduced pressure and the residue was purified by flash chromatography (40 g silica gel column, eluting with 0-50% EtOAc in hexanes) to afford the sub-title compound (258 mg, 91% yield). LC/MS (ESI) calc. for $C_{12}H_{10}F_2N_3O_2$ (M+H)$^+$: m/z=266.1; found: 266.0.

Step 2. 3-Amino-6-(2,6-difluorophenyl)pyrazine-2-carboxylic Acid

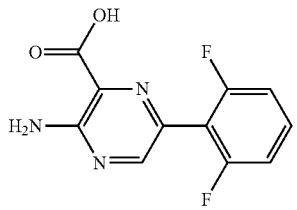 [SMILES: Nc1ncc(-c2c(F)cccc2F)nc1C(=O)O]

A solution of methyl 3-amino-6-(2,6-difluorophenyl)pyrazine-2-carboxylate (258 mg, 0.973 mmol) and lithium hydroxide monohydrate (200 mg, 4.8 mmol) in THF (4.0 mL) and water (2.0 mL) was heated at 60° C. in a sealed vial for 2 h. The reaction mixture was allowed to cool to ambient temperature and neutralized by the addition of 1.0 M hydrogen chloride in water (4.8 mL, 4.8 mmol) to form a precipitate. The precipitate was collected by filtration, washed with EtOAc (5 mL), and dried under vacuum to afford the sub-title compound (170 mg). The filtrate was diluted with EtOAc (15 mL) and the layers were separated. The organic layer was washed with H$_2$O (3 mL) and the combined aqueous phases were extracted with EtOAc (3 mL). The combined organic layers were washed with brine (3 mL), dried over Na$_2$SO$_4$, filtered and concentrated under reduced pressure to provide additional sub-title compound. The crude product was used in the subsequent reaction without further purification (70 mg). LC/MS (ESI) calc. for $C_{11}H_8F_2N_3O_2$ (M+H)$^+$: m/z=252.1; found: 251.9.

Step 3. 3-({[3-Amino-6-(2,6-difluorophenyl)pyrazin-2-yl]carbonyl}amino)-4-{(3S)-3-[(tert-butoxycarbonyl)amino]piperidin-1-yl}-6,7-dihydro-5H-cyclopenta[b]pyridin-7-yl Acetate

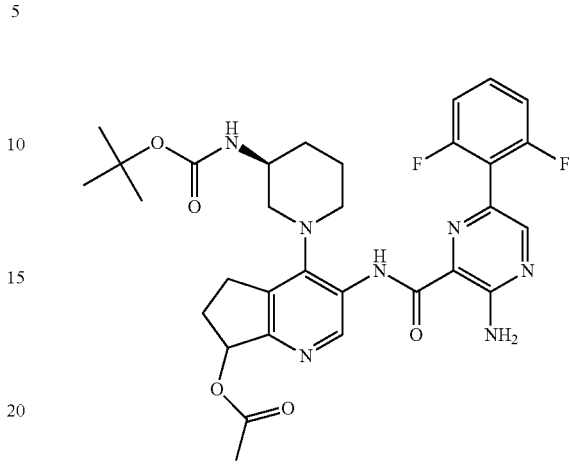

To a pre-stirred solution of 3-amino-6-(2,6-difluorophenyl)pyrazine-2-carboxylic acid (18 mg, 0.070 mmol), HATU (32 mg, 0.084 mmol), and DIPEA (36 μL, 0.21 mmol) in 1,2-dichloroethane (0.3 mL) was added a solution of 3-amino-4-{(3S)-3-[(tert-butoxycarbonyl)amino]piperidin-1-yl}-6,7-dihydro-5H-cyclopenta[b]pyridin-7-yl acetate (38 mg, 0.097 mmol) in 1,2-dichloroethane (0.5 mL). The resulting solution was stirred at ambient temperature for 3 h. The crude reaction mixture was concentrated under reduced pressure and the residue was purified by flash chromatography (20 g silica gel column, eluting with 0-10% MeOH in DCM) to afford the sub-title compound (18 mg, 41%). LC/MS (ESI) calc. for $C_{31}H_{36}F_2N_7O_5$ (M+H)$^+$: m/z=624.3; found: 624.1.

Step 4. 3-Amino-N-{4-[(3S)-3-aminopiperidin-1-yl]-7-hydroxy-6,7-dihydro-5H-cyclopenta[b]pyridin-3-yl}-6-(2,6-difluorophenyl)pyrazine-2-carboxamide A solution of 3-({[3-amino-6-(2,6-difluorophenyl)pyrazin-2-yl]carbonyl}amino)-4-{(3S)-3-[(tert-butoxycarbonyl)amino]piperidin-1-yl}-6,7-dihydro-5H-cyclopenta[b]pyridin-7-yl acetate (18 mg, 0.029 mmol) and lithium hydroxide [1.0]-water (11.1 mg, 0.264 mmol) in MeOH (300 μL) and water (300 μL) was stirred at ambient temperature for 1.5 h. The reaction mixture was diluted with EtOAc (20 mL) and neutralized with 1.0 M hydrogen chloride in water (260 μL, 0.26 mmol). The layers were separated and the organic layer was washed with H$_2$O (3 mL) and the combined aqueous phases were extracted with EtOAc (3 mL×3). The combined organic layers were washed with brine (3 mL), dried over Na$_2$SO$_4$, filtered and concentrated under reduced pressure to afford an intermediate (13 mg, 87%). The crude intermediate was dissolved in 1,2-dichloroethane (300 μL) and TFA (300 μL, 3.89 mmol), and the resulting solution was stirred at ambient temperature for 1.5 h. The crude reaction mixture was concentrated under reduced pressure and the residue was purified by preparative HPLC (XBridge™ preparative C18 5 μm OBD™ column, 30×10 mm, 60 mL/min., eluting with a gradient of MeCN and water with 0.05% TFA) to afford the tris(trifluoroacetate) salt of the title compound as two diastereoisomers. On analytical HPLC (Waters SunFire™ C18, 2.1×50 mm, 5 μm; flow rate 3 mL/min.; injection volume 2 μL; gradient from 2 to 80%

B in 3 minutes (A=water with 0.025% TFA, B=MeCN)), the diastereoisomers had the following properties:

Diastereoisomer 1. First peak. Retention time 0.88 min., LC/MS (ESI) calc. for $C_{24}H_{26}F_2N_7O_2$ (M+H)$^+$: m/z=482.2; found: 482.0.

Diastereoisomer 2. Second peak. Retention time 0.94 min., LC/MS (ESI) calc. for $C_{24}H_{26}F_2N_7O_2$ (M+H)$^+$: m/z=482.2; found: 482.0.

The diastereoisomers correspond to the (7R) and (7S) diastereoisomers of the title compound.

Example 63

N-{4-[(3R,5S)-3-Amino-4-hydroxy-4,5-dimethylpiperidin-1-yl]-7-hydroxy-6,7-dihydro-5H-cyclopenta[b]pyridin-3-yl}-6-(2,6-difluorophenyl)-5-fluoropyridine-2-carboxamide

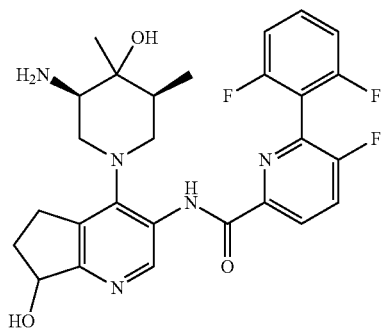 [SMILES: C[C@H]1CN(c2c(NC(=O)c3ccc(F)c(-c4c(F)cccc4F)n3)cnc3c2CCC3O)C[C@@H](N)C1(C)O]

Step 1. Benzyl-(3R,4R,5S)-3-[(tert-butoxycarbonyl)amino]-4-{[tert-butyl(dimethyl)silyl]oxy}-5-methylpiperidine-1-carboxylate

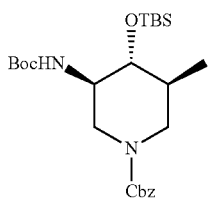 [SMILES: C[C@H]1CN(C(=O)OCc2ccccc2)C[C@@H](NC(=O)OC(C)(C)C)[C@@H]1O[Si](C)(C)C(C)(C)C]

To a solution of tert-butyl-((3R,4R,5S)-4-{[tert-butyl(dimethyl)silyl]oxy}-5-methylpiperidin-3-yl)carbamate (3.2 g, 9.4 mmol) (40% purity) in DCM (25 mL), N-(benzyloxycarbonyloxy)succinimide (2.6 g, 10 mmol) was added, followed by triethylamine (1.4 mL, 10 mmol). The mixture was stirred for 16 h at room temperature. The reaction mixture was then diluted with EtOAc, washed with water and brine and dried over Na$_2$SO$_4$. The solvent was evaporated under reduced pressure and the resulting crude product was purified by silica gel chromatography eluting with 25% EtOAc in hexanes to give the sub-title compound as a white solid (1.71 g, 38%). LCMS calc. for $C_{25}H_{42}N_2O_5SiNa$ (M+Na)$^+$ m/z=501.3; found 501.0.

Step 2. Benzyl-(3R,4R,5S)-3-[(tert-butoxycarbonyl)amino]-4-hydroxy-5-methylpiperidine-1-carboxylate

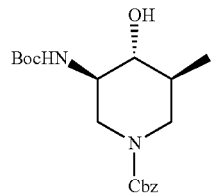 [SMILES: C[C@H]1CN(C(=O)OCc2ccccc2)C[C@@H](NC(=O)OC(C)(C)C)[C@@H]1O]

Benzyl-(3R,4R,5S)-3-[(tert-butoxycarbonyl)amino]-5-methyl-4-(1,1,2,2-tetramethylpropoxy)piperidine-1-carboxylate (1.88 g, 4.06 mmol) was dissolved in THF (20 mL) and a 1.0 M solution of tetra-n-butylammonium fluoride in THF (4.7 mL, 4.7 mmol) was added. The reaction mixture was stirred for 30 min. at room temperature and then diluted with EtOAc. The mixture was washed 2 times with brine, then dried and concentrated under reduced pressure. The crude product was purified by silica gel chromatography eluting with 25-75% EtOAc in hexanes to give the sub-title compound as a white solid (1.48 g, 82%). LCMS calc. for $C_{19}H_{28}N_2NaO_5$ (M+Na)$^+$ m/z=387.2; found 387.0.

Step 3. Benzyl-3-[(tert-butoxycarbonyl)amino]-5-methyl-4-oxopiperidine-1-carboxylate

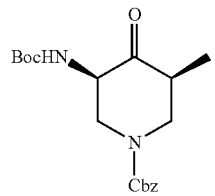 [SMILES: C[C@H]1CN(C(=O)OCc2ccccc2)C[C@@H](NC(=O)OC(C)(C)C)C1=O]

Pyridine (0.8 mL, 10 mmol) and Dess-Martin periodinane (1.8 g, 4.4 mmol) were added to a stirred solution of benzyl-3-[(tert-butoxycarbonyl)amino]-4-hydroxy-5-methylpiperidine-1-carboxylate (1.22 g, 3.35 mmol) in DCM (20 mL) at 0° C. The reaction mixture was stirred at room temperature for 16 h. A solution containing a mixture of NaHCO$_3$ and Na$_2$S$_2$O$_3$ was added and the resulting mixture was stirred for 30 min. The mixture was then extracted with DCM. The combined organic layers were dried over Na$_2$SO$_4$ and concentrated under reduced pressure. The resulting residue was purified by silica gel chromatography eluting with 40% EtOAc in hexanes to give the sub-title compound as a colorless oil (1.15 g, 95%). LCMS calc. for $C_{19}H_{26}N_2NaO_5$ (M+Na)$^+$ m/z=385.2; found 385.0.

Step 4. Benzyl-(3R,5S)-3-[(tert-butoxycarbonyl)amino]-4-hydroxy-4,5-dimethylpiperidine-1-carboxylate

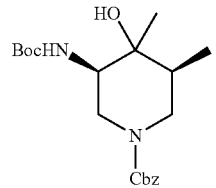 [SMILES: C[C@H]1CN(C(=O)OCc2ccccc2)C[C@@H](NC(=O)OC(C)(C)C)C1(C)O]

To a solution of benzyl-(3R,5S)-3-[(tert-butoxycarbonyl)amino]-5-methyl-4-oxopiperidine-1-carboxylate (1.61 g, 4.44 mmol) in THF (30 mL) at −78° C. a solution of methylmagnesium bromide in ether (3.0 M, 4.4 mL, 13 mmol) was added. The reaction was then quenched by adding aq. NH$_4$Cl, and the resulting mixture was extracted with EtOAc. The combined organic extracts were dried and concentrated under reduced pressure. The residue was purified by silica gel chromatography eluting with 20-80% EtOAc in hexanes to give a mixture of the two diastereoisomers of the sub-title compound as a colorless oil (0.95 g, 56%). LCMS calc. for $C_{20}H_{30}N_2NaO_5$ (M+Na)$^+$ m/z=401.2; found 401.0. 40% of unreacted starting material was also isolated.

Step 5. tert-Butyl-[(3R,5S)-4-hydroxy-4,5-dimethylpiperidin-3-yl]carbamate

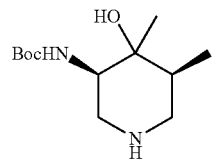 [SMILES: C[C@H]1CNC[C@@H](NC(=O)OC(C)(C)C)C1(C)O]

Benzyl-(3R,4R,5S)-3-[(tert-butoxycarbonyl)amino]-4-hydroxy-4,5-dimethylpiperidine-1-carboxylate (414 mg, 1.09 mmol) in a vial was dissolved in MeOH (10 mL) and 10% palladium on carbon (100 mg) was added. The vial was closed with septum and connected to a balloon filled with hydrogen. The reaction mixture was stirred at room temperature overnight. The solution was filtered to remove the palladium on carbon and solvent was evaporated under reduced pressure to give the sub-title compound as a colorless oil (245 mg, 92%), which was used in the next step without further purification. LCMS calc. for $C_{12}H_{25}N_2O_3$ (M+H)$^+$ m/z=245.2; found 245.1.

Step 6. tert-Butyl [(3R,5S)-4-hydroxy-4,5-dimethyl-1-(3-nitro-6,7-dihydro-5H-cyclopenta[b]pyridin-4-yl)piperidin-3-yl]carbamate

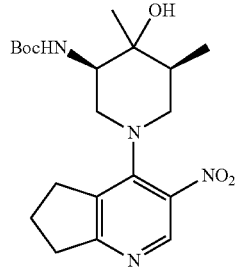 [SMILES: C[C@H]1CN(c2c([N+](=O)[O-])cnc3c2CCC3)C[C@@H](NC(=O)OC(C)(C)C)C1(C)O]

A mixture of 4-chloro-3-nitro-6,7-dihydro-5H-cyclopenta[b]pyridine (210 mg, 1.0 mmol), tert-butyl [(3R,5S)-4-hydroxy-4,5-dimethylpiperidin-3-yl]carbamate (255 mg, 1.04 mmol) and triethylamine (296 µL, 2.12 mmol) in isopropyl alcohol (1 mL) was stirred at 80° C. for 2 h. The solvent was evaporated under reduced pressure and the resulting residue was purified by chromatography on silica gel eluting with 25% EtOAc in hexanes to give the sub-title compound as a yellow oil (318 mg, 74%). LCMS calc. for $C_{20}H_{31}N_4O_5$ (M+H)+m/z=407.2; found 407.2.

Step 7. tert-Butyl [(3R,5S)-4-hydroxy-4,5-dimethyl-1-(3-nitro-1-oxido-6,7-dihydro-5H-cyclopenta[b]pyridin-4-yl)piperidin-3-yl]carbamate

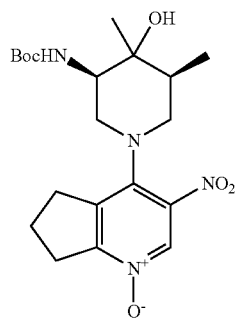 [SMILES: C[C@H]1CN(c2c([N+](=O)[O-])c[n+]([O-])c3c2CCC3)C[C@@H](NC(=O)OC(C)(C)C)C1(C)O]

mCPBA (260 mg, 1.5 mmol) was added to a mixture of tert-butyl [(3R,5S)-4-hydroxy-4,5-dimethyl-1-(3-nitro-6,7-dihydro-5H-cyclopenta[b]pyridin-4-yl)piperidin-3-yl]carbamate (312 mg, 0.768 mmol) in DCM (3.2 mL). After 2 h, LCMS showed only 30% conversion of starting material. mCPBA was added several more times (to a total amount of about 10 eq.) until LCMS showed complete consumption of starting material (after approximately 7 h). A saturated solution of NaHCO$_3$ was then added to the mixture and the resulting mixture was extracted with DCM. The combined organic extracts were dried and then concentrated to dryness under reduced pressure. The crude sub-title compound was used in the next step without further purification. LCMS calc. for $C_{20}H_{31}N_4O_6$ (M+H)$^+$ m/z=423.2; found 423.2.

Step 8. 4-{(3R,5S)-3-[(tert-Butoxycarbonyl)amino]-4-hydroxy-4,5-dimethylpiperidin-1-yl}-3-nitro-6,7-dihydro-5H-cyclopenta[b]pyridin-7-yl Acetate

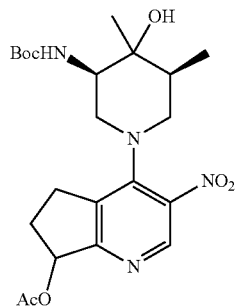 [SMILES: CC(=O)OC1CCc2c1ncc([N+](=O)[O-])c2N1C[C@H](C)C(C)(O)[C@H](NC(=O)OC(C)(C)C)C1]

A mixture of tert-butyl [(3R,5S)-4-hydroxy-4,5-dimethyl-1-(3-nitro-1-oxido-6,7-dihydro-5H-cyclopenta[b]pyridin-4-yl)piperidin-3-yl]carbamate (390 mg, 0.92 mmol) and Ac$_2$O (2 mL) was stirred at 90° C. for 1 h. The reaction mixture was cooled to room temperature and then concentrated under reduced pressure. The mixture was neutralized with aq. NaHCO$_3$ and then extracted with EtOAc. The combined organic extracts were dried and concentrated under reduced pressure. The resulting residue was purified by silica gel chromatography eluting with 20-80% EtOAc in hexanes to give the desired product as a yellow oil (196 mg, 55% in 2 steps). LCMS calc. for $C_{22}H_{33}N_4O_7$ (M+H)$^+$ m/z=465.2; found 465.1.

Step 9. 3-Amino-4-{(3R,5S)-3-[(tert-butoxycarbonyl)amino]-4-hydroxy-4,5-dimethylpiperidin-1-yl}-6,7-dihydro-5H-cyclopenta[b]pyridin-7-yl Acetate

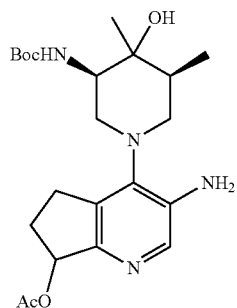 [SMILES: CC(=O)OC1CCc2c1ncc(N)c2N1C[C@H](C)C(C)(O)[C@H](NC(=O)OC(C)(C)C)C1]

4-{(3R,5S)-3-[(tert-Butoxycarbonyl)amino]-4-hydroxy-4,5-dimethylpiperidin-1-yl}-3-nitro-6,7-dihydro-5H-cyclopenta[b]pyridin-7-yl acetate (198 mg, 0.426 mmol) was dissolved in acetic acid (2.8 mL), and iron powder (0.36 g, 6.4 mmol) was added to the solution. Reaction was stirred at room temperature for 2 h. The mixture was diluted with 30 mL of EtOAc, filtered through diatomaceous earth. The filtrate was concentrated under reduced pressure and the resulting residue was dissolved in EtOAc, and neutralized with NaHCO$_3$. The layers were separated, and the aqueous layer was extracted with further EtOAc. The combined organic layers were dried and concentrated under reduced pressure to give the sub-title compound as a white solid (176 mg, 95%), which was used in the next step without further purification. LCMS calc. for $C_{22}H_{35}N_4O_5$ (M+H)$^+$ m/z=435.3; found 435.1.

Step 10. 4-{(3R,5S)-3-[(tert-Butoxycarbonyl)amino]-4-hydroxy-4,5-dimethylpiperidin-1-yl}-3-({[6-(2,6-difluorophenyl)-5-fluoropyridin-2-yl]carbonyl}amino)-6,7-dihydro-5H-cyclopenta[b]pyridin-7-yl Acetate

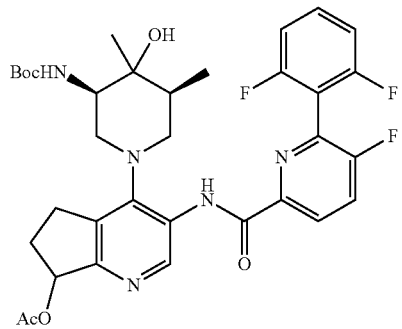 [SMILES: CC(=O)OC1CCc2c1ncc(NC(=O)c1ccc(F)c(-c3c(F)cccc3F)n1)c2N1C[C@H](C)C(C)(O)[C@H](NC(=O)OC(C)(C)C)C1]

3-Amino-4-{(3R,5S)-3-[(tert-butoxycarbonyl)amino]-4-hydroxy-4,5-dimethylpiperidin-1-yl}-6,7-dihydro-5H-cyclopenta[b]pyridin-7-ylacetate (153 mg, 0.352 mmol), 6-(2,6-difluorophenyl)-5-fluoropyridine-2-carboxylic acid (107 mg, 0.422 mmol), HATU (330 mg, 0.88 mmol), and DIPEA (180 µL, 1.0 mmol) were dissolved in DMF (4.9 mL) and the resulting mixture was stirred at room temperature for 2 h. The reaction mixture was diluted with MeCN and purified by RP-HPLC (Waters SunFire™ C18 column, 19 mm×100 mm, 5 µm particle size, eluting with a gradient of MeCN/water containing 0.1% TFA, at flow rate of 30 mL/min.) to give the sub-title compound as a white solid (118 mg, 50%). LCMS calc. for $C_{34}H_{39}F_3N_5O_6$ (M+H)$^+$ m/z=670.3; found 670.3.

Step 11. N-{4-[(3R,5S)-3-Amino-4-hydroxy-4,5-dimethylpiperidin-1-yl]-7-hydroxy-6,7-dihydro-5H-cyclopenta[b]pyridin-3-yl}-6-(2,6-difluorophenyl)-5-fluoropyridine-2-carboxamide 4-{(3R,5S)-3-[(tert-Butoxycarbonyl)amino]-4-hydroxy-4,5-dimethylpiperidin-1-yl}-3-({[6-(2,6-difluorophenyl)-5-fluoropyridin-2-yl]carbonyl}amino)-6,7-dihydro-5H-cyclopenta[b]pyridin-7-yl acetate (118 mg, 0.176 mmol) was dissolved in a mixture of MeOH (1 mL) and THF (1 mL) and 0.5 M solution of aq. NaOH (1 mL, 0.5 mmol) was added. The reaction was stirred for 1 h, and then concentrated to dry under reduced pressure. To the residue was added 4.0 M solution of hydrogen chloride in dioxane (3 mL, 10 mmol). The reaction mixture was stirred for 1 h, and then evaporated to dryness. The resulting residue was dissolved in MeCN and purified by RP-HPLC (water SunFire™ C18 column, 19 mm×100 mm, 5 µm particle size, eluting with a gradient of MeCN/water containing 0.1% TFA, at flow rate of 30 mL/min.) to give four different diastereoisomers of the bis(trifluoroacetate) of the title compound as white solids.

Diastereoisomer 1. First peak. Retention time 1.402 min. LCMS calc. for $C_{27}H_{29}F_3N_5O_3$ (M+H)$^+$ m/z=528.2; found: 528.2. $^1$H NMR (500 MHz, DMSO-d$_6$) δ 10.49 (s, 1H), 8.74 (s, 1H), 8.36 (dd, J=8.7, 4.0 Hz, 1H), 8.21 (t, J=8.8 Hz, 1H), 8.14 (s, 3H), 7.71-7.61 (m, 1H), 7.31 (t, J=8.3 Hz, 2H), 5.16

(t, J=6.9 Hz, 1H), 3.55 (d, J=9.7 Hz, 1H), 3.33 (t, J=12.1 Hz, 1H), 3.25 (d, J=11.3 Hz, 1H), 3.14 (dq, J=12.0, 4.2, and 3.4 Hz, 1H), 3.05 (s, 1H), 2.97-2.80 (m, 2H), 1.97-1.83 (m, 1H), 1.73 (dt, J=11.4 and 6.6 Hz, 1H), 0.98 (s, 3H), 0.63 (d, J=6.8 Hz, 3H) ppm.

Diastereoisomer 2. Second peak. Retention time 1.445 min. LCMS calc. for $C_{27}H_{29}F_3N_5O_3$ (M+H)$^+$ m/z=528.2; found: 528.2.

Diastereoisomer 3. Third peak. Retention time 1.587 min. LCMS calc. for $C_{27}H_{29}F_3N_5O_3$ (M+H)$^+$ m/z=528.2; found: 528.2. $^1$H NMR (500 MHz, DMSO-d$_6$) δ 10.48 (s, 1H), 8.82 (s, 1H), 8.37 (dd, J=8.6 and 3.9 Hz, 1H), 8.22 (t, J=8.8 Hz, 1H), 8.03 (s, 2H), 7.67 (p, J=8.1 Hz, 1H), 7.31 (t, J=8.2 Hz, 2H), 5.13-5.05 (m, 1H), 3.41 (d, J=10.7 Hz, 1H), 3.24 (t, J=12.1 Hz, 1H), 3.13-3.02 (m, 1H), 3.03-2.81 (m, 2H), 2.46-2.38 (m, 1H), 1.91 (dq, J=13.2, 7.1 Hz, 1H), 1.80-1.66 (m, 1H), 0.97 (s, 3H), 0.67 (d, J=6.7 Hz, 3H).

Diastereoisomer 4. Fourth peak. Retention time 1.658 min. LCMS calc. for $C_{27}H_{29}F_3N_5O_3$ (M+H)$^+$ m/z=528.2; found: 528.2.

The diastereoisomers correspond to the (3R,4R,5R,7R), (3R,4S,5R,7R), (3R,4R,5R,7S), and ((3R,4S,5R,7S) diastereoisomers of the title compound.

Example 64

N-{4-[(3S,5R)-3-Amino-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide

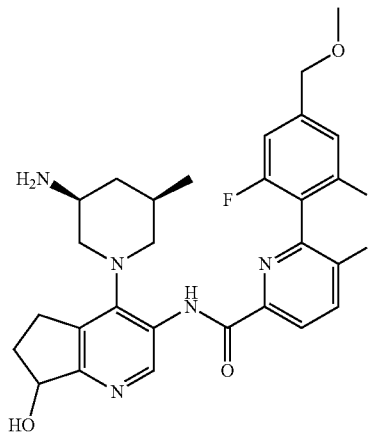

Step 1. (3,5-Difluorophenyl)methanol

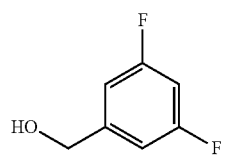

To a solution of 3,5-difluorobenzaldehyde (2.00 g, 14.1 mmol) in MeOH (20 mL) at 0-5° C. was added NaBH$_4$ (1.06 g, 28.1 mmol) portionwise. The mixture was stirred at 0-5° C. for 1 h, quenched with brine, and then extracted with EtOAc (2×). The combined organic phases were washed with water and brine, then dried over Na$_2$SO$_4$ and concentrated under reduced pressure to give sub-title compound as a colorless oil. %). $^1$H NMR (300 MHz, CDCl$_3$) δ 6.88 (m, 2H), 6.70 (m, 1H), 4.69 (s, 2H), 1.88 (br s, 1H) ppm.

Step 2. 1,3-Difluoro-5-(methoxymethyl)benzene

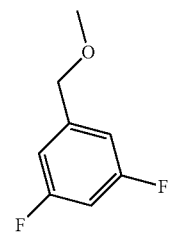

To a solution of (3,5-difluorophenyl)methanol (1.98 g, 13.7 mmol) in THF (20 mL) at 0° C. was added sodium hydride (1.0 g, 25 mmol) in portions. The mixture was stirred at 0-5° C. for 1 h, and then methyl iodide (4.3 mL, 69 mmol) was added. The reaction mixture was stirred at room temperature for 2 h. The mixture was quenched with water and extracted with EtOAc. The combined organic extracts were concentrated and the resulting residue was columned on 40 g silica gel, eluting with 0-40% EtOAc in hexanes, to give a colorless oil (2.1 g, 97%). $^1$H NMR (300 MHz, CDCl$_3$) δ 6.86 (m, 2H), 6.71 (m, 1H), 4.43 (s, 2H), 3.38 (s, 3H) ppm.

Step 3. 2-[2,6-Difluoro-4-(methoxymethyl)phenyl]-4,4,5,5-tetramethyl-1,3,2-dioxaborolane

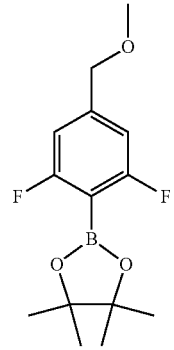 [SMILES: COCc1cc(F)c(B2OC(C)(C)C(C)(C)O2)c(F)c1]

To a solution of 1,3-difluoro-5-(methoxymethyl)benzene (0.970 g, 6.13 mmol) in THF (24 mL) at −78° C., a solution of n-BuLi in hexanes (1.6 M, 9.58 mL, 15.3 mmol) was slowly added through a dripping funnel. When addition was done, the mixture was kept at −78° C. for 1 h. 2-Isopropoxy-4,4,5,5-tetramethyl-1,3,2-dioxaborolane (3.75 mL, 18.4 mmol) was then added in one portion. The reaction mixture was allowed to warm to room temperature and stirred for 1 h. The mixture was quenched with aq. NaHCO$_3$ and extracted with EtOAc. The combined organic extracts were washed with brine, dried over Na$_2$SO$_4$, and concentrated under reduced pressure to give sub-title compound as a colorless oil. $^1$H NMR (300 MHz, CDCl$_3$) δ 6.82 (m, 2H), 4.43 (s, 2H), 3.38 (s, 3H), 1.37 (s, 12H) ppm.

Step 4. 6-[2,6-Difluoro-4-(methoxymethyl)phenyl]-5-fluoropyridine-2-carboxylic Acid

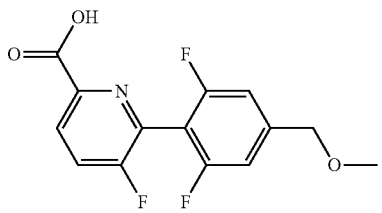 [SMILES: COCc1cc(F)c(-c2nc(C(=O)O)ccc2F)c(F)c1]

A mixture of 2-[2,6-difluoro-4-(methoxymethyl)phenyl]-4,4,5,5-tetramethyl-1,3,2-dioxaborolane (0.364 g, 1.28 mmol), methyl 6-bromo-5-fluoropyridine-2-carboxylate (0.300 g, 1.28 mmol) and DIPEA (0.67 mL, 3.8 mmol) in 1,4-dioxane (6 mL) and water (0.30 mL) was purged with nitrogen. Bis(tri-tert-butylphosphine)palladium (65.5 mg, 0.128 mmol) was added to the mixture. The resulting reaction mixture was then heated at 120° C. for 40 min. The mixture was filtered through a pad of diatomaceous earth and the filtrate was concentrated under reduced pressure. The crude product was purified by silica gel column chromatography (eluting with 0-50% EtOAc in hexanes) to give methyl 6-[2,6-difluoro-4-(methoxymethyl)phenyl]-5-fluoropyridine-2-carboxylate as a white powder.

The methyl 6-[2,6-difluoro-4-(methoxymethyl)phenyl]-5-fluoropyridine-2-carboxylate was treated with THF (2 mL), MeOH (2 mL) and 1.0 M aq. NaOH (2 mL, 2 mmol) at room temperature for 1 h. The volatile solvents were removed under reduced pressure. The residue was neutralized to pH around 5-6 with 1N HCl. The solids that precipitated were collected by filtration, rinsed with water, and dried to give the sub-title compound as a white solid (374 mg, 98.2%). LCMS calc. for $C_{14}H_{11}F_3NO_3$ (M+H)$^+$ m/z=298.1; found: 298.0.

Step 5. N-{4-[(3S,5R)-3-Amino-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (256 mg, 0.633 mmol), 6-[2,6-difluoro-4-(methoxymethyl)phenyl]-5-fluoropyridine-2-carboxylic acid (188 mg, 0.633 mmol), HATU (481 mg, 1.26 mmol) in DMF (1 mL) and DIPEA (0.330 mL, 1.90 mmol) was stirred at room temperature for 2 h. The reaction mixture was quenched with water and then extracted with EtOAc (2 times). The combined organic extracts were washed with brine, dried over $Na_2SO_4$, and concentrated under reduced pressure. The resulting residue was purified by column chromatography on silica gel using CombiFlash® apparatus eluting with EtOAc/hexanes (50-100%) to yield 4-{(3S,5R)-3-[(tert-butoxycarbonyl)amino]-5-methylpiperidin-1-yl}-3-[({6-[2,6-difluoro-4-(methoxymethyl)phenyl]-5-fluoropyridin-2-yl}carbonyl)amino]-6,7-dihydro-5H-cyclopenta[b]pyridin-7-yl acetate as an intermediate.

To the amide intermediate, THF (6 mL), MeOH (6 mL) and 1.0 M aq. NaOH (6.32 mL, 6.32 mmol) were added. The mixture was stirred at room temperature for 20 min. The volatile solvents were removed under reduced pressure. The resulting residue was extracted with EtOAc (2×). The combined organic phases were washed with brine, dried over $Na_2SO_4$, and then concentrated to dry to give tert-butyl ((3S,5R)-1-{3-[({6-[2,6-difluoro-4-(methoxymethyl)phenyl]-5-fluoropyridin-2-yl}carbonyl)amino]-7-hydroxy-6,7-dihydro-5H-cyclopenta[b]pyridin-4-yl}-5-methylpiperidin-3-yl)carbamate as a second intermediate.

The alcohol intermediated was treated with TFA (6 mL) and DCM (6 mL). The mixture was stirred at room temperature for 2 h, and then concentrated under reduced pressure. The resulting residue was purified by preparative LCMS (Waters SunFire™ C18 column, 19 mm×100 mm, 5 µm particle size, eluting with a gradient of MeCN/water containing 0.1% $NH_4OH$, at flow rate of 30 mL/min.) to afford two diastereoisomers of the title compound as white powders.

Diastereoisomer 1. First peak. Retention time 1.48 min. LCMS calc. for $C_{28}H_{31}F_3N_5O_3$ (M+H)$^+$ m/z=542.2; found: 542.1. $^1$H NMR (300 MHz, DMSO-$d_6$) δ 10.72 (s, 1H), 9.40 (s, 1H), 8.31 (m, 1H), 8.17 (m, 1H), 7.26 (d, J=9.0 Hz, 2H), 5.23 (m, 1H), 4.75 (m, 1H), 4.51 (s, 2H), 3.34 (s, 3H), 2.99 (m, 1H), 2.84 (m, 2H), 2.71 (m, 1H), 2.53 (m, 1H), 2.41 (m, 1H), 2.28 (m, 1H), 2.22 (m, 1H), 1.77 (m, 1H), 1.49 (m, 2H), 1.28 (m, 1H), 0.53 (d, J=6.0 Hz, 3H) ppm.

Diastereoisomer 2. Second peak: Retention time 1.56 min. LCMS calc. for $C_{28}H_3F_3N_5O_3$ (M+H)$^+$ m/z=542.2; found: 542.1. $^1$H NMR (300 MHz, DMSO-$d_6$) δ 10.71 (s, 1H), 9.40 (s, 1H), 8.31 (m, 1H), 8.17 (m, 1H), 7.26 (d, J=9.0 Hz, 2H), 5.24 (m, 1H), 4.78 (m, 1H), 4.51 (s, 2H), 3.34 (s, 3H), 2.97 (m, 1H), 2.83 (m, 2H), 2.71 (m, 1H), 2.53 (m, 1H), 2.41 (m, 1H), 2.29 (m, 1H), 2.25 (m, 1H), 1.72 (m, 1H), 1.51 (m, 2H), 1.28 (m, 1H), 0.52 (d, J=6.6 Hz, 3H) ppm.

The diastereoisomers correspond to the (7R) and (7S) diastereoisomers of the title compound.

Example 65

N-{4-[(3R,4R,5S)-3-Amino-4-hydroxy-5-methylpiperidin-1-yl]-2,3-dihydrofuro[2,3-b]pyridin-5-yl}-6-[2,6-difluoro-4-(1-hydroxy-1-methylethyl)phenyl]-5-fluoropyridine-2-carboxamide

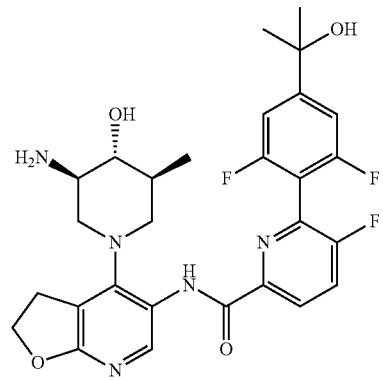 [SMILES: C[C@H]1CN(c2c(NC(=O)c3ccc(F)c(-c4c(F)cc(C(C)(C)O)cc4F)n3)cnc3c2CCO3)C[C@@H](N)[C@@H]1O]

Step 1. 1-(3,5-Difluorophenyl)ethanol

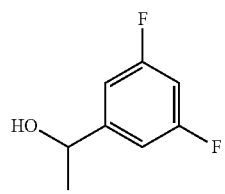

To a solution of 3,5-difluorobenzaldehyde (3.00 g, 21.1 mmol) in THF (30 mL) at 0-5° C. was added methylmagnesium bromide in THF (3.0 M; 8.44 mL, 25.3 mmol) dropwise. The mixture was stirred at 0-5° C. for 1 h, quenched with brine, and then extracted with EtOAc (2 times). The combined organic phases were washed with water and brine, dried over $Na_2SO_4$, and concentrated under reduced pressure to give the sub-title compound as a colorless oil (3.02 g, 90.4%). $^1$H NMR (300 MHz, $CDCl_3$) δ 6.89 (m, 2H), 6.69 (m, 1H), 4.88 (q, J=6.3 Hz, 1H), 1.47 (d, J=6.3 Hz, 3H) ppm.

Step 2. 1-(3,5-Difluorophenyl)ethanone

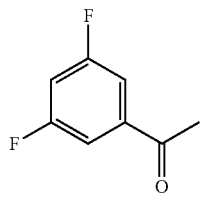

Dess-Martin periodinane (9.66 g, 22.8 mmol) was added portionwise to a solution of 1-(3,5-difluorophenyl)ethanol (3.00 g, 19.0 mmol) in DCM (40 mL) cooled in an ice bath. The mixture was stirred at room temperature for 2 h, then concentrated under reduced pressure. The residue was purified by purified by column chromatography on silica gel using CombiFlash® apparatus eluting with EtOAc/hexanes (0-40%). The purification gave 2.06 g (69.6%) of the sub-title compound as a colorless oil. $^1$H NMR (300 MHz, $CDCl_3$) δ 7.45 (m, 2H), 7.01 (m, 1H), 2.59 (s, 3H) ppm.

Step 3. 2-(3,5-Difluorophenyl)propan-2-ol

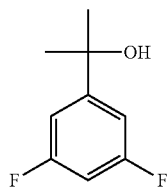

To a solution of 1-(3,5-difluorophenyl)ethanone (2.00 g, 12.8 mmol) in THF (20 mL) at 0-5° C., methylmagnesium bromide in THF (3.0 M; 5.12 mL, 15.4 mmol) was added dropwise. The mixture was stirred at 0-5° C. for 1 h, then quenched with brine, extracted with EtOAc (2 times). The combined organic phases were washed with water and brine, dried over $Na_2SO_4$, and concentrated under reduced pressure to give the sub-title compound as a colorless oil (2.12 g, 96.1%).

Step 4. 2-[3,5-Difluoro-4-(4,4,5,5-tetramethyl-1,3,2-dioxaborolan-2-yl)phenyl]propan-2-ol

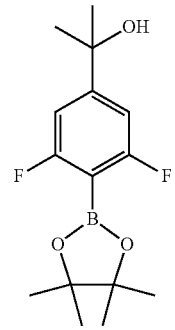 [SMILES: CC(C)(O)c1cc(F)c(B2OC(C)(C)C(C)(C)O2)c(F)c1]

To a mixture of 2-(3,5-difluorophenyl)propan-2-ol (2.00 g, 11.6 mmol) in THF (46 mL) at −78° C., n-BuLi in hexanes (1.6 M; 18.2 mL, 29.0 mmol) was slowly added through a dripping funnel. When the addition was complete, the mixture was kept at −78° C. for 1 h. 2-Isopropoxy-4,4,5,5-tetramethyl-1,3,2-dioxaborolane (7.11 mL, 34.8 mmol) was then added in one portion. The mixture was allowed to warmup room temperature and stirred for 1 h, then the reaction was quenched with water and the solution was extracted with EtOAc. The combined organic extracts were washed with brine, dried over $Na_2SO_4$, and concentrated under reduced pressure to give the sub-title compound as a colorless oil. LCMS calc. for $C_{15}H_{21}BF_2O_3Na$ $(M+Na)^+$ m/z=321.2; found: 321.0.

Step 5. Methyl 6-[2,6-difluoro-4-(1-hydroxy-1-methylethyl)phenyl]-5-fluoropyridine-2-carboxylate

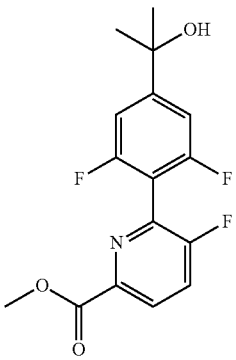 [SMILES: COC(=O)c1ccc(F)c(-c2c(F)cc(C(C)(C)O)cc2F)n1]

To a nitrogen purged mixture of 2-[3,5-difluoro-4-(4,4,5,5-tetramethyl-1,3,2-dioxaborolan-2-yl)phenyl]propan-2-ol (1.53 g, 5.13 mmol), methyl 6-bromo-5-fluoropyridine-2-carboxylate (1.20 g, 5.13 mmol) and DIPEA (2.7 mL, 15 mmol) in 1,4-dioxane (20 mL) and water (1.2 mL), bis(tri-tert-butylphosphine)palladium (262 mg, 0.513 mmol) was added. The reaction mixture was heated at 120° C. for 40 min., then cooled and filtered through a pad of diatomaceous earth. The filtrate was concentrated under reduced pressure.

The crude residue was purified by silica gel column chromatography (0-50% EtOAc in hexanes) to give methyl 6-[2,6-difluoro-4-(1-hydroxy-1-methylethyl)phenyl]-5-fluoropyridine-2-carboxylate as a white powder, which was used without further purification.

Step 6. 6-[2,6-Difluoro-4-(1-hydroxy-1-methylethyl)phenyl]-5-fluoropyridine-2-carboxylic Acid

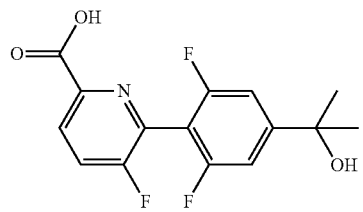 [SMILES: CC(C)(O)c1cc(F)c(-c2nc(C(=O)O)ccc2F)c(F)c1]

The methyl 6-[2,6-difluoro-4-(1-hydroxy-1-methylethyl)phenyl]-5-fluoropyridine-2-carboxylate prepared as described in Step 5 was treated with THF (8 mL), MeOH (8 mL) and 1.0 M aq. NaOH (8 mL, 8 mmol) at room temperature for 1 h. The volatile solvents were removed under reduced pressure. The residue was neutralized to pH around 6-7 with 1 M HCl. The precipitates were filtered, rinsed with water and dried to give the sub-title compound as a white solid (0.332 g, 20.8%). LCMS calc. for $C_{15}H_{13}F_3NO_3$ (M+H)$^+$ m/z=312.1; found: 312.1.

Step 7. N-{4-[(3R,4R,5S)-3-Amino-4-hydroxy-5-methylpiperidin-1-yl]-2,3-dihydrofuro[2,3-b]pyridin-5-yl}-6-[2,6-difluoro-4-(1-hydroxy-1-methylethyl)phenyl]-5-fluoropyridine-2-carboxamide A mixture of tert-butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate (200 mg, 0.418 mmol), 6-[2,6-difluoro-4-(1-hydroxy-1-methylethyl)phenyl]-5-fluoropyridine-2-carboxylic acid (130 mg, 0.418 mmol), HATU (318 mg, 0.836 mmol) in DMF (1.5 mL) and DIPEA (218 µL, 1.25 mmol) was stirred at room temperature for 2 h. After quenched with water, the mixture was extracted with EtOAc (2×). The combined organic phases were washed with brine, dried over $Na_2SO_4$, and concentrated. The residue was purified by purified by column chromatography on silica gel using CombiFlash® apparatus eluting with EtOAc/hexanes (50-100%), to yield an amide intermediate, tert-butyl ((3R,4R,5S)-4-{[tert-butyl(dimethyl)silyl]oxy}-1-{5-[({6-[2,6-difluoro-4-(1-hydroxy-1-methylethyl)phenyl]-5-fluoropyridin-2-yl}carbonyl)amino]-2,3-dihydrofuro[2,3-b]pyridin-4-yl}-5-methylpiperidin-3-yl)carbamate.

The amide intermediate prepared as described above was treated with 4.0 M HCl in dioxane (8 mL, 30 mmol) at room temperature overnight. The reaction mixture was concentrated under reduced pressure. The resulting residue was purified by preparative LCMS (Waters SunFire™ C18 column, 19 mm×100 mm, 5 µm particle size, eluting with a gradient of MeCN/water containing 0.1% $NH_4OH$, at flow rate of 30 mL/min.) to give the title compound as a white powder. LCMS calc. for $C_{28}H_{31}F_3N_5O_4$ (M+H)$^+$ m/z=558.2; found: 558.0. $^1$H NMR (300 MHz, DMSO-$d_6$) δ 10.17 (s, 1H), 8.69 (s, 1H), 8.32 (m, 1H), 8.16 (m, 1H), 7.32 (d, J=9.0 Hz, 2H), 5.27 (br s, 1H), 4.49 (m, 3H), 3.05 (m, 1H), 2.96 (m, 1H), 2.66-2.42 (m, 5H), 1.47 (s, 6H), 0.68 (d, J=6.6 Hz, 3H) ppm.

Example 66

N-{4-[(3R,4R,5S)-3-Amino-4-hydroxy-5-methylpiperidin-1-yl]-7-hydroxy-6,7-dihydro-5H-cyclopenta[b]pyridin-3-yl}-6-[2,6-difluoro-4-(methoxymethyl)phenyl]-5-fluoropyridine-2-carboxamide

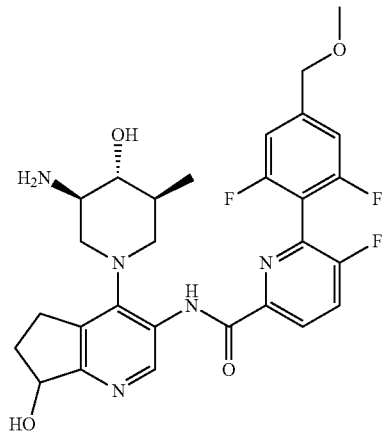 [SMILES: COCc1cc(F)c(-c2nc(C(=O)Nc3cnc4c(c3N3C[C@@H](N)[C@H](O)[C@@H](C)C3)CCC4O)ccc2F)c(F)c1]

A mixture of 3-amino-4-((3R,4R,5S)-3-[(tert-butoxycarbonyl)amino]-4-{[tert-butyl(dimethyl)silyl]oxy}-5-methylpiperidin-1-yl)-6,7-dihydro-5H-cyclopenta[b]pyridin-7-yl acetate (324 mg, 0.606 mmol), 6-[2,6-difluoro-4-(methoxymethyl)phenyl]-5-fluoropyridine-2-carboxylic acid (180 mg, 0.606 mmol) and HATU (0.460 g, 1.21 mmol) in DMF (3.0 mL) and DIPEA (0.316 mL, 1.82 mmol) was stirred at room temperature for 2 h. After quenching the reaction with water, the mixture was extracted with EtOAc (2 times). The combined organic extracts were washed with brine, dried over $Na_2SO_4$, and concentrated under reduced pressure. The residue was purified by purified by column chromatography on silica gel using CombiFlash® apparatus eluting with EtOAc/hexanes (50-100%) to give an amide intermediate, 4-((3R,4R,5S)-3-[(tert-butoxycarbonyl)amino]-4-{[tert-butyl(dimethyl)silyl]oxy}-5-methylpiperidin-1-yl)-3-[({6-[2,6-difluoro-4-(methoxymethyl)phenyl]-5-fluoropyridin-2-yl}carbonyl)amino]-6,7-dihydro-5H-cyclopenta[b]pyridin-7-yl acetate.

To the amide intermediate prepared as described above THF (5 mL), MeOH (5 mL) and 1.0 M aq. NaOH (5 mL, 5 mmol) were added. The mixture was stirred at room temperature for 20 min. The volatile organic solvents were removed under reduced pressure. The residue was extracted with EtOAc (2 times). The combined organic phases were then washed with brine, dried over $Na_2SO_4$, and concentrated under reduced pressure to give an alcohol intermediate, tert-butyl ((3R,4R,5S)-4-{[tert-butyl(dimethyl)silyl]oxy}-1-{3-[({6-[2,6-difluoro-4-(methoxymethyl)phenyl]-5-fluoropyridin-2-yl}carbonyl)amino]-7-hydroxy-6,7-dihydro-5H-cyclopenta[b]pyridin-4-yl}-5-methylpiperidin-3-yl)carbamate.

The alcohol intermediate prepared as described above was treated with 4.0 M HCl in dioxane (10 mL, 40 mmol) at room temperature overnight. The reaction mixture was concentrated under reduced pressure. The residue was purified by preparative LCMS (Waters SunFire™ C18 column, 19 mm×100 mm, 5 μm particle size, eluting with a gradient of MeCN/water containing 0.1% NH$_4$OH, at flow rate of 30 mL/min.) to afford two diastereoisomers of the title compound as white powders.

Diastereoisomer 1. First peak. Retention time: 1.452 min. LCMS calc. for $C_{28}H_{31}F_3N_5O_4$ (M+H)$^+$ m/z=558.2; found: 558.0. $^1$H NMR (400 MHz, DMSO-d$_6$) δ 10.53 (s, 1H), 9.32 (s, 1H), 8.35 (m, 1H), 8.19 (m, 1H), 7.20 (d, J=10.2 Hz, 2H), 5.29 (m, 1H), 4.82 (m, 1H), 4.52 (s, 2H), 4.49 (m, 1H), 3.35 (s, 3H), 3.04 (m, 1H), 2.92 (m, 1H), 2.84 (m, 2H), 2.71 (m, 1H), 2.60 (m, 1H), 2.57 (m, 1H), 2.43 (m, 1H), 2.29 (m, 1H), 1.78 (m, 1H), 1.45 (m, 2H), 0.68 (d, J=6.4 Hz, 3H) ppm.

Diastereoisomer 2. Second peak. Retention time: 1.563 min. LCMS calc. for $C_{28}H_{31}F_3N_5O_4$ (M+H)$^+$ m/z=558.2; found: 558.0. $^1$H NMR (400 MHz, DMSO-d$_6$) δ 10.54 (s, 1H), 9.33 (s, 1H), 8.35 (m, 1H), 8.19 (m, 1H), 7.19 (d, J=8.8 Hz, 2H), 5.28 (m, 1H), 4.80 (m, 1H), 4.52 (s, 2H), 4.49 (m, 1H), 3.35 (s, 3H), 3.04 (m, 1H), 2.93 (m, 1H), 2.84 (m, 2H), 2.70 (m, 1H), 2.60 (m, 1H), 2.56 (m, 1H), 2.43 (m, 1H), 2.26 (m, 1H), 1.79 (m, 1H), 1.44 (m, 2H), 0.69 (d, J=6.4 Hz, 3H) ppm.

The diastereoisomers correspond to the (7R) and (7S) diastereoisomers of the title compound.

Example 67

N-{4-[(3S,5R)-3-Amino-5-methylpiperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide

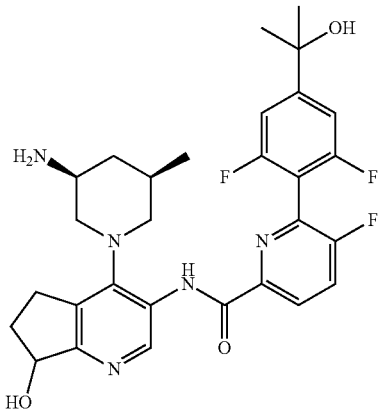 [SMILES: C[C@@H]1C[C@H](N)CN(c2c(NC(=O)c3ccc(F)c(-c4c(F)cc(C(C)(C)O)cc4F)n3)cnc3c2CCC3O)C1]

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (299 mg, 0.739 mmol), 6-[2,6-difluoro-4-(1-hydroxy-1-methylethyl)phenyl]-5-fluoropyridine-2-carboxylic acid (230 mg, 0.739 mmol) and HATU (562 mg, 1.48 mmol) in DMF (0.7 mL) and DIPEA (0.386 mL, 2.22 mmol) was stirred at room temperature for 2 h. The reaction mixture was quenched with water, the mixture was extracted with EtOAc (2 times). The combined organic phases were washed with brine, dried over Na$_2$SO$_4$ and concentrated under reduced pressure. The residue was purified by purified by column chromatography on silica gel using CombiFlash® apparatus eluting with EtOAc/hexanes (50-100%) to give an amide intermediate, 4-{(3S,5R)-3-[(tert-butoxycarbonyl)amino]-5-methylpiperidin-1-yl}-3-[({6-[2,6-difluoro-4-(1-hydroxy-1-methylethyl)phenyl]-5-fluoropyridin-2-yl}carbonyl)amino]-6,7-dihydro-5H-cyclopenta[b]pyridin-7-yl acetate.

The amide intermediate prepared as described above was treated with THF (6 mL), MeOH (6 mL) and 1.0 M aq. NaOH (7.39 mL, 7.39 mmol) at room temperature for 20 min. The volatile solvents were removed under reduced pressure. The residue was extracted with EtOAc (2 times). The combined organic phases were washed with brine, dried over Na$_2$SO$_4$, concentrated under reduced pressure to give an alcohol intermediate, tert-butyl ((3S,5R)-1-{3-[({6-[2,6-difluoro-4-(1-hydroxy-1-methylethyl)phenyl]-5-fluoropyridin-2-yl}carbonyl)amino]-7-hydroxy-6,7-dihydro-5H-cyclopenta[b]pyridin-4-yl}-5-methylpiperidin-3-yl)carbamate.

The alcohol intermediate prepared as described above was treated with TFA (6 mL) and DCM (6 mL). The solution was stirred at room temperature for 2 h, concentrated. The residue was purified by prep. LCMS (Waters SunFire™ C18 column, 19 mm×100 mm, 5 μm particle size, eluting with a gradient of MeCN/water containing 0.1% NH$_4$OH, at flow rate of 30 mL/min.) to provide two diastereoisomers as white powders.

Diastereoisomer 1. First peak. Retention time: 1.505 min. LCMS calc. for $C_{29}H_{33}F_3N_5O_3$ (M+H)$^+$ m/z=556.3; found: 556.0. $^1$H NMR (400 MHz, DMSO-d$_6$) δ 10.77 (s, 1H), 9.46 (s, 1H), 8.36 (m, 1H), 8.21 (m, 1H), 7.41 (d, J=10.2 Hz, 1H), 5.47 (m, 1H), 5.30 (m, 1H), 4.84 (m, 1H), 3.01 (m, 1H), 2.92 (m, 1H), 2.84 (m, 1H), 2.78 (m, 1H), 2.63 (m, 1H), 2.51 (m, 1H), 2.33 (m, 1H), 2.30 (m, 1H), 1.77 (m, 1H), 1.59 (m, 1H), 1.50 (s, 6H), 1.37 (m, 1H), 0.56 (d, J=6.4 Hz, 3H) ppm.

Diastereoisomer 2. Second peak. Retention time: 1.599 min. LCMS calc. for $C_{29}H_{33}F_3N_5O_3$ (M+H)$^+$ m/z=556.3; found: 556.0. $^1$H NMR (400 MHz, DMSO-d$_6$) δ 10.79 (s, 1H), 9.46 (s, 1H), 8.35 (m, 1H), 8.21 (m, 1H), 7.40 (d, J=8.8 Hz, 2H), 5.47 (m, 1H), 5.28 (m, 1H), 4.80 (m, 1H), 3.05 (m, 1H), 2.90 (m, 1H), 2.84 (m, 1H), 2.75 (m, 1H), 2.61 (m, 1H), 2.46 (m, 1H), 2.32 (m, 1H), 2.26 (m, 1H), 1.81 (m, 1H), 1.56 (m, 1H), 1.50 (s, 6H), 1.35 (m, 1H), 0.57 (d, J=6.4 Hz, 3H) ppm.

The diastereoisomers correspond to the (7R) and (7S) diastereoisomers of the title compound.

Example 68

N-{4-[(3R,4R,5S)-3-Amino-5-cyclopropyl-4-hydroxypiperidin-1-yl]-7-hydroxy-6,7-dihydro-5H-cyclopenta[b]pyridin-3-yl}-6-(2,6-difluorophenyl)-5-fluoropyridine-2-carboxamide

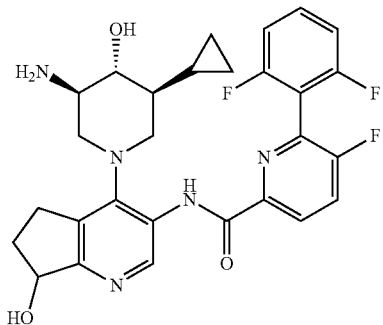 [SMILES: N[C@@H]1CN(c2c(NC(=O)c3ccc(F)c(-c4c(F)cccc4F)n3)cnc3c2CCC3O)C[C@H](C2CC2)[C@H]1O]

Step 1. tert-Butyl (4R)-4-{(1R,2R)-3-[(4R)-4-benzyl-2-oxo-1,3-oxazolidin-3-yl]-2-cyclopropyl-1-hydroxy-3-oxopropyl}-2,2-dimethyl-1,3-oxazolidine-3-carboxylate

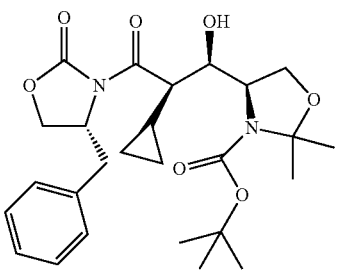 [SMILES: CC(C)(C)OC(=O)N1[C@@H]([C@H](O)[C@H](C(=O)N2C(=O)OC[C@H]2Cc2ccccc2)C2CC2)COC1(C)C]

To a −40° C. solution of (4R)-4-benzyl-3-(cyclopropylacetyl)-1,3-oxazolidin-2-one (2.0 g, 7.7 mmol) in anhydrous DCM (45 mL), a solution of 1.0 M titanium tetrachloride in DCM (9.3 mL) was added drop-wise under an atmosphere of nitrogen to form a yellow slurry. After 10 min., DIPEA (3.36 mL, 19.3 mmol) was added drop-wise, changing the color from yellow to deep purple. The reaction mixture was allowed to warm gradually to −20° C. while stirring over 1 h. The reaction mixture was again cooled to −40° C., and a solution of tert-butyl (4R)-4-formyl-2,2-dimethyl-1,3-oxazolidine-3-carboxylate (1.8 g, 7.85 mmol) (Aldrich) in anhydrous DCM (5 mL) was added drop-wise. The reaction mixture was allowed to warm gradually to 0° C. over 1 h and then allowed to stir for an additional 1.5 h at 0° C. The reaction was quenched by the addition of saturated NH$_4$Cl (aq.) (15 mL). After separation of the two layers that resulted, the organic layer was washed with water and brine, dried over Na$_2$SO$_4$, concentrated under reduced pressure and purified by flash chromatography (120 g silica gel, eluting with 0-60% EtOAc/hexanes) to afford the sub-title compound (1.9 g, 50%). LC/MS (ESI) m/z calc. for C$_{26}$H$_{36}$N$_2$O$_7$Na: 511.2 [M+Na]$^+$, found 511.1.

Step 2. tert-Butyl (4R)-4-((1R,2R)-3-[(4R)-4-benzyl-2-oxo-1,3-oxazolidin-3-yl]-1-{[tert-butyl(dimethyl)silyl]oxy}-2-cyclopropyl-3-oxopropyl)-2,2-dimethyl-1,3-oxazolidine-3-carboxylate

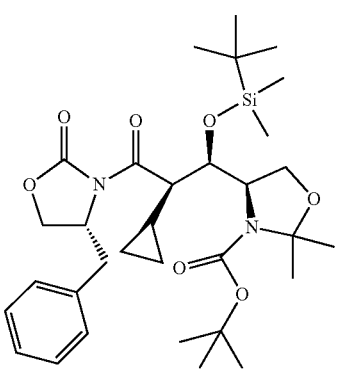 [SMILES: CC(C)(C)OC(=O)N1[C@@H]([C@H](O[Si](C)(C)C(C)(C)C)[C@H](C(=O)N2C(=O)OC[C@H]2Cc2ccccc2)C2CC2)COC1(C)C]

To a −40° C. solution of tert-butyl (4R)-4-{(1R,2R)-3-[(4R)-4-benzyl-2-oxo-1,3-oxazolidin-3-yl]-2-cyclopropyl-1-hydroxy-3-oxopropyl}-2,2-dimethyl-1,3-oxazolidine-3-carboxylate (1.80 g, 3.68 mmol) in anhydrous DCM (10 mL), 2,6-lutidine (0.85 mL, 7.3 mmol) was added under an atmosphere of nitrogen. After 10 min., a solution of tert-butyldimethylsilyl trifluoromethanesulfonate (1.1 mL, 4.9 mmol) in anhydrous DCM (1 mL) was added. The reaction mixture was allowed to warm gradually to ambient temperature while stirring overnight. The crude reaction mixture was diluted with 1,2-dichloroethane and cooled to 0° C. prior to quenching with saturated NaHCO$_3$ (aq.). Upon separation of the two layers that resulted, the organic layer was washed with water and brine, dried over Na$_2$SO$_4$, concentrated under reduced pressure and purified by flash chromatography (120 g silica gel, eluting with 0-30% EtOAc/hexanes) to afford the sub-title compound (2.1 g, 95%). LC/MS (ESI) m/z calc. for C$_{32}$H$_{50}$N$_2$O$_7$SiNa: 625.3 [M+Na]$^+$, found 625.1.

Step 3. tert-Butyl (4R)-4-((1R,2S)-1-{[tert-butyl(dimethyl)silyl]oxy}-2-cyclopropyl-3-hydroxypropyl)-2,2-dimethyl-1,3-oxazolidine-3-carboxylate

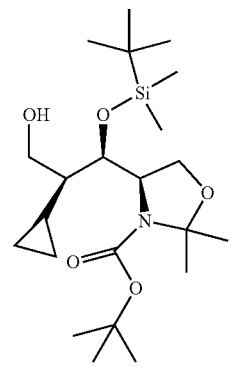 [SMILES: CC(C)(C)OC(=O)N1[C@@H]([C@H](O[Si](C)(C)C(C)(C)C)[C@H](CO)C2CC2)COC1(C)C]

A solution of tert-butyl (4R)-4-((1R,2R)-3-[(4R)-4-benzyl-2-oxo-1,3-oxazolidin-3-yl]-1-{[tert-butyl(dimethyl)silyl]oxy}-2-cyclopropyl-3-oxopropyl)-2,2-dimethyl-1,3-oxazolidine-3-carboxylate (3.3 g, 5.5 mmol) in anhydrous THF (50 mL) and EtOH (1 mL) was cooled to −30° C. prior to the addition of lithium tetrahydroborate (0.24 g, 11 mmol) under an atmosphere of nitrogen. The reaction mixture was allowed to gradually warm to ambient temperature while stirring for 20 h. The crude reaction mixture was diluted with diethyl ether (36 mL) and cooled to 0° C. prior to the addition of 1 M NaOH (aq.) (36 mL). Upon separation of the layers that resulted, the aqueous layer was extracted with EtOAc several times and the combined organic extracts were washed with brine, dried over Na$_2$SO$_4$, filtered, and concentrated under reduced pressure. The crude product was purified by flash column chromatography (120 g silica gel, eluting with 0-40% EtOAc/hexanes) to afford the sub-title compound (1.27 g, 54%). LC/MS (ESI) m/z calc. for C$_{22}$H$_{43}$NO$_5$SiNa: 452.3 [M+Na]$^+$, found 452.0.

Step 4. tert-Butyl (4R)-4-((1R,2S)-3-azido-1-{[tert-butyl(dimethyl)silyl]oxy}-2-cyclopropylpropyl)-2,2-dimethyl-1,3-oxazolidine-3-carboxylate

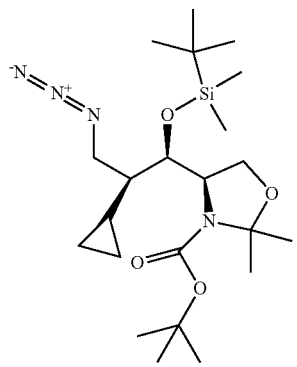

To a solution of tert-butyl (4R)-4-((1R,2S)-1-{[tert-butyl(dimethyl)silyl]oxy}-2-cyclopropyl-3-hydroxypropyl)-2,2-dimethyl-1,3-oxazolidine-3-carboxylate (1.3 g, 3.0 mmol) and triphenylphosphine (1.6 g, 6.1 mmol) in anhydrous THF (20 mL), DIAD (1.2 mL, 5.9 mmol) was added drop-wise under an atmosphere of nitrogen. Upon completion of addition, a precipitate was formed. The reaction mixture was stirred for 30 min. then diphenylphosphonic azide (1.3 mL, 6.2 mmol) in anhydrous THF (1.0 mL) was added. After stirring at ambient temperature for 3 h, the volatile organic solvents were removed under reduced pressure and the crude product was purified by flash column chromatography (120 g of silica gel, eluting with 0-15% EtOAc-hexanes) to afford the sub-title compound as a light yellow oil (1.18 g, 86%). LC/MS (ESI) m/z calc. for $C_{17}H_{35}N_4O_2Si$: 355.30 [M−Boc+H]$^+$, found: 355.1.

Step 5. tert-Butyl (2R,3R,4S)-5-azido-4-cyclopropyl-1,3-dihydroxypentan-2-ylcarbamate

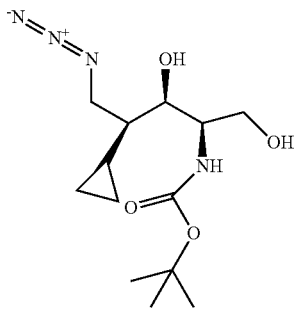

A solution of tert-butyl (4R)-4-((1R,2S)-3-azido-1-{[tert-butyl(dimethyl)silyl]oxy}-2-cyclopropylpropyl)-2,2-dimethyl-1,3-oxazolidine-3-carboxylate (1.16 g, 2.55 mmol) in MeOH (5 mL) was cooled on an ice bath, then TFA (4.9 mL, 64 mmol) was added. The reaction mixture was allowed to warm to ambient temperature and stirred for 30 min. The volatile organic solvents were removed under reduced pressure and the residue was azeotropically evaporated with toluene several times. The residue was then dissolved in anhydrous DCM (18 mL) and DIPEA (0.99 g, 7.6 mmol) and di-tert-butyl dicarbonate (0.84 g, 3.8 mmol) were added. The solution was stirred at ambient temperature for 4 h. The crude reaction mixture was concentrated under reduced pressure and the residue was purified by flash column chromatography (40 g silica gel, eluting with 0-100% EtOAc/DCM) to afford the desired product (0.33 g, 43%) and tert-butyl [(1R,2R,3S)-4-azido-2-{[tert-butyl(dimethyl)silyl]oxy}-3-cyclopropyl-1-(hydroxymethyl)butyl]carbamate (0.50 g, 50%). LCMS (ESI) calc. for $C_{13}H_{25}N_4O_4$ [M+H]$^+$ m/z=301.2, found: 301.2. For tert-butyl [(1R,2R,3S)-4-azido-2-{[tert-butyl(dimethyl)silyl]oxy}-3-cyclopropyl-1-(hydroxymethyl)butyl]carbamate: LCMS (ESI) calc. for $C_{19}H_{38}N_4O_4SiNa$ [M+Na]$^+$ m/z=437.3, found 437.0.

Step 6. (2R,3R,4S)-5-Azido-2-[(tert-butoxycarbonyl)amino]-4-cyclopropyl-3-hydroxypentyl 4-methylbenzenesulfonate

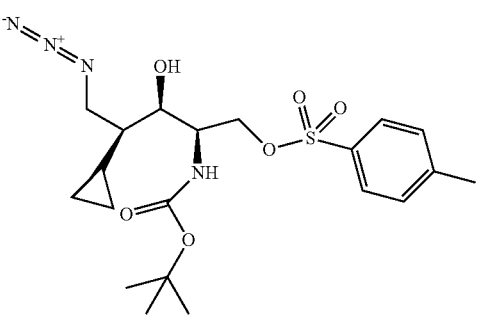

To a solution of tert-butyl [(1R,2R,3S)-4-azido-3-cyclopropyl-2-hydroxy-1-(hydroxymethyl)butyl]carbamate (0.435 g, 1.45 mmol) in anhydrous pyridine (5 mL) was added 4-dimethylaminopyridine (0.055 g, 0.20 mmol) and para-toluenesulfonyl chloride (0.55 g, 2.8 mmol). After stirring at ambient temperature for 2 h, the reaction mixture was diluted with EtOAc (40 mL) and H$_2$O (3 mL). The layers were separated, the organic layer was washed with H$_2$O (3×3 mL) and the combined aqueous phases were extracted with EtOAc (3 mL). The combined organic layers were washed with brine (3 mL), dried over Na$_2$SO$_4$, filtered, and concentrated under reduced pressure. The crude product was purified by flash column chromatography (40 g silica gel column, eluting with 0-30% EtOAc/hexanes) to afford the sub-title compound (506 mg, 77%). LCMS (ESI) calc. for $C_{15}H_{23}N_4O_4S$ [M+H−Boc+H]$^+$ m/z=355.2, found 355.1.

Step 7. tert-Butyl [(3R,4R,5S)-5-cyclopropyl-4-hydroxypiperidin-3-yl]carbamate

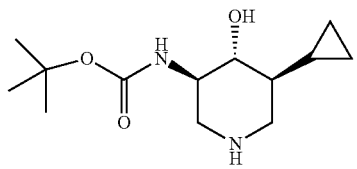 [SMILES: CC(C)(C)OC(=O)N[C@@H]1CNC[C@H](C2CC2)[C@H]1O]

A mixture of (2R,3R,4S)-5-azido-2-[(tert-butoxycarbonyl)amino]-4-cyclopropyl-3-hydroxypentyl 4-methylbenzenesulfonate (0.506 g, 1.11 mmol), DIPEA (0.31 mL, 1.8 mmol), and 10% palladium (dry basis) on activated carbon (wet, Degussa type E101 NE/W) (0.1 g) in MeOH (5 mL)

was stirred under an atmosphere of hydrogen introduced via a balloon. After 3 h, the crude reaction mixture was filtered through a pad of diatomaceous earth and the solids were washed thoroughly with MeOH. The volatile organic solvents were removed under reduced pressure and the residue was dried under high vacuum to afford the sub-title compound as a solid. The crude product was used directly in the subsequent displacement reaction without further purification. LCMS (ESI) m/z calc. for $C_{13}H_{25}N_2O_3$ 257.2 [M+H]$^+$, found 257.2.

Step 8. tert-Butyl [(3R,4R,5S)-5-cyclopropyl-4-hydroxy-1-(3-nitro-6,7-dihydro-5H-cyclopenta[b]pyridin-4-yl)piperidin-3-yl]carbamate

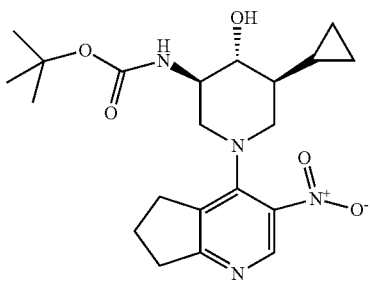 [SMILES: CC(C)(C)OC(=O)N[C@@H]1CN(c2c([N+](=O)[O-])cnc3c2CCC3)C[C@H](C2CC2)[C@H]1O]

A mixture of 4-chloro-3-nitro-6,7-dihydro-5H-cyclopenta[b]pyridine (0.094 g, 0.47 mmol), tert-butyl [(3R,4R,5S)-5-cyclopropyl-4-hydroxypiperidin-3-yl]carbamate (0.13 g, 0.51 mmol), and triethylamine (0.26 mL, 1.9 mmol) in isopropyl alcohol (2 mL) was heated at 90° C. for 2 days. The desired product partially precipitated from the reaction mixture and was collected by filtration, washed with hexanes and dried under reduced pressure to afford pure sub-title compound (0.080 g). The filtrate was concentrated under reduced pressure and purified by flash column chromatography (20 g silica gel column, eluting with 0-15% MeOH/DCM) to afford further sub-title compound (0.034 g, total 0.114 g, 58%). LCMS (ESI) m/z calc. for $C_{21}H_{31}N_4O_5$ 419.2 [M+H]$^+$, found 419.1.

Step 9. tert-Butyl[(3R,4R,5S)-5-cyclopropyl-4-hydroxy-1-(3-nitro-1-oxido-6,7-dihydro-5H-cyclopenta[b]pyridin-4-yl)piperidin-3-yl]carbamate

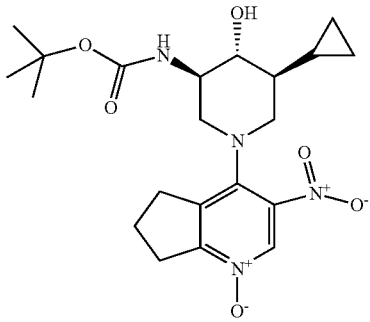 [SMILES: CC(C)(C)OC(=O)N[C@@H]1CN(c2c([N+](=O)[O-])c[n+]([O-])c3c2CCC3)C[C@H](C2CC2)[C@H]1O]

A solution of tert-butyl [(3R,4R,5S)-5-cyclopropyl-4-hydroxy-1-(3-nitro-6,7-dihydro-5H-cyclopenta[b]pyridin-4-yl)piperidin-3-yl]carbamate (0.113 g, 0.270 mmol) in anhydrous DCM (2.5 mL) was cooled to 0° C. and mCPBA (0.080 g, 0.33 mmol, 4×0.020 g) was added portion-wise. After 15 min., the reaction mixture was allowed to warm to ambient temperature and was stirred for 2 h. The reaction was quenched by the addition of a solution of $Na_2S_2O_3$ (0.051 g, 0.32 mmol) in water (1 mL) followed by 4 M aq. NaOH (1 mL). The layers were separated and the organic fraction was concentrated and purified by flash column chromatography (20 g silica gel column, eluting with 0-30% MeOH/EtOAc) to afford the sub-title compound (0.050 g, 43%). LCMS (ESI) m/z calc. for $C_{21}H_{31}N_4O_6$ 435.2 [M+H]$^+$, found 435.0.

Step 10. 4-{(3R,4R,5S)-4-(Acetyloxy)-3-[(tert-butoxycarbonyl)amino]-5-cyclopropylpiperidin-1-yl}-3-nitro-6,7-dihydro-5H-cyclopenta[b]pyridin-7-yl Acetate

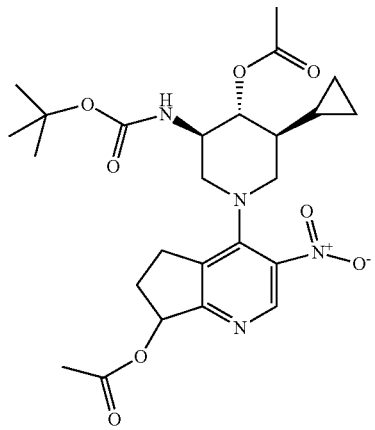 [SMILES: CC(=O)OC1CCc2c1ncc([N+](=O)[O-])c2N1C[C@H](C2CC2)[C@@H](OC(C)=O)[C@H](NC(=O)OC(C)(C)C)C1]

Ac$_2$O (1.30 mL, 13.8 mmol) was added to tert-butyl [(3R,4R,5S)-5-cyclopropyl-4-hydroxy-1-(3-nitro-1-oxido-6,7-dihydro-5H-cyclopenta[b]pyridin-4-yl)piperidin-3-yl]carbamate (0.050 g, 0.12 mmol) and the resulting solution was heated at 90° C. in a sealed vial for 16 h. The volatiles were removed under reduced pressure and the residue was dissolved in EtOAc and cooled to 0° C. and saturated aq.NaHCO$_3$ was added. After stirring for 15 min., the layers were separated and the organic fraction was washed with brine, dried over Na$_2$SO$_4$, filtered and concentrated under reduced pressure to afford the sub-title compound (0.055 g, 92%), which was used without further purification in the subsequent reaction. LCMS (ESI) m/z calc. for $C_{25}H_{35}N_4O_8$ 519.2 [M+H]$^+$, found 519.1.

Step 11. (3R,4R,5S)-1-[7-(Acetyloxy)-3-amino-6,7-dihydro-5H-cyclopenta[b]pyridin-4-yl]-3-[(tert-butoxycarbonyl)amino]-5-cyclopropylpiperidin-4-yl Acetate

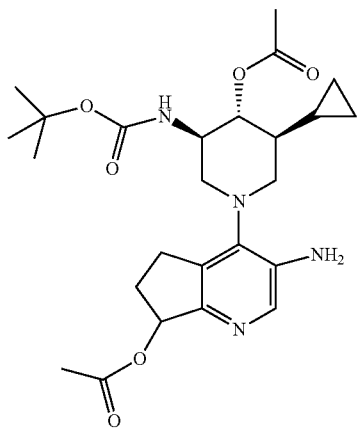 [SMILES: CC(=O)OC1CCc2c1ncc(N)c2N1C[C@H](C2CC2)[C@@H](OC(C)=O)[C@H](NC(=O)OC(C)(C)C)C1]

A solution of 4-{(3R,4R,5S)-4-(acetyloxy)-3-[(tert-butoxycarbonyl)amino]-5-cyclopropylpiperidin-1-yl}-3-nitro-6,7-dihydro-5H-cyclopenta[b]pyridin-7-yl acetate (0.055 g, 0.11 mmol) in MeOH (5.0 mL) and EtOAc (1.0 mL) was deoxygenated and purged with nitrogen prior to the addition of 10% palladium (dry basis) on activated carbon (wet, Degussa type E101 NE/W) (0.025 g). The reaction mixture was stirred under an atmosphere of hydrogen, introduced via a balloon, for 2 h. The crude reaction mixture was filtered through a pad of diatomaceous earth and the solids were washed thoroughly with EtOAc and MeOH. The filtrate was concentrated under reduced pressure to afford the sub-title compound (0.052 g, 100%). LCMS (ESI) m/z calc. for $C_{25}H_{37}N_4O_6$ 489.3 [M+H]$^+$, found 489.0.

Step 12. N-{4-[(3R,4R,5S)-3-Amino-5-cyclopropyl-4-hydroxypiperidin-1-yl]-7-hydroxy-6,7-dihydro-5H-cyclopenta[b]pyridin-3-yl}-6-(2,6-difluorophenyl)-5-fluoropyridine-2-carboxamide To a mixture of 6-(2,6-difluorophenyl)-5-fluoropyridine-2-carboxylic acid (0.028 g, 0.11 mmol), HATU (0.056 g, 0.15 mmol) and DIPEA (0.051 mL, 0.29 mmol) in 1,2-dichloroethane (0.4 mL) was added a solution of (3R,4R,5S)-1-[7-(acetyloxy)-3-amino-6,7-dihydro-5H-cyclopenta[b]pyridin-4-yl]-3-[(tert-butoxycarbonyl)amino]-5-cyclopropylpiperidin-4-yl acetate (0.050 g, 0.10 mmol) in 1,2-dichloroethane (0.5 mL). The reaction mixture was stirred at 45° C. for 1 h and then at ambient temperature overnight. The reaction mixture was diluted with EtOAc (40 mL) and H$_2$O (3 mL). The layers were separated and the organic layer was washed with H$_2$O (3×3 mL). The combined aqueous phases were extracted with EtOAc (3 mL). The combined organic extracts were washed with brine (3 mL), dried over Na$_2$SO$_4$, filtered and concentrated under reduced pressure. The crude product was dissolved in THF (1.3 mL) and MeOH (0.4 mL) and to this was added 1 M aq. NaOH (1 mL) and the resulting mixture was stirred for 2.5 h at ambient temperature. The reaction mixture was diluted with EtOAc (40 mL) and neutralized by the addition of 1 M aq. HCl to adjust the pH to ~7. The layers were separated, the organic layer was washed with H$_2$O (3×3 mL) and the combined aqueous phases were extracted with EtOAc (3 mL). The combined organic extracts were washed with brine (3 mL), dried over Na$_2$SO$_4$, filtered and concentrated under reduced pressure. The crude product was dissolved in 4 M HCl in 1,4-dioxane (2 mL) and stirred at ambient temperature for 30 min. The volatile organic solvents were removed under reduced pressure and the residue was re-dissolved in MeOH (5 mL) and neutralized by the addition of saturated NH$_4$OH. The crude reaction mixture was purified by mass triggered preparative-HPLC (Waters SunFire™ C18 column, 19 mm×100 mm, 5 μm particle size, eluting with a gradient of MeCN/water containing 0.1% NH$_4$OH, at flow rate of 30 mL/min.) to afford the two 7-hydroxyl diastereoisomers of the title compound as two peaks.

Diastereoisomer 1. First peak (12.4 mg). Retention time 1.09 min., LCMS (ESI) m/z calc. for $C_{28}H_{29}F_3N_5O_3$ 540.2 [M+H]$^+$, found 540.0.

Diastereoisomer 2. Second peak (10.4 mg) Retention time 1.16 min, LCMS (ESI) m/z calc. for $C_{28}H_{29}F_3N_5O_3$ 540.2 [M+H]$^+$, found 540.0.

The diastereoisomers correspond to the (7R) and (7S) diastereoisomers of the title compound.

Example 69

N-{4-[(3R,4R,5S)-3-amino-4-hydroxy-5-methylpiperidin-1-yl]-2,3-dihydrofuro[2,3-b]pyridin-5-yl}-6-[2,6-difluoro-4-(tetrahydro-2H-pyran-3-yloxy)phenyl]-5-fluoropyridine-2-carboxamide

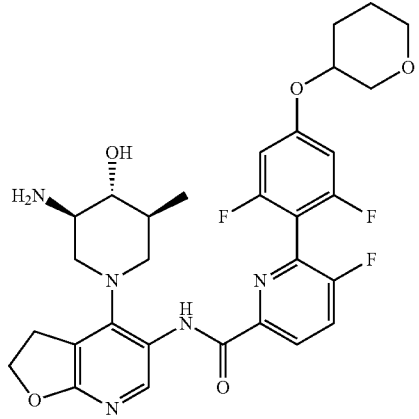 [SMILES: C[C@H]1CN(c2c(NC(=O)c3ccc(F)c(-c4c(F)cc(OC5CCCOC5)cc4F)n3)cnc3c2CCO3)C[C@@H](N)[C@@H]1O]

Step 1.
3-(3,5-Difluorophenoxy)tetrahydro-2H-pyran

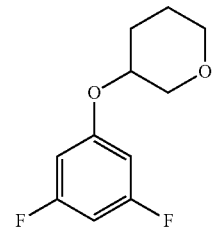

A solution of 3,5-difluorophenol (1.15 g, 8.81 mmol), tetrahydro-2H-pyran-3-ol (0.900 g, 8.81 mmol), triphenylphosphine (2.31 g, 8.81 mmol) and DIAD (1.74 mL, 8.81 mmol) in THF (10 mL) was stirred overnight. The solution was then concentrated under reduced pressure and the residue was purified by purified by column chromatography on silica gel using CombiFlash® apparatus eluting with EtOAc/hexanes (0-30%). The purification afforded 1.43 g (75.8%) of the sub-title compound as a colorless oil.

Step 2.3-[3,5-Difluoro-4-(4,4,5,5-tetramethyl-1,3,2-dioxaborolan-2-yl)phenoxy]tetrahydro-2H-pyran

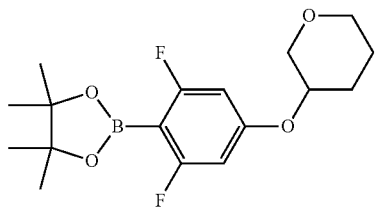 [SMILES: CC1(C)OB(c2c(F)cc(OC3CCCOC3)cc2F)OC1(C)C]

To a mixture of 3-(3,5-difluorophenoxy)tetrahydro-2H-pyran (1.42 g, 6.63 mmol) in THF (26 mL) at −78° C., a solution of n-BuLi in hexanes (1.6 M; 10.4 mL, 16.6 mmol) was added slowly through a dripping funnel. When addition was complete, the mixture was kept at −78° C. for 1 h. 2-Isopropoxy-4,4,5,5-tetramethyl-1,3,2-dioxaborolane (4.06 mL, 19.9 mmol) was then added in one portion. The mixture was allowed to warm to room temperature and stirred for 1 h. The mixture was quenched with NaHCO$_3$ solution and extracted with EtOAc. The organic extract was washed with brine, dried over Na$_2$SO$_4$, and concentrated under reduced pressure to give sub-title compound as a colorless oil. LCMS calc. for $C_{17}H_{24}BF_2O_4$ (M+H)$^+$ m/z=341.2; found: 341.1.

Step 3. 6-[2,6-Difluoro-4-(tetrahydro-2H-pyran-3-yloxy)phenyl]-5-fluoropyridine-2-carboxylic Acid

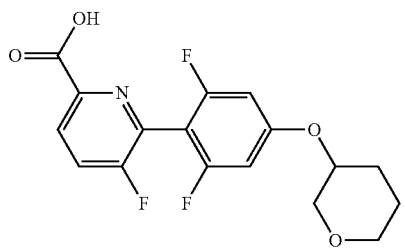 [SMILES: O=C(O)c1ccc(F)c(-c2c(F)cc(OC3CCCOC3)cc2F)n1]

A mixture of 3-[3,5-difluoro-4-(4,4,5,5-tetramethyl-1,3,2-dioxaborolan-2-yl)phenoxy]tetrahydro-2H-pyran (0.436 g, 1.28 mmol), methyl 6-bromo-5-fluoropyridine-2-carboxylate (0.300 g, 1.28 mmol) and DIPEA (0.67 mL, 3.8 mmol) in 1,4-dioxane (6 mL) and water (0.3 mL) was purged with nitrogen and then bis(tri-tert-butylphosphine)palladium (65.5 mg, 0.128 mmol) was added. The reaction mixture was sealed and heated at 120° C. for 40 min., then cooled and filtered through a pad of diatomaceous earth. The filtrate was concentrated under reduced pressure and the resulting residue was purified by silica gel column chromatography (0-50% EtOAc in hexanes) to give methyl 6-[2,6-difluoro-4-(tetrahydro-2H-pyran-3-yloxy)phenyl]-5-fluoropyridine-2-carboxylate.

The methyl 6-[2,6-difluoro-4-(tetrahydro-2H-pyran-3-yloxy)phenyl]-5-fluoropyridine-2-carboxylate was treated with THF (2 mL), MeOH (2 mL) and 1.0 M aq. NaOH (2 mL, 2 mmol) at room temperature for 1 h. The volatile organic solvents were removed and the residue was neutralized to pH-5-6 with 1 M HCl. The solid that precipitated was filtered, rinsed with water, and dried to give sub-title compound as a white solid. LCMS calc. for $C_{17}H_{15}F_3NO_4$ (M+H)$^+$ m/z=354.1; found: 353.9.

Step 4. N-{4-[(3R,4R,5S)-3-amino-4-hydroxy-5-methylpiperidin-1-yl]-2,3-dihydrofuro[2,3-b]pyridin-5-yl}-6-[2,6-difluoro-4-(tetrahydro-2H-pyran-3-yloxy)phenyl]-5-fluoropyridine-2-carboxamide A mixture of tert-butyl((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate (20 mg, 0.042 mmol), 6-[2,6-difluoro-4-(tetrahydro-2H-pyran-3-yloxy)phenyl]-5-fluoropyridine-2-carboxylic acid (18 mg, 0.050 mmol) and HATU (32 mg, 0.084 mmol) in DMF (0.10 mL) and DIPEA (22 µL, 0.13 mmol) was stirred at room temperature for 2 h. The reaction was quenched with water and the mixture was extracted with EtOAc (2×). The combined organic extracts were washed with brine, dried over Na$_2$SO$_4$, and concentrated under reduced pressure. The residue was purified by purified by column chromatography on silica gel using CombiFlash® apparatus eluting with EtOAc/hexanes (50-100%) to yield the amide intermediate, tert-butyl ((3R,4R,5S)-4-{[tert-butyl(dimethyl)silyl]oxy}-1-{5-[({6-[2,6-difluoro-4-(tetrahydro-2H-pyran-3-yloxy)phenyl]-5-fluoropyridin-2-yl}carbonyl)amino]-2,3-dihydrofuro[2,3-b]pyridin-4-yl}-5-methylpiperidin-3-yl)carbamate.

The amide intermediate prepared as described above was treated with 4.0 M HCl in dioxane (1 mL, 4 mmol) at room temperature overnight. The solution was then concentrated and the residue was purified by preparative LCMS (Waters SunFire™ C18 column, 19 mm×100 mm, 5 µm particle size, eluting with a gradient of MeCN/water containing 0.1% NH$_4$OH, at flow rate of 30 mL/min.) to afford a mixture of diastereoisomers of the title compound (S) and (R) configuration of the tetrahydropyran) as a white powder. LCMS calc. for $C_{30}H_{33}F_3N_5O_5$ (M+H)$^+$ m/z=600.2; found: 600.2. $^1$H NMR (300 MHz, DMSO-d$_6$) δ 10.15 (s, 1H), 8.70 (m, 1H), 8.24 (dd, J=8.7 and 4.2 Hz, 1H), 8.09 (dd, J=8.7 and 8.7 Hz, 1H), 6.87 (d, J=10.2 Hz, 2H), 4.46 (m, 4H), 3.78 (m, 1H), 3.52 (m, 3H), 3.31 (m, 1H), 3.16 (m, 1H), 3.00 (m, 1H), 2.90 (m, 1H), 2.52 (m, 2H), 1.99 (m, 1H), 1.72 (m, 2H), 1.43 (m, 3H), 0.65 (2 d, 3H) ppm.

Example 70

N-{4-[(3S,5R)-3-Amino-5-methylpiperidin-1-yl]-7-hydroxy-6,7-dihydro-5H-cyclopenta[b]pyridin-3-yl}-6-[2,6-difluoro-4-(tetrahydro-2H-pyran-3-yloxy)phenyl]-5-fluoropyridine-2-carboxamide

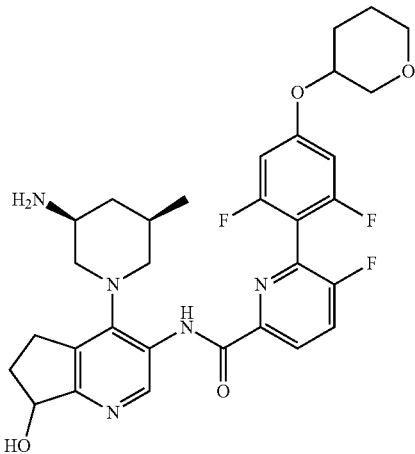 [SMILES: C[C@@H]1C[C@H](N)CN(c2c(NC(=O)c3ccc(F)c(-c4c(F)cc(OC5CCCOC5)cc4F)n3)cnc3c2CCC3O)C1]

A mixture of 3-amino-4-{(3S,5R)-3-[(tert-butoxycarbonyl)amino]-5-methylpiperidin-1-yl}-6,7-dihydro-5H-cyclopenta[b]pyridin-7-yl acetate (30 mg, 0.074 mmol), 6-[2,6-difluoro-4-(tetrahydro-2H-pyran-3-yloxy)phenyl]-5-fluoropyridine-2-carboxylic acid (26 mg, 0.074 mmol) and HATU (56 mg, 0.15 mmol) in DMF (0.3 mL) and DIPEA (39 µL, 0.22 mmol) was stirred at room temperature for 2 h. The reaction mixture was quenched with water and the resulting mixture was extracted with EtOAc (2 times). The combined organic phases were washed with brine, dried over Na$_2$SO$_4$ and concentrated under reduced pressure. The residue was purified by purified by column chromatography on silica gel using CombiFlash® apparatus eluting with EtOAc/hexanes (50-100%) to afford an amide intermediate, 4-{(3S,5R)-3-[(tert-butoxycarbonyl)amino]-5-methylpiperidin-1-yl}-3-[({6-[2,6-difluoro-4-(tetrahydro-2H-pyran-3-yloxy)phenyl]-5-fluoropyridin-2-yl}carbonyl)amino]-6,7-dihydro-5H-cyclopenta[b]pyridin-7-yl acetate.

The amide intermediate was treated with THF (0.7 mL), MeOH (0.7 mL) and 1.0 M aq. NaOH (0.74 mL, 0.74 mmol) at room temperature for 20 min. The volatile organic solvents were removed. The residue was extracted with EtOAc (2 times). The combined organic extracts were washed with brine, dried over Na$_2$SO$_4$, and concentrated to give an alcohol intermediate, tert-butyl ((3S,5R)-1-{3-[({6-[2,6-difluoro-4-(tetrahydro-2H-pyran-3-yloxy)phenyl]-5-fluoropyridin-2-yl}carbonyl)amino]-7-hydroxy-6,7-dihydro-5H-cyclopenta[b]pyridin-4-yl}-5-methylpiperidin-3-yl)carbamate.

The alcohol intermediate made above was treated with 4.0 M HCl in dioxane (1 mL, mmol) at room temperature overnight. The solution was concentrated under reduced pressure and the resulting residue was purified by preparative LCMS (Waters SunFire™ C18 column, 19 mm×100 mm, 5 µm particle size, eluting with a gradient of MeCN/water containing 0.1% NH$_4$OH, at flow rate of 30 m/min.) to give two separated diastereoisomers of the title compound as white powders.

Diastereoisomer 1. First peak. Retention time: 1.204 min. LCMS calc. for $C_{31}H_{35}F_3N_5O_4$ (M+H)$^+$ m/z=598.3; found: 598.0.

Diastereoisomer 2. Second peak. Retention time: 1.283 min. LCMS calc. for $C_{31}H_{35}F_3N_5O_4$ (M+H)$^+$ m/z=598.3; found: 598.0.

The diastereoisomers are tentatively assigned as the separated (7R) and (7S) diastereoisomers of the title compound, each being a mixture of diastereoisomers having (R) and (S) configuration of tetrahydropyran ring.

Example 71

3-Amino-N-{4-[(3R,4R,5S)-3-amino-4-hydroxy-5-methylpiperidin-1-yl]-2,3-dihydrofuro[2,3-b]pyridin-5-yl}-6-(2,6-difluorophenyl)-5-fluoropyridine-2-carboxamide

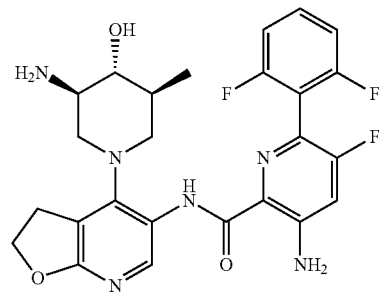 [SMILES: C[C@H]1CN(c2c(NC(=O)c3nc(-c4c(F)cccc4F)c(F)cc3N)cnc3c2CCO3)C[C@@H](N)[C@@H]1O]

A mixture of tert-butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate (62 mg, 0.13 mmol), 3-[(tert-butoxycarbonyl)amino]-6-(2,6-difluorophenyl)-5-fluoropyridine-2-carboxylic acid (48 mg, 0.13 mmol) and HATU (99 mg, 0.26 mmol) in DMF (0.20 mL, 2.6 mmol) and DIPEA (68 µL, 0.39 mmol) was stirred at room temperature for 2 h. The reaction was quenched with water, and the mixture was extracted with EtOAc (2 times). The combined organic phases were washed with brine, dried over Na$_2$SO$_4$, and concentrated under reduced pressure. The residue was purified by purified by column chromatography on silica gel using CombiFlash® apparatus eluting with EtOAc/hexanes (50-100%) to generate an amide intermediate, tert-butyl [2-({[4-((3R,4R,5S)-3-[(tert-butoxycarbonyl)amino]-4-{[tert-butyl(dimethyl)silyl]oxy}-5-methylpiperidin-1-yl)-2,3-dihydrofuro[2,3-b]pyridin-5-yl]amino}carbonyl)-6-(2,6-difluorophenyl)-5-fluoropyridin-3-yl]carbamate.

The amide intermediate prepared as described above was treated with 4.0 M HCl in dioxane (2 mL, 8 mmol) at room temperature overnight. The solution was concentrated under reduced pressure, and the residue was purified by preparative LCMS (Waters SunFire™ C18 column, 19 mm×100 mm, 5 µm particle size, eluting with a gradient of MeCN/water containing 0.1% NH$_4$OH, at flow rate of 30 mL/min.) to afford the desired product as a white powder. LCMS calc. for $C_{25}H_{26}F_3N_6O_3$ (M+H)$^+$ m/z=515.2; found: 515.0. $^1$H NMR (400 MHz, DMSO-d$_6$) δ 9.98 (s, 1H), 8.67 (s, 1H), 7.52 (m, 1H), 7.39 (br s, 2H), 7.20 (s, 2H), 7.18 (m, 2H), 4.46 (m, 2H), 4.41 (m, 1H), 3.02 (m, 1H), 2.90 (m, 1H), 2.59 (m, 1H), 2.52 (m, 1H), 2.37 (m, 1H), 1.47 (m, 2H), 1.35 (m, 1H), 0.68 (d, J=6.8 Hz, 3H) ppm.

Example 72

N-{4-[(3S,5R)-3-Amino-5-(trifluoromethyl)piperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide

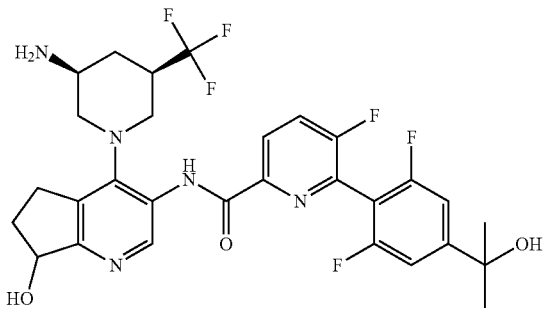 [SMILES: CC(C)(O)c1cc(F)c(-c2nc(C(=O)Nc3cnc4c(c3N3C[C@@H](N)C[C@@H](C(F)(F)F)C3)CCC4O)ccc2F)c(F)c1]

Step 1. tert-Butyl [1-(3-nitro-6,7-dihydro-5H-cyclopenta[b]pyridin-4-yl)-5-(trifluoromethyl)piperidin-3-yl]carbamate

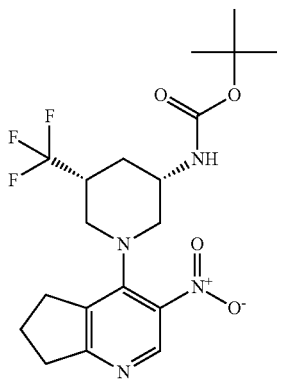 [SMILES: CC(C)(C)OC(=O)N[C@H]1C[C@@H](C(F)(F)F)CN(c2c([N+](=O)[O-])cnc3c2CCC3)C1]

A mixture of 4-chloro-3-nitro-6,7-dihydro-5H-cyclopenta[b]pyridine (0.34 g, 1.7 mmol), cis-tert-butyl [5-(trifluoromethyl)piperidin-3-yl]carbamate (0.50 g, 1.9 mmol) in isopropyl alcohol (1.0 g) and DIPEA (1.0 mL, 5.7 mmol) was stirred at 110° C. for 2 h. The solution was allowed to cool to room temperature, then the mixture was concentrated under reduced pressure. The residue was purified by purified by column chromatography on silica gel using Combi-Flash® apparatus (40 g column, eluting with 0 to 70% EtOAc in hexanes) to give the sub-title compound as a pale yellow powder (0.37 g, 50%). LCMS calc. for $C_{19}H_{26}F_3N_4O_4$ $(M+H)^+$ m/z=431.2; found: 431.0. The material was subjected to chiral HPLC (Phenomenex Lux® Cellulose 4 column, 21.2×250 mm, 5 micron particle size; Mobile phase: 7% EtOH in hexanes; Flow rate: 18 mL/min. isocratic; Column loading: 10 mg/injection; Run time: 24 minutes) to give two separated enantiomers of the sub-title compound.

Enantiomer 1. First peak. Retention time 16.2 min.
Enantiomer 2. Second peak. Retention time 19.1 min.
Enantiomer 1 is tentatively assigned as tert-butyl [(3R,5S)-1-(3-nitro-6,7-dihydro-5H-cyclopenta[b]pyridin-4-yl)-5-(trifluoromethyl)piperidin-3-yl]carbamate and enantiomer 2 is tentatively assigned as the tert-butyl [(3S,5R)-1-(3-nitro-6,7-dihydro-5H-cyclopenta[b]pyridin-4-yl)-5-(trifluoromethyl)piperidin-3-yl]carbamate.

Step 2. tert-Butyl [(3S,5R)-1-(3-nitro-1-oxido-6,7-dihydro-5H-cyclopenta[b]pyridin-4-yl)-5-(trifluoromethyl)piperidin-3-yl]carbamate

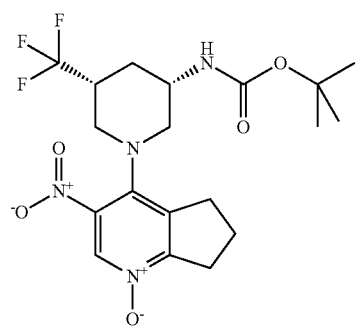

mCPBA (0.16 g, 0.93 mmol) was added to a solution of tert-butyl [(3S,5R)-1-(3-nitro-6,7-dihydro-5H-cyclopenta[b]pyridin-4-yl)-5-(trifluoromethyl)piperidin-3-yl]carbamate (0.16 g, 0.37 mmol) (second peak, pure product resolved on chiral HPLC from previous step) in DCM (2.0 mL) at room temperature. The reaction mixture was stirred at room temperature for 2 h. The mixture was treated with aq. $Na_2S_2O_3$, then 1 M NaOH, and extracted with EtOAc. The combined organic layers were concentrated under reduced pressure. The residue was purified by column chromatography on silica gel using CombiFlash® apparatus (20 g column) eluting with 0-100% EtOAc in hexanes followed by MeOH/EtOAc (0-30%) to give 0.10 g (60%) of the sub-title compound as a reddish solid. 0.033 g of unreacted starting material was recovered. LCMS calc. for $C_{19}H_{26}F_3N_4O_5$ $(M+H)+$ m/z=447.2; found: 446.9.

Step 3. 4-[(3S,5R)-3-[(tert-Butoxycarbonyl)amino]-5-(trifluoromethyl)piperidin-1-yl]-3-nitro-6,7-dihydro-5H-cyclopenta[b]pyridin-7-yl Acetate

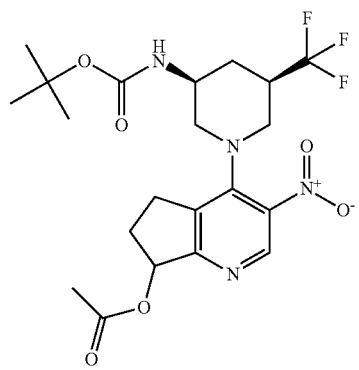 [SMILES: CC(=O)OC1CCc2c1ncc([N+](=O)[O-])c2N1C[C@@H](NC(=O)OC(C)(C)C)C[C@@H](C(F)(F)F)C1]

A mixture of tert-butyl [(3S,5R)-1-(3-nitro-1-oxido-6,7-dihydro-5H-cyclopenta[b]pyridin-4-yl)-5-(trifluoromethyl)piperidin-3-yl]carbamate (0.100 g, 0.224 mmol) in $Ac_2O$ (1.5 mL, 16 mmol) was stirred at 90° C. for 1 h. The solution was allowed to cool to room temperature, then concentrated under reduced pressure at 60° C. The residue was diluted with EtOAc (5 mL), washed quickly with 1N NaOH. The aqueous phase was extracted with EtOAc twice. The combined organic phases were condensed and columned on 20 g silica gel, eluting with 0-50% EtOAc in hexanes to give the sub-title compound as a brown solid (0.085 g, 78%). LCMS calc. for $C_{21}H_{28}F_3N_4O_6$ (M+H)+ m/z=489.2; found: 489.0.

Step 4. 4-[(3S,5R)-3-[(tert-Butoxycarbonyl)amino]-5-(trifluoromethyl)piperidin-1-yl]-3-[({6-[2,6-difluoro-4-(1-hydroxy-1-methylethyl)phenyl]-5-fluoropyridin-2-yl}carbonyl)amino]-6,7-dihydro-5H-cyclopenta[b]pyridin-7-yl Acetate

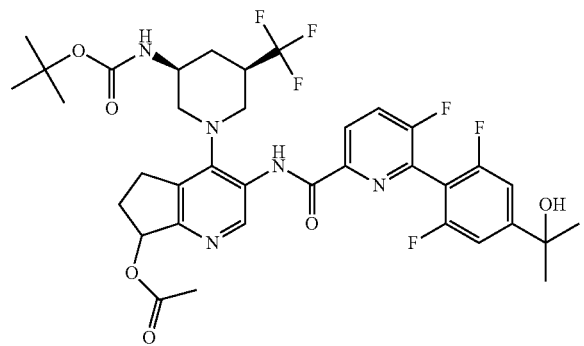 [SMILES: CC(=O)OC1CCc2c1ncc(NC(=O)c1ccc(F)c(-c3c(F)cc(C(C)(C)O)cc3F)n1)c2N1C[C@@H](NC(=O)OC(C)(C)C)C[C@@H](C(F)(F)F)C1]

A mixture of 3-amino-4-[(3S,5R)-3-[(tert-butoxycarbonyl)amino]-5-(trifluoromethyl)piperidin-1-yl]-6,7-dihydro-5H-cyclopenta[b]pyridin-7-yl acetate (0.010 g, 0.022 mmol), 6-[2,6-difluoro-4-(1-hydroxy-1-methylethyl)phenyl]-5-fluoropyridine-2-carboxylic acid (0.0082 g, 0.026 mmol), HATU (0.022 g, 0.057 mmol) in DMF (0.06 mL) and DIPEA (0.011 mL, 0.065 mmol) was stirred at room temperature for 1 h. The mixture was quenched with 1N NaOH solution and extracted with EtOAc. The organics were combined, dried over $Na_2SO_4$ and concentrated to give the sub-title compound as a brown solid. LCMS calc. for $C_{36}H_{40}F_6N_5O_6$ (M+H)+ m/z=752.3; found: 752.0.

Step 5. N-{4-[(3S,5R)-3-Amino-5-(trifluoromethyl) piperidin-1-yl]-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide

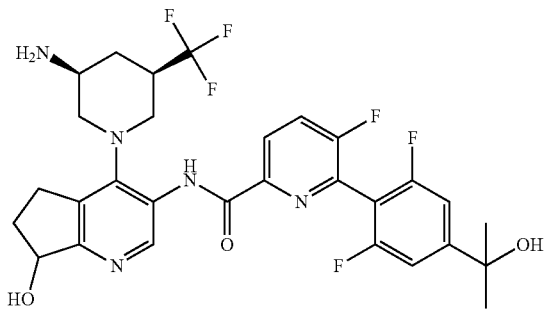 [SMILES: CC(C)(O)c1cc(F)c(-c2nc(C(=O)Nc3cnc4c(c3N3C[C@@H](N)C[C@@H](C(F)(F)F)C3)CCC4O)ccc2F)c(F)c1]

A mixture of 4-[(3S,5R)-3-[(tert-butoxycarbonyl)amino]-5-(trifluoromethyl)piperidin-1-yl]-3-[({6-[2,6-difluoro-4-(1-hydroxy-1-methylethyl)phenyl]-5-fluoropyridin-2-yl}carbonyl)amino]-6,7-dihydro-5H-cyclopenta[b]pyridin-7-yl acetate (0.015 g, 0.020 mmol) in MeOH (0.8 mL), THF (0.8 mL) and 1.0 M aq. NaOH (0.8 mL, 0.8 mmol) was stirred at room temperature for 0.5 h. The solution was then concentrated under reduced pressure and the remaining aqueous phase was extracted with EtOAc. The organic extract was concentrated to dryness under reduced pressure. The residue was treated with 4.0 M HCl in dioxane (0.20 mL, 0.80 mmol) for 20 min. The reaction mixture was then concentrated under reduced pressure. The residue was dissolved in 4.5 mL of MeOH, neutralized with $NH_4OH$ solution, and purified by preparative LCMS (Waters SunFire™ C18 column, 19 mm×100 mm, 5 μm particle size, eluting with a gradient of MeCN/water containing 0.1% $NH_4OH$, at flow rate of 30 mL/min.) to afford two separated diastereoisomers of the title compound as white powders.

Diastereoisomer 1. First peak. Retention time 1.24 min., LCMS calc. for $C_{29}H_3F_6N_5O_3$ (M+H)+ m/z=610.2; found: 610.0.

Diastereoisomer 2. Second peak. Retention time 1.32 min., LCMS calc. for $C_{29}H_3F_6N_5O_3$ (M+H)+ m/z=610.2; found: 610.0.

The diastereoisomers correspond to the (7R) and (7S) diastereoisomers of the title compound, N-{4-[(3S,5R)-3-amino-5-(trifluoromethyl)piperidin-1-yl]-(7R)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide and N-{4-[(3S,5R)-3-amino-5-(trifluoromethyl)piperidin-1-yl]-(7S)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide. The alternative enantiomers, N-{4-[(3R,5S)-3-amino-5-(trifluoromethyl)piperidin-1-yl]-(7R)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide and N-{4-[(3R,5S)-3-amino-5-(trifluoromethyl)piperidin-1-yl]-(7S)-7-hydroxy-6,7-dihydro-5H-cyclopenta[b]pyridin-3-yl}-6-[2,6-difluoro-4-(1-hydroxy-1-methylethyl)phenyl]-5-fluoropyridine-2-carboxamide, are prepared by an analogous route starting from using tert-butyl [(3R,5S)-1-(3-nitro-6,7-dihydro-5H-cyclopenta[b]pyridin-4-yl)-5-(trifluoromethyl)piperidin-3-yl]carbamate (Enantiomer 1) from step 1.

Example 73

N-{4-[(3S,5R)-3-Amino-5-methylpiperidin-1-yl]-2,3-dihydrofuro[2,3-b]pyridin-5-yl}-6-(2,6-difluoro-3-methoxyphenyl)-5-fluoropyridine-2-carboxamide

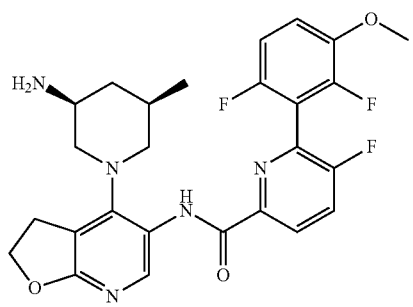 [SMILES: COc1ccc(F)c(-c2nc(C(=O)Nc3cnc4c(c3N3C[C@H](C)C[C@H](N)C3)CCO4)ccc2F)c1F]

To a mixture of 6-(2,6-difluoro-3-methoxyphenyl)-5-fluoropyridine-2-carboxylic acid (232 mg, 0.492 mmol), tert-butyl [(3S,5R)-1-(5-amino-2,3-dihydrofuro[2,3-b]pyridin-4-yl)-5-methylpiperidin-3-yl]carbamate (152 mg, 0.436 mmol), and HATU (513 mg, 1.35 mmol) in DMF (3.0 mL), DIPEA (298 mg, 2.30 mmol) was added. The reaction mixture was stirred at room temperature for 2 h, and then concentrated under reduced pressure. To the resulting residue, DCM (2.0 mL) was added followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (65.9 mg, 29%). LCMS calc. for C$_{26}$H$_{27}$F$_3$N$_5$O$_3$ (M+H)$^+$: m/z=514.2; found 514.0. $^1$H NMR (500 MHz, DMSO-d$_6$) δ 10.42 (s, 1H), 8.90 (s, 1H), 8.34 (dd, J=8.7, 4.0 Hz, 1H), 8.20 (t, J=8.8 Hz, 1H), 7.50-7.41 (m, 1H), 7.33-7.26 (m, 1H), 4.55-4.43 (m, 2H), 3.93 (s, 3H), 3.35 (t, J=8.5 Hz, 2H), 3.05-2.95 (m, 1H), 2.90-2.82 (m, 1H), 2.64-2.54 (m, 1H), 2.39 (t, J=10.4 Hz, 1H), 2.26 (t, J=11.2 Hz, 1H), 1.64-1.51 (m, 1H), 1.41-1.17 (m, 3H), 0.64-0.55 (m, 4H) ppm.

Example 74

N-{4-[(3R,4R,5S)-3-Amino-4-hydroxy-5-methylpiperidin-1-yl]-2,3-dihydrofuro[2,3-b]pyridin-5-yl}-6-(2,6-difluoro-3-methoxyphenyl)-5-fluoropyridine-2-carboxamide

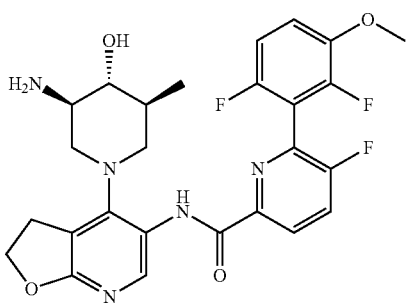 [SMILES: COc1ccc(F)c(-c2nc(C(=O)Nc3cnc4c(c3N3C[C@@H](N)[C@H](O)[C@@H](C)C3)CCO4)ccc2F)c1F]

To a mixture of 6-(2,6-difluoro-3-methoxyphenyl)-5-fluoropyridine-2-carboxylic acid (176 mg, 0.372 mmol), tert-butyl ((3R,4R,5S)-1-(5-amino-2,3-dihydrofuro[2,3-b]pyridin-4-yl)-4-{[tert-butyl(dimethyl)silyl]oxy}-5-methylpiperidin-3-yl)carbamate (152 mg, 0.317 mmol), and HATU (374 mg, 0.983 mmol) in DMF (3.0 mL) DIPEA (238 mg, 1.84 mmol) was added. The reaction mixture was stirred at room temperature for 2 h, and then concentrated under reduced pressure. To the resulting residue, DCM (2.0 mL) was added followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH$_4$OH, at flow rate of 30 mL/min.) to afford the title compound as a white solid (54 mg, 32%). LCMS calc. for C$_{26}$H$_{27}$F$_3$N$_5$O$_4$ (M+H)$^+$: m/z=530.2; found 530.0. $^1$H NMR (500 MHz, DMSO-d$_6$) δ 10.18 (s, 1H), 8.70 (s, 1H), 8.34 (dd, J=8.7, 4.0 Hz, 1H), 8.18 (t, J=8.8 Hz, 1H), 7.39-7.32 (m, 1H), 7.24-7.17 (m, 1H), 4.53-4.44 (m, 2H), 4.41 (d, J=3.8 Hz, 1H), 3.89 (s, 3H), 3.36 (t, J=8.5 Hz, 2H), 3.10-3.04 (m, 1H), 3.00-2.93 (m, 1H), 2.63 (t, J=10.8 Hz, 1H), 2.58-2.51 (m, 2H), 2.46-2.38 (m, 1H), 1.66 (br, 2H), 1.48-1.36 (m, 1H), 0.69 (d, J=6.5 Hz, 3H) ppm.

Example 75

5-Amino-N-{4-[(3R,4S,5S)-3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide

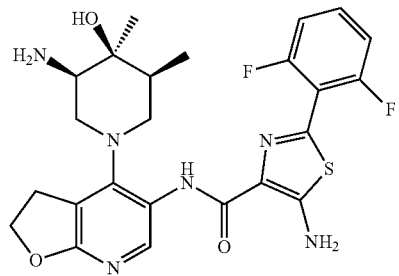 [SMILES: C[C@H]1CN(c2c(NC(=O)c3nc(-c4c(F)cccc4F)sc3N)cnc3c2CCO3)C[C@@H](N)[C@@]1(C)O]

Step 1. Benzyl(3R,4R,5S)-3-[(tert-butoxycarbonyl)amino]-4-hydroxy-4,5-dimethylpiperidine-1-carboxylate

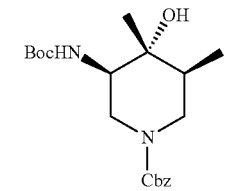

and Benzyl(3R,4S,5S)-3-[(tert-butoxycarbonyl)amino]-4-hydroxy-4,5-dimethylpiperidine-1-carboxylate

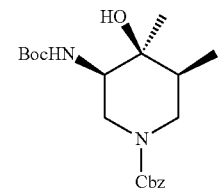 [SMILES: C[C@H]1CN(C(=O)OCc2ccccc2)C[C@@H](NC(=O)OC(C)(C)C)[C@@]1(C)O]

Benzyl (3R,5S)-3-[(tert-butoxycarbonyl)amino]-5-methyl-4-oxopiperidine-1-carboxylate (466 mg, 1.29 mmol) was added to an oven-dried vial equipped with a magnetic stirring bar. The vial was sealed with a PTFE-lined septum and kept under an N$_2$ atmosphere. A solution of LaCl$_3$.2LiCl in THF (from Aldrich, 0.6 M, 6.50 mL, 3.90 mmol) was added. The reaction mixture was stirred at room temperature for 1 h, and then cooled to −10° C. A solution of methylmagnesium chloride in THF (3.0 M; 1.30 mL, 3.90 mmol) was added slowly. After stirring at −10° C. for 1.5 h, the reaction was quenched with saturated aq. NH$_4$C and the solution was extracted with EtOAc (3 times). The combined organic layers were washed with brine, dried over anhydrous Na₂SO₄, and concentrated under reduced pressure. The resulting residue was purified using RP-HPLC (XBridge™ C18 column, eluting with a gradient of MeCN/water containing 0.05% TFA, at flow rate of 30 mL/min.) to afford benzyl (3R,4R,5S)-3-[(tert-butoxycarbonyl)amino]-4-hydroxy-4,5-dimethylpiperidine-1-carboxylate as a colorless oil (81 mg, 17%), Retention time 2.085 min.: LCMS calc. for $C_{20}H_{30}N_2NaO_5$ (M+Na)⁺: m/z=401.2; found 401.0; and benzyl (3R,4S,5S)-3-[(tert-butoxycarbonyl)amino]-4-hydroxy-4,5-dimethylpiperidine-1-carboxylate as a colorless oil (100 mg, 21%), retention time: 2.247 min., LCMS calc. for $C_{20}H_{30}N_2NaO_5$ (M+Na)⁺: m/z=401.2; found 401.0.

Step 2. tert-Butyl [(3R,4S,5S)-4-hydroxy-4,5-dimethylpiperidin-3-yl]carbamate

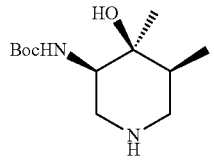 [SMILES: C[C@H]1CNC[C@@H](NC(=O)OC(C)(C)C)[C@@]1(C)O]

To a stirred solution of benzyl (3R,4S,5S)-3-[(tert-butoxycarbonyl)amino]-4-hydroxy-4,5-dimethylpiperidine-1-carboxylate (100 mg, 0.265 mmol) in MeOH (5.0 mL), 10 wt % Pd on carbon (33 mg) was added. The reaction mixture was stirred at room temperature under a hydrogen atmosphere (balloon pressure) for 3 h. The reaction was filtered through a pad of diatomaceous earth (eluted with MeOH), and then concentrated under reduced pressure. The resulting crude product was used directly in the next step without further purification (60 mg, 92%). LCMS calc. for $C_{12}H_{25}N_2O_3$ (M+H)⁺: m/z=245.2; found 245.0.

Step 3. tert-Butyl [(3R,4S,5S)-4-hydroxy-4,5-dimethyl-1-(5-nitro-2,3-dihydrofuro[2,3-b]pyridin-4-yl)piperidin-3-yl]carbamate

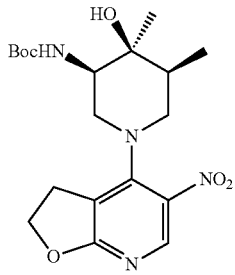 [SMILES: C[C@H]1CN(c2c([N+](=O)[O-])cnc3c2CCO3)C[C@@H](NC(=O)OC(C)(C)C)[C@@]1(C)O]

To a vial containing 4-iodo-5-nitro-2,3-dihydrofuro[2,3-b]pyridine (76 mg, 0.26 mmol) and tert-butyl [(3R,4S,5S)-4-hydroxy-4,5-dimethylpiperidin-3-yl]carbamate (60 mg, 0.24 mmol), EtOH was added (2.0 mL), followed by DIPEA (114 mg, 0.883 mmol). The mixture was stirred at 110° C. for 12 h. After cooling to room temperature, the reaction mixture was concentrated under reduced pressure. The resulting residue was purified on silica gel (0-100% EtOAc in hexanes) to give the sub-title compound as a yellow foamy solid (68 mg, 69%). LCMS calc. for $C_{19}H_{29}N_4O_6$ (M+H)⁺: m/z=409.2; found 409.0.

Step 4. tert-Butyl [(3R,4S,5S)-1-(5-amino-2,3-dihydrofuro[2,3-b]pyridin-4-yl)-4-hydroxy-4,5-dimethylpiperidin-3-yl]carbamate

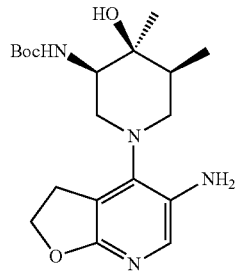

To a stirred solution of tert-butyl [(3R,4S,5S)-4-hydroxy-4,5-dimethyl-1-(5-nitro-2,3-dihydrofuro[2,3-b]pyridin-4-yl)piperidin-3-yl]carbamate (68 mg, 0.17 mmol) in MeOH (3.0 mL), 10 wt % Pd on carbon (25 mg) was added. The reaction mixture was stirred at room temperature under a hydrogen atmosphere (balloon pressure) for 6 h. The mixture was filtered through a pad of diatomaceous earth (eluted with MeOH), and then concentrated under reduced pressure. The resulting crude product was used directly in the next step without further purification (62 mg, 98%). LCMS calc. for $C_{19}H_{31}N_4O_4$ (M+H)⁺: m/z=379.2; found 379.0.

Step 5. 5-Amino-N-{4-[(3R,4S,5S)-3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide

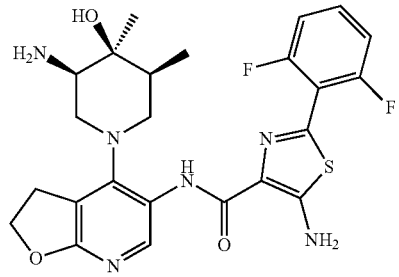 [SMILES: C[C@H]1CN(c2c(NC(=O)c3nc(-c4c(F)cccc4F)sc3N)cnc3c2CCO3)C[C@@H](N)[C@@]1(C)O]

To a mixture of 5-[(tert-butoxycarbonyl)amino]-2-(2,6-difluorophenyl)-1,3-thiazole-4-carboxylic acid (75 mg, 0.21 mmol), tert-butyl [(3R,4S,5S)-1-(5-amino-2,3-dihydrofuro[2,3-b]pyridin-4-yl)-4-hydroxy-4,5-dimethylpiperidin-3-yl]carbamate (62 mg, 0.16 mmol) and HATU (196 mg, 0.515 mmol) in DMF (2.0 mL), DIPEA (123 mg, 0.952 mmol) was added. The reaction mixture was stirred at room temperature for 3 h, and then concentrated under reduced pressure. DCM (2.0 mL) was added to the resulting residue followed by TFA (2.0 mL). The mixture was stirred at room temperature for 30 min., and then concentrated under reduced pressure. The resulting residue was purified using RP-HPLC (XBridge™ C18 column, eluting with a gradient of MeCN/water containing 0.1% NH₄OH, at flow rate of 30 mL/min.) to afford the title compound as a white solid (25 mg, 29%). LCMS calc. for $C_{24}H_{27}F_2N_6O_3S$ (M+H)+: m/z=517.2; found 517.0. 1H NMR (500 MHz, DMSO-$d_6$) δ 9.34 (s, 1H), 8.78 (s, 1H), 7.64-7.46 (m, 3H), 7.24 (t, J=8.6 Hz, 2H), 4.47 (t, J=9.1 Hz, 2H), 3.97 (s, 1H), 3.37 (t, J=8.5 Hz, 2H), 2.87-2.79 (m, 2H), 2.79-2.72 (m, 1H), 2.63 (dd, J=10.8, 4.6 Hz, 1H), 2.60-2.55 (m, 1H), 1.85-1.76 (m, 1H), 1.39 (br, 2H), 0.98 (s, 3H), 0.73 (d, J=6.8 Hz, 3H) ppm.

Example 76

5-Amino-N-{4-[(3R,4R,5S)-3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide

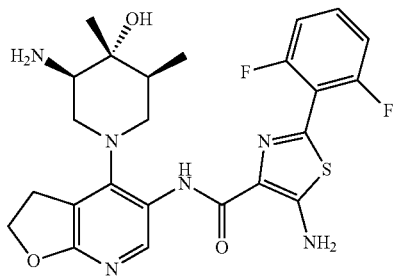 [SMILES: C[C@H]1CN(c2c(NC(=O)c3nc(-c4c(F)cccc4F)sc3N)cnc3c2CCO3)C[C@@H](N)[C@]1(C)O]

Step 1. tert-Butyl [(3R,4R,5S)-4-hydroxy-4,5-dimethylpiperidin-3-yl]carbamate

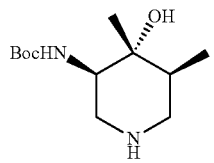 [SMILES: C[C@H]1CNC[C@@H](NC(=O)OC(C)(C)C)[C@]1(C)O]

To a stirred solution of benzyl (3R,4R,5S)-3-[(tert-butoxycarbonyl)amino]-4-hydroxy-4,5-dimethylpiperidine-1-carboxylate (81 mg, 0.21 mmol) in MeOH (4.0 mL), 10 wt % Pd on carbon (29 mg) was added. The reaction mixture was stirred at room temperature under a hydrogen atmosphere (balloon pressure) for 3 h. The reaction mixture was filtered through a pad of diatomaceous earth (eluted with MeOH), and then concentrated under reduced pressure. The resulting crude product was used directly in the next step without further purification (46 mg, 88%). LCMS calc. for $C_{12}H_{25}N_2O_3$ (M+H)+: m/z=245.2; found 245.0.

Step 2. tert-Butyl [(3R,4R,5S)-4-hydroxy-4,5-dimethyl-1-(5-nitro-2,3-dihydrofuro[2,3-b]pyridin-4-yl)piperidin-3-yl]carbamate

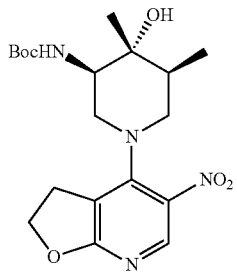 [SMILES: C[C@H]1CN(c2c([N+](=O)[O-])cnc3c2CCO3)C[C@@H](NC(=O)OC(C)(C)C)[C@]1(C)O]

To a vial containing 4-iodo-5-nitro-2,3-dihydrofuro[2,3-b]pyridine (59 mg, 0.20 mmol) and tert-butyl [(3R,4R,5S)-4-hydroxy-4,5-dimethylpiperidin-3-yl]carbamate (46 mg, 0.19 mmol) was added EtOH (2.0 mL), followed by DIPEA (100 mg, 0.772 mmol). The mixture was stirred at 110° C. for 15 h. After cooling to the room temperature, the reaction was concentrated under reduced pressure. The resulting residue was purified on silica gel (0-100% EtOAc in hexanes) to give the sub-title compound as a yellow foamy solid (51 mg, 67%). LCMS calc. for $C_{19}H_{29}N_4O_6$ (M+H)+: m/z=409.2; found 409.0.

Step 3. tert-Butyl [(3R,4R,5S)-1-(5-Amino-2,3-dihydrofuro[2,3-b]pyridin-4-yl)-4-hydroxy-4,5-dimethylpiperidin-3-yl]carbamate

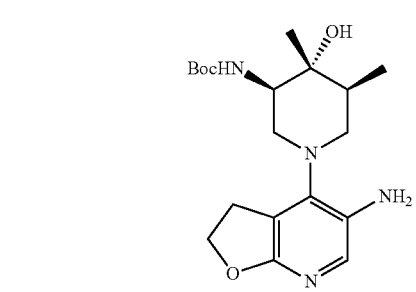 [SMILES: C[C@H]1CN(c2c(N)cnc3c2CCO3)C[C@@H](NC(=O)OC(C)(C)C)[C@]1(C)O]

To a stirred solution of tert-butyl [(3R,4R,5S)-4-hydroxy-4,5-dimethyl-1-(5-nitro-2,3-dihydrofuro[2,3-b]pyridin-4-yl)piperidin-3-yl]carbamate (51 mg, 0.13 mmol) in MeOH (3.0 mL), 10 wt % Pd on carbon (19 mg) was added. The reaction mixture was stirred at room temperature under a hydrogen atmosphere (balloon pressure) for 6 h. The mixture was filtered through a pad of diatomaceous earth (eluted with MeOH), and then concentrated under reduced pressure. The resulting crude product was used directly in the next step without further purification (44 mg, 92%). LCMS calc. for $C_{19}H_{31}N_4O_4$ (M+H)+: m/z=379.2; found 379.0.

Step 4. 5-Amino-N-{4-[(3R,4R,5S)-3-amino-4-hydroxy-4,5-dimethylpiperidin-1-yl]-2,3-dihydrofuro[2,3-b]pyridin-5-yl}-2-(2,6-difluorophenyl)-1,3-thiazole-4-carboxamide

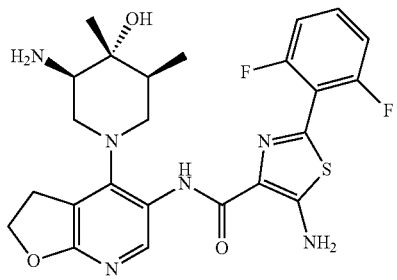 [SMILES: C[C@H]1CN(c2c(NC(=O)c3nc(-c4c(F)cccc4F)sc3N)cnc3c2CCO3)C[C@@H](N)[C@]1(C)O]

To a mixture of 5-[(tert-butoxycarbonyl)amino]-2-(2,6-difluorophenyl)-1,3-thiazole-4-carboxylic acid (55 mg, 0.15 mmol), tert-butyl [(3R,4R,5S)-1-(5-amino-2,3-dihydrofuro[2,3-b]pyridin-4-yl)-4-hydroxy-4,5-dimethylpiperidin-3-yl]carbamate (44 mg, 0.12 mmol) and HATU (134 mg, 0.353 mmol), DMF (2.0 mL) was added, followed by DIPEA (86 mg, 0.67 mmol). The reaction mixture was stirred at room temperature for 3 h, and then concentrated under reduced pressure. DCM (2.0 mL) was added to the resulting residue followed by TFA (2.0 mL). The mixture was stirred at room temperature for 30 min. and then concentrated under reduced pressure. The resulting residue was purified using RP-HPLC (XBridge™ C18 column, eluting with a gradient of MeCN/water containing 0.1% ammonium hydroxide, at flow rate of 30 mL/min.) to afford the title compound as a white solid (20 mg, 34%). LCMS calc. for $C_{24}H_{27}F_2N_6O_3S$ (M+H)$^+$: m/z=517.2; found 517.0. $^1$H NMR (500 MHz, DMSO-d$_6$) δ 9.17 (s, 1H), 8.61 (s, 1H), 7.59-7.45 (m, 3H), 7.21 (t, J=8.6 Hz, 2H), 4.52-4.42 (m, 2H), 4.06 (s, 1H), 3.37 (t, J=8.5 Hz, 2H), 2.99-2.92 (m, 1H), 2.90-2.79 (m, 2H), 2.77-2.64 (m, 2H), 1.93-1.82 (m, 1H), 1.46 (br, 2H), 0.92 (s, 3H), 0.71 (d, J=6.9 Hz, 3H) ppm.

Example A. Pim Enzyme Assays

Pim-1 and Pim-3 kinase assays-20 μL reactions were run in white 384 well polystyrene plates dotted with 0.8 μL compound/DMSO in the assay buffer (50 mM Tris, pH 7.5, 0.01% Tween-20, 5 mM MgCl$_2$, 0.01% BSA, 5 mM DTT), containing 0.05 μM Biotin-labeled BAD peptide substrate (AnaSpec 62269), 1 mM ATP, and 2.5 pM (Pim-1, Invitrogen PV3503) or 1.25 pM (Pim-3, Millipore 14-738) enzyme for 1 h at 25° C. Reactions were stopped by addition of 10 μL STOP Buffer (150 mM Tris, pH=7.5, 150 mM NaCl, 75 mM EDTA, 0.01% Tween-20, 0.3% BSA) supplemented with Phospho-Bad (Ser112) Antibody (Cell Signaling 9291) diluted 666-fold, and Streptavidin donor beads (PerkinElmer 6760002) along with Protein-A acceptor beads (PerkinElmer 6760137) at 15 μg/mL each. Supplementation of the STOP buffer with beads and stopping the reactions were done under reduced light. Prior to the stopping reactions STOP buffer with beads was pre-incubated for 1 h in the dark at room temperature. After stopping the reactions, plates were incubated for 1 h in the dark at room temperature before reading on a PHERAstar FS plate reader (BMG Labtech) under reduced light.

Pim-2 kinase assay-20 μL reactions were run in white 384 well polystyrene plates dotted with 0.8 μL compound/DMSO in the assay buffer (50 mM Tris, pH 7.5, 0.01% Tween-20, 5 mM MgCl$_2$, 0.01% BSA, 5 mM DTT), containing 0.05 μM Fluorescein-labeled CREBtide peptide substrate (Invitrogen PV3508), 1 mM ATP, and 1 nM enzyme (Invitrogen PV3649) for 2 h at 25° C. Reactions were stopped by addition of 10 μL TR-FRET Dilution Buffer (Invitrogen PV3574) with 30 mM EDTA and 1.5 nM LanthaScreen Tb-CREB pSer133 antibody (Invitrogen PV3566). After 30 min. incubation at room temperature, plates were read on a PHERAstar FS plate reader (BMG Labtech).

Compounds of the invention having an IC$_{50}$ of 2 μM or less when tested for PIM kinase activity under the assay conditions disclosed above are considered active.

Although the above in vitro assays are conducted at 1 mM ATP compounds can also be evaluated for potency and in vitro activity against PIM targets utilizing K$_m$ conditions, where the concentration of ATP is set to the K$_m$ value and the assay is more sensitive to PIM inhibition activity.

Example B. Pim Cellular Assays

One or more compounds of the invention were tested for inhibitory activity of PIM according to at least one of the following cellular assays. Compounds of the invention having an IC$_{50}$ of 10 μM or less when tested for PIM kinase activity under the cellular assay conditions disclosed below would be and were considered active.

Pim Cell Proliferation Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS (Roswell Park Memorial Institute 1640 Medium supplemented with 10% fetal bovine serum) and IMDM 20% FBS (Iscove's Modified Dulbecco's Medium (MDM) with 20% fetal bovine strum) (Mediatech, Manassas, Va.) respectively. To measure the anti-proliferation activity of test compounds, both cell lines are plated with the culture medium (2×10$^3$ cells/well/in 200 μL) into 96-well polystyrene ultralow binding (Costar) in the presence or absence of a concentration range of test compounds. After 4 days, [$^3$H]-thymidine, 1 μCi/10 μL/well (PerkinElmer, Boston, Mass.) in culture medium is then added to the cell culture for an additional 16 h before the incorporated radioactivity is separated by filtration with a Packard Microplate Harvester with water through a 0.3% polyethylenimine pre-wetted glass fiber GF/B filter plates (Packard Bioscience/PerkinElmer, Boston, Mass.). The plate is measured by liquid scintillation counting with a TopCount® scintillation sounter (PerkinElmer). IC$_{50}$ determination is performed by fitting the curve of percent inhibition versus the log of the inhibitor concentration using GraphPad Prism® 5.0 software.

Pim pBAD Signaling Assays

KG-1A cells are purchased from ATCC (Manassas, Va.) and KMS.12.BM cells are purchased from NIBIO, JCRB cell bank (Tokyo, Japan) and maintained in the culture mediums recommended, RPMI, 10% FBS and IMDM 20% FBS (Mediatech, Manassas, Va.) respectively. To measure the pBAD inhibitory activity of the compounds, both cell lines are plated with the culture medium (1×10$^6$/well/100 μL for KG1A and 4×10$^5$ cells/well/in 100 μL for KMS12BM) into 96-well V bottom polypropylene plates (Matrix, Thermo Fisher, USA) and incubated 30 min. at 37° C. to normalize cell signaling from handling. Test compounds are added at an appropriate concentration range and further incubated for 2.5 h for KMS.2.BM cells and 4h for KG1-A cells. Plates are centrifuged at 2000 RPM for 10 min. and supernatants aspirated. 100 μL lysis buffer with protease inhibitors (Cell Signaling Technologies, Danver, Mass., Sigma, St Louis Mo., EMD, USA) is added to the pellets, mixed well and set on ice for 30 min. Lysates are frozen overnight at −80'C. To measure the pBAD activity, a Cell Signaling ELISA (enzyme-linked immunosorbant assay) kit (Cell Signaling Path Scan phosphor pBAD ELISA) is utilized. 50 μL of the lysate is tested per the ELISA protocol and the data analysis is performed by software on a SpectraMax® M5 plate reader (Molecular Devices, Sunnyvale, Calif.). $IC_{50}$ determination is performed by fitting the curve of percent inhibition versus the log of the inhibitor concentration using GraphPad Prism® 5.0 software.

Data obtained for the Example compounds, obtained using the methods described in Example A, are provided in Table 1.

TABLE 1

Pim Enzyme Assay Data

| Example | Pim1 $IC_{50}$ (nM) | Pim2 $IC_{50}$ (nM) | Pim3 $IC_{50}$ (nM) |
|---|---|---|---|
| 1 | + | 277 | + |
| 2 | >40 | >2000[1] | >40 |
| 3 | + | + | + |
| 4 | + | >2000 | + |
| 5 | + | + | + |
| 6 | + | >2000 | + |
| 7 | + | + | + |
| 8 | + | >2000 | + |
| 9 | + | + | + |
| 10 | + | ++ | + |
| 11 | + | ++ | + |
| 12 | + | + | + |
| 13 | + | >2000 | + |
| 14 | + | + | + |
| 15 (Diastereoisomer 1) | + | + | + |
| 15 (Diastereoisomer 2) | + | + | + |
| 16 (Diastereoisomer 1) | + | >2000 | + |
| 16 (Diastereoisomer 2) | + | >2000 | + |
| 17 | + | ++ | + |
| 18 (Diastereoisomer 1) | + | ++ | + |
| 18 (Diastereoisomer 2) | + | ++ | + |
| 19 (Diastereoisomer 1) | + | >2000 | ++ |
| 19 (Diastereoisomer 2) | + | ++ | + |
| 20 | + | + | + |
| 21 | + | + | + |
| 22 (Diastereoisomer 1) | + | ++ | + |
| 22 (Diastereoisomer 2) | + | + | + |
| 23 (Diastereoisomer 1) | + | + | + |
| 23 (Diastereoisomer 2) | + | + | + |
| 24 | + | >2000 | + |
| 25 | + | + | + |
| 26 | + | >2000 | + |
| 27 | + | + | + |
| 28 | + | + | + |
| 29 | + | ++ | + |
| 30 | + | ++ | + |
| 31 | + | + | + |
| 32 | + | + | + |
| 33 | + | ++ | + |
| 34 | + | >2000 | + |
| 35 | >40 | >2000[2] | >40 |
| 36 | + | + | + |
| 37 (mixture of diastereoisomers) | + | + | + |
| 37 (Diastereoisomer 1) | + | + | + |
| 37 (Diastereoisomer 2) | + | + | + |
| 38 | + | + | + |
| 39 | + | + | + |
| 40 | + | + | + |
| 41 | + | + | + |
| 42 | + | + | + |
| 43 | + | + | + |
| 44 (Diastereoisomer 1) | + | + | + |
| 44 (Diastereoisomer 2) | + | + | + |
| 45 (Diastereoisomer 1) | + | + | + |
| 45 (Diastereoisomer 2) | + | + | + |
| 46 (Diastereoisomer 1) | + | + | + |
| 46 (Diastereoisomer 2) | + | + | + |
| 47 (Diastereoisomer 1) | + | + | + |
| 47 (Diastereoisomer 2) | + | + | + |
| 48 (Diastereoisomer 1) | + | ++ | + |
| 48 (Diastereoisomer 2) | + | + | + |
| 49 (Diastereoisomer 1) | + | + | + |
| 49 (Diastereoisomer 2) | + | + | + |
| 50 | + | ++ | + |
| 51 (Diastereoisomer 1) | + | + | + |
| 51 (Diastereoisomer 2) | + | + | + |
| 52 | + | + | + |
| 53 (Diastereoisomer 1) | + | + | + |
| 53 (Diastereoisomer 2) | + | + | + |
| 54 (Diastereoisomer 1) | + | + | + |
| 54 (Diastereoisomer 2) | + | + | + |
| 55 (Diastereoisomer 1) | + | ++ | + |
| 55 (Diastereoisomer 2) | + | + | + |
| 56 (Diastereoisomer 1) | + | + | + |
| 56 (Diastereoisomer 2) | + | + | + |
| 57 | + | ++ | + |
| 58 (Diastereoisomer 1) | + | ++ | + |
| 58 (Diastereoisomer 2) | + | ++ | + |
| 59 (Diastereoisomer 1) | + | ++ | + |
| 59 (Diastereoisomer 2) | + | ++ | + |
| 60 (Diastereoisomer 1) | + | ++ | + |
| 60 (Diastereoisomer 2) | + | ++ | + |
| 61 (Diastereoisomer 1) | + | >2000 | >40 |

TABLE 1-continued

Pim Enzyme Assay Data

| Example | Pim1 IC$_{50}$ (nM) | Pim2 IC$_{50}$ (nM) | Pim3 IC$_{50}$ (nM) |
|---|---|---|---|
| 61 (Diastereoisomer 2) | + | ++ | + |
| 62 (Diastereoisomer 1) | + | ++ | + |
| 62 (Diastereoisomer 2) | + | ++ | + |
| 63 (Diastereoisomer 1) | + | + | + |
| 63 (Diastereoisomer 2) | + | + | + |
| 63 (Diastereoisomer 3) | + | + | + |
| 63 (Diastereoisomer 4) | + | + | + |
| 64 (Diastereoisomer 1) | + | + | + |
| 64 (Diastereoisomer 2) | + | + | + |
| 65 | + | + | + |
| 66 (Diastereoisomer 1) | + | + | + |
| 66 (Diastereoisomer 2) | + | + | + |
| 67 (Diastereoisomer 1) | + | + | + |
| 67 (Diastereoisomer 2) | + | + | + |
| 68 (Diastereoisomer 1) | + | + | + |
| 68 (Diastereoisomer 2) | + | + | + |
| 69 | + | + | + |
| 70 (Diastereoisomer 1) | + | + | + |
| 70 (Diastereoisomer 2) | + | + | + |
| 71 | + | + | + |
| 72 (Diastereoisomer 1) | + | + | + |
| 72 (Diastereoisomer 2) | + | + | + |
| 73 | + | + | + |
| 74 | + | + | + |
| 75 | + | + | + |
| 76 | + | + | + |

1000 nM < IC$_{50}$ ≤ 10000 nM: +++
100 nM < IC$_{50}$ ≤ 1000 nM: ++
IC$_{50}$ ≤ 100 nM: +.
[1, 2] Compound 2 inhibited Pim2 (100 nM < IC$_{50}$ ≤ 1000 nM) and compound 35 inhibited PIM2 (1000 nM < IC$_{50}$ ≤ 10000 nM) at K$_m$ ATP concentration rather than at 1 mM concentration.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound, which is N-{4-[3-amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, wherein one or more hydrogen atoms are replaced by deuterium, or a pharmaceutically acceptable salt thereof.

2. A pharmaceutical composition comprising a compound of claim 1, or a pharmaceutically acceptable salt thereof, and a pharmaceutically acceptable carrier.

3. A compound, which is N-{4-[(3R,4R,5S)-3-Amino-4-hydroxy-5-methylpiperidin-1-yl]-7-hydroxy-6,7-dihydro-5H-cyclopenta[b]pyridin-3-yl}-6-(2,6-difluorophenyl)-5-fluoropyridine-2-carboxamide, wherein one or more hydrogen atoms are replaced by deuterium, or a pharmaceutically acceptable salt thereof.

4. A pharmaceutical composition comprising a compound of claim 3, or a pharmaceutically acceptable salt thereof, and a pharmaceutically acceptable carrier.

* * * * *